United States Patent
Kling et al.

(10) Patent No.: US 9,150,545 B2
(45) Date of Patent: Oct. 6, 2015

(54) CARBOXAMIDE COMPOUNDS AND THEIR USE AS CALPAIN INHIBITORS V

(71) Applicants: ABBVIE DEUTSCHLAND GMBH & CO. KG, Wiesbaden (DE); ABBVIE INC., North Chicago, IL (US)

(72) Inventors: Andreas Kling, Wiesbaden (DE); Katja Jantos, Wiesbaden (DE); Helmut Mack, Wiesbaden (DE); Achim Möller, Wiesbaden (DE); Wilfried Hornberger, Wiesbaden (DE); Gisela Backfisch, Wiesbaden (DE); Yanbin Lao, North Chicago, IL (US); Marjoleen Nijsen, Wiesbaden (DE)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 14/390,381

(22) PCT Filed: Mar. 14, 2013

(86) PCT No.: PCT/EP2013/055291
§ 371 (c)(1),
(2) Date: Oct. 2, 2014

(87) PCT Pub. No.: WO2013/149800
PCT Pub. Date: Oct. 10, 2013

(65) Prior Publication Data
US 2015/0065477 A1     Mar. 5, 2015

Related U.S. Application Data

(60) Provisional application No. 61/619,590, filed on Apr. 3, 2012.

(51) Int. Cl.
*A61K 31/44* (2006.01)
*C07D 221/18* (2006.01)
(Continued)

(52) U.S. Cl.
CPC ............ *C07D 401/14* (2013.01); *C07D 401/04* (2013.01); *C07D 405/14* (2013.01);
(Continued)

(58) Field of Classification Search
None
See application file for complete search history.

(56) References Cited

U.S. PATENT DOCUMENTS 4,826,835 A    5/1989  Kuhla et al.
7,728,012 B2 *  6/2010  Kling et al. ................. 514/341
(Continued)

FOREIGN PATENT DOCUMENTS

WO    WO-8800468 A1    1/1988
WO    WO-9816512 A1    4/1998
(Continued)

OTHER PUBLICATIONS

Barrett M.J., et al., "Effect of Substrate on Ca2(+)-Concentration Required for Activity of the Ca2(+)-Dependent Proteinases, mu- and m-Calpain," Life Science, 1991, vol. 48 (17), pp. 1659-1669.
(Continued)

Primary Examiner — Timothy R Rozof
(74) Attorney, Agent, or Firm — Lisa V. Mueller; Michael Best & Friedrich LLP

(57) ABSTRACT

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity. The carboxamide compounds are compounds of the general formula (I) in which $R^1$, $R^2$ and n have the meanings mentioned in the claims and the description, Y is a radical of the formulae (Y1) or (Y2) where # indicates the point of attachment of Y to the pyridine ring, $R^3$, $R^4$, $R^5$, $R^y$ and m have the meanings mentioned in the claims and the description, A is $(CH_2)_p$ with p being 1, 2, 3 or 4, where one or two hydrogen atoms may be replaced by a radical $R^6$, where A is attached to the 3- or 4-position of the pyrazole radical and $R^6$ has the meaning mentioned in the claims and the description; $A^1$ is $(CH_2)q$ with q being 0, 1, 2 or 3, where one or two hydrogen atoms may be replaced by halogen or $C_1$-$C_4$-alkyl; and $A^2$ is $(CH_2)r$ with r being 0, 1, 2 or 3, where one or two hydrogen atoms may be replaced by halogen or $C_1$-$C_4$-alkyl, provided that that r+q is 2, 3, 4, 5 or 6; their tautomers, the hydrates thereof, the pharmaceutically suitable salts of the carboxamide compounds (I), the prodrugs of (I) and the pharmaceutically suitable salts of the prodrugs, tautomers or hydrates of (I).

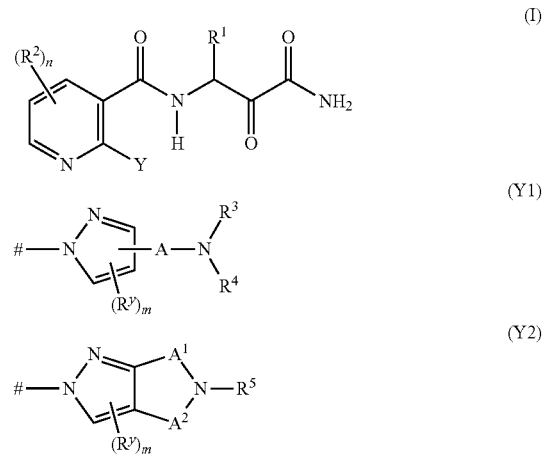

22 Claims, No Drawings

(51) Int. Cl.
| | |
|---|---|
| C07D 401/00 | (2006.01) |
| C07D 401/14 | (2006.01) |
| C07D 405/14 | (2006.01) |
| C07D 401/04 | (2006.01) |
| C07D 471/04 | (2006.01) |
| C07D 487/04 | (2006.01) |
| C07D 413/14 | (2006.01) |
| C07D 491/048 | (2006.01) |
| C07D 491/107 | (2006.01) |

(52) U.S. Cl.
CPC .......... *C07D413/14* (2013.01); *C07D 471/04* (2013.01); *C07D 487/04* (2013.01); *C07D 491/048* (2013.01); *C07D 491/107* (2013.01)

(56) References Cited

U.S. PATENT DOCUMENTS

| | | | |
|---|---|---|---|
| 8,598,211 B2* | 12/2013 | Kling et al. | 514/341 |
| 2011/0059968 A1* | 3/2011 | Hornberger et al. | 514/235.5 |

FOREIGN PATENT DOCUMENTS

| | | |
|---|---|---|
| WO | WO-9825883 A1 | 6/1998 |
| WO | WO-9825899 A1 | 6/1998 |
| WO | WO-9917775 A1 | 4/1999 |
| WO | WO-9954293 A1 | 10/1999 |
| WO | WO-9954294 A1 | 10/1999 |
| WO | WO-9954304 A1 | 10/1999 |
| WO | WO-9954305 A1 | 10/1999 |
| WO | WO-9954310 A2 | 10/1999 |
| WO | WO-9954320 A1 | 10/1999 |
| WO | WO-9961423 A1 | 12/1999 |
| WO | WO-03080182 A1 | 10/2003 |
| WO | WO-2007016589 A2 | 2/2007 |
| WO | WO-2008080969 A1 | 7/2008 |
| WO | WO-2008106130 A2 | 9/2008 |
| WO | WO-2011076811 A1 | 6/2011 |
| WO | WO-2011076812 A1 | 6/2011 |

OTHER PUBLICATIONS

Bartus R.T., et al., "Calpain as a Novel Target for Treating Acute Neurodegenerative Disorders," Neurological Research, 1995, vol. 17 (4), pp. 249-258.
Carragher N.O., "Calpain Inhibition: A Therapeutic Strategy Targeting Multiple Disease States," Current Pharmaceutical Design, 2006, vol. 12 (5), pp. 615-638.
Chatterjee P.K., et al., "Inhibitors of Calpain Activation (PD150606 and E-64) and Renal Ischemia-Reperfusion Injury," Biochemical Pharmacology, 2005, vol. 69 (7), pp. 1121-1131.
Cuzzocrea S., et al., "Calpain Inhibitor I Reduces the Development of Acute and Chronic Inflammation," American Journal of Pathology, 2000, vol. 157 (6), pp. 2065-2079.
Dnyanmote A.V., et al., "Calpastatin Overexpression Prevents Progression of S-1, 2-Dichlorovinyl-L-Cysteine (DCVC)-Initiated Acute Renal Injury and Renal Failure (ARF) in Diabetes," Toxicology and Applied Pharmacology, 2006, vol. 215 (2), pp. 146-157.
Donkor I.O., "Calpain Inhibitors: A Survey of Compounds Reported In the Patent and Scientific Literature," Expert Opinion on Therapeutic Patents, 2011, vol. 21 (5), pp. 601-636.
Edelstein C.L., et al., "The Role of Cystein Protease in Hyproxia-Induced Rat Renal Proximal Tubular Injury," Proceedings of the National Academy of Sciences, 1995, vol. 92 (17), pp. 7662-7666.
Fehrentz J.A., et al., "An Efficient Synthesis of Optically Active A-(T-Butoxycarbonylamino)-Aldehydes from A-Amino Acids," Synthesis, 1983, vol. 8, pp. 676-678.
Goll D.E., et al., "The Calpain System," Physiological Reviews, 2003, vol. 83 (3), pp. 731-801.
Greenbaum D.C., et al., "Apicomplexan Parasites Co-Opt Host Calpains to Facilitate their Escape from Infected Cells," Science, 2009, vol. 324 (5928), pp. 794-797.

Groshong J.S., et al., "Calpain Activation Impairs Neuromuscular Transmission in a Mouse Model of the Slow-Channel Myasthenic Syndrome," Journal of Clinical Investigation, 2007, vol. 117 (10), pp. 2903-2912.
Hassen G.W., et al., "A Novel Calpain Inhibitor for the Treatment of Acute Experimental Autoimmune Encephalomyelitis.," Journal of Neuroimmunology, 2006, vol. 180 (1-2), pp. 135-146.
Higaki J., et al., "Inhibition of Beta-Amloid Formation Identifies Proteolytic Precursors and Subcellular Site of Catabolism," Neuron, 1995, vol. 14 (3), pp. 651-659.
Higuchi M., et al., "Distinct Mechanistic Roles of Calpain and Caspase Activation in Neurodegeneratio as Revealed in Mice Overexpressing their Specific Inhibitor," The Journal of Biological Chemistry, 2005, vol. 280 (15), pp. 15229-15237.
Hoffmann F., et al., "Carbonyl Reductases and Pluripotent Hydroxysteroid Dehydrogenases of the Short-Chain Dehydrogenase/Reductase Superfamily," Drug Metabolism Reviews, 2007, vol. 39 (1), pp. 87-144.
Hong S.C., et al., "Neuroprotection with a Calpain Inhibitor in a Model of Focal Cerebral lschemia," Stroke, 1994, vol. 25 (3), pp. 663-669.
International Search Report and Written Opinion for Application No. PCT/EP2013/055291, mailed on Jul. 3, 2013, 14 pages.
Jung S.Y., et al., "Antimalarial Effect of N-Acetyl-L-Leucyl-L-Leucyl-L-Norleucinal by the Inhibition of Plasmodium Falciparum Calpain," Archives of Pharmacal Research, 2009, vol. 32 (6), pp. 899-906.
Kunz S., et al., "The Calpain Inhibitor MDL 28170 Prevents Inflammation-Induced Neurofilament Light Chain Breakdown in the Spinal Cord and Reduces Thermal Hyperalgesia," Pain, 2004, vol. 110 (1-2), pp. 409-418.
Li X., et al., "BDA-410: A Novel Synthetic Calpain Inhibitor Active Against Blood Stage Malaria," Molecular and Biochemical Parasitology, 2007, vol. 155 (1), pp. 26-32.
Medana I.M., et al., "Cerebral Calpain in Fatal Falciparum Malaria," Neuropathology and Applied Neurobiology, 2007, vol. 33 (2), pp. 179-192.
Monaco E.A., 3rd., "Recent Evidence Regarding A Role for Cdk5 Dysregulation in Alzheimer's Disease," Current Alzheimer Research, 2004, vol. 1 (1), pp. 33-38.
O'Donnell L.A., et al., "Human Immunodeficiency Virus (HIV)-Induced Neurotoxicity: Roles for the NMDA Receptor Subtypes 2A and 2B and the Calcium-Activated Protease Calpain by a CSF-derived HIV-1 Strain," The Journal of Neuroscience, 2006, vol. 26 (3), pp. 981-990.
Park S.Y., et al., "The Generation of a 17 KDa Neurotoxic Fragment: An Alternative Mechanism by which Tau Mediates Beta-Amyloid-Induced Neurodegeneration," The Journal of Neuroscience, 2005, vol. 25 (22), pp. 5365-5375.
Patrick G.N., et al., "Conversion of P35 to P25 Deregulates Cdk5 Activity and Promotes Neurodegeneration," Nature, 1999, vol. 402 (6762), pp. 615-622.
Peltier J., et al., "Calpain Activation and Secretion Promote Glomerular Injury in Experimental Glomerulonephritis: Evidence From Calpastatin-Transgenic Mice," Journal of the American Society of Nephrology, 2006, vol. 17 (12), pp. 3415-3423.
Pietsch M., et al., "Calpains: Attractive Targets for the Development of Synthetic Inhibitors," Current Topics in Medicinal Chemistry, 2010, vol. 10 (3), pp. 270-293.
Rosemond M.J., et al., "Human Carbonyl Reduction Pathways and A Strategy for their Study in Vitro," Drug Metabolism Reviews, 2004, vol. 36 (2), pp. 335-361.
Saatman et al., "Calpain Inhibitor AK95 Attenuated Motor and Cognitive Deficits Following Experimental Brain Injury in the Rat," Proceedings of the National Academy of Sciences, 1996, vol. 93 (8), pp. 3428-3433.
Saez M.E., et al., "The Therapeutic Potential of the Calpain Family: New Aspects," Drug Discovery Today, 2006, vol. 11 (19-20), pp. 917-923.
Shi Y., et al., "Downregulation of the Calpain Inhibitor Protein Calpastatin by Caspases During Renal lschemia-Reperfusion," American Journal of Physiology Renal Physiology, 2000, vol. 279 (3), pp. F509-F517.

(56) References Cited

OTHER PUBLICATIONS

Shiba et al., "Mechanism of Growth Inhibition of MCF-7 by a Cell Permeable Calpain Inhibitor," International Journal of Oncology, 1994, vol. 5, pp. 353-420.

Spencer M.J., et al., "Overexpression of a Calpastatin Transgene in Mdx Muscle Reduces Dystrophic Pathology," Human Molecular Genetics, 2002, vol. 11 (21), pp. 2645-2655.

Suzuki et al., "Calpain: Novel Family Members, Activation and Physiological Function," Biological Chemistry Hoppe-Seyler, 1995, vol. 376 (9), pp. 523-529.

Takano J., et al., "Calpain Mediates Excitotoxic DNA Fragmentation via Mitochondrial Pathways in Adult Brains: Evidence from Calpastatin Mutant Mice," The Journal of Biological Chemistry, 2005, vol. 280 (16), pp. 16175-16184.

Teranishi F., et al., "Calpain is Involved in the HIV Replication from the Latently Infected OM10.1 Cells," Biochemical and Biophysical Research Communications, 2003, vol. 303 (3), pp. 940-946.

Wang et al., "Calpain Inhibition an Overview of its Therapeutic Potential," Trends in Pharmacological Sciences, 1994, vol. 15 (11), pp. 412-419.

Wang K.K.W., et al., "Calpain Inhibitors: Novel Neuroprotectants and Potential Anticataractic Agents," Drug of the Future, 1998, vol. 23 (7), pp. 741-749.

Wang M.S., et al., "Calpain Inhibition Protects against Taxol-Induced Sensory Neuropathy," Brain, 2004, vol. 127 (Pt 3), pp. 671-679.

Watanabe N., et al., "Selective Release of a Processed Form of Interleukin 1 alpha," Cytokine, 1994, vol. 6 (6), pp. 597-601.

Yoshida K., et al., "Calpain is Implicated in Rat Myocardial Injury after Ischemia of Reperfusion," Japanese Circulation Journal, 1995, vol. 59 (1), pp. 40-48.

\* cited by examiner

CARBOXAMIDE COMPOUNDS AND THEIR USE AS CALPAIN INHIBITORS V

CROSS-REFERENCE TO RELATED APPLICATIONS

This is a U.S. national stage entry of International Patent Application No. PCT/EP2013/055291, filed on Mar. 14, 2013, which claims priority to U.S. Patent Application No. 61/619,590, filed on Apr. 3, 2012, the entire contents of all of which are fully incorporated herein by reference.

DESCRIPTION

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

Calpains are intracellular, proteolytic enzymes from the cysteine protease group and are found in many cells. The enzyme calpain is activated by elevated calcium concentration, with a distinction being made between calpain I or µ-calpain, which is activated by µ-molar concentrations of calcium ions, and calpain II or m-calpain, which is activated by m-molar concentrations of calcium ions. Currently, further calpain isoenzymes are also postulated (M. E. Saez et al.; Drug Discovery Today 2006, 11 (19/20), pp. 917-923; Goll et al., Physiol. Rev. 2003, 83, oo. 731-801; K. Suzuki et al., Biol. Chem. Hoppe-Seyler, 1995, 376 (9), pp. 523-9).

Calpains play an important role in various physiological processes. These processes include the cleavage of different regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and others which are listed in: M. J. Barrett et al., Life Sci. 1991, 48, pp. 1659-69; K. Wang et al., Trends in Pharmacol. Sci. 1994, 15, pp. 412-419.

Elevated calpain levels have been measured in various pathophysiological processes, for example: ischemias of the heart (e.g. myocardial infarction), the kidney, the lung, the liver or the central nervous system (e.g. stroke), inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above) and infectious diseases such as malaria (I M Medana et al., Neuropath and Appl. Neurobiol. 2007, 33, pp. 179-192). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes.

For this reason, it was postulated that inhibitors of calpain could be of use for treating these diseases. This postulate was confirmed by a variety of investigations. Thus, Seung-Chyul Hong et al., Stroke 1994, 25 (3), pp. 663-669, and R. T. Bartus et al., Neurological Res. 1995, 17, pp. 249-258, have demonstrated that calpain inhibitors have a neuroprotective effect in acute neurodegenerative impairments or ischemias such as occur after cerebral stroke. K. E. Saatman et al., Proc. Natl. Acad. Sci. USA, 1996, 93, pp. 3428-3433 describe that following experimental brain trauma, calpain inhibitors also improved recovery from the memory performance deficits and neuromotor impairments. C. L. Edelstein et al., Proc. Natl. Acad. Sci. USA, 1995, 92, pp. 7662-6, found that calpain inhibitors have a protective effect on hypoxia-damaged kidneys. Yoshida, Ken Ischi et al., Jap. Circ. J. 1995, 59 (1), pp. 40-48, pointed out that calpain inhibitors had favorable effects following cardiac damage which was produced by ischemia or reperfusion. The calpain inhibitor BDA-410 delayed the progression of malaria infection in a mouse model of malaria pathogenesis as shown by X. Li et al., Mol. Biochem. Parasitol. 2007, 155 (1), pp 26-32.

More recent studies have shown in calpastatin transgenic animals that the expression of the natural inhibitor of calpain significantly attenuates the pathophysiological effects of activated calpain in experimental glomerulonephritis shown by J. Peltier et al., J A, Soc Nephrol. 2006, 17, pp. 3415-3423, in cardiovascular remodeling in angiotensin II-induced hypertension, in impaired synaptic transmission in slow-channel congenital myasthenic syndrome shown by Groshong J S et al., J Clin Invest. 2007, 117 (10), pp 2903-2912, in excitotoxic DNA fragmentation via mitochondrial pathways shown by J Takano et al., J Biol Chem. 2005, 280 (16) pp. 16175-16184, and in necrotic processes in dystrophic muscles shown by M J Spencer et al., Hum Mol Gen, 2002, 11(21), pp 2645-2655.

It has been shown in recent years that both the function and the metabolism of a number of important proteins involved in the development of Alzheimer's disease are modulated by calpain. Various external influences such as, for example, excitotoxins, oxidative stress or else the action of amyloid protein lead to hyperactivation of calpain in the nerve cell, causing, as cascade, a dysregulation of the CNS-specific kinase cdk5 and subsequently a hyperphosphorylation of the so-called tau protein. Whereas the actual task of the tau protein consists of stabilizing the microtubules and thus the cytoskeleton, phosphorylated tau is no longer able to fulfil this function; the cytoskeleton collapses, axonal transport of matter is impaired and thus eventually the nerve cell degenerates (G. Patrick et al., Nature 1999, 402, pp. 615-622; E. A. Monaco et al.; Curr. Alzheimer Res. 2004, 1 (1), pp. 33-38). Accumulation of phosphorylated tau additionally leads to the formation of so-called neurofibrillary tangles (NFTs) which, together with the well-known amyloid plaques, represent a pathological hallmark of Alzheimer's disease. Similar changes in the tau protein, generally referred to important feature of as tauopathies are also observed in other (neuro) degenerative disorders such as, for example, following stroke, inflammations of the brain, Parkinsonism, in normal-pressure hydrocephalus and Creutzfeldt-Jakob disease.

The involvement of calpain in neurodegenerative processes has been demonstrated in transgenic mice with the aid of calpastatin, a specific and natural inhibitor of calpains (Higuchi et al.; J. Biol. Chem. 2005, 280 (15), pp. 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, Vol. 180, pp. 135-146). It has further been shown that calpain inhibitors on the one hand block the Aβ-induced degeneration of neurons (Park et al.; J. Neurosci. 2005, 25, pp. 5365-5375), and in addition reduce the release of the β-amyloid precursor protein (β APP) (J. Higaki et al., Neuron, 1995, 14, pp. 651-659). With this background, calpain inhibitors having sufficient CNS availability represent a novel therapeutic principle for the treatment of neurodegenerative disorders in general and in particular also of Alzheimer's disease.

The release of interleukin-1α is likewise inhibited by calpain inhibitors (N. Watanabe et al., Cytokine 1994, 6(6), pp. 597-601). It has additionally been found that calpain inhibitors show cytotoxic effects on tumor cells (E. Shiba et al. 20th Meeting Int. Ass. Breast Cancer Res., Sendai Jp, 1994, 25.-28. Sep., Int. J. Oncol. S(Suppl.), 1994, 381).

The involvement of calpain in HIV disorders has only recently been shown. Thus, it has been demonstrated that the HIV-induced neurotoxicity is mediated by calpain (O'Donnell et al.; J. Neurosci. 2006, 26 (3), pp. 981-990). Calpain involvement in the replication of the HIV virus has also been shown (Teranishi et al.; Biochem. Biophys. Res. Comm. 2003, 303 (3), pp. 940-946).

Recent investigations indicate that calpain plays a part in so-called nociception, the perception of pain. Calpain inhibitors showed a distinctly beneficial effect in various preclinically relevant models of pain, e.g. in the thermally induced hyperalgesia in rats (Kunz et al.; Pain 2004, 110, pp. 409-418), in Taxol-induced neuropathy (Wang et al.; Brain 2004, 127, pp. 671-679) and in acute and chronic inflammatory processes (Cuzzocrea et al.; American Journal of Pathololgy 2000, 157 (6), pp. 2065-2079).

The involvement of calpain in the development of kidney diseases, such as chronic kidney diseases, e.g. diabetic nephropathy, has also been shown recently. Thus, it has been demonstrated by Y. Shi et al. in animal models that the natural calpain inhibitor calpastatin is down regulated during renal ischemia reperfusion (Am. J. Physiol. Renal Physiol. 2000, 279, pp. 509-517). Furthermore, A. Dnyanmote et al., Toxicology and Applied Pharmacology 2006, 215, pp. 146-157, have shown that inhibition of calpain via overexpression of calpastatin reduces the progression of DCVC-induced renal injury in a model of acute renal failure. In addition, Peltier et al. have demonstrated that calpain activation and secretion promotes glomerular injury in experimental glomerulonephritis (J. Am. Soc. Nephrol. 2006, 17, pp. 3415-3423). It has also been shown that calpain inhibitors reduce renal dysfunction and injury caused by renal ischemia-reperfusion and thus may be useful in enhancing the tolerance of the kidney against renal injury associated with aortovascular surgery or renal transplantation (P. Chatterjee et al., Biochem. Pharmacol. 2005, 7, pp. 1121-1131).

Calpain has also been identified as a central mediator essential for parasitic activity. Parasites like *Plasmodium falciparum* and *Toxoplasma gondii* exploit host cell calpains to facilitate escape from the intracellular parasitophorous vacuole and/or host plasma membrane Inhibition of calpain-1 in hypotonically lysed and resealed erythrocytes prevented the escape of *P. falciparum* parasites, which was restored by adding purified calpain-1. Similarly, efficient egress of *T. gondii* from mammalian fibroblasts was blocked by either small interfering RNA—mediated suppression or genetic deletion of calpain activity and could be restored by genetic complementation (D. Greenbaum et al., Science 324, 794 (2009). Because parasites that fail to escape from their host cells are unable to proliferate, suggesting a strategy for anti-parasitic therapeutics. Pharmacological inhibition of calpain has been shown to exert anti-malarial activity, and hence presents a novel strategy for anti-parasitic strategy such as diseases caused by protest infections like malaria or toxoplasmosis (Li et al., *Mol Biochem Parasitol*. 2007; 155(1): 26-32; Jung et al. Archives of Pharmacal Research (2009), 32(6), 899-906, Chandramohanadas et al. Science (2009), 324, 794).

Further possible applications of calpain inhibitors are detailed in: M. Pietsch et al. Current Topics in Medicinal Chemistry, 2010, 10, 270-293; M. E. Saez et al.; Drug Discovery Today 2006, 11 (19/20), pp. 917-923; N. 0. Carragher, Curr. Pharm. Design 2006, 12, pp. 615-638; K. K. Wang et al.; Drugs of the Future 1998, 23 (7), pp. 741-749; and Trends in Pharmacol. Sci. 1994, 15, pp. 412-419.

A comprehensive review of calpain inhibitors reported in the literature is given in: Donkor et al, Expert Opin. Ther. Patents 2011, 21 (5). pp. 601-636.

With the calpain inhibitors described to date a general distinction is made between irreversible and reversible inhibitors, and peptide and non-peptide inhibitors.

Irreversible inhibitors are usually alkylating substances. They have the disadvantage that they firstly react unselectively and/or are unstable in the body. Thus, corresponding inhibitors often show unwanted side effects such as toxicity, and application thereof is therefore markedly restricted. The irreversible inhibitors include for example epoxides such as E64, α-halo ketones, and disulfides.

A large number of known reversible calpain inhibitors are peptide aldehydes which are derived in particular from di- or tripeptides such as, for example, Z-Val-Phe-H (MDL 28170). Derivatives and prodrugs structurally derived from aldehydes are also described, especially corresponding acetals and hemiacetals (e.g. hydroxytetrahydrofurans, hydroxyoxazolindines, hydroxymorpholines and the like), but also imines or hydrazones. However, under physiological conditions, peptide aldehydes and related compounds usually have the disadvantage that, owing to their reactivity, they are frequently unstable, are rapidly metabolized and are prone to unspecific reactions which may likewise cause toxic effects (J. A. Fehrentz and B. Castro, Synthesis 1983, pp. 676-78).

In recent years, a number of non-peptide carboxamides having a β-keto function in the amine moiety and inhibiting calpain have been described. Thus, WO 98/16512 describes 3-amino-2-oxo carboxylic acid derivatives whose amino group is amidated with a 4-piperidinecarboxylic acid compound. WO 99/17775 describes similar compounds which are amidated with a quinolinecarboxylic acid. WO 98/25883, WO 98/25899 and WO 99/54294 describe 3-amino-2-oxo carboxylic acid derivatives whose amino group is amidated with a substituted benzoic acid. WO 99/61423 describes 3-amino-2-oxo carboxylic acid derivatives whose amino group is amidated with an aromatic carboxylic acid carrying a tetrahydroquinoline/isoquinoline and 2,3-dihydroindole/isoindole residue. Similar compounds in which the aromatic carboxylic acid residue carries a heterocyloalkyl radical or (hetero)aryl radical which is optionally connected via a linker are described in WO 99/54320, WO 99/54310, WO 99/54304 and WO 99/54305. Likewise, WO 08/080969 describes nicotinamides of 3-amino-2-oxo carboxylic acid derivatives that in position 2 of the pyridine ring are linked to a substituted pyrazole via a nitrogen atom. WO 03/080182 describes the use of the aforementioned amides for the treatment of pulmonary diseases. The nonpeptide calpain inhibitors mentioned therein also have a number of disadvantages, in particular a low or absent selectivity in respect of related cysteine proteases, such as various cathepsins, likewise possibly leading to unwanted side effects.

WO 07/016589 and WO 08/106130 describe 2-oxo carboxylic acid derivatives carrying a N-acylated 2-pyrrolidinecarboxylamido group in the 3-position. Also disclosed is their use for treating hepatitis C virus infections.

Carboxamides comprising an α-ketoamide moiety in the amine component, in particular those described in WO 08/080969, have been demonstrated to be highly effective and selective calpain inhibitors. However, as found out by the inventors of the present invention, in some cases they have limited cytosolic stability, namely in humans, possibly resulting in their premature clearance from the cytosol. As a consequence, the pharmacokinetics of these compounds may be insufficient.

The cytosolic degradation of said carboxamide compounds having an α-ketoamide moiety is believed to be mainly caused by metabolic reduction of the carbonyl function in the α-position. Carbonyl reduction is an important step in Phase I metabolism of carbonyl-containing drugs by converting aldehyde, ketone or quinone moieties to alcohols to facilitate the elimination by Phase II conjugation or direct excretion (M. J. C. Rosemond and J. S. Walsh: "Human carbonyl reduction pathways and a strategy for their study in vitro", Drug Metabolism Reviews, 2004, 36, 335-361). Human carbonyl-reducing activities are ubiquitous, found in many tissues including liver, lung, brain, heart, kidney, and blood. Multiple human carbonyl-reducing enzymes have been characterized, including medium-chain (MDR), and short-chain (SDR) dehydrogenases/reductases, aldo-keto reductases (AKR), and quinone reductases (QR), most of these are present in liver cytosols, except for some SDR family present in liver microsomes and mitochondria as described in F. Hoffmann and E. Maser: "Carbonyl reductases and pluripotent hydroxysteroid dehydrogenases of the shortchain dehydrogenases/reductases superfamily", Drug Metabolism Reviews 2007, 39, 87-144.

The present invention is thus based on the object of providing compounds which inhibit calpain with high affinity and selectivity. The compounds are further intended to display enhanced cytosolic stability in human cells, such as hepatocytes, and in consequence improved pharmacokinetics.

This object and further objects are achieved by the carboxamide compounds of the general formula I described below, the tautomers, the hydrates, the pharmaceutically suitable salts and the prodrugs thereof:

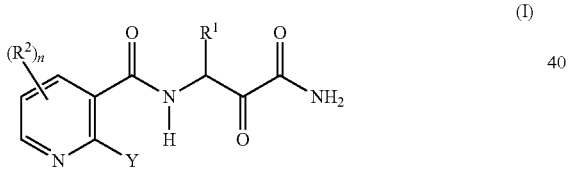
(I)

in which
$R^1$ is $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$,
  $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$,
  aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or may carry 1, 2, 3 or 4 identical or different radicals $R^{1c}$; where
    $R^{1a}$ is selected independently of one another from the group consisting of OH, SH, COOH, CN, OCH$_2$COOH, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOR$^{a1}$, CONR$^{a2}$R$^{a3}$, SO$_2$NR$^{a2}$R$^{a3}$, —NR$^{a2}$—SO$_2$—R$^{a4}$, NR$^{a2}$—CO—R$^{a5}$, SO$_2$—R$^{a4}$ and NR$^{a6}$R$^{a7}$;

$R^{1b}$ is selected independently of one another from the group consisting of OH, SH, COOH, CN, OCH$_2$COOH, halogen, phenyl which optionally has 1, 2 or 3 substituents $R^{1d}$,
  $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$,
  COOR$^{b1}$, CONR$^{b2}$R$^{b3}$, SO$_2$NR$^{b2}$R$^{b3}$, NR$^{b2}$—SO$_2$—R$^{b4}$, NR$^{b2}$—CO—R$^{b5}$, SO$_2$—R$^{b4}$ and NR$^{b6}$R$^{b7}$,
  in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring, $R^{1c}$ is selected independently of one another from the group consisting of OH, SH, halogen, NO$_2$, NH$_2$, CN, COOH, OCH$_2$COOH, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$,
  $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals,
  aryl, hetaryl, O-aryl, O—CH$_2$-aryl, where the last three radicals mentioned are unsubstituted in the aryl moiety or may carry 1, 2, 3 or 4 $R^{1d}$ radicals,
  COOR$^{c1}$, CONR$^{c2}$R$^{c3}$, SO$_2$NR$^{c2}$R$^{c3}$, NR$^{c2}$—SO$_2$—R$^{c4}$, NR$^{c2}$—CO—R$^{c5}$, SO$_2$—R$^{c4}$,
  —(CH$_2$)$_p$—NR$^{c6}$R$^{c7}$ with p=0, 1, 2, 3, 4, 5 or 6 and O—(CH$_2$)$_q$—NR$^{c6}$R$^{c7}$ with q=2, 3, 4, 5 or 6; where or two radicals $R^{1b}$ or two radicals $R^{1c}$ bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N and S as ring members;

$R^{1d}$ is selected from the group consisting of halogen, OH, SH, NO$_2$, COOH, C(O)NH$_2$, CHO, CN, NH$_2$, OCH$_2$COOH, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and SO$_2$—$C_1$-$C_6$-alkyl;

$R^2$ is selected from the group consisting of halogen, NH$_2$, CN, CF$_3$, CHF$_2$, CH$_2$F, O—CF$_3$, O—CHF$_2$, O—CH$_2$F, COOH, OCH$_2$COOH, $C_1$-$C_2$-alkyl, $C_1$-$C_2$-alkoxy, $C_1$-$C_2$-alkoxy-$C_1$-$C_2$-alkyl, $C_1$-$C_2$-alkylthio and CH$_2$NRR', where
  R and R' are selected independently of one another from the group consisting of hydrogen and $C_1$-$C_4$-alkyl;
n is 0, 1 or 2;
Y is a radical of the formulae Y1 or Y2

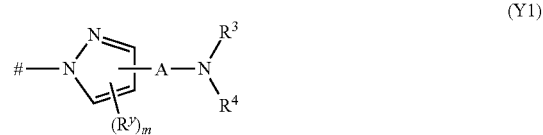
(Y1)

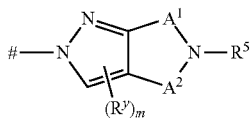

(Y2)

where # indicates the point of attachment of Y to the pyridine ring;

A is $(CH_2)_p$ with p being 1, 2, 3 or 4, where one or two hydrogen atoms may be replaced by a radical $R^6$, where A is attached to the 3- or 4-position of the pyrazole radical;

$A^1$ is $(CH_2)_q$ with q being 0, 1, 2 or 3, where one or two hydrogen atoms may be replaced by halogen or $C_1$-$C_4$-alkyl;

$A^2$ is $(CH_2)_r$ with r being 0, 1, 2 or 3, where one or two hydrogen atoms may be replaced by halogen or $C_1$-$C_4$-alkyl;

provided that r+q is 2, 3, 4, 5 or 6;

m is 0 or 1;

$R^y$ is selected from the group consisting of halogen, $NH_2$, CN, $CF_3$, $CHF_2$, $CH_2F$, O—$CF_3$, O—$CHF_2$, O—$CH_2F$, COOH, $OCH_2COOH$, $C_1$-$C_2$-alkyl, $C_1$-$C_2$-alkoxy, $C_1$-$C_2$-alkoxy-$C_1$-$C_2$-alkyl and $C_1$-$C_2$-alkylthio;

$R^3$ is selected from the group consisting of hydrogen, $C_1$-$C_6$-alkyl, $C_1$-$C_6$-haloalkyl, $C_1$-$C_6$-alkyl which has 1, 2 or 3 substituents $R^{3a}$, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals $R^{3b}$, $C_2$-$C_6$-alkenyl or $C_2$-$C_6$-alkynyl, where alkenyl and alkynyl, in the last 2 radicals mentioned are unsubstituted or have 1, 2 or 3 substituents $R^{3a}$, phenyl or phenyl-$C_1$-$C_4$-alkyl, where phenyl in the last 2 radicals mentioned are unsubstituted or have 1, 2 or 3 substituents $R^{3c}$, and a radical $C(=)R^{3d}$;

$R^{3a}$ is selected from the group consisting of OH, SH, CN, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, —$NR^{a2}$—$SO_2$—$R^{a4}$, $NR^{a2}$—CO—$R^{a5}$, $SO_2$—$R^{a4}$ and $NR^{a6}R^{a7}$, $R^{3b}$ is selected from the group consisting of OH, SH, CN, halogen, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{3a}$, phenyl which optionally has 1, 2 or 3 substituents $R^{3c}$, $COOR^{b1}$, $CONR^{b2}R^{b3}$ $SO_2NR^{b2}R^{b3}$, $NR^{b2}$—$SO_2$—$R^{b4}$, $NR^{b2}$—CO—$R^{b5}$, $SO_2$—$R^{b4}$ and $NR^{b6}R^{b7}$, or two $R^{3b}$ radicals may together also form a $C_1$-$C_4$-alkylene group, or 2$R^{3b}$ radicals bonded to adjacent C atoms of cycloalkyl may form together with the carbon atoms to which they are bonded also a benzene ring, $R^{3c}$ is selected from the group consisting of halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—$C(O)C_1$-$C_6$-alkyl, and $SO_2$—$C_1$-$C_6$-alkyl;

$R^{3d}$ is selected from the group consisting of $C_1$-$C_6$-alkyl, $C_1$-$C_6$-haloalkyl, $C_1$-$C_6$-alkyl which has 1, 2 or 3 substituents $R^{3a}$, $C_3$-$C_7$-cycloalkyl, $C_3$-$C_7$-cycloalkyl-$C_1$-$C_4$-alkyl, where the cycloalkyl moiety of the last 2 radicals mentioned is unsubstituted or may have 1, 2, 3 or 4 radicals $R^{3b}$, phenyl which optionally has 1, 2 or 3 substituents $R^{3c}$, $R^4$ is selected from the group consisting of hydrogen, $C_1$-$C_6$-alkyl, $C_1$-$C_6$-haloalkyl, $C_1$-$C_6$-alkyl which has 1, 2 or 3 substituents $R^{4a}$, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals $R^{4b}$, $C_2$-$C_6$-alkenyl or $C_2$-$C_6$-alkynyl, where alkenyl and alkynyl, in the last 2 radicals mentioned are unsubstituted or have 1, 2 or 3 substituents $R^{4a}$, phenyl and phenyl-$C_1$-$C_4$-alkyl, where phenyl in the last 2 radicals mentioned are unsubstituted or have 1, 2 or 3 substituents $R^{4c}$, where $R^{4a}$ is as defined for $R^{3a}$, $R^{4b}$ is as defined for $R^{3b}$, and $R^{4c}$ is as defined for $R^{3c}$, or the moiety $NR^3R^4$ in formula Y1 is a saturated, N-bound 4-, 5-, 6-, or 7-membered heteromonocyclic or 7-, 8-, 9-, or 10-membered heterobicyclic radical, where said heteromonocyclic and the heterobicyclic radical, in addition to the nitrogen atom, may have 1 or 2 further heteroatoms or heteroatom moieties as ring members, which are selected from O, S, S(O), $S(O)_2$ and $NR^{4d}$, where said heteromonocyclic radical may carry a fused benzene ring and where said heteromonocyclic and the heterobicyclic radical are unsubstutitued or may be substituted by 1, 2, 3 or 4 radicals $R^{4e}$;

$R^{4d}$ is selected from the group consisting of hydrogen, $C_1$-$C_6$-alkyl, $C_1$-$C_6$-haloalkyl, $C_1$-$C_6$-alkyl which has 1, 2 or 3 substituents $R^{4a}$, $C_3$-$C_7$-cycloalkyl, $C_3$-$C_7$-cycloalkyl-$C_1$-$C_4$-alkyl, where the cycloalkyl moiety of the last 2 radicals mentioned is unsubstituted or may have 1, 2, 3 or 4 radicals $R^{4b}$, phenyl and phenyl-$C_1$-$C_4$-alkyl where the phenyl ring of the last 2 radicals mentioned is unsubstituted or may have 1, 2 or 3 substituents $R^{4c}$, $R^{4e}$ is selected from the group consisting of halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $COOR^{b1}$, $CONR^{b2}R^{b3}$, $SO_2NR^{b2}R^{b3}$, $NR^{b2}$—$SO_2$—$R^{b4}$, $NR^{b2}$—CO—$R^{b5}$, $SO_2$—$R^{b4}$, and phenyl which optionally has 1, 2 or 3 substituents $R^{4c}$;

$R^5$ has one of the meanings given for $R^3$ or is a radical $COOR^{b1}$;

$R^6$ if present, is selected from halogen or $C_1$-$C_4$-alkyl, or $R^6$ together with $R^4$ forms a bivalent radical $(CH_2)_s$ with s being 1, 2 or 3, where one or two hydrogen atoms may be replaced by halogen or $C_1$-$C_4$-alkyl;

and where $R^{a1}$, $R^{b1}$ and $R^{c1}$ are independently of one another selected from the group consisting of $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocloalkyl-$C_1$-$C_4$-alkyl, $C_1$-$C_6$-alkoxy-$C_1$-$C_4$-alkyl, aryl, aryl-$C_1$-$C_4$-alkyl, hetaryl and hetaryl-$C_1$-$C_4$-alkyl, where aryl and hetaryl in the last 4 radicals mentioned are unsubstituted or have 1, 2 or 3 substituents $R^{1d}$, $R^{a2}$, $R^{b2}$ and $R^{c2}$ are independently of one another selected from the group consisting of H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl and hetaryl-$C_1$-$C_4$-alkyl, where aryl and hetaryl in the last 4 radicals mentioned are unsubstituted or have 1, 2 or 3 substituents $R^{1d}$, $R^{a3}$, $R^{b3}$ and $R^{c3}$ are independently of one another selected from the group consisting of H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl and hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members, $R^{a4}$, $R^{b4}$ and $R^{c4}$ are independently of one another selected from the group consisting of $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl and hetaryl-$C_1$-$C_4$-alkyl, where aryl and hetaryl in the last 4 radicals mentioned are unsubstituted or have 1, 2 or 3 substituents $R^{1d}$, and $R^{a5}$, $R^{b5}$ and $R^{c5}$ have independently of one another the meanings mentioned for $R^{a1}$, $R^{b1}$ and $R^{c1}$;

$R^{a6}$, $R^{b6}$ and $R^{c6}$ are independently of one another selected from the group consisting of H, $C_1$-$C_6$-alkyl, $C_1$-$C_6$-alkoxy, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, aryl, hetaryl, O-aryl, $OCH_2$-aryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) and $SO_2$-(hetaryl-$C_1$-$C_4$-alkyl), where aryl and hetaryl in the last 18 radicals mentioned are unsubstituted or have 1, 2 or 3 substituents $R^{1d}$, and $R^{a7}$, $R^{b7}$ and $R^{c7}$ are independently of one another selected from the group consisting of H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl and hetaryl-$C_1$-$C_4$-alkyl, where aryl and hetaryl in the last 4 radicals mentioned are unsubstituted or have 1, 2 or 3 substituents $R^{1d}$, or the two radicals $R^{a6}$ and $R^{a7}$, or $R^{b6}$ and $R^{b7}$ or $R^{c6}$ and $R^{c7}$ form together with the N atom a 3 to 7-membered, optionally substituted nitrogen heterocycle which may optionally have 1, 2 or 3 further different or identical heteroatoms from the group of O, N and S as ring members.

The present invention therefore relates to the carboxamide compounds of the general formula I, their tautomers, the hydrates thereof, the pharmaceutically suitable salts of the carboxamide compounds I, the prodrugs of I and the pharmaceutically suitable salts of the prodrugs, tautomers or hydrates of I.

The carboxamide compounds of the invention of the formula I, their salts, their prodrugs, their hydrates and their tautomers effectively inhibit calpain even at low concentrations. They are additionally distinguished by a high selectivity in relation to the inhibition of the calpain compared with other cysteine proteases, such as cathepsin B, cathepsin K, cathepsin L and cathepsin S, and by their improved stability against cytosolic degradation.

The carboxamide compounds of the invention of the formula I, their salts, their prodrugs, their hydrates and their tautomers are therefore particularly suitable for treating disorders and conditions in creatures, especially human creatures, which are associated with an elevated calpain activity.

The invention therefore also relates to the use of carboxamide compounds of the formula I, their tautomers, their hydrates and their pharmaceutically suitable salts for the manufacture of a medicament, in particular of a medicament which is suitable for the treatment of a disorder or a condition which is associated with an elevated calpain activity.

The invention further relates to a medicament, in particular a medicament which is suitable for the treatment of a disorder or a condition which is associated with an elevated calpain activity. The medicament comprises at least one carboxamide compound of the formula I, as described herein, the tautomer, the hydrate or a prodrug of compound I, or a pharmaceutically suitable salt of compound I or of the tautomer, the hydrate or a prodrug of I.

This carboxamide compound, its salts, prodrugs, hydrates and tautomers like the compounds of formula I effectively inhibit calpain even at low concentrations. They are additionally distinguished by a high selectivity in relation to the inhibition of the calpain compared with other cysteine proteases, such as cathepsin B, cathepsin K, cathepsin L and cathepsin S, and by their improved stability against cytosolic degradation. Therefore, these carboxamide compounds are particularly suitable for treating disorders and conditions in creatures, especially human creatures, which are associated with an elevated calpain activity. The invention therefore also relates to the use of these carboxamide compounds, their tautomers, their hydrates and their pharmaceutically suitable salts for the manufacture of a medicament, in particular of a medicament which is suitable for the treatment of a disorder or a condition which is associated with an elevated calpain activity as described herein for the compounds of formula I. As regards the tautomers, the hydrates, the pharmaceutically suitable salts or the prodrugs reference is made to the compounds of formula I.

The carboxamide compounds of the formula I may be present in the form of the α-ketoamide, as shown in the formula I. Alternatively they may also be present in the form of a hydrate, i.e. the keto group in the α-position relative to the carbamoyl moiety $CONH_2$ in the amine component is transformed into two geminal hydroxy groups, as shown in the formula I-H below. $R^1$, $R^2$, Y and n in formula I-H have the aforementioned meanings

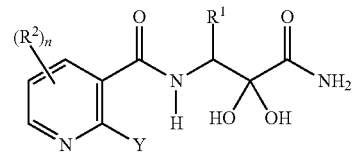
(I-H)

In the presence of water, especially under physiological conditions, usually both the α-ketoamide form and the hydrate form are present in a mixture.

Where only the α-ketoamide form is indicated in the following formulae and descriptions, it is intended to include also the hydrate and mixtures thereof with the α-ketoamide form unless indicated otherwise. Hydrates and α-ketoamide forms are equally suitable as calpain inhibitors.

The carboxamide compounds of the invention of the formula I are also able to form tautomers which are equally suitable as calpain inhibitors. Particular examples of tautomers to be mentioned are the compounds of the formula I-T:

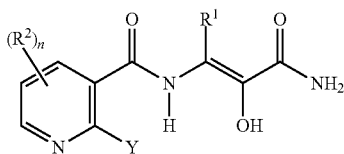

(I-H)

$R^1$, $R^2$, Y and n in formula I-T have the aforementioned meanings.

The carboxamide compounds of the invention of the formula I can also form hemiacetals, hemiketals, acetals or ketals with alkanols. These compounds are equally suitable as calpain inhibitors as they are prodrugs of the compounds I. Accordingly, compounds where one or both of the geminal hydroxy groups shown in formula I-H are a radical derived from an alkanol, and especially $C_1$-$C_6$-alkoxy, can also be used according to the invention.

The term prodrug, as used herein and in the claims refers to a compound which is transformed under metabolic conditions into a compound of the formula I. Apart from the aforementioned hemiacetals, hemiketals, acetals and ketals prodrugs of the compounds I include the compounds of the formula I, wherein the oxygen atom of the keto group in α-position to the carbamoyl moiety $CONH_2$ is replaced with a group O-Alk-O, S-Alk-O or S-Alk-S, where Alk is linear $C_2$-$C_5$-alkandiyl, which may be unsubstituted or substituted with 1, 2, 3 or 4 radicals selected from $C_1$-$C_4$-alkyl or halogen, examples for such groups including $O(CH_2)_2O$, $O(CH_2)_5O$, $O(CH_2)_4O$, $S(CH_2)_2O$, $S(CH_2)_5O$, $S(CH_2)_4O$, etc. Further prodrugs or the compounds I include the compounds of the formula I, wherein the keto group in α-position to the carbamoyl moiety $CONH_2$ is replaced with a group C=$NR^α$, where $R^α$ is selected from H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C_2$-$C_6$-alkenyloxy, $C_3$-$C_6$-cycloalkyloxy, $C_3$-$C_6$-cycloalkyl-$C_1$-$C_4$-alkyloxy. Under metabolic conditions, the aforementioned prodrugs are transformed into the corresponding α-ketoamide compounds of the formula I or into the corresponding hydrates of formula I-H. Therefore, said prodrugs and their pharmaceutically acceptable salts are also part of the invention.

It is equally possible to use pharmaceutically suitable salts of the carboxamide compounds of the formula I, of their tautomers, their hydrates or of their prodrugs, especially acid addition salts with physiologically tolerated organic or inorganic acids. Examples of suitable physiologically tolerated organic and inorganic acids are hydrochloric acid, hydrobromic acid, phosphoric acid, nitric acid, sulfuric acid, organic sulfonic acids having 1 to 12 carbon atoms, e.g. $C_1$-$C_4$-alkylsulfonic acids such as methanesulfonic acid, cycloaliphatic sulfonic acids such as S-(+)-10-camphorsulfonic acids, and aromatic sulfonic acids such as benzenesulfonic acid and toluenesulfonic acid, di- and tricarboxylic acids and hydroxy carboxylic acids having 2 to 10 carbon atoms, such as oxalic acid, malonic acid, maleic acid, fumaric acid, mucic acid, lactic acid, tartaric acid, citric acid, glycolic acid and adipic acid, as well as cis- and trans-cinnamic acid, furan-2-carboxylic acid and benzoic acid. Further suitable acids are described in Fortschritte der Arzneimittelforschung, Volume 10, pages 224 et seq., Birkhäuser Verlag, Basel and Stuttgart, 1966. The physiologically tolerated salts of the compounds of the formula I may be in the form of mono-, di-, tri- or tetrasalts, meaning that they may comprise 1, 2, 3 or 4 of the aforementioned acid molecules per molecule of the formula I. The acid molecules may be present in their acidic form or as anion.

The compounds of the invention may be in the form of a mixture of diastereomers, or of a mixture of diastereomers in which one of the two diastereomers is enriched, or of essentially diastereomerically pure compounds (diastereomeric excess de >90%). The compounds are preferably in the form of essentially diastereomerically pure compounds (diastereomeric excess de >90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee >90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

In the context of the present description, unless stated otherwise, the terms "alkyl", "alkoxy", "alkylthio", "haloalkyl", "haloalkoxy", "haloalkylthio", "alkenyl", "alkynyl", "alkylene" and radicals derived therefrom always include both unbranched and branched "alkyl", "alkoxy", "alkylthio", "haloalkyl", "haloalkoxy", "haloalkylthio", "alkenyl", "alkynyl" and "alkylene", respectively.

The prefix $C_n$-$C_m$- indicates the respective number of carbons in the hydrocarbon unit. Unless indicated otherwise, halogenated substituents preferably have one to five identical or different halogen atoms, especially fluorine atoms or chlorine atoms. $C_0$-Alkylene or $(CH_2)_0$ or similar expressions in the context of the description designate, unless indicated otherwise, a single bond.

The term "halogen" designates in each case, fluorine, bromine, chlorine or iodine, specifically fluorine, chlorine or bromine.

Examples of other meanings are:

Alkyl, and the alkyl moieties for example in alkoxy, alkylthio, arylalkyl, hetarylalkyl, cycloalkylalkyl or alkoxyalkyl: saturated, straight-chain or branched hydrocarbon radicals having one or more C atoms, e.g. 1 to 4, 1 to 6 or 1 to 10 carbon atoms, e.g. $C_1$-$C_6$-alkyl such as methyl, ethyl, propyl, 1-methylethyl, butyl, 1-methylpropyl(sec.-butyl), 2-methylpropyl (isobutyl), 1,1-dimethylethyl(tert.-butyl), pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1- methylpropyl, 1-ethyl-2-methylpropyl. In one embodiment of the invention, alkyl stands for small alkyl groups such as $C_1$-$C_4$-alkyl. In another embodiment of the invention, alkyl stands for larger alkyl groups such as $C_5$-$C_{10}$-alkyl.

Haloalkyl: an alkyl radical having ordinarily 1 to 6 or 1 to 4 C atoms as mentioned above, whose hydrogen atoms are partly or completely replaced by halogen atoms such as fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl, and the cycloalkyl moieties for example in cycloalkoxy or cycloalkyl-$C_1$-$C_6$-alkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl.

Alkenyl, and alkenyl moieties for example in aryl-($C_2$-$C_6$)-alkenyl: monounsaturated, straight-chain or branched hydrocarbon radicals having two or more C atoms, e.g. 2 to 4, 2 to 6 or 2 to 10 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl: straight-chain or branched hydrocarbon groups having two or more C atoms, e.g. 2 to 4, 2 to 6 or 2 to 10 carbon atoms and one or two triple bonds in any position but nonadjacent, e.g. $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy or alkoxy moieties for example in alkoxyalkyl:

Alkyl as defined above having preferably 1 to 6 or 1 to 4 C atoms, which is linked via an O atom: e.g. methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: alkoxy as described above, in which the hydrogen atoms of these groups are partly or completely replaced by halogen atoms, i.e. for example $C_1$-$C_6$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, specifically chloromethoxy, fluoromethoxy, difluoromethoxy, trifluoromethoxy, 2-fluoroethoxy, 2-chloroethoxy or 2,2,2-trifluoroethoxy.

Alkoxyalkyl: an alkyl radical ordinarily having 1 to 4 C atoms, in which one hydrogen atom is replaced by an alkoxy radical ordinarily having 1 to 6 or 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxyl)ethyl, 2-(2-methylpropoxyl)ethyl, 2-(1,1-dimethylethoxyl)ethyl, 2-(methoxy)propyl, 2-(ethoxy)propyl, 2-(n-propoxy)propyl, 2-(1-methylethoxyl)propyl, 2-(n-butoxy)propyl, 2-(1-methylpropoxyl)propyl, 2-(2-methylpropoxyl)propyl, 2-(1,1-dimethylethoxyl)propyl, 3-(methoxy)propyl, 3-(ethoxy)propyl, 3-(n-propoxy)propyl, 3-(1-methylethoxyl)propyl, 3-(n-butoxy)propyl, 3-(1-methylpropoxyl)propyl, 3-(2-methylpropoxyl)propyl, 3-(1,1-dimethylethoxyl)propyl, 2-(methoxy)butyl, 2-(ethoxy)butyl, 2-(n-propoxy)butyl, 2-(1-methylethoxyl)butyl, 2-(n-butoxy)butyl, 2-(1-methylpropoxyl)butyl, 2-(2-methylpropoxyl)butyl, 2-(1,1-dimethylethoxyl)butyl, 3-(methoxy)butyl, 3-(ethoxy)butyl, 3-(n- propoxy)butyl, 3-(1-methylethoxy)butyl, 3-(n-butoxy) butyl, 3-(1-methylpropoxyl)butyl, 3-(2-methylpropoxyl) butyl, 3-(1,1-dimethylethoxyl)butyl, 4-(methoxy)butyl, 4-(ethoxy)butyl, 4-(n-propoxy)butyl, 4-(1-methylethoxyl) butyl, 4-(n-butoxy)butyl, 4-(1-methylpropoxyl)butyl, 4-(2-methylpropoxyl)butyl, 4-(1,1-dimethylethoxyl)butyl, etc.

Alkylthio: alkyl as defined above preferably having 1 to 6 or 1 to 4 C atoms, which is linked via an S atom, e.g. methylthio, ethylthio, n-propylthio and the like.

Haloalkylthio: haloalkyl as defined above preferably having 1 to 6 or 1 to 4 C atoms, which is linked via an S atom, e.g. fluoromethylthio, difluoromethylthio, trifluoromethylthio, 2-fluoroethylthio, 2,2-difluoroethylthio, 2,2,2-trifluoroethylthio, pentafluoroethylthio, 2-fluoropropylthio, 3-fluoropropylthio, 2,2-difluoropropylthio, 2,3-difluoropropylthio, and heptafluoropropylthio.

Aryl: a mono-, bi- or tricyclic aromatic hydrocarbon radical such as phenyl or naphthyl, especially phenyl.

Heterocyclyl: a heterocyclic radical which may be saturated or partly unsaturated or aromatic and which ordinarily has 3, 4, 5, 6, 7 or 8 ring atoms, where ordinarily 1, 2, 3 or 4, in particular 1, 2 or 3, of the ring atoms are heteroatoms such as N, S or O, besides carbon atoms as ring members.

Examples of saturated heterocycles are in particular:

Heterocycloalkyl: i.e. a saturated heterocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3-4-membered saturated rings such as
2-oxiranyl, 2-oxetanyl, 3-oxetanyl, 2-aziridinyl, 3-thiethanyl, 1-azetidinyl, 2-azetidinyl.

C-bonded, 5-membered saturated rings such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heterocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:

2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:

1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heterocyclic radical which ordinarily has 1, 2, 3 or 4 nitrogen atoms or a heteroatom selected from oxygen and sulfur and, if appropriate, 1, 2 or 3 nitrogen atoms as ring members besides carbon atoms as ring members: for example C-bonded, 5-membered heteroaromatic radicals having 1, 2, 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol- 4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered heteroaromatic radicals having 1, 2, 3 or 4 nitrogen atoms as ring members, such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:
pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles which have one of the aforementioned 5- or 6-membered heterocyclic rings and a further saturated, unsaturated or aromatic carbocycle fused thereto, for example a benzene, cyclohexane, cyclohexene or cyclohexadiene ring, or a further 5- or 6-membered heterocyclic ring fused thereto, where the latter may likewise be saturated, unsaturated or aromatic. These bicyclic heterocycles include for example quinolinyl, isoquinolinyl, indolyl, indolizynyl, isoindolyl, indazolyl, benzofuryl, benzothienyl, benzo[b]thiazolyl, benzoxazolyl, benzthiazolyl, benzimidazolyl and 3,5,6,7-tetrahydro-indazolyl. Examples of 5- to 6-membered non-aromatic heterocyclic radicals comprising a fused benzene ring include dihydroindolyl, dihydroindolizynyl, dihydroisoindolyl, dihydroquinolinyl, dihydroisoquinolinyl, chromenyl and chromanyl.

Arylalkyl: an aryl radical as defined above which is linked via an alkylene group, in particular via a methylene, 1,1-ethylene or 1,2-ethylene group, e.g. benzyl, 1-phenylethyl and 2-phenylethyl(=phenethyl).

Arylalkenyl: an aryl radical as defined above, which is linked via an alkenylene group, in particular via a 1,1-ethenyl, 1,2-ethenyl or 1,3-propenyl group, e.g. 2-phenylethen-1-yl and 1-phenylethen-1-yl.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Heterocyclylalkyl and hetarylalkyl: a heterocyclyl or hetaryl radical as defined above which is linked via an alkylene group, in particular via a methylene, 1,1-ethylene or 1,2-ethylene group.

The expression "optionally substituted" means in the context of the present invention that the respective moiety is substituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$-$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

According to a particular embodiment of the invention the compounds of the formula I are predominately in the S-configuration at the carbon atom carrying the radical $R^1$, and according to a particular preferred embodiment the compounds I are completely S-configurated at said position.

According to one aspect of the invention the hydrogen atom linked to the carbon atom carrying the radical $R^1$ of a compound I is replaced by a deuterium atom, as shown in formula I-D below. $R^1$, $R^2$, Y and n in formula I-D have the aforementioned meanings, and where $R^1$, $R^2$, Y and n alone or in combination, have in particular the preferred or special meanings given below.

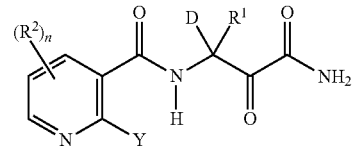

(I-D)

The degree of deuteration at said position usually exceeds 80%, preferably exceeds 90% and in particular exceeds 95%. The deuterated diasteromers of formula I-D often show a markedly higher stability against racematisation than their counterparts of formula I, probably due to a kinetic isotope effect (see F. Maltais et al. J. Med. Chem, DOI 10.1021/jm901023f). Thus, it is generally possible to stabilize the S-configuration at the carbon atom carrying radical $R^1$ of compounds I according to the aforementioned preferred embodiments of the invention, by introducing a deuterium at that carbon atom.

In relation to their use as calpain inhibitors, the variables n, m, Y, $R^1$, $R^2$ and $R^y$ preferably have the following meanings, where these represent, both considered on their own and in combination with at least one other or all, special embodiments of the compounds of the formula I:

$R^1$ is $C_1$-$C_{10}$-alkyl, preferably $C_3$-$C_8$-alkyl, which may be partly or completely halogenated and/or have 1, 2 or 3 substituents $R^{1a}$, in particular is unsubstituted $C_1$-$C_{10}$-alkyl, specifically unsubstituted $C_3$-$C_8$-alkyl, $C_3$-$C_7$-cycloalkyl-$C_1$-$C_4$-alkyl, where the cycloalkyl moiety may have 1, 2, 3 or 4 radicals $R^{1b}$, in particular $C_3$-$C_7$-cycloalkylmethyl, 1-($C_3$-$C_7$-cycloalkyl)ethyl or 2-($C_3$-$C_7$-cycloalkyl)ethyl, specifically cyclohexylmethyl, or phenyl-$C_1$-$C_4$-alkyl or hetaryl-$C_1$-$C_4$-alkyl, in particular benzyl, 1-phenylethyl, 2-phenylethyl, hetarylmethyl, 1-hetarylethyl, 2-hetarylethyl, such as thienylmethyl, pyridinylmethyl, where phenyl and hetaryl in the last radicals mentioned may be unsubstituted or carry 1, 2, 3 or 4 identical or different radicals $R^{1c}$.

More preferably $R^1$ is $C_1$-$C_{10}$-alkyl, preferably $C_3$-$C_8$-alkyl, which may be partly or completely halogenated and/or have 1, 2 or 3 substituents $R^{1a}$ as defined herein, where $R^{1a}$ is in particular selected from $C_1$-$C_4$-alkoxy and $C_1$-$C_4$-haloalkoxy;

$C_3$-$C_7$-cycloalkyl-methyl, where the cycloalkyl moiety may have 1, 2, 3 or 4 radicals $R^{1b}$, as defined herein, where $R^{1b}$ is in particular selected from halogen, $C_1$-$C_3$-alkyl, $C_1$-$C_4$-haloalkyl, $C_1$-$C_4$-alkoxy or $C_1$-$C_4$-haloalkoxy; or benzyl or hetaryl-methyl, where phenyl and hetaryl in the last 2 radicals mentioned may be unsubstituted or carry 1, 2, 3 or 4 identical or different radicals $R^{1c}$ as defined herein, where $R^{1c}$ is in particular selected from halogen, specifically fluorine and chlorine, $C_1$-$C_4$-alkyl, $C_1$-$C_4$-haloalkyl, $C_1$-$C_4$-alkoxy, $C_1$-$C_4$-haloalkoxy and $(CH_2)_p$NR$^{c6}$R$^{c7}$, where p is 0 or 1 and $R^{c6}$ and $R^{c7}$ are as defined above, and in particular are selected form hydrogen and $C_1$-$C_4$-alkyl or NR$^{c6}$R$^{c7}$ together form a saturated N-bound heterocycle such as 4-morpholinyl, 1-pyrrolidinyl, 1-piperidinyl or 1-piperazinly or 4-methylpiperazin-1-yl.

In particular, $R^1$ is benzyl, where the phenyl group of benzyl may be unsubstituted or carry 1 or 2 identical or different radicals $R^{1c}$ as defined herein, where $R^{1c}$ is in particular selected from halogen, specifically fluorine and chlorine, $C_1$-$C_4$-alkyl, $C_1$-$C_4$-haloalkyl, $C_1$-$C_4$-alkoxy, $C_1$-$C_4$-haloalkoxy and $(CH_2)_p$NR$^{c6}$R$^{c7}$, where p is 0 or 1 and $R^{c6}$ and $R^{c7}$ are as defined above, and in particular are selected form hydrogen and $C_1$-$C_4$-alkyl or NR$^{c6}$R$^{c7}$ together form a saturated N-bound heterocycle such as 4-morpholinyl, 1-pyrrolidinyl, 1-piperidinyl or 1-piperazinly or 4-methylpiperazin-1-yl and where $R^{1c}$ is especially selected from fluorine, chlorine, methyl, methoxy, $CF_3$, $CHF_2$, $CH_2F$, O—$CF_3$, O—$CHF_2$ and O—$CH_2F$.

In this connection, $R^{1a}$, $R^{1b}$ and $R^{1c}$ where present have the aforementioned meanings. In particular:

$R^{1a}$ is $C_1$-$C_4$-alkoxy or $C_1$-$C_4$-haloalkoxy;

$R^{1b}$ is halogen, $C_1$-$C_4$-alkyl, $C_1$-$C_4$-haloalkyl, $C_1$-$C_4$-alkoxy or $C_1$-$C_4$-haloalkoxy; and $R^{1c}$ is halogen, $C_1$-$C_4$-alkyl, OH, SH, CN, $C_1$-$C_4$-haloalkyl, $C_1$-$C_4$-haloalkoxy, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, CONH$_2$, CONH—$C_1$-$C_6$-alkyl, SO$_2$NH-$C_1$-$C_6$-alkyl, CON—($C_1$-$C_6$-alkyl)$_2$, SO$_2$N—($C_1$-$C_6$-alkyl)$_2$, NH—SO$_2$—$C_1$-$C_6$-alkyl, NH—CO—$C_1$-$C_6$-alkyl, SO$_2$—$C_1$-$C_6$-alkyl, O-phenyl, O—$CH_2$-phenyl, CONH-phenyl, SO$_2$NH-phenyl, CONH-hetaryl, SO$_2$NH-hetaryl, SO$_2$-phenyl, NH—SO$_2$-phenyl, NH—CO-phenyl, NH—SO$_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —$(CH_2)_p$—NR$^{c6}$R$^{c7}$ with p=0, 1, 2, 3, 4, 5 or 6, in particular 0, and —O—$(CH_2)_q$—NR$^{c6}$R$^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded, are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{1c}$ is in particular selected from halogen, $C_1$-$C_4$-alkyl, $C_1$-$C_4$-alkoxy, $CF_3$, $CHF_2$, $CH_2F$, O—$CHF_2$, O—$CH_2F$, O—$CF_3$ and —$(CH_2)_p$—NR$^{c6}$R$^{c7}$ with p=0, 1 or 2, where $R^{c6}$ is selected from the group consisting of H and $C_1$-$C_4$-alkyl and.

$R^{c7}$ is selected from the group consisting of H and $C_1$-$C_4$-alkyl or the two radicals $R^{c6}$ and $R^{c7}$ form together with the N atom a 5, 6 or 7-membered, saturated nitrogen heterocycle which may optionally have further different or identical heteroatom from the group of O, N and S as ring member and where the nitrogen heterocycle is unsubstituted or carries 1, 2 or 3 substituents selected from $C_1$-$C_4$-alkyl.

$R^{1c}$ is particularly preferred halogen, specifically fluorine and chlorine, $C_1$-$C_4$-alkyl, $C_1$-$C_4$-haloalkyl, $C_1$-$C_4$-alkoxy, $C_1$-$C_4$-haloalkoxy and $(CH_2)_p$NR$^{c6}$R$^{c7}$, where p is 0 or 1 and $R^{c6}$ and $R^{c7}$ are as defined above, and in particular are selected form hydrogen and $C_1$-$C_4$-alkyl or NR$^{c6}$R$^{c7}$ together form a saturated N-bound heterocycle such as 4-morpholinyl, 1-pyrrolidinyl, 1-piperidinyl or 1-piperazinyl or 4-methylpiperazin-1-yl and where $R^{1c}$ is especially selected from halogen, $C_1$-$C_4$-alkyl, such as methyl, $CF_3$, $CHF_2$, $CH_2F$, $C_1$-$C_4$-alkoxy, such as methoxy, O—$CF_3$, O—$CHF_2$ and O—$CH_2F$.

$R^1$ is in particular benzyl, which may be unsubstituted or carry 1 or 2 identical or different radicals $R^{1c}$, where the radicals $R^{1c}$ are as defined above and in particular selected from halogen, $C_1$-$C_2$-alkyl and $C_1$-$C_2$-alkoxy.

n is preferably 0 or 1 and specifically 0.

Depending on its occurrence, $R^2$ is in particular halogen, specifically fluorine or chlorine, CN, $CF_3$, $CHF_2$, $CH_2F$, $C_1$-$C_2$-alkyl or $C_1$-$C_2$-alkoxy. In particular, $R^2$, if present, is fluorine, chlorine, methyl, ethyl or methoxy, and specifically fluorine or methyl.

m is preferably 0.

Depending on its occurrence, $R^y$ is in particular halogen, specifically fluorine or chlorine, CN, $CF_3$, $CHF_2$, $CH_2F$, $C_1$-$C_2$-alkyl or $C_1$-$C_2$-alkoxy. In particular, $R^y$, if present, is fluorine, chlorine, methyl, ethyl or methoxy, and specifically fluorine or methyl.

A first group of embodiments of the invention relates to compounds of the formula I, wherein Y is a radical of the formula Y1.

Amongst the compounds of the formula I, wherein Y is a radical of the formula Y1, a particular group of embodiments relates to compounds, where the moiety A-NR$^3$R$^4$ in formula Y1 is located in the 3-position of the pyrazole ring.

Amongst the compounds of the formula I, wherein Y is a radical of the formula Y1, another particular group of embodiments relates to compounds, where the moiety A-NR$^3$R$^4$ in formula Y1 is located in the 4-position of the pyrazole ring.

In the compounds of the formula I, where Y is a radical Y1, the variables A, R$^3$ and R$^4$ preferably have the following meanings, where these represent, both considered on their own and in combination with at least one other or all, special embodiments of the compounds of the formula I.

A is a bivalent radical of the formula CH—R$^p$(CH$_2$)$_z$, where the carbon atom which carries R$^p$ is bound to the pyrazole ring, where z is 0, 1 or 2 and where R$^p$ is hydrogen or has one of the meanings given for R$^6$, or R$^p$ together with R$^4$ forms a bivalent radical of the formula (CH$_2$)$_s$ with s being 1, 2 or 3. In particular z is 0, 1 or 2, R$^p$ is hydrogen or methyl, or R$^p$ together with R$^4$ forms a bivalent radical of the formula (CH$_2$)$_s$ with s being 1, 2 or 3.

A particular group of the compounds of formula I, where Y is Y1 and where A is a bivalent radical of the formula CH—R$^p$(CH$_2$)$_z$ and where the carbon atom which carries R$^p$ is bound to the pyrazole ring, where z is 0, 1 or 2, where R$^p$ is hydrogen or has one of the meanings given for R$^6$, and where R$^p$ is in particular hydrogen, methyl or ethyl, especially hydrogen.

A special group of the compounds of formula I, where Y is Y1 and where A is a bivalent radical of the formula CH—R$^p$ $(CH_2)_z$ and where the carbon atom which carries $R^p$ is bound to the pyrazole ring, are the compounds of the formula Ia, the tautomers thereof, the hydrates thereof, the prodrugs thereof and the pharmaceutically suitable salts thereof:

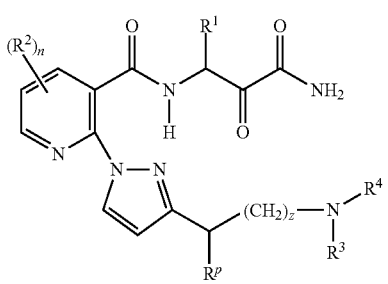

(Ia)

where $R^1$, $R^2$, $R^3$, $R^4$ and n are as defined herein,
$R^p$ is hydrogen, methyl or ethyl, or
$R^p$ together with $R^4$ forms a bivalent radical of the formula $(CH_2)_s$ with s being 1, 2 or 3, and
z is 0, 1 or 2.

In the compounds of the formulae I and Ia, where Y is Y1, the variables $R^3$ and $R^4$ preferably have the following meanings, where these represent, both considered on their own and in combination with at least one other or all, special embodiments of the compounds of the formulae I and Ia:
$R^3$ is preferably $C_1$-$C_6$-alkyl, $C_1$-$C_6$-haloalkyl, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals $R^{3b}$,
phenyl or phenyl-$C_1$-$C_4$-alkyl, where phenyl in the last 2 radicals mentioned are unsubstituted or have 1, 2 or 3 substituents $R^{3c}$, where
$R^{3b}$ and $R^{3c}$ are as defined above.
In this connection, $R^{3b}$ and $R^{3c}$ where present have the aforementioned meanings. In particular:
$R^{3b}$ is selected from the group consisting of halogen, $C_1$-$C_6$-alkyl, which may be partly or completely halogenated,
phenyl which optionally has 1, 2 or 3 substituents $R^{3c}$,
$R^{3b}$ is in particular fluorine or methyl;
$R^{3c}$ is selected from halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—$C(O)C_1$-$C_6$-alkyl, and $SO_2$—$C_1$-$C_6$-alkyl;
$R^{3c}$ is in particular selected from halogen, CN, $C_1$-$C_4$-alkyl, $C_1$-$C_2$-fluoroalkyl, $C_1$-$C_2$-alkoxy and $C_1$-$C_2$-fluoroalkoxy.
$R^3$ is in particular $C_1$-$C_6$-alkyl, $C_1$-$C_4$-fluoroalkyl, $C_3$-$C_7$-cycloalkyl, $C_3$-$C_7$-cycloalkyl-$C_1$-alkyl, where the cycloalkyl moiety of the last 2 radicals mentioned may have 1, 2, 3 or 4 radicals $R^{3b}$, which are in particular selected from the group consisting of fluorine or methyl;
phenyl or benzyl, where phenyl in the last 2 radicals mentioned are unsubstituted or have 1, 2 or 3 substituents $R^{3c}$, where
$R^{3b}$ and $R^{3c}$ are as defined above.
$R^4$ is preferably hydrogen, $C_1$-$C_6$-alkyl or $C_1$-$C_6$-haloalkyl, in particular hydrogen or $C_1$-$C_4$-alkyl.

In the moiety of the formula Y1, the moiety $NR^3R^4$ may also form a saturated, N-bound 4-, 5-, 6-, or 7-membered heteromonocyclic or 7-, 8-, 9-, or 10-membered heterobicyclic radical as defined above. In particular, the moiety $NR^3R^4$ is a saturated, N-bound 4-, 5-, 6-, or 7-membered heteromonocyclic or 7-, 8-, 9-, or 10-membered heterobicyclic radical, where said heteromonocyclic and the heterobicyclic radical, in addition to the nitrogen atom, may have 1 further heteroatom or heteroatom moiety as ring member, which are selected from O, S, $S(O)_2$ and $NR^{4d}$, where said heteromonocyclic radical may carry a fused benzene ring and where said heteromonocyclic and the heterobicyclic radical are unsubstituted or may be substituted by 1, 2, 3 or 4 radicals $R^{4e}$, where $R^{4d}$ and $R^{4e}$ are as defined above and where $R^{4d}$ is selected from the group consisting of hydrogen, $C_1$-$C_6$-alkyl, $C_1$-$C_6$-haloalkyl, $C_1$-$C_6$-alkyl which has 1, 2 or 3 substituents $R^{4a}$,
$C_3$-$C_7$-cycloalkyl, $C_3$-$C_7$-cycloalkyl-$C_1$-$C_4$-alkyl, where the cycloalkyl moiety of the last 2 radicals mentioned is unsubstituted or may have 1, 2, 3 or 4 radicals $R^{4b}$, phenyl and benzyl where the phenyl ring of the last 2 radicals mentioned is unsubstituted or may have 1, 2 or 3 substituents $R^{4c}$;
In this connection, $R^{4d}$ and $R^{4e}$ where present have the aforementioned meanings. In particular:
$R^{4d}$ is selected from the group consisting of hydrogen, $C_1$-$C_6$-alkyl, $C_1$-$C_6$-haloalkyl, $C_1$-$C_6$-alkyl which has 1, 2 or 3 substituents $R^{4a}$,
$C_3$-$C_7$-cycloalkyl, $C_3$-$C_7$-cycloalkyl-$C_1$-$C_4$-alkyl, where the cycloalkyl moiety of the last 2 radicals mentioned is unsubstituted or may have 1, 2, 3 or 4 radicals $R^{4b}$,
phenyl and benzyl where the phenyl ring of the last 2 radicals mentioned is unsubstituted or may have 1, 2 or 3 substituents $R^{4c}$;
$R^{4e}$ is selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio and phenyl.
In this connection, $R^{4a}$, $R^{4b}$ and $R^{4c}$ where present have the aforementioned meanings. In particular:
$R^{4a}$ is selected from the group consisting of halogen and $C_1$-$C_4$-alkoxy, in particular fluorine, methoxy or ethoxy;
$R^{4b}$ is selected from the group consisting of halogen, $C_1$-$C_6$-alkyl, which may be partly or completely halogenated,
phenyl which optionally has 1, 2 or 3 substituents $R^{3c}$,
$R^{4b}$ is in particular fluorine or methyl;
$R^{4c}$ is selected from halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—$C(O)C_1$-$C_6$-alkyl, and $SO_2$—$C_1$-$C_6$-alkyl;
$R^{4c}$ is in particular selected from halogen, CN, $C_1$-$C_4$-alkyl, $C_1$-$C_2$-fluoroalkyl, $C_1$-$C_2$-alkoxy and $C_1$-$C_2$-fluoroalkoxy.

Particular examples of the moiety $NR^3R^4$ include, but are not limited to the following radicals:
4-morpholinyl, 4-thiomorpholinyl, 1,1-dioxothiomorpholin-4-yl, 2,6-dimethylmorpholin-4-yl, 2-phenylmorpholin-4-yl, 1-azetidinyl, 1-azepanyl, 1-pyrrolidinyl, 3-phenylpyrrolidin-1-yl, 1-piperidinyl, 4-methylpiperidin-1-yl, 4-phenylpiperidin-1-yl, 4,4-difluoropiperidin-1-yl, 4-(trifluoromethyl)piperidin-1-yl, 4-(tert.-butyl)piperidin-1-yl, 4-methylpiperazin-1-yl, 4-ethylpiperazin-1-yl, 4-propylpiperazin-1-yl, 4-cyclopropylmethylpiperazin-1-yl, 4-cyclopropylpiperazin-1-yl, 4-phenylpiperazin-1-yl, dimethylamino, diethylamino, diisopropylamino, N-phenylamino, N-methyl- N-phenylamino, N-methyl-N-isopropylamino, N-cyclopropyl-N-methylamino, N-cyclopropyl-N-phenylamino, N-cyclopropyl-N-benzylamino, N-cyclohexyl-N-methylamino, N-benzyl-N-methylamino, N-cyclohexylmethyl-N-methylamino, N-(4-trifluoromethylcyclohexyl)methyl-N-methylamino, 3,4-dihydro-2H-1,4-benzoxazin-4-yl, cis-octahydrobenzo-[1,4]oxazin-4-yl, trans-octahydrobenzo[1,4]oxazin-4-yl, 5,5-difluoroocta-hydrocyclopenta[c]pyrrol-2-yl, hexahydrofuro[3,4-c]pyrrol-5-yl, 2,3-dihydroindol-1-yl, 2-oxa-7-azaspiro[3.5]nonane-7-yl, 2,3-dihydro-1H-isoindole-2-yl, 5-trifluoromethyl-2,3-dihydro-1H-isoindole-2-yl, 4-trifluoro-2,3-dihydro-1H-isoindole-2-yl, 2,3-dihydroisoindole-1-one-2-yl, 1,2,3,4-tetrahydroisoquinoline-2-yl, 3-azabicyclo[3.2.0]heptane-3-yl and 6-(4-fluorophenyl)-3-azabicyclo[3.2.0]heptane-3-yl.

A further group of embodiments of the present invention relate to compounds of the formula I, where Y is a radical Y1, $R^p$ together with $R^4$ forms a bivalent radical of the formula $(CH_2)_s$ with s being 1, 2 or 3. In this group of embodiments, n, $R^1$, $R^2$ and $R^3$ are as defined above. In this group of embodiments, $R^3$ has in particular the following meanings:

$R^3$ is preferably $C_1$-$C_6$-alkyl, $C_1$-$C_6$-haloalkyl, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals $R^{3b}$,
phenyl or phenyl-$C_1$-$C_4$-alkyl, where phenyl in the last 2 radicals mentioned are unsubstituted or have 1, 2 or 3 substituents $R^{3c}$, where
$R^{3b}$ and $R^{3c}$ are as defined above.

In this connection, $R^{3b}$ and $R^{3c}$ where present have the aforementioned meanings. In particular:

$R^{3b}$ is selected from the group consisting of halogen, $C_1$-$C_6$-alkyl, which may be partly or completely halogenated,
phenyl which optionally has 1, 2 or 3 substituents $R^{3c}$,
$R^{3b}$ is in particular fluorine or methyl;
$R^{3c}$ is selected from halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—C(O)$C_1$-$C_6$-alkyl, and $SO_2$—$C_1$-$C_6$-alkyl;
$R^{3c}$ is in particular selected from halogen, CN, $C_1$-$C_4$-alkyl, $C_1$-$C_2$-fluoroalkyl, $C_1$-$C_2$-alkoxy and $C_1$-$C_2$-fluoroalkoxy.

In this group of embodiments, $R^3$ is especially selected from the group consisting of $C_1$-$C_6$-alkyl, $C_1$-$C_4$-fluoroalkyl, $C_3$-$C_7$-cycloalkyl, $C_3$-$C_7$-cycloalkyl-$C_1$-alkyl, where the cycloalkyl moiety of the last 2 radicals mentioned may have 1, 2, 3 or 4 radicals $R^{3b}$, which are in particular selected from the group consisting of fluorine or methyl, phenyl or benzyl, where phenyl in the last 2 radicals mentioned are unsubstituted or have 1, 2 or 3 substituents $R^{3c}$, where $R^{3b}$ and $R^{3c}$ are as defined above.

In this group of embodiments, particular examples of the moiety A-$NR^3R^4$ include, but are not limited to the following radicals: azetidin-3-yl, pyrrolidin-3-yl, 1-methylpyrrolidin-3-yl, piperidin-3-yl, 1-methylpiperidin-3-yl, piperidin-4-yl, 1-methylpiperidin-4-yl, 1-ethylpiperidin-4-yl, 1-propylpiperidin-4-yl, 1-cyclopropylpiperidin-4-yl, and 1-benzylpiperidin-4-yl,.

A second group of embodiments of the invention relates to compounds of the formula I, where Y is a radical of the formula Y2.

In the compounds of the formulae I, where Y is Y2, the variables $A^1$, $A^2$ and $R^5$ preferably have the following meanings, where these represent, both considered on their own and in combination with at least one other or all, special embodiments of the compounds of the formulae I and Ib:

$A^1$ is preferably a single bond, $CH_2$ or $CH_2CH_2$.
$A^2$ is preferably $CH_2$, $CH_2CH_2$ or $CH_2CH_2CH_2$.
$R^5$ is preferably $C_1$-$C_6$-alkyl, $C_1$-$C_6$-haloalkyl, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals $R^{3b}$,
a radical $C(=O)R^{3d}$, a radical $COOR^{b1}$,
phenyl or phenyl-$C_1$-$C_4$-alkyl, where phenyl in the last 2 radicals mentioned are unsubstituted or have 1, 2 or 3 substituents $R^{3c}$, where
$R^{b1}$, $R^{3b}$, $R^{3c}$ and $R^{3d}$ are as defined above.

In this context, $R^{b1}$, $R^{3b}$, $R^{3c}$ and $R^{3d}$ where present have the aforementioned meanings. In particular:

$R^{3b}$ is selected from the group consisting of halogen, $C_1$-$C_6$-alkyl, which may be partly or completely halogenated,
phenyl which optionally has 1, 2 or 3 substituents $R^{3c}$,
$R^{3b}$ is in particular fluorine or methyl;
$R^{3c}$ is selected from halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—C(O)$C_1$-$C_6$-alkyl, and $SO_2$—$C_1$-$C_6$-alkyl;
$R^{3c}$ is in particular selected from halogen, CN, $C_1$-$C_4$-alkyl, $C_1$-$C_2$-fluoroalkyl, $C_1$-$C_2$-alkoxy and $C_1$-$C_2$-fluoroalkoxy;
$R^{b1}$ is selected from the group consisting of $C_1$-$C_6$-alkyl, $C_3$-$C_7$-cycloalkyl, $C_3$-$C_7$-cycloalkyl-$C_1$-$C_4$-alkyl, phenyl and phenyl-$C_1$-$C_4$-alkyl, where phenyl in the last 2 radicals mentioned is unsubstituted or has 1, 2 or 3 substituents $R^{1d}$, which are selected from the group consisting of halogen, $C_1$-$C_6$-alkyl, $C_1$-$C_6$-alkoxy and $C_1$-$C_6$-haloalkyl. $R^{1b}$ is in particular $C_1$-$C_6$-alkyl.

$R^5$ is in particular $C_1$-$C_6$-alkyl, $C_1$-$C_4$-fluoroalkyl, $C_3$-$C_7$-cycloalkyl, $C_3$-$C_7$-cycloalkyl-$C_1$-alkyl, where the cycloalkyl moiety of the last 2 radicals mentioned may have 1, 2, 3 or 4 radicals $R^{3b}$, which are in particular selected from the group consisting of fluorine or methyl; phenyl or benzyl, where phenyl in the last 2 radicals mentioned are unsubstituted or have 1, 2 or 3 substituents $R^{3c}$, where
$R^{3b}$ and $R^{3c}$ are as defined above.

Particular examples of the moiety Y2 include, but are not limited to the following radicals:

4,5,6,7-tetrahydropyrazolo[3,4-c]pyridin-2-yl, 6-($C_1$-$C_4$-alkyl)-4,5,6,7-tetrahydropyrazolo[3,4-c]pyridin-2-yl, 6-(tert.-butoxycarbonyl)-4,5,6,7-tetrahydropyrazolo[3,4-c]pyridin-2-yl, 6-benzyl-4,5,6,7-tetrahydropyrazolo[3,4-c]pyridin-2-yl, 6-cyclopropylmethyl-4,5,6,7-tetrahydropyrazolo[3,4-c]pyridin-2-yl, 4,5,6,7-tetrahydropyrazolo[4,3-c]pyridin-2-yl, 5-($C_1$-$C_4$-alkyl)-4,5,6,7-tetrahydropyrazolo[4,3-c]pyridin-2-yl, 5-(tert.-butoxycarbonyl)-4,5,6,7-tetrahydropyrazolo[4,3-c]pyridin-2-yl, 5-benzyl-4,5,6,7-tetrahydropyrazolo[4,3-c]pyridin-2-yl, 5-cyclopropylmethyl-4,5,6,7-tetrahydropyrazolo[4,3-c]pyridin-2-yl, 2,4,5,6-tetrahydropyrrolo[3,4-c]pyrazol-2-yl, 5-($C_1$-$C_4$-alkyl)-2,4,5,6-tetrahydropyrrolo[3,4-c]pyrazol-2-yl, 5-benzyl-2,4,5,6-tetrahydropyrrolo[3,4-c]pyrazol-2-yl, 5-(tert.-butoxycarbonyl)-2,4,5,6-tetrahydropyrrolo[3,4-c]pyrazol-2-yl, 4,5,6,7-tetrahydropyrazolo[4,3-c]pyridin- 2-yl, 5-(C$_1$-C$_4$-alkyl)-4,5,6,7-tetrahydropyrazolo[4,3-b]pyridin-2-yl, 5-(tert.-butoxycarbonyl)-4,5,6,7-tetrahydropyrazolo[4,3-b]pyridin-2-yl, 5-benzyl-4,5,6,7-tetrahydropyrazolo[4,3-b]pyridin-2-yl and 5-cyclopropylmethyl-4,5,6,7-tetrahydropyrazolo[4,3-b]pyridin-2-yl.

A special group of the compounds of formula I, where Y is Y2 are the compounds of the formula Ib, the tautomers thereof, the hydrates thereof, the prodrugs thereof and the pharmaceutically suitable salts thereof:

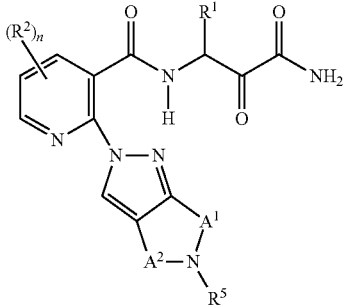

(Ib)

where R$^1$, R$^2$, R$^5$ and n are as defined above and where
A$^1$ is (CH$_2$)$_q$ with q being 0, 1 or 2;
A$^2$ is (CH$_2$)$_r$ with r being 1, 2 or 3; and
where q+r is 1, 2 or 3.

If not stated otherwise, the radicals R$^{1d}$, R$^{a1}$, R$^{b1}$, R$^{c1}$, R$^{a2}$, R$^{b2}$, R$^{c2}$, R$^{a3}$, R$^{b3}$, R$^{c3}$, R$^{a4}$, R$^{b4}$, R$^{c4}$, R$^{a5}$, R$^{b5}$, R$^{c5}$, R$^{a6}$, R$^{b6}$, R$^{c6}$, R$^{a7}$, R$^{b7}$ and R$^{c7}$ have unless otherwise indicated, independently of one another preferably one of the following meanings:

R$^{1d}$: halogen, C$_1$-C$_4$-alkyl, C$_1$-C$_4$-haloalkyl, C$_1$-C$_4$-alkoxy or C$_1$-C$_4$-haloalkoxy.

R$^{a1}$, R$^{b1}$, R$^{c1}$ independently of one another: hydrogen, C$_1$-C$_6$-alkyl, C$_1$-C$_6$-haloalkyl, phenyl, benzyl, hetaryl or hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a2}$, R$^{b2}$, R$^{c2}$ independently of one another: hydrogen, C$_1$-C$_6$-alkyl, phenyl, benzyl, hetaryl or hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a3}$, R$^{b3}$, R$^{c3}$ independently of one another: hydrogen or C$_1$-C$_6$-alkyl, or R$^{a2}$ with R$^{a3}$ (and likewise R$^{b2}$ with R$^{b3}$ and R$^{c2}$ with R$^{c3}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from C$_1$-C$_4$-alkyl, C$_1$-C$_4$-haloalkyl, C$_1$-C$_4$-alkoxy and C$_1$-C$_4$-haloalkoxy.

R$^{a4}$, R$^{b4}$, R$^{c4}$ independently of one another: C$_1$-C$_6$-alkyl, phenyl, benzyl, hetaryl or hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a5}$, R$^{b5}$, R$^{c5}$ independently of one another: hydrogen, C$_1$-C$_6$-alkyl, phenyl, benzyl, hetaryl or hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a6}$, R$^{b6}$, R$^{c6}$ independently of one another: hydrogen, C$_1$-C$_6$-alkyl, phenyl, benzyl, hetaryl or hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a7}$, R$^{b7}$, R$^{c7}$ independently of one another: hydrogen or C$_1$-C$_6$-alkyl, or R$^{a6}$ with R$^{a7}$ (and likewise R$^{b6}$ with R$^{b7}$ and R$^{c6}$ with R$^{c7}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from C$_1$-C$_4$-alkyl, C$_1$-C$_4$-haloalkyl, C$_1$-C$_4$-alkoxy and C$_1$-C$_4$-haloalkoxy.

The compounds of the general formulae Ia and Ia-H, Ib and Ib-H which are indicated in Tables 1 to 12 below, and their tautomers, prodrugs and pharmaceutically acceptable salts, represent per se preferred embodiments of the present invention.

The meanings for R$^1$, CH—R$^p$(CH$_2$)$_z$ and NR$^3$R$^4$ indicated in Table A below represent embodiments of the invention which are likewise preferred independently of one another and especially in combination.

The meanings for R$^1$, A$^1$, A$^2$ and R$^5$ indicated in Table B below represent embodiments of the invention which are likewise preferred independently of one another and especially in combination.

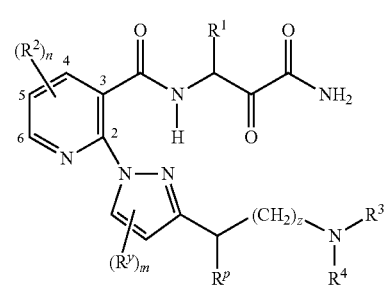

(Ia)

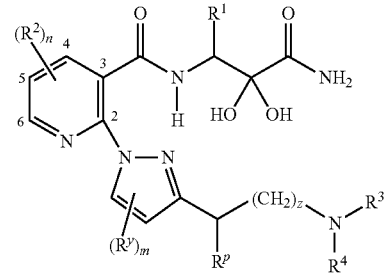

(Ia-H)

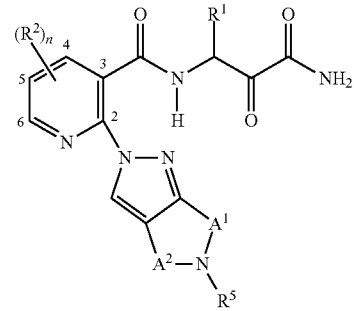

(Ib)

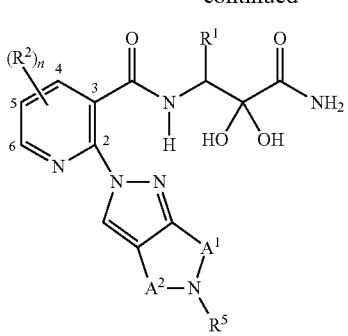

(Ib-H)

Table 1
Compounds of the formulae Ia and Ia-H in which n=0, i.e. $(R^2)_n$ is absent, m=0, i.e. $(R^y)_m$ is absent, and the combination of $R^1$ and CH—$R^p(CH_2)_z$ and $NR^3R^4$ for a compound in each case corresponds to one line of Table A.

Table 2
Compounds of the formulae Ia and Ia-H in which n=1, $(R^2)_n$ is 4-fluoro, m=0, i.e. $(R^y)_m$ is absent, and the combination of $R^1$ and CH—$R^p(CH_2)_z$ and $NR^3R^4$ for a compound in each case corresponds to one line of Table A.

Table 3
Compounds of the formulae Ia and Ia-H in which n=1, $(R^2)_n$ is 5-cyano, m=0, i.e. $(R^y)_m$ is absent, and the combination of $R^1$ and CH—$R^p(CH_2)_z$ and $NR^3R^4$ for a compound in each case corresponds to one line of Table A.

Table 4
Compounds of the formulae Ia and Ia-H in which n=1, $(R^2)_n$ is 5-fluoro, m=0, i.e. $(R^y)_m$ is absent, and the combination of $R^1$ and CH—$R^p(CH_2)_z$ and $NR^3R^4$ for a compound in each case corresponds to one line of Table A.

Table 5
Compounds of the formulae Ia and Ia-H in which n=1, $(R^2)_n$ is 5-chloro, m=0, i.e. $(R^y)_m$ is absent, and the combination of $R^1$ and CH—$R^p(CH_2)_z$ and $NR^3R^4$ for a compound in each case corresponds to one line of Table A.

Table 6
Compounds of the formulae Ia and Ia-H in which n=1, $(R^2)_n$ is 6-fluoro, m=0, i.e. $(R^y)_m$ is absent, and the combination of $R^1$ and CH—$R^p(CH_2)_z$ and $NR^3R^4$ for a compound in each case corresponds to one line of Table A.

Table 7
Compounds of the formulae Ib and Ib-H in which n=0, i.e. $(R^2)_n$ is absent and the combination of $R^1, A^1, A^2$ and $R^5$ for a compound in each case corresponds to one line of Table B.

Table 8 Compounds of the formulae Ib and Ib-H in which n=1, $(R^2)_n$ is 4-fluoro and the combination of $R^1, A^1, A^2$ and $R^5$ for a compound in each case corresponds to one line of Table B.

Table 9
Compounds of the formulae Ib and Ib-H in which n=1, $(R^2)_n$ is 5-cyano and the combination of $R^1, A^1, A^2$ and $R^5$ for a compound in each case corresponds to one line of Table B.

Table 10
Compounds of the formulae Ib and Ib-H in which n=1, $(R^2)_n$ is 5-fluoro and the combination of $R^1, A^1, A^2$ and $R^5$ for a compound in each case corresponds to one line of Table B.

Table 11
Compounds of the formulae Ib and Ib-H in which n=1, $(R^2)_n$ is 5-chloro and the combination of $R^1, A^1, A^2$ and $R^5$ for a compound in each case corresponds to one line of Table B.

Table 12
Compounds of the formulae Ib and Ib-H in which n=1, $(R^2)_n$ is 6-fluoro and the combination of $R^1, A^1, A^2$ and $R^5$ for a compound in each case corresponds to one line of Table B.

TABLE A

| # | $R^1$ | CH—$R^p(CH_2)_z$ | $NR^3R^4$ |
|---|---|---|---|
| 1 | $CH_2$—Ph | $CH_2$ | 4-morpholinyl |
| 2 | $CH_2$—Ph | $CH_2$ | 4-thiomorpholinyl |
| 3 | $CH_2$—Ph | $CH_2$ | 1,1-dioxothiomorpholin-4-yl |
| 4 | $CH_2$—Ph | $CH_2$ | 2,6-dimethylmorpholin-4-yl |
| 5 | $CH_2$—Ph | $CH_2$ | 2-phenylmorpholin-4-yl |
| 6 | $CH_2$—Ph | $CH_2$ | 1-azetidinyl |
| 7 | $CH_2$—Ph | $CH_2$ | 1-pyrrolidinyl |
| 8 | $CH_2$—Ph | $CH_2$ | 3-phenylpyrrolidin-1-yl |
| 9 | $CH_2$—Ph | $CH_2$ | 1-piperidinyl |
| 10 | $CH_2$—Ph | $CH_2$ | 1-azepanyl |
| 11 | $CH_2$—Ph | $CH_2$ | 4-methylpiperidin-1-yl |
| 12 | $CH_2$—Ph | $CH_2$ | 4-phenylpiperidin-1-yl |
| 13 | $CH_2$—Ph | $CH_2$ | 4,4-difluoropiperidin-1-yl |
| 14 | $CH_2$—Ph | $CH_2$ | 4-(trifluoromethyl)piperidin-1-yl |
| 15 | $CH_2$—Ph | $CH_2$ | 4-(tert.-butyl)piperidin-1-yl |
| 16 | $CH_2$—Ph | $CH_2$ | 4-methylpiperazin-1-yl |
| 17 | $CH_2$—Ph | $CH_2$ | 4-ethylpiperazin-1-yl |
| 18 | $CH_2$—Ph | $CH_2$ | 4-propylpiperazin-1-yl |
| 19 | $CH_2$—Ph | $CH_2$ | 4-cyclopropylmethylpiperazin-1-yl |
| 20 | $CH_2$—Ph | $CH_2$ | 4-cyclopropylpiperazin-1-yl |
| 21 | $CH_2$—Ph | $CH_2$ | 4-phenylpiperazin-1-yl |
| 22 | $CH_2$—Ph | $CH_2$ | dimethylamino |
| 23 | $CH_2$—Ph | $CH_2$ | diethylamino |
| 24 | $CH_2$—Ph | $CH_2$ | diisopropylamino |
| 25 | $CH_2$—Ph | $CH_2$ | N-phenylamino |
| 26 | $CH_2$—Ph | $CH_2$ | N-methyl-N-phenylamino |
| 27 | $CH_2$—Ph | $CH_2$ | N-cyclopropyl-N-methylamino |
| 28 | $CH_2$—Ph | $CH_2$ | N-cyclohexyl-N-methylamino |
| 29 | $CH_2$—Ph | $CH_2$ | N-benzyl-N-methylamino |
| 30 | $CH_2$—Ph | $CH_2$ | N-cyclohexylmethyl-N-methylamino |
| 31 | $CH_2$—Ph | $CH_2$ | N-methyl-N-isopropylamino |
| 32 | $CH_2$—Ph | $CH_2$ | N-cyclopropyl-N-phenylamino |
| 33 | $CH_2$—Ph | $CH_2$ | N-cyclopropyl-N-benzylamino |
| 34 | $CH_2$—Ph | $CH_2$ | N-(4-trifluoromethylcyclohexyl)-methyl-N-methylamino |
| 35 | $CH_2$—Ph | $CH_2$ | 3,4-dihydro-2H-1,4-benzoxazin-4-yl |
| 36 | $CH_2$—Ph | $CH_2$ | cis-octahydrobenzo-[1,4]oxazin-4-yl |
| 37 | $CH_2$—Ph | $CH_2$ | trans-octahydrobenzo[1,4]oxazin-4-yl |
| 38 | $CH_2$—Ph | $CH_2$ | 5,5-difluorooctahydrocyclopenta[c]pyrrol-2-yl |
| 39 | $CH_2$—Ph | $CH_2$ | hexahydrofuro[3,4-c]pyrrol-5-yl |
| 40 | $CH_2$—Ph | $CH_2$ | 2,3-dihydroindol-1-yl |
| 41 | $CH_2$—Ph | $CH_2$ | 2-oxa-7-azaspiro[3.5]nonane-7-yl |
| 42 | $CH_2$—Ph | $CH_2$ | 2,3-dihydro-1H-isoindole-2-yl |
| 43 | $CH_2$—Ph | $CH_2$ | 5-trifluoromethyl-2,3-dihydro-1H-isoindole-2-yl |
| 44 | $CH_2$—Ph | $CH_2$ | 4-trifluoro-2,3-dihydro-1H-isoindole-2-yl |
| 45 | $CH_2$—Ph | $CH_2$ | 2,3-dihydroisoindole-1-one-2-yl |
| 46 | $CH_2$—Ph | $CH_2$ | 1,2,3,4-tetrahydroisoquinoline-2-yl |
| 47 | $CH_2$—Ph | $CH_2$ | 3-azabicyclo[3.2.0]heptane-3-yl |
| 48 | $CH_2$—Ph | $CH_2$ | 6-(4-fluorophenyl)-3-azabicyclo[3.2.0]heptane-3-yl |
| 49 | $CH_2$—Ph | $CH_2CH_2$ | 4-morpholinyl |
| 50 | $CH_2$—Ph | $CH_2CH_2$ | 4-thiomorpholinyl |
| 51 | $CH_2$—Ph | $CH_2CH_2$ | 1,1-dioxothiomorpholin-4-yl |
| 52 | $CH_2$—Ph | $CH_2CH_2$ | 2,6-dimethylmorpholin-4-yl |
| 53 | $CH_2$—Ph | $CH_2CH_2$ | 2-phenylmorpholin-4-yl |
| 54 | $CH_2$—Ph | $CH_2CH_2$ | 1-azetidinyl |
| 55 | $CH_2$—Ph | $CH_2CH_2$ | 1-pyrrolidinyl |
| 56 | $CH_2$—Ph | $CH_2CH_2$ | 3-phenylpyrrolidin-1-yl |
| 57 | $CH_2$—Ph | $CH_2CH_2$ | 1-piperidinyl |
| 58 | $CH_2$—Ph | $CH_2CH_2$ | 1-azepanyl |
| 59 | $CH_2$—Ph | $CH_2CH_2$ | 4-methylpiperidin-1-yl |
| 60 | $CH_2$—Ph | $CH_2CH_2$ | 4-phenylpiperidin-1-yl |
| 61 | $CH_2$—Ph | $CH_2CH_2$ | 4,4-difluoropiperidin-1-yl |
| 62 | $CH_2$—Ph | $CH_2CH_2$ | 4-(trifluoromethyl)piperidin-1-yl |

TABLE A-continued

| # | R¹ | CH—R$^p$(CH$_2$)$_z$ | NR³R⁴ |
|---|---|---|---|
| 63 | CH$_2$—Ph | CH$_2$CH$_2$ | 4-(tert.-butyl)piperidin-1-yl |
| 64 | CH$_2$—Ph | CH$_2$CH$_2$ | 4-methylpiperazin-1-yl |
| 65 | CH$_2$—Ph | CH$_2$CH$_2$ | 4-ethylpiperazin-4-yl |
| 66 | CH$_2$—Ph | CH$_2$CH$_2$ | 4-propylpiperazin-4-yl |
| 67 | CH$_2$—Ph | CH$_2$CH$_2$ | 4-cyclopropylmethylpiperazin-1-yl |
| 68 | CH$_2$—Ph | CH$_2$CH$_2$ | 4-cyclopropylpiperazin-1-yl |
| 69 | CH$_2$—Ph | CH$_2$CH$_2$ | 4-phenylpiperazin-1-yl |
| 70 | CH$_2$—Ph | CH$_2$CH$_2$ | dimethylamino |
| 71 | CH$_2$—Ph | CH$_2$CH$_2$ | diethylamino |
| 72 | CH$_2$—Ph | CH$_2$CH$_2$ | diisopropylamino |
| 73 | CH$_2$—Ph | CH$_2$CH$_2$ | N-phenylamino |
| 74 | CH$_2$—Ph | CH$_2$CH$_2$ | N-methyl-N-isopropylamino |
| 75 | CH$_2$—Ph | CH$_2$CH$_2$ | N-methyl-N-phenylamino |
| 76 | CH$_2$—Ph | CH$_2$CH$_2$ | N-cyclopropyl-N-methylamino |
| 77 | CH$_2$—Ph | CH$_2$CH$_2$ | N-cyclopropyl-N-phenylamino |
| 78 | CH$_2$—Ph | CH$_2$CH$_2$ | N-cyclopropyl-N-benzylamino |
| 79 | CH$_2$—Ph | CH$_2$CH$_2$ | N-cyclohexyl-N-methylamino |
| 80 | CH$_2$—Ph | CH$_2$CH$_2$ | N-benzyl-N-methylamino |
| 81 | CH$_2$—Ph | CH$_2$CH$_2$ | N-cyclohexylmethyl-N-methylamino |
| 82 | CH$_2$—Ph | CH$_2$CH$_2$ | N-(4-trifluoromethylcyclohexyl)-methyl-N-methylamino |
| 83 | CH$_2$—Ph | CH$_2$CH$_2$ | 3,4-dihydro-2H-1,4-benzoxazin-4-yl |
| 84 | CH$_2$—Ph | CH$_2$CH$_2$ | cis-octahydrobenzo-[1,4]oxazin-4-yl |
| 85 | CH$_2$—Ph | CH$_2$CH$_2$ | trans-octahydrobenzo[1,4]oxazin-4-yl |
| 86 | CH$_2$—Ph | CH$_2$CH$_2$ | 5,5-difluoroocta-hydrocyclopenta[c]pyrrol-2-yl |
| 87 | CH$_2$—Ph | CH$_2$CH$_2$ | hexahydrofuro[3,4-c]pyrrol-5-yl |
| 88 | CH$_2$—Ph | CH$_2$CH$_2$ | 2,3-dihydroindol-1-yl |
| 89 | CH$_2$—Ph | CH$_2$CH$_2$ | 2-oxa-7-azaspiro[3.5]nonane-7-yl |
| 90 | CH$_2$—Ph | CH$_2$CH$_2$ | 2,3-dihydro-1H-isoindole-2-yl |
| 91 | CH$_2$—Ph | CH$_2$CH$_2$ | 5-trifluoromethyl-2,3-dihydro-1H-isoindole-2-yl |
| 92 | CH$_2$—Ph | CH$_2$CH$_2$ | 4-trifluoro-2,3-dihydro-1H-isoindole-2-yl |
| 93 | CH$_2$—Ph | CH$_2$CH$_2$ | 2,3-dihydroisoindole-1-one-2-yl |
| 94 | CH$_2$—Ph | CH$_2$CH$_2$ | 1,2,3,4-tetrahydroisoquinoline-2-yl |
| 95 | CH$_2$—Ph | CH$_2$CH$_2$ | 3-azabicyclo[3.2.0]heptane-3-yl |
| 96 | CH$_2$—Ph | CH$_2$CH$_2$ | 6-(4-fluorophenyl)-3-azabicyclo[3.2.0]heptane-3-yl |
| 97 | CH$_2$—Ph | | azetin-3-yl |
| 98 | CH$_2$—Ph | | pyrrolidin-3-yl |
| 99 | CH$_2$—Ph | | 1-methylpyrrolidin-3-yl |
| 100 | CH$_2$—Ph | | piperidin-3-yl |
| 101 | CH$_2$—Ph | | 1-methylpiperidin-3-yl |
| 102 | CH$_2$—Ph | | piperidin-4-yl |
| 103 | CH$_2$—Ph | | 1-methylpiperidin-4-yl |
| 104 | CH$_2$—Ph | | 1-ethylpiperidin-4-yl |
| 105 | CH$_2$—Ph | | 1-propylpiperidin-4-yl |
| 106 | CH$_2$—Ph | | 1-benzylpiperidin-4-yl |
| 107 | CH$_2$—Ph | | 1-cyclopropylpiperidin-4-yl |
| 108 | 4-Cl-Bz | CH$_2$ | 4-morpholinyl |
| 109 | 4-Cl-Bz | CH$_2$ | 4-thiomorpholinyl |
| 110 | 4-Cl-Bz | CH$_2$ | 1,1-dioxothiomorpholin-4-yl |
| 111 | 4-Cl-Bz | CH$_2$ | 2,6-dimethylmorpholin-4-yl |
| 112 | 4-Cl-Bz | CH$_2$ | 2-phenylmorpholin-4-yl |
| 113 | 4-Cl-Bz | CH$_2$ | 1-azetidinyl |
| 114 | 4-Cl-Bz | CH$_2$ | 1-pyrrolidinyl |
| 115 | 4-Cl-Bz | CH$_2$ | 3-phenylpyrrolidin-1-yl |
| 116 | 4-Cl-Bz | CH$_2$ | 1-piperidinyl |
| 117 | 4-Cl-Bz | CH$_2$ | 1-azepanyl |
| 118 | 4-Cl-Bz | CH$_2$ | 4-methylpiperidin-1-yl |
| 119 | 4-Cl-Bz | CH$_2$ | 4-phenylpiperidin-1-yl |
| 120 | 4-Cl-Bz | CH$_2$ | 4,4-difluoropiperidin-1-yl |
| 121 | 4-Cl-Bz | CH$_2$ | 4-(trifluoromethyl)piperidin-1-yl |
| 122 | 4-Cl-Bz | CH$_2$ | 4-(tert.-butyl)piperidin-1-yl |
| 123 | 4-Cl-Bz | CH$_2$ | 4-methylpiperazin-1-yl |
| 124 | 4-Cl-Bz | CH$_2$ | 4-ethylpiperazin-1-yl |
| 125 | 4-Cl-Bz | CH$_2$ | 4-propylpiperazin-1-yl |
| 126 | 4-Cl-Bz | CH$_2$ | 4-cyclopropylmethylpiperazin-1-yl |
| 127 | 4-Cl-Bz | CH$_2$ | 4-cyclopropylpiperazin-1-yl |
| 128 | 4-Cl-Bz | CH$_2$ | 4-phenylpiperazin-1-yl |
| 129 | 4-Cl-Bz | CH$_2$ | dimethylamino |
| 130 | 4-Cl-Bz | CH$_2$ | diethylamino |
| 131 | 4-Cl-Bz | CH$_2$ | diisopropylamino |
| 132 | 4-Cl-Bz | CH$_2$ | N-phenylamino |
| 133 | 4-Cl-Bz | CH$_2$ | N-methyl-N-phenylamino |
| 134 | 4-Cl-Bz | CH$_2$ | N-cyclopropyl-N-methylamino |
| 135 | 4-Cl-Bz | CH$_2$ | N-cyclohexyl-N-methylamino |
| 136 | 4-Cl-Bz | CH$_2$ | N-benzyl-N-methylamino |
| 137 | 4-Cl-Bz | CH$_2$ | N-cyclohexylmethyl-N-methylamino |
| 138 | 4-Cl-Bz | CH$_2$ | N-methyl-N-isopropylamino |
| 139 | 4-Cl-Bz | CH$_2$ | N-cyclopropyl-N-phenylamino |
| 140 | 4-Cl-Bz | CH$_2$ | N-cyclopropyl-N-benzylamino |
| 141 | 4-Cl-Bz | CH$_2$ | N-(4-trifluoromethylcyclohexyl)-methyl-N-methylamino |
| 142 | 4-Cl-Bz | CH$_2$ | 3,4-dihydro-2H-1,4-benzoxazin-4-yl |
| 143 | 4-Cl-Bz | CH$_2$ | cis-octahydrobenzo-[1,4]oxazin-4-yl |
| 144 | 4-Cl-Bz | CH$_2$ | trans-octahydrobenzo[1,4]oxazin-4-yl |
| 145 | 4-Cl-Bz | CH$_2$ | 5,5-difluoroocta-hydrocyclopenta[c]pyrrol-2-yl |
| 146 | 4-Cl-Bz | CH$_2$ | hexahydrofuro[3,4-c]pyrrol-5-yl |
| 147 | 4-Cl-Bz | CH$_2$ | 2,3-dihydroindol-1-yl |
| 148 | 4-Cl-Bz | CH$_2$ | 2-oxa-7-azaspiro[3.5]nonane-7-yl |
| 149 | 4-Cl-Bz | CH$_2$ | 2,3-dihydro-1H-isoindole-2-yl |
| 150 | 4-Cl-Bz | CH$_2$ | 5-trifluoromethyl-2,3-dihydro-1H-isoindole-2-yl |
| 151 | 4-Cl-Bz | CH$_2$ | 4-trifluoro-2,3-dihydro-1H-isoindole-2-yl |
| 152 | 4-Cl-Bz | CH$_2$ | 2,3-dihydroisoindole-1-one-2-yl |
| 153 | 4-Cl-Bz | CH$_2$ | 1,2,3,4-tetrahydroisoquinoline-2-yl |
| 154 | 4-Cl-Bz | CH$_2$ | 3-azabicyclo[3.2.0]heptane-3-yl |
| 155 | 4-Cl-Bz | CH$_2$ | 6-(4-fluorophenyl)-3-azabicyclo[3.2.0]heptane-3-yl |
| 156 | 4-Cl-Bz | CH$_2$CH$_2$ | 4-morpholinyl |
| 157 | 4-Cl-Bz | CH$_2$CH$_2$ | 4-thiomorpholinyl |
| 158 | 4-Cl-Bz | CH$_2$CH$_2$ | 1,1-dioxothiomorphin-4-yl |
| 159 | 4-Cl-Bz | CH$_2$CH$_2$ | 2,6-dimethylmorpholin-4-yl |
| 160 | 4-Cl-Bz | CH$_2$CH$_2$ | 2-phenylmorpholin-4-yl |
| 161 | 4-Cl-Bz | CH$_2$CH$_2$ | 1-azetidinyl |
| 162 | 4-Cl-Bz | CH$_2$CH$_2$ | 1-pyrrolidinyl |
| 163 | 4-Cl-Bz | CH$_2$CH$_2$ | 3-phenylpyrrolidin-1-yl |
| 164 | 4-Cl-Bz | CH$_2$CH$_2$ | 1-piperidinyl |
| 165 | 4-Cl-Bz | CH$_2$CH$_2$ | 1-azepanyl |
| 166 | 4-Cl-Bz | CH$_2$CH$_2$ | 4-methylpiperidin-1-yl |
| 167 | 4-Cl-Bz | CH$_2$CH$_2$ | 4-phenylpiperidin-1-yl |
| 168 | 4-Cl-Bz | CH$_2$CH$_2$ | 4,4-difluoropiperidin-1-yl |
| 169 | 4-Cl-Bz | CH$_2$CH$_2$ | 4-(trifluoromethyl)piperidin-1-yl |
| 170 | 4-Cl-Bz | CH$_2$CH$_2$ | 4-(tert.-butyl)piperidin-1-yl |
| 171 | 4-Cl-Bz | CH$_2$CH$_2$ | 4-methylpiperazin-1-yl |
| 172 | 4-Cl-Bz | CH$_2$CH$_2$ | 4-ethylpiperazin-1-yl |
| 173 | 4-Cl-Bz | CH$_2$CH$_2$ | 4-propylpiperazin-1-yl |
| 174 | 4-Cl-Bz | CH$_2$CH$_2$ | 4-cyclopropylmethylpiperazin-1-yl |
| 175 | 4-Cl-Bz | CH$_2$CH$_2$ | 4-cyclopropylpiperazin-1-yl |
| 176 | 4-Cl-Bz | CH$_2$CH$_2$ | 4-phenylpiperazin-1-yl |
| 177 | 4-Cl-Bz | CH$_2$CH$_2$ | dimethylamino |
| 178 | 4-Cl-Bz | CH$_2$CH$_2$ | diethylamino |
| 179 | 4-Cl-Bz | CH$_2$CH$_2$ | diisopropylamino |
| 180 | 4-Cl-Bz | CH$_2$CH$_2$ | N-phenylamino |
| 181 | 4-Cl-Bz | CH$_2$CH$_2$ | N-methyl-N-phenylamino |
| 182 | 4-Cl-Bz | CH$_2$CH$_2$ | N-cyclopropyl-N-methylamino |
| 183 | 4-Cl-Bz | CH$_2$CH$_2$ | N-cyclohexyl-N-methylamino |
| 184 | 4-Cl-Bz | CH$_2$CH$_2$ | N-benzyl-N-methylamino |
| 185 | 4-Cl-Bz | CH$_2$CH$_2$ | N-cyclohexylmethyl-N-methylamino |
| 186 | 4-Cl-Bz | CH$_2$CH$_2$ | N-methyl-N-isopropylamino |
| 187 | 4-Cl-Bz | CH$_2$CH$_2$ | N-cyclopropyl-N-phenylamino |
| 188 | 4-Cl-Bz | CH$_2$CH$_2$ | N-cyclopropyl-N-benzylamino |
| 189 | 4-Cl-Bz | CH$_2$CH$_2$ | N-(4-trifluoromethylcyclohexyl)-methyl-N-methylamino |
| 190 | 4-Cl-Bz | CH$_2$CH$_2$ | 3,4-dihydro-2H-1,4-benzoxazin-4-yl |
| 191 | 4-Cl-Bz | CH$_2$CH$_2$ | cis-octahydrobenzo-[1,4]oxazin-4-yl |
| 192 | 4-Cl-Bz | CH$_2$CH$_2$ | trans-octahydrobenzo[1,4]oxazin-4-yl |
| 193 | 4-Cl-Bz | CH$_2$CH$_2$ | 5,5-difluoroocta-hydrocyclopenta[c]pyrrol-2-yl |
| 194 | 4-Cl-Bz | CH$_2$CH$_2$ | hexahydrofuro[3,4-c]pyrrol-5-yl |

TABLE A-continued

| # | R¹ | CH—R$^p$(CH$_2$)$_z$ | NR³R⁴ |
|---|---|---|---|
| 195 | 4-Cl-Bz | CH$_2$CH$_2$ | 2,3-dihydroindol-1-yl |
| 196 | 4-Cl-Bz | CH$_2$CH$_2$ | 2-oxa-7-azaspiro[3.5]nonane-7-yl |
| 197 | 4-Cl-Bz | CH$_2$CH$_2$ | 2,3-dihydro-1H-isoindole-2-yl |
| 198 | 4-Cl-Bz | CH$_2$CH$_2$ | 5-trifluoromethyl-2,3-dihydro-1H-isoindole-2-yl |
| 199 | 4-Cl-Bz | CH$_2$CH$_2$ | 4-trifluoro-2,3-dihydro-1H-isoindole-2-yl |
| 200 | 4-Cl-Bz | CH$_2$CH$_2$ | 2,3-dihydroisoindole-1-one-2-yl |
| 201 | 4-Cl-Bz | CH$_2$CH$_2$ | 1,2,3,4-tetrahydroisoquinoline-2-yl |
| 202 | 4-Cl-Bz | CH$_2$CH$_2$ | 3-azabicyclo[3.2.0]heptane-3-yl |
| 203 | 4-Cl-Bz | CH$_2$CH$_2$ | 6-(4-fluorophenyl)-3-azabicyclo[3.2.0]heptane-3-yl |
| 204 | 4-Cl-Bz | | azetin-3-yl |
| 205 | 4-Cl-Bz | | pyrrolidin-3-yl |
| 206 | 4-Cl-Bz | | 1-methylpyrrolidin-3-yl |
| 207 | 4-Cl-Bz | | piperidin-3-yl |
| 208 | 4-Cl-Bz | | 1-methylpiperidin-3-yl |
| 209 | 4-Cl-Bz | | piperidin-4-yl |
| 210 | 4-Cl-Bz | | 1-methylpiperidin-4-yl |
| 211 | 4-Cl-Bz | | 1-ethylpiperidin-4-yl |
| 212 | 4-Cl-Bz | | 1-propylpiperidin-4-yl |
| 213 | 4-Cl-Bz | | 1-cyclopropylpiperidin-4-yl |
| 214 | 4-Cl-Bz | | 1-benzylpiperidin-4-yl |
| 215 | 4-F-Bz | CH$_2$ | 4-morpholinyl |
| 216 | 4-F-Bz | CH$_2$ | 4-thiomorpholinyl |
| 217 | 4-F-Bz | CH$_2$ | 1,1-dioxothiomorpholin-4-yl |
| 218 | 4-F-Bz | CH$_2$ | 2,6-dimethylmorpholin-4-yl |
| 219 | 4-F-Bz | CH$_2$ | 2-phenylmorpholin-4-yl |
| 220 | 4-F-Bz | CH$_2$ | 1-azetidinyl |
| 221 | 4-F-Bz | CH$_2$ | 1-pyrrolidinyl |
| 222 | 4-F-Bz | CH$_2$ | 3-phenylpyrrolidin-1-yl |
| 223 | 4-F-Bz | CH$_2$ | 1-piperidinyl |
| 224 | 4-F-Bz | CH$_2$ | 1-azepanyl |
| 225 | 4-F-Bz | CH$_2$ | 4-methylpiperidin-1-yl |
| 226 | 4-F-Bz | CH$_2$ | 4-phenylpiperidin-1-yl |
| 227 | 4-F-Bz | CH$_2$ | 4,4-difluoropiperidin-1-yl |
| 228 | 4-F-Bz | CH$_2$ | 4-(trifluoromethyl)piperidin-1-yl |
| 229 | 4-F-Bz | CH$_2$ | 4-(tert.-butyl)piperidin-1-yl |
| 230 | 4-F-Bz | CH$_2$ | 4-methylpiperazin-1-yl |
| 231 | 4-F-Bz | CH$_2$ | 4-ethylpiperazin-1-yl |
| 232 | 4-F-Bz | CH$_2$ | 4-propylpiperazin-1-yl |
| 233 | 4-F-Bz | CH$_2$ | 4-cyclopropylmethylpiperazin-1-yl |
| 234 | 4-F-Bz | CH$_2$ | 4-cyclopropylpiperazin-1-yl |
| 235 | 4-F-Bz | CH$_2$ | 4-phenylpiperazin-1-yl |
| 236 | 4-F-Bz | CH$_2$ | dimethylamino |
| 237 | 4-F-Bz | CH$_2$ | diethylamino |
| 238 | 4-F-Bz | CH$_2$ | diisopropylamino |
| 239 | 4-F-Bz | CH$_2$ | N-phenylamino |
| 240 | 4-F-Bz | CH$_2$ | N-methyl-N-phenylamino |
| 241 | 4-F-Bz | CH$_2$ | N-cyclopropyl-N-methylamino |
| 242 | 4-F-Bz | CH$_2$ | N-cyclohexyl-N-methylamino |
| 243 | 4-F-Bz | CH$_2$ | N-benzyl-N-methylamino |
| 244 | 4-F-Bz | CH$_2$ | N-cyclohexylmethyl-N-methylamino |
| 245 | 4-F-Bz | CH$_2$ | N-methyl-N-isopropylamino |
| 246 | 4-F-Bz | CH$_2$ | N-cyclopropyl-N-phenylamino |
| 247 | 4-F-Bz | CH$_2$ | N-cyclopropyl-N-benzylamino |
| 248 | 4-F-Bz | CH$_2$ | N-(4-trifluoromethylcyclohexyl)-methyl-N-methylamino |
| 249 | 4-F-Bz | CH$_2$ | 3,4-dihydro-2H-1,4-benzoxazin-4-yl |
| 250 | 4-F-Bz | CH$_2$ | cis-octahydrobenzo-[1,4]oxazin-4-yl |
| 251 | 4-F-Bz | CH$_2$ | trans-octahydrobenzo[1,4]oxazin-4-yl |
| 252 | 4-F-Bz | CH$_2$ | 5,5-difluoroocta-hydrocyclopenta[c]pyrrol-2-yl |
| 253 | 4-F-Bz | CH$_2$ | hexahydrofuro[3,4-c]pyrrol-5-yl |
| 254 | 4-F-Bz | CH$_2$ | 2,3-dihydroindol-1-yl |
| 255 | 4-F-Bz | CH$_2$ | 2-oxa-7-azaspiro[3.5]nonane-7-yl |
| 256 | 4-F-Bz | CH$_2$ | 2,3-dihydro-1H-isoindole-2-yl |
| 257 | 4-F-Bz | CH$_2$ | 5-trifluoromethyl-2,3-dihydro-1H-isoindole-2-yl |
| 258 | 4-F-Bz | CH$_2$ | 4-trifluoro-2,3-dihydro-1H-isoindole-2-yl |
| 259 | 4-F-Bz | CH$_2$ | 2,3-dihydroisoindole-1-one-2-yl |
| 260 | 4-F-Bz | CH$_2$ | 1,2,3,4-tetrahydroisoquinoline-2-yl |
| 261 | 4-F-Bz | CH$_2$ | 3-azabicyclo[3.2.0]heptane-3-yl |
| 262 | 4-F-Bz | CH$_2$ | 6-(4-fluorophenyl)-3-azabicyclo[3.2.0]heptane-3-yl |
| 263 | 4-F-Bz | CH$_2$CH$_2$ | 4-morpholinyl |
| 264 | 4-F-Bz | CH$_2$CH$_2$ | 4-thiomorpholinyl |
| 265 | 4-F-Bz | CH$_2$CH$_2$ | 1,1-dioxothiomorpholin-4-yl |
| 266 | 4-F-Bz | CH$_2$CH$_2$ | 2,6-dimethylmorpholin-4-yl |
| 267 | 4-F-Bz | CH$_2$CH$_2$ | 2-phenylmorpholin-4-yl |
| 268 | 4-F-Bz | CH$_2$CH$_2$ | 1-azetidinyl |
| 269 | 4-F-Bz | CH$_2$CH$_2$ | 1-pyrrolidinyl |
| 270 | 4-F-Bz | CH$_2$CH$_2$ | 3-phenylpyrrolidin-1-yl |
| 271 | 4-F-Bz | CH$_2$CH$_2$ | 1-piperidinyl |
| 272 | 4-F-Bz | CH$_2$CH$_2$ | 1-azepanyl |
| 273 | 4-F-Bz | CH$_2$CH$_2$ | 4-methylpiperidin-1-yl |
| 274 | 4-F-Bz | CH$_2$CH$_2$ | 4-phenylpiperidin-1-yl |
| 275 | 4-F-Bz | CH$_2$CH$_2$ | 4,4-difluoropiperidin-1-yl |
| 276 | 4-F-Bz | CH$_2$CH$_2$ | 4-(trifluoromethyl)piperidin-1-yl |
| 277 | 4-F-Bz | CH$_2$CH$_2$ | 4-(tert.-butyl)piperidin-1-yl |
| 278 | 4-F-Bz | CH$_2$CH$_2$ | 4-methylpiperazin-1-yl |
| 279 | 4-F-Bz | CH$_2$CH$_2$ | 4-ethylpiperazin-1-yl |
| 280 | 4-F-Bz | CH$_2$CH$_2$ | 4-propylpiperazin-1-yl |
| 281 | 4-F-Bz | CH$_2$CH$_2$ | 4-cyclopropylmethylpiperazin-1-yl |
| 282 | 4-F-Bz | CH$_2$CH$_2$ | 4-cyclopropylpiperazin-1-yl |
| 283 | 4-F-Bz | CH$_2$CH$_2$ | 4-phenylpiperazin-1-yl |
| 284 | 4-F-Bz | CH$_2$CH$_2$ | dimethylamino |
| 285 | 4-F-Bz | CH$_2$CH$_2$ | diethylamino |
| 286 | 4-F-Bz | CH$_2$CH$_2$ | diisopropylamino |
| 287 | 4-F-Bz | CH$_2$CH$_2$ | N-phenylamino |
| 288 | 4-F-Bz | CH$_2$CH$_2$ | N-methyl-N-phenylamino |
| 289 | 4-F-Bz | CH$_2$CH$_2$ | N-cyclopropyl-N-methylamino |
| 290 | 4-F-Bz | CH$_2$CH$_2$ | N-cyclohexyl-N-methylamino |
| 291 | 4-F-Bz | CH$_2$CH$_2$ | N-benzyl-N-methylamino |
| 292 | 4-F-Bz | CH$_2$CH$_2$ | N-cyclohexylmethyl-N-methylamino |
| 293 | 4-F-Bz | CH$_2$CH$_2$ | N-methyl-N-isopropylamino |
| 294 | 4-F-Bz | CH$_2$CH$_2$ | N-cyclopropyl-N-phenylamino |
| 295 | 4-F-Bz | CH$_2$CH$_2$ | N-cyclopropyl-N-benzylamino |
| 296 | 4-F-Bz | CH$_2$CH$_2$ | N-(4-trifluoromethylcyclohexyl)-methyl-N-methylamino |
| 297 | 4-F-Bz | CH$_2$CH$_2$ | 3,4-dihydro-2H-1,4-benzoxazin-4-yl |
| 298 | 4-F-Bz | CH$_2$CH$_2$ | cis-octahydrobenzo-[1,4]oxazin-4-yl |
| 299 | 4-F-Bz | CH$_2$CH$_2$ | trans-octahydrobenzo[1,4]oxazin-4-yl |
| 300 | 4-F-Bz | CH$_2$CH$_2$ | 5,5-difluoroocta-hydrocyclopenta[c]pyrrol-2-yl |
| 301 | 4-F-Bz | CH$_2$CH$_2$ | hexahydrofuro[3,4-c]pyrrol-5-yl |
| 302 | 4-F-Bz | CH$_2$CH$_2$ | 2,3-dihydroindol-1-yl |
| 303 | 4-F-Bz | CH$_2$CH$_2$ | 2-oxa-7-azaspiro[3.5]nonane-7-yl |
| 304 | 4-F-Bz | CH$_2$CH$_2$ | 2,3-dihydro-1H-isoindole-2-yl |
| 305 | 4-F-Bz | CH$_2$CH$_2$ | 5-trifluoromethyl-2,3-dihydro-1H-isoindole-2-yl |
| 306 | 4-F-Bz | CH$_2$CH$_2$ | 4-trifluoro-2,3-dihydro-1H-isoindole-2-yl |
| 307 | 4-F-Bz | CH$_2$CH$_2$ | 2,3-dihydroisoindole-1-one-2-yl |
| 308 | 4-F-Bz | CH$_2$CH$_2$ | 1,2,3,4-tetrahydroisoquinoline-2-yl |
| 309 | 4-F-Bz | CH$_2$CH$_2$ | 3-azabicyclo[3.2.0]heptane-3-yl |
| 310 | 4-F-Bz | CH$_2$CH$_2$ | 6-(4-fluorophenyl)-3-azabicyclo[3.2.0]heptane-3-yl |
| 311 | 4-F-Bz | | azetin-3-yl |
| 312 | 4-F-Bz | | pyrrolidin-3-yl |
| 313 | 4-F-Bz | | 1-methylpyrrolidin-3-yl |
| 314 | 4-F-Bz | | piperidin-3-yl |
| 315 | 4-F-Bz | | 1-methylpiperidin-3-yl |
| 316 | 4-F-Bz | | piperidin-4-yl |
| 317 | 4-F-Bz | | 1-methylpiperidin-4-yl |
| 318 | 4-F-Bz | | 1-ethylpiperidin-4-yl |
| 319 | 4-F-Bz | | 1-propylpiperidin-4-yl |
| 320 | 4-F-Bz | | 1-benzylpiperidin-4-yl |
| 321 | 4-F-Bz | | 1-cyclopropylpiperidin-4-yl |
| 322 | 2-F-Bz | CH$_2$ | 4-morpholinyl |
| 323 | 2-F-Bz | CH$_2$ | 4-thiomorpholinyl |
| 324 | 2-F-Bz | CH$_2$ | 1,1-dioxothiomorpholin-4-yl |
| 325 | 2-F-Bz | CH$_2$ | 2,6-dimethylmorpholin-4-yl |
| 326 | 2-F-Bz | CH$_2$ | 2-phenylmorpholin-4-yl |
| 327 | 2-F-Bz | CH$_2$ | 1-azetidinyl |
| 328 | 2-F-Bz | CH$_2$ | 1-pyrrolidinyl |
| 329 | 2-F-Bz | CH$_2$ | 3-phenylpyrrolidin-1-yl |

TABLE A-continued

| # | R¹ | CH—R^p(CH₂)_z | NR³R⁴ |
|---|---|---|---|
| 330 | 2-F-Bz | CH₂ | 1-piperidinyl |
| 331 | 2-F-Bz | CH₂ | 1-azepanyl |
| 332 | 2-F-Bz | CH₂ | 4-methylpiperidin-1-yl |
| 333 | 2-F-Bz | CH₂ | 4-phenylpiperidin-1-yl |
| 334 | 2-F-Bz | CH₂ | 4,4-difluoropiperidin-1-yl |
| 335 | 2-F-Bz | CH₂ | 4-(trifluoromethyl)piperidin-1-yl |
| 336 | 2-F-Bz | CH₂ | 4-(tert.-butyl)piperidin-1-yl |
| 337 | 2-F-Bz | CH₂ | 4-methylpiperazin-1-yl |
| 338 | 2-F-Bz | CH₂ | 4-ethylpiperazin-1-yl |
| 339 | 2-F-Bz | CH₂ | 4-propylpiperazin-1-yl |
| 340 | 2-F-Bz | CH₂ | 4-cyclopropylmethylpiperazin-1-yl |
| 341 | 2-F-Bz | CH₂ | 4-cyclopropylpiperazin-1-yl |
| 342 | 2-F-Bz | CH₂ | 4-phenylpiperazin-1-yl |
| 343 | 2-F-Bz | CH₂ | dimethylamino |
| 344 | 2-F-Bz | CH₂ | diethylamino |
| 345 | 2-F-Bz | CH₂ | diisopropylamino |
| 346 | 2-F-Bz | CH₂ | N-phenylamino |
| 347 | 2-F-Bz | CH₂ | N-methyl-N-phenylamino |
| 348 | 2-F-Bz | CH₂ | N-cyclopropyl-N-methylamino |
| 349 | 2-F-Bz | CH₂ | N-cyclohexyl-N-methylamino |
| 350 | 2-F-Bz | CH₂ | N-benzyl-N-methylamino |
| 351 | 2-F-Bz | CH₂ | N-cyclohexylmethyl-N-methylamino |
| 352 | 2-F-Bz | CH₂ | N-methyl-N-isopropylamino |
| 353 | 2-F-Bz | CH₂ | N-cyclopropyl-N-phenylamino |
| 354 | 2-F-Bz | CH₂ | N-cyclopropyl-N-benzylamino |
| 355 | 2-F-Bz | CH₂ | N-(4-trifluoromethylcyclohexyl)-methyl-N-methylamino |
| 356 | 2-F-Bz | CH₂ | 3,4-dihydro-2H-1,4-benzoxazin-4-yl |
| 357 | 2-F-Bz | CH₂ | cis-octahydrobenzo-[1,4]oxazin-4-yl |
| 358 | 2-F-Bz | CH₂ | trans-octahydrobenzo[1,4]oxazin-4-yl |
| 359 | 2-F-Bz | CH₂ | 5,5-difluorooctahydrocyclopenta[c]pyrrol-2-yl |
| 360 | 2-F-Bz | CH₂ | hexahydrofuro[3,4-c]pyrrol-5-yl |
| 361 | 2-F-Bz | CH₂ | 2,3-dihydroindol-1-yl |
| 362 | 2-F-Bz | CH₂ | 2-oxa-7-azaspiro[3.5]nonane-7-yl |
| 363 | 2-F-Bz | CH₂ | 2,3-dihydro-1H-isoindole-2-yl |
| 364 | 2-F-Bz | CH₂ | 5-trifluoromethyl-2,3-dihydro-1H-isoindole-2-yl |
| 365 | 2-F-Bz | CH₂ | 4-trifluoro-2,3-dihydro-1H-isoindole-2-yl |
| 366 | 2-F-Bz | CH₂ | 2,3-dihydroisoindole-1-one-2-yl |
| 367 | 2-F-Bz | CH₂ | 1,2,3,4-tetrahydroisoquinoline-2-yl |
| 368 | 2-F-Bz | CH₂ | 3-azabicyclo[3.2.0]heptane-3-yl |
| 369 | 2-F-Bz | CH₂ | 6-(4-fluorophenyl)-3-azabicyclo[3.2.0]heptane-3-yl |
| 370 | 2-F-Bz | CH₂CH₂ | 4-morpholinyl |
| 371 | 2-F-Bz | CH₂CH₂ | 4-thiomorpholinyl |
| 372 | 2-F-Bz | CH₂CH₂ | 1,1-dioxothiomorpholin-4-yl |
| 373 | 2-F-Bz | CH₂CH₂ | 2,6-dimethylmorpholin-4-yl |
| 374 | 2-F-Bz | CH₂CH₂ | 2-phenylmorpholin-4-yl |
| 375 | 2-F-Bz | CH₂CH₂ | 1-azetidinyl |
| 376 | 2-F-Bz | CH₂CH₂ | 1-pyrrolidinyl |
| 377 | 2-F-Bz | CH₂CH₂ | 3-phenylpyrrolidin-1-yl |
| 378 | 2-F-Bz | CH₂CH₂ | 1-piperidinyl |
| 379 | 2-F-Bz | CH₂CH₂ | 1-azepanyl |
| 380 | 2-F-Bz | CH₂CH₂ | 4-methylpiperidin-1-yl |
| 381 | 2-F-Bz | CH₂CH₂ | 4-phenylpiperidin-1-yl |
| 382 | 2-F-Bz | CH₂CH₂ | 4,4-difluoropiperidin-1-yl |
| 383 | 2-F-Bz | CH₂CH₂ | 4-(trifluoromethyl)piperidin-1-yl |
| 384 | 2-F-Bz | CH₂CH₂ | 4-(tert.-butyl)piperidin-1-yl |
| 385 | 2-F-Bz | CH₂CH₂ | 4-methylpiperazin-1-yl |
| 386 | 2-F-Bz | CH₂CH₂ | 4-ethylpiperazin-1-yl |
| 387 | 2-F-Bz | CH₂CH₂ | 4-propylpiperazin-1-yl |
| 388 | 2-F-Bz | CH₂CH₂ | 4-cyclopropylmethylpiperazin-1-yl |
| 389 | 2-F-Bz | CH₂CH₂ | 4-cyclopropylpiperazin-1-yl |
| 390 | 2-F-Bz | CH₂CH₂ | 4-phenylpiperazin-1-yl |
| 391 | 2-F-Bz | CH₂CH₂ | dimethylamino |
| 392 | 2-F-Bz | CH₂CH₂ | diethylamino |
| 393 | 2-F-Bz | CH₂CH₂ | diisopropylamino |
| 394 | 2-F-Bz | CH₂CH₂ | N-phenylamino |
| 395 | 2-F-Bz | CH₂CH₂ | N-methyl-N-phenylamino |
| 396 | 2-F-Bz | CH₂CH₂ | N-cyclopropyl-N-methylamino |
| 397 | 2-F-Bz | CH₂CH₂ | N-cyclohexyl-N-methylamino |
| 398 | 2-F-Bz | CH₂CH₂ | N-benzyl-N-methylamino |
| 399 | 2-F-Bz | CH₂CH₂ | N-cyclohexylmethyl-N-methylamino |
| 400 | 2-F-Bz | CH₂CH₂ | N-methyl-N-isopropylamino |
| 401 | 2-F-Bz | CH₂CH₂ | N-cyclopropyl-N-phenylamino |
| 402 | 2-F-Bz | CH₂CH₂ | N-cyclopropyl-N-benzylamino |
| 403 | 2-F-Bz | CH₂CH₂ | N-(4-trifluoromethylcyclohexyl)-methyl-N-methylamino |
| 404 | 2-F-Bz | CH₂CH₂ | 3,4-dihydro-2H-1,4-benzoxazin-4-yl |
| 405 | 2-F-Bz | CH₂CH₂ | cis-octahydrobenzo-[1,4]oxazin-4-yl |
| 406 | 2-F-Bz | CH₂CH₂ | trans-octahydrobenzo[1,4]oxazin-4-yl |
| 407 | 2-F-Bz | CH₂CH₂ | 5,5-difluorooctahydrocyclopenta[c]pyrrol-2-yl |
| 408 | 2-F-Bz | CH₂CH₂ | hexahydrofuro[3,4-c]pyrrol-5-yl |
| 409 | 2-F-Bz | CH₂CH₂ | 2,3-dihydroindol-1-yl |
| 410 | 2-F-Bz | CH₂CH₂ | 2-oxa-7-azaspiro[3.5]nonane-7-yl |
| 411 | 2-F-Bz | CH₂CH₂ | 2,3-dihydro-1H-isoindole-2-yl |
| 412 | 2-F-Bz | CH₂CH₂ | 5-trifluoromethyl-2,3-dihydro-1H-isoindole-2-yl |
| 413 | 2-F-Bz | CH₂CH₂ | 4-trifluoro-2,3-dihydro-1H-isoindole-2-yl |
| 414 | 2-F-Bz | CH₂CH₂ | 2,3-dihydroisoindole-1-one-2-yl |
| 415 | 2-F-Bz | CH₂CH₂ | 1,2,3,4-tetrahydroisoquinoline-2-yl |
| 416 | 2-F-Bz | CH₂CH₂ | 3-azabicyclo[3.2.0]heptane-3-yl |
| 417 | 2-F-Bz | CH₂CH₂ | 6-(4-fluorophenyl)-3-azabicyclo[3.2.0]heptane-3-yl |
| 418 | 2-F-Bz | | azetin-3-yl |
| 419 | 2-F-Bz | | pyrrolidin-3-yl |
| 420 | 2-F-Bz | | 1-methylpyrrolidin-3-yl |
| 421 | 2-F-Bz | | piperidin-3-yl |
| 422 | 2-F-Bz | | 1-methylpiperidin-3-yl |
| 423 | 2-F-Bz | | piperidin-4-yl |
| 424 | 2-F-Bz | | 1-methylpiperidin-4-yl |
| 425 | 2-F-Bz | | 1-ethylpiperidin-4-yl |
| 426 | 2-F-Bz | | 1-propylpiperidin-4-yl |
| 427 | 2-F-Bz | | 1-benzylpiperidin-4-yl |
| 428 | 2-F-Bz | | 1-cyclopropylpiperidin-4-yl |
| 429 | 3-F-Bz | CH₂ | 4-morpholinyl |
| 430 | 3-F-Bz | CH₂ | 4-thiomorpholinyl |
| 431 | 3-F-Bz | CH₂ | 1,1-dioxothiomorpholin-4-yl |
| 432 | 3-F-Bz | CH₂ | 2,6-dimethylmorpholin-4-yl |
| 433 | 3-F-Bz | CH₂ | 2-phenylmorpholin-4-yl |
| 434 | 3-F-Bz | CH₂ | 1-azetidinyl |
| 435 | 3-F-Bz | CH₂ | 1-pyrrolidinyl |
| 436 | 3-F-Bz | CH₂ | 3-phenylpyrrolidin-1-yl |
| 437 | 3-F-Bz | CH₂ | 1-piperidinyl |
| 438 | 3-F-Bz | CH₂ | 1-azepanyl |
| 439 | 3-F-Bz | CH₂ | 4-methylpiperidin-1-yl |
| 440 | 3-F-Bz | CH₂ | 4-phenylpiperidin-1-yl |
| 441 | 3-F-Bz | CH₂ | 4,4-difluoropiperidin-1-yl |
| 442 | 3-F-Bz | CH₂ | 4-(trifluoromethyl)piperidin-1-yl |
| 443 | 3-F-Bz | CH₂ | 4-(tert.-butyl)piperidin-1-yl |
| 444 | 3-F-Bz | CH₂ | 4-methylpiperazin-1-yl |
| 445 | 3-F-Bz | CH₂ | 4-ethylpiperazin-1-yl |
| 446 | 3-F-Bz | CH₂ | 4-propylpiperazin-1-yl |
| 447 | 3-F-Bz | CH₂ | 4-cyclopropylmethylpiperazin-1-yl |
| 448 | 3-F-Bz | CH₂ | 4-cyclopropylpiperazin-1-yl |
| 449 | 3-F-Bz | CH₂ | 4-phenylpiperazin-1-yl |
| 450 | 3-F-Bz | CH₂ | dimethylamino |
| 451 | 3-F-Bz | CH₂ | diethylamino |
| 452 | 3-F-Bz | CH₂ | diisopropylamino |
| 453 | 3-F-Bz | CH₂ | N-phenylamino |
| 454 | 3-F-Bz | CH₂ | N-methyl-N-phenylamino |
| 455 | 3-F-Bz | CH₂ | N-cyclopropyl-N-methylamino |
| 456 | 3-F-Bz | CH₂ | N-cyclohexyl-N-methylamino |
| 457 | 3-F-Bz | CH₂ | N-benzyl-N-methylamino |
| 458 | 3-F-Bz | CH₂ | N-cyclohexylmethyl-N-methylamino |
| 459 | 3-F-Bz | CH₂ | N-methyl-N-isopropylamino |
| 460 | 3-F-Bz | CH₂ | N-cyclopropyl-N-phenylamino |
| 461 | 3-F-Bz | CH₂ | N-cyclopropyl-N-benzylamino |
| 462 | 3-F-Bz | CH₂ | N-(4-trifluoromethylcyclohexyl)-methyl-N-methylamino |
| 463 | 3-F-Bz | CH₂ | 3,4-dihydro-2H-1,4-benzoxazin-4-yl |

TABLE A-continued

| # | R¹ | CH—R^p(CH₂)_z | NR³R⁴ |
|---|---|---|---|
| 464 | 3-F-Bz | CH₂ | cis-octahydrobenzo-[1,4]oxazin-4-yl |
| 465 | 3-F-Bz | CH₂ | trans-octahydrobenzo[1,4]oxazin-4-yl |
| 466 | 3-F-Bz | CH₂ | 5,5-difluoroocta-hydrocyclopenta[c]pyrrol-2-yl |
| 467 | 3-F-Bz | CH₂ | hexahydrofuro[3,4-c]pyrrol-5-yl |
| 468 | 3-F-Bz | CH₂ | 2,3-dihydroindol-1-yl |
| 469 | 3-F-Bz | CH₂ | 2-oxa-7-azaspiro[3.5]nonane-7-yl |
| 470 | 3-F-Bz | CH₂ | 2,3-dihydro-1H-isoindole-2-yl |
| 471 | 3-F-Bz | CH₂ | 5-trifluoromethyl-2,3-dihydro-1H-isoindole-2-yl |
| 472 | 3-F-Bz | CH₂ | 4-trifluoro-2,3-dihydro-1H-isoindole-2-yl |
| 473 | 3-F-Bz | CH₂ | 2,3-dihydroisoindole-1-one-2-yl |
| 474 | 3-F-Bz | CH₂ | 1,2,3,4-tetrahydroisoquinoline-2-yl |
| 475 | 3-F-Bz | CH₂ | 3-azabicyclo[3.2.0]heptane-3-yl |
| 476 | 3-F-Bz | CH₂ | 6-(4-fluorophenyl)-3-azabicyclo[3.2.0]heptane-3-yl |
| 477 | 3-F-Bz | CH₂CH₂ | 4-morpholinyl |
| 478 | 3-F-Bz | CH₂CH₂ | 4-thiomorpholinyl |
| 479 | 3-F-Bz | CH₂CH₂ | 1,1-dioxothiomorpholin-4-yl |
| 480 | 3-F-Bz | CH₂CH₂ | 2,6-dimethylmorpholin-4-yl |
| 481 | 3-F-Bz | CH₂CH₂ | 2-phenylmorpholin-4-yl |
| 482 | 3-F-Bz | CH₂CH₂ | 1-azetidinyl |
| 483 | 3-F-Bz | CH₂CH₂ | 1-pyrrolidinyl |
| 484 | 3-F-Bz | CH₂CH₂ | 3-phenylpyrrolidin-1-yl |
| 485 | 3-F-Bz | CH₂CH₂ | 1-piperidinyl |
| 486 | 3-F-Bz | CH₂CH₂ | 1-azepanyl |
| 487 | 3-F-Bz | CH₂CH₂ | 4-methylpiperidin-1-yl |
| 488 | 3-F-Bz | CH₂CH₂ | 4-phenylpiperidin-1-yl |
| 489 | 3-F-Bz | CH₂CH₂ | 4,4-difluoropiperidin-1-yl |
| 490 | 3-F-Bz | CH₂CH₂ | 4-(trifluoromethyl)piperidin-1-yl |
| 491 | 3-F-Bz | CH₂CH₂ | 4-(tert.-butyl)piperidin-1-yl |
| 492 | 3-F-Bz | CH₂CH₂ | 4-methylpiperazin-1-yl |
| 493 | 3-F-Bz | CH₂CH₂ | 4-ethylpiperazin-1-yl |
| 494 | 3-F-Bz | CH₂CH₂ | 4-propylpiperazin-1-yl |
| 495 | 3-F-Bz | CH₂CH₂ | 4-cyclopropylmethylpiperazin-1-yl |
| 496 | 3-F-Bz | CH₂CH₂ | 4-cyclopropylpiperazin-1-yl |
| 497 | 3-F-Bz | CH₂CH₂ | 4-phenylpiperazin-1-yl |
| 498 | 3-F-Bz | CH₂CH₂ | dimethylamino |
| 499 | 3-F-Bz | CH₂CH₂ | diethylamino |
| 500 | 3-F-Bz | CH₂CH₂ | diisopropylamino |
| 501 | 3-F-Bz | CH₂CH₂ | N-phenylamino |
| 502 | 3-F-Bz | CH₂CH₂ | N-methyl-N-phenylamino |
| 503 | 3-F-Bz | CH₂CH₂ | N-cyclopropyl-N-methylamino |
| 504 | 3-F-Bz | CH₂CH₂ | N-cyclohexyl-N-methylamino |
| 505 | 3-F-Bz | CH₂CH₂ | N-benzyl-N-methylamino |
| 506 | 3-F-Bz | CH₂CH₂ | N-cyclohexylmethyl-N-methylamino |
| 507 | 3-F-Bz | CH₂CH₂ | N-methyl-N-isopropylamino |
| 508 | 3-F-Bz | CH₂CH₂ | N-cyclopropyl-N-phenylamino |
| 509 | 3-F-Bz | CH₂CH₂ | N-cyclopropyl-N-benzylamino |
| 510 | 3-F-Bz | CH₂CH₂ | N-(4-trifluoromethylcyclohexyl)-methyl-N-methylamino |
| 511 | 3-F-Bz | CH₂CH₂ | 3,4-dihydro-2H-1,4-benzoxazin-4-yl |
| 512 | 3-F-Bz | CH₂CH₂ | cis-octahydrobenzo-[1,4]oxazin-4-yl |
| 513 | 3-F-Bz | CH₂CH₂ | trans-octahydrobenzo[1,4]oxazin-4-yl |
| 514 | 3-F-Bz | CH₂CH₂ | 5,5-difluoroocta-hydrocyclopenta[c]pyrrol-2-yl |
| 515 | 3-F-Bz | CH₂CH₂ | hexahydrofuro[3,4-c]pyrrol-5-yl |
| 516 | 3-F-Bz | CH₂CH₂ | 2,3-dihydroindol-1-yl |
| 517 | 3-F-Bz | CH₂CH₂ | 2-oxa-7-azaspiro[3.5]nonane-7-yl |
| 518 | 3-F-Bz | CH₂CH₂ | 2,3-dihydro-1H-isoindole-2-yl |
| 519 | 3-F-Bz | CH₂CH₂ | 5-trifluoromethyl-2,3-dihydro-1H-isoindole-2-yl |
| 520 | 3-F-Bz | CH₂CH₂ | 4-trifluoro-2,3-dihydro-1H-isoindole-2-yl |
| 521 | 3-F-Bz | CH₂CH₂ | 2,3-dihydroisoindole-1-one-2-yl |
| 522 | 3-F-Bz | CH₂CH₂ | 1,2,3,4-tetrahydroisoquinoline-2-yl |
| 523 | 3-F-Bz | CH₂CH₂ | 3-azabicyclo[3.2.0]heptane-3-yl |
| 524 | 3-F-Bz | CH₂CH₂ | 6-(4-fluorophenyl)-3-azabicyclo[3.2.0]heptane-3-yl |
| 525 | 3-F-Bz | | azetin-3-yl |
| 526 | 3-F-Bz | | pyrrolidin-3-yl |
| 527 | 3-F-Bz | | 1-methylpyrrolidin-3-yl |
| 528 | 3-F-Bz | | piperidin-3-yl |
| 529 | 3-F-Bz | | 1-methylpiperidin-3-yl |
| 530 | 3-F-Bz | | piperidin-4-yl |
| 531 | 3-F-Bz | | 1-methylpiperidin-4-yl |
| 532 | 3-F-Bz | | 1-ethylpiperidin-4-yl |
| 533 | 3-F-Bz | | 1-propylpiperidin-4-yl |
| 534 | 3-F-Bz | | 1-benzylpiperidin-4-yl |
| 535 | 3-F-Bz | | 1-cyclopropylpiperidin-4-yl |
| 536 | CH₂—c-Hex | CH₂ | 4-morpholinyl |
| 537 | CH₂—c-Hex | CH₂ | 4-thiomorpholinyl |
| 538 | CH₂—c-Hex | CH₂ | 1,1-dioxothiomorpholin-4-yl |
| 539 | CH₂—c-Hex | CH₂ | 2,6-dimethylmorpholin-4-yl |
| 540 | CH₂—c-Hex | CH₂ | 2-phenylmorpholin-4-yl |
| 541 | CH₂—c-Hex | CH₂ | 1-azetidinyl |
| 542 | CH₂—c-Hex | CH₂ | 1-pyrrolidinyl |
| 543 | CH₂—c-Hex | CH₂ | 3-phenylpyrrolidin-1-yl |
| 544 | CH₂—c-Hex | CH₂ | 1-piperidinyl |
| 545 | CH₂—c-Hex | CH₂ | 1-azepanyl |
| 546 | CH₂—c-Hex | CH₂ | 4-methylpiperidin-1-yl |
| 547 | CH₂—c-Hex | CH₂ | 4-phenylpiperidin-1-yl |
| 548 | CH₂—c-Hex | CH₂ | 4,4-difluoropiperidin-1-yl |
| 549 | CH₂—c-Hex | CH₂ | 4-(trifluoromethyl)piperidin-1-yl |
| 550 | CH₂—c-Hex | CH₂ | 4-(tert.-butyl)piperidin-1-yl |
| 551 | CH₂—c-Hex | CH₂ | 4-methylpiperazin-1-yl |
| 552 | CH₂—c-Hex | CH₂ | 4-ethylpiperazin-1-yl |
| 553 | CH₂—c-Hex | CH₂ | 4-propylpiperazin-1-yl |
| 554 | CH₂—c-Hex | CH₂ | 4-cyclopropylmethylpiperazin-1-yl |
| 555 | CH₂—c-Hex | CH₂ | 4-cyclopropylpiperazin-1-yl |
| 556 | CH₂—c-Hex | CH₂ | 4-phenylpiperazin-1-yl |
| 557 | CH₂—c-Hex | CH₂ | dimethylamino |
| 558 | CH₂—c-Hex | CH₂ | diethylamino |
| 559 | CH₂—c-Hex | CH₂ | diisopropylamino |
| 560 | CH₂—c-Hex | CH₂ | N-phenylamino |
| 561 | CH₂—c-Hex | CH₂ | N-methyl-N-phenylamino |
| 562 | CH₂—c-Hex | CH₂ | N-cyclopropyl-N-methylamino |
| 563 | CH₂—c-Hex | CH₂ | N-cyclohexyl-N-methylamino |
| 564 | CH₂—c-Hex | CH₂ | N-benzyl-N-methylamino |
| 565 | CH₂—c-Hex | CH₂ | N-cyclohexylmethyl-N-methylamino |
| 566 | CH₂—c-Hex | CH₂ | N-methyl-N-isopropylamino |
| 567 | CH₂—c-Hex | CH₂ | N-cyclopropyl-N-phenylamino |
| 568 | CH₂—c-Hex | CH₂ | N-cyclopropyl-N-benzylamino |
| 569 | CH₂—c-Hex | CH₂ | N-(4-trifluoromethylcyclohexyl)-methyl-N-methylamino |
| 570 | CH₂—c-Hex | CH₂ | 3,4-dihydro-2H-1,4-benzoxazin-4-yl |
| 571 | CH₂—c-Hex | CH₂ | cis-octahydrobenzo-[1,4]oxazin-4-yl |
| 572 | CH₂—c-Hex | CH₂ | trans-octahydrobenzo[1,4]oxazin-4-yl |
| 573 | CH₂—c-Hex | CH₂ | 5,5-difluoroocta-hydrocyclopenta[c]pyrrol-2-yl |
| 574 | CH₂—c-Hex | CH₂ | hexahydrofuro[3,4-c]pyrrol-5-yl |
| 575 | CH₂—c-Hex | CH₂ | 2,3-dihydroindol-1-yl |
| 576 | CH₂—c-Hex | CH₂ | 2-oxa-7-azaspiro[3.5]nonane-7-yl |
| 577 | CH₂—c-Hex | CH₂ | 2,3-dihydro-1H-isoindole-2-yl |
| 578 | CH₂—c-Hex | CH₂ | 5-trifluoromethyl-2,3-dihydro-1H-isoindole-2-yl |
| 579 | CH₂—c-Hex | CH₂ | 4-trifluoro-2,3-dihydro-1H-isoindole-2-yl |
| 580 | CH₂—c-Hex | CH₂ | 2,3-dihydroisoindole-1-one-2-yl |
| 581 | CH₂—c-Hex | CH₂ | 1,2,3,4-tetrahydroisoquinoline-2-yl |
| 582 | CH₂—c-Hex | CH₂ | 3-azabicyclo[3.2.0]heptane-3-yl |
| 583 | CH₂—c-Hex | CH₂ | 6-(4-fluorophenyl)-3-azabicyclo[3.2.0]heptane-3-yl |
| 584 | CH₂—c-Hex | CH₂CH₂ | 4-morpholinyl |
| 585 | CH₂—c-Hex | CH₂CH₂ | 4-thiomorpholinyl |
| 586 | CH₂—c-Hex | CH₂CH₂ | 1,1-dioxothiomorpholin-4-yl |
| 587 | CH₂—c-Hex | CH₂CH₂ | 2,6-dimethylmorpholin-4-yl |
| 588 | CH₂—c-Hex | CH₂CH₂ | 2-phenylmorpholin-4-yl |
| 589 | CH₂—c-Hex | CH₂CH₂ | 1-azetidinyl |
| 590 | CH₂—c-Hex | CH₂CH₂ | 1-pyrrolidinyl |
| 591 | CH₂—c-Hex | CH₂CH₂ | 3-phenylpyrrolidin-1-yl |
| 592 | CH₂—c-Hex | CH₂CH₂ | 1-piperidinyl |
| 593 | CH₂—c-Hex | CH₂CH₂ | 1-azepanyl |
| 594 | CH₂—c-Hex | CH₂CH₂ | 4-methylpiperidin-1-yl |
| 595 | CH₂—c-Hex | CH₂CH₂ | 4-phenylpiperidin-1-yl |

TABLE A-continued

| # | R¹ | CH—R$^p$(CH$_2$)$_z$ | NR³R⁴ |
|---|---|---|---|
| 596 | CH$_2$—c-Hex | CH$_2$CH$_2$ | 4,4-difluoropiperidin-1-yl |
| 597 | CH$_2$—c-Hex | CH$_2$CH$_2$ | 4-(trifluoromethyl)piperidin-1-yl |
| 598 | CH$_2$—c-Hex | CH$_2$CH$_2$ | 4-(tert.-butyl)piperidin-1-yl |
| 599 | CH$_2$—c-Hex | CH$_2$CH$_2$ | 4-methylpiperazin-1-yl |
| 600 | CH$_2$—c-Hex | CH$_2$CH$_2$ | 4-ethylpiperazin-1-yl |
| 601 | CH$_2$—c-Hex | CH$_2$CH$_2$ | 4-propylpiperazin-1-yl |
| 602 | CH$_2$—c-Hex | CH$_2$CH$_2$ | 4-cyclopropylmethylpiperazin-1-yl |
| 603 | CH$_2$—c-Hex | CH$_2$CH$_2$ | 4-cyclopropylpiperazin-1-yl |
| 604 | CH$_2$—c-Hex | CH$_2$CH$_2$ | 4-phenylpiperazin-1-yl |
| 605 | CH$_2$—c-Hex | CH$_2$CH$_2$ | dimethylamino |
| 606 | CH$_2$—c-Hex | CH$_2$CH$_2$ | diethylamino |
| 607 | CH$_2$—c-Hex | CH$_2$CH$_2$ | diisopropylamino |
| 608 | CH$_2$—c-Hex | CH$_2$CH$_2$ | N-phenylamino |
| 609 | CH$_2$—c-Hex | CH$_2$CH$_2$ | N-methyl-N-phenylamino |
| 610 | CH$_2$—c-Hex | CH$_2$CH$_2$ | N-cyclopropyl-N-methylamino |
| 611 | CH$_2$—c-Hex | CH$_2$CH$_2$ | N-cyclohexyl-N-methylamino |
| 612 | CH$_2$—c-Hex | CH$_2$CH$_2$ | N-benzyl-N-methylamino |
| 613 | CH$_2$—c-Hex | CH$_2$CH$_2$ | N-cyclohexylmethyl-N-methylamino |
| 614 | CH$_2$—c-Hex | CH$_2$CH$_2$ | N-methyl-N-isopropylamino |
| 615 | CH$_2$—c-Hex | CH$_2$CH$_2$ | N-cyclopropyl-N-phenylamino |
| 616 | CH$_2$—c-Hex | CH$_2$CH$_2$ | N-cyclopropyl-N-benzylamino |
| 617 | CH$_2$—c-Hex | CH$_2$CH$_2$ | N-(4-trifluoromethylcyclohexyl)-methyl-N-methylamino |
| 618 | CH$_2$—c-Hex | CH$_2$CH$_2$ | 3,4-dihydro-2H-1,4-benzoxazin-4-yl |
| 619 | CH$_2$—c-Hex | CH$_2$CH$_2$ | cis-octahydrobenzo-[1,4]oxazin-4-yl |
| 620 | CH$_2$—c-Hex | CH$_2$CH$_2$ | trans-octahydrobenzo[1,4]oxazin-4-yl |
| 621 | CH$_2$—c-Hex | CH$_2$CH$_2$ | 5,5-difluoroocta-hydrocyclopenta[c]pyrrol-2-yl |
| 622 | CH$_2$—c-Hex | CH$_2$CH$_2$ | hexahydrofuro[3,4-c]pyrrol-5-yl |
| 623 | CH$_2$—c-Hex | CH$_2$CH$_2$ | 2,3-dihydroindol-1-yl |
| 624 | CH$_2$—c-Hex | CH$_2$CH$_2$ | 2-oxa-7-azaspiro[3.5]nonane-7-yl |
| 625 | CH$_2$—c-Hex | CH$_2$CH$_2$ | 2,3-dihydro-1H-isoindole-2-yl |
| 626 | CH$_2$—c-Hex | CH$_2$CH$_2$ | 5-trifluoromethyl-2,3-dihydro-1H-isoindole-2-yl |
| 627 | CH$_2$—c-Hex | CH$_2$CH$_2$ | 4-trifluoro-2,3-dihydro-1H-isoindole-2-yl |
| 628 | CH$_2$—c-Hex | CH$_2$CH$_2$ | 2,3-dihydroisoindole-1-one-2-yl |
| 629 | CH$_2$—c-Hex | CH$_2$CH$_2$ | 1,2,3,4-tetrahydroisoquinoline-2-yl |
| 630 | CH$_2$—c-Hex | CH$_2$CH$_2$ | 3-azabicyclo[3.2.0]heptane-3-yl |
| 631 | CH$_2$—c-Hex | CH$_2$CH$_2$ | 6-(4-fluorophenyl)-3-azabicyclo[3.2.0]heptane-3-yl |
| 632 | CH$_2$—c-Hex | | azetin-3-yl |
| 633 | CH$_2$—c-Hex | | pyrrolidin-3-yl |
| 634 | CH$_2$—c-Hex | | 1-methylpyrrolidin-3-yl |
| 635 | CH$_2$—c-Hex | | piperidin-3-yl |
| 636 | CH$_2$—c-Hex | | 1-methylpiperidin-3-yl |
| 637 | CH$_2$—c-Hex | | piperidin-4-yl |
| 638 | CH$_2$—c-Hex | | 1-methylpiperidin-4-yl |
| 639 | CH$_2$—c-Hex | | 1-ethylpiperidin-4-yl |
| 640 | CH$_2$—c-Hex | | 1-propylpiperidin-4-yl |
| 641 | CH$_2$—c-Hex | | 1-benzylpiperidin-4-yl |
| 642 | CH$_2$—c-Hex | | 1-cyclopropylpiperidin-4-yl |
| 643 | (CH$_2$)$_3$CH$_3$ | CH$_2$ | 4-morpholinyl |
| 644 | (CH$_2$)$_3$CH$_3$ | CH$_2$ | 4-thiomorpholinyl |
| 645 | (CH$_2$)$_3$CH$_3$ | CH$_2$ | 1,1-dioxothiomorpholin-4-yl |
| 646 | (CH$_2$)$_3$CH$_3$ | CH$_2$ | 2,6-dimethylmorpholin-4-yl |
| 647 | (CH$_2$)$_3$CH$_3$ | CH$_2$ | 2-phenylmorpholin-4-yl |
| 648 | (CH$_2$)$_3$CH$_3$ | CH$_2$ | 1-azetidinyl |
| 649 | (CH$_2$)$_3$CH$_3$ | CH$_2$ | 1-pyrrolidinyl |
| 650 | (CH$_2$)$_3$CH$_3$ | CH$_2$ | 3-phenylpyrrolidin-1-yl |
| 651 | (CH$_2$)$_3$CH$_3$ | CH$_2$ | 1-piperidinyl |
| 652 | (CH$_2$)$_3$CH$_3$ | CH$_2$ | 1-azepanyl |
| 653 | (CH$_2$)$_3$CH$_3$ | CH$_2$ | 4-methylpiperidin-1-yl |
| 654 | (CH$_2$)$_3$CH$_3$ | CH$_2$ | 4-phenylpiperidin-1-yl |
| 655 | (CH$_2$)$_3$CH$_3$ | CH$_2$ | 4,4-difluoropiperidin-1-yl |
| 656 | (CH$_2$)$_3$CH$_3$ | CH$_2$ | 4-(trifluoromethyl)piperidin-1-yl |
| 657 | (CH$_2$)$_3$CH$_3$ | CH$_2$ | 4-(tert.-butyl)piperidin-1-yl |
| 658 | (CH$_2$)$_3$CH$_3$ | CH$_2$ | 4-methylpiperazin-1-yl |
| 659 | (CH$_2$)$_3$CH$_3$ | CH$_2$ | 4-ethylpiperazin-1-yl |
| 660 | (CH$_2$)$_3$CH$_3$ | CH$_2$ | 4-propylpiperazin-1-yl |
| 661 | (CH$_2$)$_3$CH$_3$ | CH$_2$ | 4-cyclopropylmethylpiperazin-1-yl |
| 662 | (CH$_2$)$_3$CH$_3$ | CH$_2$ | 4-cyclopropylpiperazin-1-yl |
| 663 | (CH$_2$)$_3$CH$_3$ | CH$_2$ | 4-phenylpiperazin-1-yl |
| 664 | (CH$_2$)$_3$CH$_3$ | CH$_2$ | dimethylamino |
| 665 | (CH$_2$)$_3$CH$_3$ | CH$_2$ | diethylamino |
| 666 | (CH$_2$)$_3$CH$_3$ | CH$_2$ | diisopropylamino |
| 667 | (CH$_2$)$_3$CH$_3$ | CH$_2$ | N-phenylamino |
| 668 | (CH$_2$)$_3$CH$_3$ | CH$_2$ | N-methyl-N-phenylamino |
| 669 | (CH$_2$)$_3$CH$_3$ | CH$_2$ | N-cyclopropyl-N-methylamino |
| 670 | (CH$_2$)$_3$CH$_3$ | CH$_2$ | N-cyclohexyl-N-methylamino |
| 671 | (CH$_2$)$_3$CH$_3$ | CH$_2$ | N-benzyl-N-methylamino |
| 672 | (CH$_2$)$_3$CH$_3$ | CH$_2$ | N-cyclohexylmethyl-N-methylamino |
| 673 | (CH$_2$)$_3$CH$_3$ | CH$_2$ | N-methyl-N-isopropylamino |
| 674 | (CH$_2$)$_3$CH$_3$ | CH$_2$ | N-cyclopropyl-N-phenylamino |
| 675 | (CH$_2$)$_3$CH$_3$ | CH$_2$ | N-cyclopropyl-N-benzylamino |
| 676 | (CH$_2$)$_3$CH$_3$ | CH$_2$ | N-(4-trifluoromethylcyclohexyl)-methyl-N-methylamino |
| 677 | (CH$_2$)$_3$CH$_3$ | CH$_2$ | 3,4-dihydro-2H-1,4-benzoxazin-4-yl |
| 678 | (CH$_2$)$_3$CH$_3$ | CH$_2$ | cis-octahydrobenzo-[1,4]oxazin-4-yl |
| 679 | (CH$_2$)$_3$CH$_3$ | CH$_2$ | trans-octahydrobenzo[1,4]oxazin-4-yl |
| 680 | (CH$_2$)$_3$CH$_3$ | CH$_2$ | 5,5-difluoroocta-hydrocyclopenta[c]pyrrol-2-yl |
| 681 | (CH$_2$)$_3$CH$_3$ | CH$_2$ | hexahydrofuro[3,4-c]pyrrol-5-yl |
| 682 | (CH$_2$)$_3$CH$_3$ | CH$_2$ | 2,3-dihydroindol-1-yl |
| 683 | (CH$_2$)$_3$CH$_3$ | CH$_2$ | 2-oxa-7-azaspiro[3.5]nonane-7-yl |
| 684 | (CH$_2$)$_3$CH$_3$ | CH$_2$ | 2,3-dihydro-1H-isoindole-2-yl |
| 685 | (CH$_2$)$_3$CH$_3$ | CH$_2$ | 5-trifluoromethyl-2,3-dihydro-1H-isoindole-2-yl |
| 686 | (CH$_2$)$_3$CH$_3$ | CH$_2$ | 4-trifluoro-2,3-dihydro-1H-isoindole-2-yl |
| 687 | (CH$_2$)$_3$CH$_3$ | CH$_2$ | 2,3-dihydroisoindole-1-one-2-yl |
| 688 | (CH$_2$)$_3$CH$_3$ | CH$_2$ | 1,2,3,4-tetrahydroisoquinoline-2-yl |
| 689 | (CH$_2$)$_3$CH$_3$ | CH$_2$ | 3-azabicyclo[3.2.0]heptane-3-yl |
| 690 | (CH$_2$)$_3$CH$_3$ | CH$_2$ | 6-(4-fluorophenyl)-3-azabicyclo[3.2.0]heptane-3-yl |
| 691 | (CH$_2$)$_3$CH$_3$ | CH$_2$CH$_2$ | 4-morpholinyl |
| 692 | (CH$_2$)$_3$CH$_3$ | CH$_2$CH$_2$ | 4-thiomorpholinyl |
| 693 | (CH$_2$)$_3$CH$_3$ | CH$_2$CH$_2$ | 1,1-dioxothiomorpholin-4-yl |
| 694 | (CH$_2$)$_3$CH$_3$ | CH$_2$CH$_2$ | 2,6-dimethylmorpholin-4-yl |
| 695 | (CH$_2$)$_3$CH$_3$ | CH$_2$CH$_2$ | 2-phenylmorpholin-4-yl |
| 696 | (CH$_2$)$_3$CH$_3$ | CH$_2$CH$_2$ | 1-azetidinyl |
| 697 | (CH$_2$)$_3$CH$_3$ | CH$_2$CH$_2$ | 1-pyrrolidinyl |
| 698 | (CH$_2$)$_3$CH$_3$ | CH$_2$CH$_2$ | 3-phenylpyrrolidin-1-yl |
| 699 | (CH$_2$)$_3$CH$_3$ | CH$_2$CH$_2$ | 1-piperidinyl |
| 700 | (CH$_2$)$_3$CH$_3$ | CH$_2$CH$_2$ | 1-azepanyl |
| 701 | (CH$_2$)$_3$CH$_3$ | CH$_2$CH$_2$ | 4-methylpiperidin-1-yl |
| 702 | (CH$_2$)$_3$CH$_3$ | CH$_2$CH$_2$ | 4-phenylpiperidin-1-yl |
| 703 | (CH$_2$)$_3$CH$_3$ | CH$_2$CH$_2$ | 4,4-difluoropiperidin-1-yl |
| 704 | (CH$_2$)$_3$CH$_3$ | CH$_2$CH$_2$ | 4-(trifluoromethyl)piperidin-1-yl |
| 705 | (CH$_2$)$_3$CH$_3$ | CH$_2$CH$_2$ | 4-(tert.-butyl)piperidin-1-yl |
| 706 | (CH$_2$)$_3$CH$_3$ | CH$_2$CH$_2$ | 4-methylpiperazin-1-yl |
| 707 | (CH$_2$)$_3$CH$_3$ | CH$_2$CH$_2$ | 4-ethylpiperazin-1-yl |
| 708 | (CH$_2$)$_3$CH$_3$ | CH$_2$CH$_2$ | 4-propylpiperazin-1-yl |
| 709 | (CH$_2$)$_3$CH$_3$ | CH$_2$CH$_2$ | 4-cyclopropylmethylpiperazin-1-yl |
| 710 | (CH$_2$)$_3$CH$_3$ | CH$_2$CH$_2$ | 4-cyclopropylpiperazin-1-yl |
| 711 | (CH$_2$)$_3$CH$_3$ | CH$_2$CH$_2$ | 4-phenylpiperazin-1-yl |
| 712 | (CH$_2$)$_3$CH$_3$ | CH$_2$CH$_2$ | dimethylamino |
| 713 | (CH$_2$)$_3$CH$_3$ | CH$_2$CH$_2$ | diethylamino |
| 714 | (CH$_2$)$_3$CH$_3$ | CH$_2$CH$_2$ | diisopropylamino |
| 715 | (CH$_2$)$_3$CH$_3$ | CH$_2$CH$_2$ | N-phenylamino |
| 716 | (CH$_2$)$_3$CH$_3$ | CH$_2$CH$_2$ | N-methyl-N-phenylamino |
| 717 | (CH$_2$)$_3$CH$_3$ | CH$_2$CH$_2$ | N-cyclopropyl-N-methylamino |
| 718 | (CH$_2$)$_3$CH$_3$ | CH$_2$CH$_2$ | N-cyclohexyl-N-methylamino |
| 719 | (CH$_2$)$_3$CH$_3$ | CH$_2$CH$_2$ | N-benzyl-N-methylamino |
| 720 | (CH$_2$)$_3$CH$_3$ | CH$_2$CH$_2$ | N-cyclohexylmethyl-N-methylamino |
| 721 | (CH$_2$)$_3$CH$_3$ | CH$_2$CH$_2$ | N-methyl-N-isopropylamino |
| 722 | (CH$_2$)$_3$CH$_3$ | CH$_2$CH$_2$ | N-cyclopropyl-N-phenylamino |
| 723 | (CH$_2$)$_3$CH$_3$ | CH$_2$CH$_2$ | N-cyclopropyl-N-benzylamino |
| 724 | (CH$_2$)$_3$CH$_3$ | CH$_2$CH$_2$ | N-(4-trifluoromethylcyclohexyl)-methyl-N-methylamino |
| 725 | (CH$_2$)$_3$CH$_3$ | CH$_2$CH$_2$ | 3,4-dihydro-2H-1,4-benzoxazin-4-yl |
| 726 | (CH$_2$)$_3$CH$_3$ | CH$_2$CH$_2$ | cis-octahydrobenzo-[1,4]oxazin-4-yl |
| 727 | (CH$_2$)$_3$CH$_3$ | CH$_2$CH$_2$ | trans-octahydrobenzo[1,4]oxazin-4-yl |

TABLE A-continued

| # | R¹ | CH—R$^p$(CH$_2$)$_z$ | NR³R⁴ |
|---|---|---|---|
| 728 | (CH$_2$)$_3$CH$_3$ | CH$_2$CH$_2$ | 5,5-difluoroocta-hydrocyclopenta[c]pyrrol-2-yl |
| 729 | (CH$_2$)$_3$CH$_3$ | CH$_2$CH$_2$ | hexahydrofuro[3,4-c]pyrrol-5-yl |
| 730 | (CH$_2$)$_3$CH$_3$ | CH$_2$CH$_2$ | 2,3-dihydroindol-1-yl |
| 731 | (CH$_2$)$_3$CH$_3$ | CH$_2$CH$_2$ | 2-oxa-7-azaspiro[3.5]nonane-7-yl |
| 732 | (CH$_2$)$_3$CH$_3$ | CH$_2$CH$_2$ | 2,3-dihydro-1H-isoindole-2-yl |
| 733 | (CH$_2$)$_3$CH$_3$ | CH$_2$CH$_2$ | 5-trifluoromethyl-2,3-dihydro-1H-isoindole-2-yl |
| 734 | (CH$_2$)$_3$CH$_3$ | CH$_2$CH$_2$ | 4-trifluoro-2,3-dihydro-1H-isoindole-2-yl |
| 735 | (CH$_2$)$_3$CH$_3$ | CH$_2$CH$_2$ | 2,3-dihydroisoindole-1-one-2-yl |
| 736 | (CH$_2$)$_3$CH$_3$ | CH$_2$CH$_2$ | 1,2,3,4-tetrahydroisoquinoline-2-yl |
| 737 | (CH$_2$)$_3$CH$_3$ | CH$_2$CH$_2$ | 3-azabicyclo[3.2.0]heptane-3-yl |
| 738 | (CH$_2$)$_3$CH$_3$ | CH$_2$CH$_2$ | 6-(4-fluorophenyl)-3-azabicyclo[3.2.0]heptane-3-yl |
| 739 | (CH$_2$)$_3$CH$_3$ | | azetin-3-yl |
| 740 | (CH$_2$)$_3$CH$_3$ | | pyrrolidin-3-yl |
| 741 | (CH$_2$)$_3$CH$_3$ | | 1-methylpyrrolidin-3-yl |
| 742 | (CH$_2$)$_3$CH$_3$ | | piperidin-3-yl |
| 743 | (CH$_2$)$_3$CH$_3$ | | 1-methylpiperidin-3-yl |
| 744 | (CH$_2$)$_3$CH$_3$ | | piperidin-4-yl |
| 745 | (CH$_2$)$_3$CH$_3$ | | 1-methylpiperidin-4-yl |
| 746 | (CH$_2$)$_3$CH$_3$ | | 1-ethylpiperidin-4-yl |
| 747 | (CH$_2$)$_3$CH$_3$ | | 1-propylpiperidin-4-yl |
| 748 | (CH$_2$)$_3$CH$_3$ | | 1-benzylpiperidin-4-yl |
| 749 | (CH$_2$)$_3$CH$_3$ | | 1-cyclopropylpiperidin-4-yl |

Ph: Phenyl
4-F-Bz: 4-Fluorobenzyl
4-Cl-Bz: 4-Chlorobenzyl
3-F-Bz: 3-Fluorobenzyl
2-F-Bz: 2-Fluorobenzyl
c-Hex: Cyclohexyl

TABLE B

| # | R¹ | A¹ | A² | R⁵ |
|---|---|---|---|---|
| 1 | CH$_2$—Ph | CH$_2$ | CH$_2$ | H |
| 2 | CH$_2$—Ph | CH$_2$ | CH$_2$ | CH$_3$ |
| 3 | CH$_2$—Ph | CH$_2$ | CH$_2$ | CH$_2$CH$_3$ |
| 4 | CH$_2$—Ph | CH$_2$ | CH$_2$ | CH$_2$CH$_2$CH$_3$ |
| 5 | CH$_2$—Ph | CH$_2$ | CH$_2$ | isopropyl |
| 6 | CH$_2$—Ph | CH$_2$ | CH$_2$ | cyclopropyl |
| 7 | CH$_2$—Ph | CH$_2$ | CH$_2$ | CH$_2$-cyclopropyl |
| 8 | CH$_2$—Ph | CH$_2$ | CH$_2$ | acetyl |
| 9 | CH$_2$—Ph | CH$_2$ | CH$_2$ | CO$_2$—t-Bu |
| 10 | CH$_2$—Ph | CH$_2$ | CH$_2$ | CH$_2$—Ph |
| 11 | CH$_2$—Ph | CH$_2$ | CH$_2$CH$_2$ | H |
| 12 | CH$_2$—Ph | CH$_2$ | CH$_2$CH$_2$ | CH$_3$ |
| 13 | CH$_2$—Ph | CH$_2$ | CH$_2$CH$_2$ | CH$_2$CH$_3$ |
| 14 | CH$_2$—Ph | CH$_2$ | CH$_2$CH$_2$ | CH$_2$CH$_2$CH$_3$ |
| 15 | CH$_2$—Ph | CH$_2$ | CH$_2$CH$_2$ | isopropyl |
| 16 | CH$_2$—Ph | CH$_2$ | CH$_2$CH$_2$ | cyclopropyl |
| 17 | CH$_2$—Ph | CH$_2$ | CH$_2$CH$_2$ | CH$_2$-cyclopropyl |
| 18 | CH$_2$—Ph | CH$_2$ | CH$_2$CH$_2$ | acetyl |
| 19 | CH$_2$—Ph | CH$_2$ | CH$_2$CH$_2$ | CO$_2$—t-Bu |
| 20 | CH$_2$—Ph | CH$_2$ | CH$_2$CH$_2$ | CH$_2$—Ph |
| 21 | CH$_2$—Ph | — | CH$_2$CH$_2$CH$_2$ | H |
| 22 | CH$_2$—Ph | — | CH$_2$CH$_2$CH$_2$ | CH$_3$ |
| 23 | CH$_2$—Ph | — | CH$_2$CH$_2$CH$_2$ | CH$_2$CH$_3$ |
| 24 | CH$_2$—Ph | — | CH$_2$CH$_2$CH$_2$ | CH$_2$CH$_2$CH$_3$ |
| 25 | CH$_2$—Ph | — | CH$_2$CH$_2$CH$_2$ | isopropyl |
| 26 | CH$_2$—Ph | — | CH$_2$CH$_2$CH$_2$ | cyclopropyl |
| 27 | CH$_2$—Ph | — | CH$_2$CH$_2$CH$_2$ | CH$_2$-cyclopropyl |
| 28 | CH$_2$—Ph | — | CH$_2$CH$_2$CH$_2$ | acetyl |
| 29 | CH$_2$—Ph | — | CH$_2$CH$_2$CH$_2$ | CO$_2$—t-Bu |
| 30 | CH$_2$—Ph | — | CH$_2$CH$_2$CH$_2$ | CH$_2$—Ph |
| 31 | CH$_2$—Ph | CH$_2$CH$_2$ | CH$_2$CH$_2$ | H |
| 32 | CH$_2$—Ph | CH$_2$CH$_2$ | CH$_2$CH$_2$ | CH$_3$ |
| 33 | CH$_2$—Ph | CH$_2$CH$_2$ | CH$_2$CH$_2$ | CH$_2$CH$_3$ |
| 34 | CH$_2$—Ph | CH$_2$CH$_2$ | CH$_2$CH$_2$ | CH$_2$CH$_2$CH$_3$ |
| 35 | CH$_2$—Ph | CH$_2$CH$_2$ | CH$_2$CH$_2$ | isopropyl |
| 36 | CH$_2$—Ph | CH$_2$CH$_2$ | CH$_2$CH$_2$ | cyclopropyl |
| 37 | CH$_2$—Ph | CH$_2$CH$_2$ | CH$_2$CH$_2$ | CH$_2$-cyclopropyl |
| 38 | CH$_2$—Ph | CH$_2$CH$_2$ | CH$_2$CH$_2$ | acetyl |
| 39 | CH$_2$—Ph | CH$_2$CH$_2$ | CH$_2$CH$_2$ | CO$_2$—t-Bu |
| 40 | CH$_2$—Ph | CH$_2$CH$_2$ | CH$_2$CH$_2$ | CH$_2$—Ph |
| 41 | CH$_2$—Ph | CH$_2$CH$_2$ | CH$_2$ | H |
| 42 | CH$_2$—Ph | CH$_2$CH$_2$ | CH$_2$ | CH$_3$ |
| 43 | CH$_2$—Ph | CH$_2$CH$_2$ | CH$_2$ | CH$_2$CH$_3$ |
| 44 | CH$_2$—Ph | CH$_2$CH$_2$ | CH$_2$ | CH$_2$CH$_2$CH$_3$ |
| 45 | CH$_2$—Ph | CH$_2$CH$_2$ | CH$_2$ | isopropyl |
| 46 | CH$_2$—Ph | CH$_2$CH$_2$ | CH$_2$ | cyclopropyl |
| 47 | CH$_2$—Ph | CH$_2$CH$_2$ | CH$_2$ | CH$_2$-cyclopropyl |
| 48 | CH$_2$—Ph | CH$_2$CH$_2$ | CH$_2$ | acetyl |
| 49 | CH$_2$—Ph | CH$_2$CH$_2$ | CH$_2$ | CO$_2$—t-Bu |
| 50 | CH$_2$—Ph | CH$_2$CH$_2$ | CH$_2$ | CH$_2$—Ph |
| 51 | CH$_2$—Ph | CH$_2$CH$_2$CH$_2$ | — | H |
| 52 | CH$_2$—Ph | CH$_2$CH$_2$CH$_2$ | — | CH$_3$ |
| 53 | CH$_2$—Ph | CH$_2$CH$_2$CH$_2$ | — | CH$_2$CH$_3$ |
| 54 | CH$_2$—Ph | CH$_2$CH$_2$CH$_2$ | — | CH$_2$CH$_2$CH$_3$ |
| 55 | CH$_2$—Ph | CH$_2$CH$_2$CH$_2$ | — | isopropyl |
| 56 | CH$_2$—Ph | CH$_2$CH$_2$CH$_2$ | — | cyclopropyl |
| 57 | CH$_2$—Ph | CH$_2$CH$_2$CH$_2$ | — | CH$_2$-cyclopropyl |
| 58 | CH$_2$—Ph | CH$_2$CH$_2$CH$_2$ | — | acetyl |
| 59 | CH$_2$—Ph | CH$_2$CH$_2$CH$_2$ | — | CO$_2$—t-Bu |
| 60 | CH$_2$—Ph | CH$_2$CH$_2$CH$_2$ | — | CH$_2$—Ph |
| 61 | 4-Cl-Bz | CH$_2$ | CH$_2$ | H |
| 62 | 4-Cl-Bz | CH$_2$ | CH$_2$ | CH$_3$ |
| 63 | 4-Cl-Bz | CH$_2$ | CH$_2$ | CH$_2$CH$_3$ |
| 64 | 4-Cl-Bz | CH$_2$ | CH$_2$ | CH$_2$CH$_2$CH$_3$ |
| 65 | 4-Cl-Bz | CH$_2$ | CH$_2$ | isopropyl |
| 66 | 4-Cl-Bz | CH$_2$ | CH$_2$ | cyclopropyl |
| 67 | 4-Cl-Bz | CH$_2$ | CH$_2$ | CH$_2$-cyclopropyl |
| 68 | 4-Cl-Bz | CH$_2$ | CH$_2$ | acetyl |
| 69 | 4-Cl-Bz | CH$_2$ | CH$_2$ | CO$_2$—t-Bu |
| 70 | 4-Cl-Bz | CH$_2$ | CH$_2$ | CH$_2$—Ph |
| 71 | 4-Cl-Bz | CH$_2$ | CH$_2$CH$_2$ | H |
| 72 | 4-Cl-Bz | CH$_2$ | CH$_2$CH$_2$ | CH$_3$ |
| 73 | 4-Cl-Bz | CH$_2$ | CH$_2$CH$_2$ | CH$_2$CH$_3$ |
| 74 | 4-Cl-Bz | CH$_2$ | CH$_2$CH$_2$ | CH$_2$CH$_2$CH$_3$ |
| 75 | 4-Cl-Bz | CH$_2$ | CH$_2$CH$_2$ | isopropyl |
| 76 | 4-Cl-Bz | CH$_2$ | CH$_2$CH$_2$ | cyclopropyl |
| 77 | 4-Cl-Bz | CH$_2$ | CH$_2$CH$_2$ | CH$_2$-cyclopropyl |
| 78 | 4-Cl-Bz | CH$_2$ | CH$_2$CH$_2$ | acetyl |
| 79 | 4-Cl-Bz | CH$_2$ | CH$_2$CH$_2$ | CO$_2$—t-Bu |
| 80 | 4-Cl-Bz | CH$_2$ | CH$_2$CH$_2$ | CH$_2$—Ph |
| 81 | 4-Cl-Bz | — | CH$_2$CH$_2$CH$_2$ | H |
| 82 | 4-Cl-Bz | — | CH$_2$CH$_2$CH$_2$ | CH$_3$ |
| 83 | 4-Cl-Bz | — | CH$_2$CH$_2$CH$_2$ | CH$_2$CH$_3$ |
| 84 | 4-Cl-Bz | — | CH$_2$CH$_2$CH$_2$ | CH$_2$CH$_2$CH$_3$ |
| 85 | 4-Cl-Bz | — | CH$_2$CH$_2$CH$_2$ | isopropyl |
| 86 | 4-Cl-Bz | — | CH$_2$CH$_2$CH$_2$ | cyclopropyl |
| 87 | 4-Cl-Bz | — | CH$_2$CH$_2$CH$_2$ | CH$_2$-cyclopropyl |
| 88 | 4-Cl-Bz | — | CH$_2$CH$_2$CH$_2$ | acetyl |
| 89 | 4-Cl-Bz | — | CH$_2$CH$_2$CH$_2$ | CO$_2$—t-Bu |
| 90 | 4-Cl-Bz | — | CH$_2$CH$_2$CH$_2$ | CH$_2$—Ph |
| 91 | 4-Cl-Bz | CH$_2$CH$_2$ | CH$_2$CH$_2$ | H |
| 92 | 4-Cl-Bz | CH$_2$CH$_2$ | CH$_2$CH$_2$ | CH$_3$ |
| 93 | 4-Cl-Bz | CH$_2$CH$_2$ | CH$_2$CH$_2$ | CH$_2$CH$_3$ |
| 94 | 4-Cl-Bz | CH$_2$CH$_2$ | CH$_2$CH$_2$ | CH$_2$CH$_2$CH$_3$ |
| 95 | 4-Cl-Bz | CH$_2$CH$_2$ | CH$_2$CH$_2$ | isopropyl |
| 96 | 4-Cl-Bz | CH$_2$CH$_2$ | CH$_2$CH$_2$ | cyclopropyl |
| 97 | 4-Cl-Bz | CH$_2$CH$_2$ | CH$_2$CH$_2$ | CH$_2$-cyclopropyl |
| 98 | 4-Cl-Bz | CH$_2$CH$_2$ | CH$_2$CH$_2$ | acetyl |
| 99 | 4-Cl-Bz | CH$_2$CH$_2$ | CH$_2$CH$_2$ | CO$_2$—t-Bu |
| 100 | 4-Cl-Bz | CH$_2$CH$_2$ | CH$_2$CH$_2$ | CH$_2$—Ph |
| 101 | 4-Cl-Bz | CH$_2$CH$_2$ | CH$_2$ | H |
| 102 | 4-Cl-Bz | CH$_2$CH$_2$ | CH$_2$ | CH$_3$ |
| 103 | 4-Cl-Bz | CH$_2$CH$_2$ | CH$_2$ | CH$_2$CH$_3$ |
| 104 | 4-Cl-Bz | CH$_2$CH$_2$ | CH$_2$ | CH$_2$CH$_2$CH$_3$ |
| 105 | 4-Cl-Bz | CH$_2$CH$_2$ | CH$_2$ | isopropyl |
| 106 | 4-Cl-Bz | CH$_2$CH$_2$ | CH$_2$ | cyclopropyl |
| 107 | 4-Cl-Bz | CH$_2$CH$_2$ | CH$_2$ | CH$_2$-cyclopropyl |
| 108 | 4-Cl-Bz | CH$_2$CH$_2$ | CH$_2$ | acetyl |
| 109 | 4-Cl-Bz | CH$_2$CH$_2$ | CH$_2$ | CO$_2$—t-Bu |
| 110 | 4-Cl-Bz | CH$_2$CH$_2$ | CH$_2$ | CH$_2$—Ph |
| 111 | 4-Cl-Bz | CH$_2$CH$_2$CH$_2$ | — | H |
| 112 | 4-Cl-Bz | CH$_2$CH$_2$CH$_2$ | — | CH$_3$ |
| 113 | 4-Cl-Bz | CH$_2$CH$_2$CH$_2$ | — | CH$_2$CH$_3$ |
| 114 | 4-Cl-Bz | CH$_2$CH$_2$CH$_2$ | — | CH$_2$CH$_2$CH$_3$ |
| 115 | 4-Cl-Bz | CH$_2$CH$_2$CH$_2$ | — | isopropyl |
| 116 | 4-Cl-Bz | CH$_2$CH$_2$CH$_2$ | — | cyclopropyl |
| 117 | 4-Cl-Bz | CH$_2$CH$_2$CH$_2$ | — | CH$_2$-cyclopropyl |
| 118 | 4-Cl-Bz | CH$_2$CH$_2$CH$_2$ | — | acetyl |

TABLE B-continued

| # | R¹ | A¹ | A² | R⁵ |
|---|---|---|---|---|
| 119 | 4-Cl-Bz | CH₂CH₂CH₂ | — | CO₂—t-Bu |
| 120 | 4-Cl-Bz | CH₂CH₂CH₂ | — | CH₂—Ph |
| 121 | 4-F-Bz | CH₂ | CH₂ | H |
| 122 | 4-F-Bz | CH₂ | CH₂ | CH₃ |
| 123 | 4-F-Bz | CH₂ | CH₂ | CH₂CH₃ |
| 124 | 4-F-Bz | CH₂ | CH₂ | CH₂CH₂CH₃ |
| 125 | 4-F-Bz | CH₂ | CH₂ | isopropyl |
| 126 | 4-F-Bz | CH₂ | CH₂ | cyclopropyl |
| 127 | 4-F-Bz | CH₂ | CH₂ | CH₂-cyclopropyl |
| 128 | 4-F-Bz | CH₂ | CH₂ | acetyl |
| 129 | 4-F-Bz | CH₂ | CH₂ | CO₂—t-Bu |
| 130 | 4-F-Bz | CH₂ | CH₂ | CH₂—Ph |
| 131 | 4-F-Bz | CH₂ | CH₂CH₂ | H |
| 132 | 4-F-Bz | CH₂ | CH₂CH₂ | CH₃ |
| 133 | 4-F-Bz | CH₂ | CH₂CH₂ | CH₂CH₃ |
| 134 | 4-F-Bz | CH₂ | CH₂CH₂ | CH₂CH₂CH₃ |
| 135 | 4-F-Bz | CH₂ | CH₂CH₂ | isopropyl |
| 136 | 4-F-Bz | CH₂ | CH₂CH₂ | cyclopropyl |
| 137 | 4-F-Bz | CH₂ | CH₂CH₂ | CH₂-cyclopropyl |
| 138 | 4-F-Bz | CH₂ | CH₂CH₂ | acetyl |
| 139 | 4-F-Bz | CH₂ | CH₂CH₂ | CO₂—t-Bu |
| 140 | 4-F-Bz | CH₂ | CH₂CH₂ | CH₂—Ph |
| 141 | 4-F-Bz | — | CH₂CH₂CH₂ | H |
| 142 | 4-F-Bz | — | CH₂CH₂CH₂ | CH₃ |
| 143 | 4-F-Bz | — | CH₂CH₂CH₂ | CH₂CH₃ |
| 144 | 4-F-Bz | — | CH₂CH₂CH₂ | CH₂CH₂CH₃ |
| 145 | 4-F-Bz | — | CH₂CH₂CH₂ | isopropyl |
| 146 | 4-F-Bz | — | CH₂CH₂CH₂ | cyclopropyl |
| 147 | 4-F-Bz | — | CH₂CH₂CH₂ | CH₂-cyclopropyl |
| 148 | 4-F-Bz | — | CH₂CH₂CH₂ | acetyl |
| 149 | 4-F-Bz | — | CH₂CH₂CH₂ | CO₂—t-Bu |
| 150 | 4-F-Bz | — | CH₂CH₂CH₂ | CH₂—Ph |
| 151 | 4-F-Bz | CH₂CH₂ | CH₂CH₂ | H |
| 152 | 4-F-Bz | CH₂CH₂ | CH₂CH₂ | CH₃ |
| 153 | 4-F-Bz | CH₂CH₂ | CH₂CH₂ | CH₂CH₃ |
| 154 | 4-F-Bz | CH₂CH₂ | CH₂CH₂ | CH₂CH₂CH₃ |
| 155 | 4-F-Bz | CH₂CH₂ | CH₂CH₂ | isopropyl |
| 156 | 4-F-Bz | CH₂CH₂ | CH₂CH₂ | cyclopropyl |
| 157 | 4-F-Bz | CH₂CH₂ | CH₂CH₂ | CH₂-cyclopropyl |
| 158 | 4-F-Bz | CH₂CH₂ | CH₂CH₂ | acetyl |
| 159 | 4-F-Bz | CH₂CH₂ | CH₂CH₂ | CO₂—t-Bu |
| 160 | 4-F-Bz | CH₂CH₂ | CH₂CH₂ | CH₂—Ph |
| 161 | 4-F-Bz | CH₂CH₂ | CH₂ | H |
| 162 | 4-F-Bz | CH₂CH₂ | CH₂ | CH₃ |
| 163 | 4-F-Bz | CH₂CH₂ | CH₂ | CH₂CH₃ |
| 164 | 4-F-Bz | CH₂CH₂ | CH₂ | CH₂CH₂CH₃ |
| 165 | 4-F-Bz | CH₂CH₂ | CH₂ | isopropyl |
| 166 | 4-F-Bz | CH₂CH₂ | CH₂ | cyclopropyl |
| 167 | 4-F-Bz | CH₂CH₂ | CH₂ | CH₂-cyclopropyl |
| 168 | 4-F-Bz | CH₂CH₂ | CH₂ | acetyl |
| 169 | 4-F-Bz | CH₂CH₂ | CH₂ | CO₂—t-Bu |
| 170 | 4-F-Bz | CH₂CH₂ | CH₂ | CH₂—Ph |
| 171 | 4-F-Bz | CH₂CH₂CH₂ | — | H |
| 172 | 4-F-Bz | CH₂CH₂CH₂ | — | CH₃ |
| 173 | 4-F-Bz | CH₂CH₂CH₂ | — | CH₂CH₃ |
| 174 | 4-F-Bz | CH₂CH₂CH₂ | — | CH₂CH₂CH₃ |
| 175 | 4-F-Bz | CH₂CH₂CH₂ | — | isopropyl |
| 176 | 4-F-Bz | CH₂CH₂CH₂ | — | cyclopropyl |
| 177 | 4-F-Bz | CH₂CH₂CH₂ | — | CH₂-cyclopropyl |
| 178 | 4-F-Bz | CH₂CH₂CH₂ | — | acetyl |
| 179 | 4-F-Bz | CH₂CH₂CH₂ | — | CO₂—t-Bu |
| 180 | 4-F-Bz | CH₂CH₂CH₂ | — | CH₂—Ph |
| 181 | 2-F-Bz | CH₂ | CH₂ | H |
| 182 | 2-F-Bz | CH₂ | CH₂ | CH₃ |
| 183 | 2-F-Bz | CH₂ | CH₂ | CH₂CH₃ |
| 184 | 2-F-Bz | CH₂ | CH₂ | CH₂CH₂CH₃ |
| 185 | 2-F-Bz | CH₂ | CH₂ | isopropyl |
| 186 | 2-F-Bz | CH₂ | CH₂ | cyclopropyl |
| 187 | 2-F-Bz | CH₂ | CH₂ | CH₂-cyclopropyl |
| 188 | 2-F-Bz | CH₂ | CH₂ | acetyl |
| 189 | 2-F-Bz | CH₂ | CH₂ | CO₂—t-Bu |
| 190 | 2-F-Bz | CH₂ | CH₂ | CH₂—Ph |
| 191 | 2-F-Bz | CH₂ | CH₂CH₂ | H |
| 192 | 2-F-Bz | CH₂ | CH₂CH₂ | CH₃ |
| 193 | 2-F-Bz | CH₂ | CH₂CH₂ | CH₂CH₃ |
| 194 | 2-F-Bz | CH₂ | CH₂CH₂ | CH₂CH₂CH₃ |
| 195 | 2-F-Bz | CH₂ | CH₂CH₂ | isopropyl |
| 196 | 2-F-Bz | CH₂ | CH₂CH₂ | cyclopropyl |
| 197 | 2-F-Bz | CH₂ | CH₂CH₂ | CH₂-cyclopropyl |
| 198 | 2-F-Bz | CH₂ | CH₂CH₂ | acetyl |
| 199 | 2-F-Bz | CH₂ | CH₂CH₂ | CO₂—t-Bu |
| 200 | 2-F-Bz | CH₂ | CH₂CH₂ | CH₂—Ph |
| 201 | 2-F-Bz | — | CH₂CH₂CH₂ | H |
| 202 | 2-F-Bz | — | CH₂CH₂CH₂ | CH₃ |
| 203 | 2-F-Bz | — | CH₂CH₂CH₂ | CH₂CH₃ |
| 204 | 2-F-Bz | — | CH₂CH₂CH₂ | CH₂CH₂CH₃ |
| 205 | 2-F-Bz | — | CH₂CH₂CH₂ | isopropyl |
| 206 | 2-F-Bz | — | CH₂CH₂CH₂ | cyclopropyl |
| 207 | 2-F-Bz | — | CH₂CH₂CH₂ | CH₂-cyclopropyl |
| 208 | 2-F-Bz | — | CH₂CH₂CH₂ | acetyl |
| 209 | 2-F-Bz | — | CH₂CH₂CH₂ | CO₂—t-Bu |
| 210 | 2-F-Bz | — | CH₂CH₂CH₂ | CH₂—Ph |
| 211 | 2-F-Bz | CH₂CH₂ | CH₂CH₂ | H |
| 212 | 2-F-Bz | CH₂CH₂ | CH₂CH₂ | CH₃ |
| 213 | 2-F-Bz | CH₂CH₂ | CH₂CH₂ | CH₂CH₃ |
| 214 | 2-F-Bz | CH₂CH₂ | CH₂CH₂ | CH₂CH₂CH₃ |
| 215 | 2-F-Bz | CH₂CH₂ | CH₂CH₂ | isopropyl |
| 216 | 2-F-Bz | CH₂CH₂ | CH₂CH₂ | cyclopropyl |
| 217 | 2-F-Bz | CH₂CH₂ | CH₂CH₂ | CH₂-cyclopropyl |
| 218 | 2-F-Bz | CH₂CH₂ | CH₂CH₂ | acetyl |
| 219 | 2-F-Bz | CH₂CH₂ | CH₂CH₂ | CO₂—t-Bu |
| 220 | 2-F-Bz | CH₂CH₂ | CH₂CH₂ | CH₂—Ph |
| 221 | 2-F-Bz | CH₂CH₂ | CH₂ | H |
| 222 | 2-F-Bz | CH₂CH₂ | CH₂ | CH₃ |
| 223 | 2-F-Bz | CH₂CH₂ | CH₂ | CH₂CH₃ |
| 224 | 2-F-Bz | CH₂CH₂ | CH₂ | CH₂CH₂CH₃ |
| 225 | 2-F-Bz | CH₂CH₂ | CH₂ | isopropyl |
| 226 | 2-F-Bz | CH₂CH₂ | CH₂ | cyclopropyl |
| 227 | 2-F-Bz | CH₂CH₂ | CH₂ | CH₂-cyclopropyl |
| 228 | 2-F-Bz | CH₂CH₂ | CH₂ | acetyl |
| 229 | 2-F-Bz | CH₂CH₂ | CH₂ | CO₂—t-Bu |
| 230 | 2-F-Bz | CH₂CH₂ | CH₂ | CH₂—Ph |
| 231 | 2-F-Bz | CH₂CH₂CH₂ | — | H |
| 232 | 2-F-Bz | CH₂CH₂CH₂ | — | CH₃ |
| 233 | 2-F-Bz | CH₂CH₂CH₂ | — | CH₂CH₃ |
| 234 | 2-F-Bz | CH₂CH₂CH₂ | — | CH₂CH₂CH₃ |
| 235 | 2-F-Bz | CH₂CH₂CH₂ | — | isopropyl |
| 236 | 2-F-Bz | CH₂CH₂CH₂ | — | cyclopropyl |
| 237 | 2-F-Bz | CH₂CH₂CH₂ | — | CH₂-cyclopropyl |
| 238 | 2-F-Bz | CH₂CH₂CH₂ | — | acetyl |
| 239 | 2-F-Bz | CH₂CH₂CH₂ | — | CO₂—t-Bu |
| 240 | 2-F-Bz | CH₂CH₂CH₂ | — | CH₂—Ph |
| 241 | 3-F-Bz | CH₂ | CH₂ | H |
| 242 | 3-F-Bz | CH₂ | CH₂ | CH₃ |
| 243 | 3-F-Bz | CH₂ | CH₂ | CH₂CH₃ |
| 244 | 3-F-Bz | CH₂ | CH₂ | CH₂CH₂CH₃ |
| 245 | 3-F-Bz | CH₂ | CH₂ | isopropyl |
| 246 | 3-F-Bz | CH₂ | CH₂ | cyclopropyl |
| 247 | 3-F-Bz | CH₂ | CH₂ | CH₂-cyclopropyl |
| 248 | 3-F-Bz | CH₂ | CH₂ | acetyl |
| 249 | 3-F-Bz | CH₂ | CH₂ | CO₂—t-Bu |
| 250 | 3-F-Bz | CH₂ | CH₂ | CH₂—Ph |
| 251 | 3-F-Bz | CH₂ | CH₂CH₂ | H |
| 252 | 3-F-Bz | CH₂ | CH₂CH₂ | CH₃ |
| 253 | 3-F-Bz | CH₂ | CH₂CH₂ | CH₂CH₃ |
| 254 | 3-F-Bz | CH₂ | CH₂CH₂ | CH₂CH₂CH₃ |
| 255 | 3-F-Bz | CH₂ | CH₂CH₂ | isopropyl |
| 256 | 3-F-Bz | CH₂ | CH₂CH₂ | cyclopropyl |
| 257 | 3-F-Bz | CH₂ | CH₂CH₂ | CH₂-cyclopropyl |
| 258 | 3-F-Bz | CH₂ | CH₂CH₂ | acetyl |
| 259 | 3-F-Bz | CH₂ | CH₂CH₂ | CO₂—t-Bu |
| 260 | 3-F-Bz | CH₂ | CH₂CH₂ | CH₂—Ph |
| 261 | 3-F-Bz | — | CH₂CH₂CH₂ | H |
| 262 | 3-F-Bz | — | CH₂CH₂CH₂ | CH₃ |
| 263 | 3-F-Bz | — | CH₂CH₂CH₂ | CH₂CH₃ |
| 264 | 3-F-Bz | — | CH₂CH₂CH₂ | CH₂CH₂CH₃ |
| 265 | 3-F-Bz | — | CH₂CH₂CH₂ | isopropyl |
| 266 | 3-F-Bz | — | CH₂CH₂CH₂ | cyclopropyl |
| 267 | 3-F-Bz | — | CH₂CH₂CH₂ | CH₂-cyclopropyl |
| 268 | 3-F-Bz | — | CH₂CH₂CH₂ | acetyl |
| 269 | 3-F-Bz | — | CH₂CH₂CH₂ | CO₂—t-Bu |
| 270 | 3-F-Bz | — | CH₂CH₂CH₂ | CH₂—Ph |
| 271 | 3-F-Bz | CH₂CH₂ | CH₂CH₂ | H |
| 272 | 3-F-Bz | CH₂CH₂ | CH₂CH₂ | CH₃ |
| 273 | 3-F-Bz | CH₂CH₂ | CH₂CH₂ | CH₂CH₃ |
| 274 | 3-F-Bz | CH₂CH₂ | CH₂CH₂ | CH₂CH₂CH₃ |

TABLE B-continued

| # | R¹ | A¹ | A² | R⁵ |
|---|---|---|---|---|
| 275 | 3-F-Bz | CH₂CH₂ | CH₂CH₂ | isopropyl |
| 276 | 3-F-Bz | CH₂CH₂ | CH₂CH₂ | cyclopropyl |
| 277 | 3-F-Bz | CH₂CH₂ | CH₂CH₂ | CH₂-cyclopropyl |
| 278 | 3-F-Bz | CH₂CH₂ | CH₂CH₂ | acetyl |
| 279 | 3-F-Bz | CH₂CH₂ | CH₂CH₂ | CO₂—t-Bu |
| 280 | 3-F-Bz | CH₂CH₂ | CH₂CH₂ | CH₂—Ph |
| 281 | 3-F-Bz | CH₂CH₂ | CH₂ | H |
| 282 | 3-F-Bz | CH₂CH₂ | CH₂ | CH₃ |
| 283 | 3-F-Bz | CH₂CH₂ | CH₂ | CH₂CH₃ |
| 284 | 3-F-Bz | CH₂CH₂ | CH₂ | CH₂CH₂CH₃ |
| 285 | 3-F-Bz | CH₂CH₂ | CH₂ | isopropyl |
| 286 | 3-F-Bz | CH₂CH₂ | CH₂ | cyclopropyl |
| 287 | 3-F-Bz | CH₂CH₂ | CH₂ | CH₂-cyclopropyl |
| 288 | 3-F-Bz | CH₂CH₂ | CH₂ | acetyl |
| 289 | 3-F-Bz | CH₂CH₂ | CH₂ | CO₂—t-Bu |
| 290 | 3-F-Bz | CH₂CH₂ | CH₂ | CH₂—Ph |
| 291 | 3-F-Bz | CH₂CH₂CH₂ | — | H |
| 292 | 3-F-Bz | CH₂CH₂CH₂ | — | CH₃ |
| 293 | 3-F-Bz | CH₂CH₂CH₂ | — | CH₂CH₃ |
| 294 | 3-F-Bz | CH₂CH₂CH₂ | — | CH₂CH₂CH₃ |
| 295 | 3-F-Bz | CH₂CH₂CH₂ | — | isopropyl |
| 296 | 3-F-Bz | CH₂CH₂CH₂ | — | cyclopropyl |
| 297 | 3-F-Bz | CH₂CH₂CH₂ | — | CH₂-cyclopropyl |
| 298 | 3-F-Bz | CH₂CH₂CH₂ | — | acetyl |
| 299 | 3-F-Bz | CH₂CH₂CH₂ | — | CO₂—t-Bu |
| 300 | 3-F-Bz | CH₂CH₂CH₂ | — | CH₂—Ph |
| 301 | CH₂—c-Hex | CH₂ | CH₂ | H |
| 302 | CH₂—c-Hex | CH₂ | CH₂ | CH₃ |
| 303 | CH₂—c-Hex | CH₂ | CH₂ | CH₂CH₃ |
| 304 | CH₂—c-Hex | CH₂ | CH₂ | CH₂CH₂CH₃ |
| 305 | CH₂—c-Hex | CH₂ | CH₂ | isopropyl |
| 306 | CH₂—c-Hex | CH₂ | CH₂ | cyclopropyl |
| 307 | CH₂—c-Hex | CH₂ | CH₂ | CH₂-cyclopropyl |
| 308 | CH₂—c-Hex | CH₂ | CH₂ | acetyl |
| 309 | CH₂—c-Hex | CH₂ | CH₂ | CO₂—t-Bu |
| 310 | CH₂—c-Hex | CH₂ | CH₂ | CH₂—Ph |
| 311 | CH₂—c-Hex | CH₂ | CH₂CH₂ | H |
| 312 | CH₂—c-Hex | CH₂ | CH₂CH₂ | CH₃ |
| 313 | CH₂—c-Hex | CH₂ | CH₂CH₂ | CH₂CH₃ |
| 314 | CH₂—c-Hex | CH₂ | CH₂CH₂ | CH₂CH₂CH₃ |
| 315 | CH₂—c-Hex | CH₂ | CH₂CH₂ | isopropyl |
| 316 | CH₂—c-Hex | CH₂ | CH₂CH₂ | cyclopropyl |
| 317 | CH₂—c-Hex | CH₂ | CH₂CH₂ | CH₂-cyclopropyl |
| 318 | CH₂—c-Hex | CH₂ | CH₂CH₂ | acetyl |
| 319 | CH₂—c-Hex | CH₂ | CH₂CH₂ | CO₂—t-Bu |
| 320 | CH₂—c-Hex | CH₂ | CH₂CH₂ | CH₂—Ph |
| 321 | CH₂—c-Hex | — | CH₂CH₂CH₂ | H |
| 322 | CH₂—c-Hex | — | CH₂CH₂CH₂ | CH₃ |
| 323 | CH₂—c-Hex | — | CH₂CH₂CH₂ | CH₂CH₃ |
| 324 | CH₂—c-Hex | — | CH₂CH₂CH₂ | CH₂CH₂CH₃ |
| 325 | CH₂—c-Hex | — | CH₂CH₂CH₂ | isopropyl |
| 326 | CH₂—c-Hex | — | CH₂CH₂CH₂ | cyclopropyl |
| 327 | CH₂—c-Hex | — | CH₂CH₂CH₂ | CH₂-cyclopropyl |
| 328 | CH₂—c-Hex | — | CH₂CH₂CH₂ | acetyl |
| 329 | CH₂—c-Hex | — | CH₂CH₂CH₂ | CO₂—t-Bu |
| 330 | CH₂—c-Hex | — | CH₂CH₂CH₂ | CH₂—Ph |
| 331 | CH₂—c-Hex | CH₂CH₂ | CH₂CH₂ | H |
| 332 | CH₂—c-Hex | CH₂CH₂ | CH₂CH₂ | CH₃ |
| 333 | CH₂—c-Hex | CH₂CH₂ | CH₂CH₂ | CH₂CH₃ |
| 334 | CH₂—c-Hex | CH₂CH₂ | CH₂CH₂ | CH₂CH₂CH₃ |
| 335 | CH₂—c-Hex | CH₂CH₂ | CH₂CH₂ | isopropyl |
| 336 | CH₂—c-Hex | CH₂CH₂ | CH₂CH₂ | cyclopropyl |
| 337 | CH₂—c-Hex | CH₂CH₂ | CH₂CH₂ | CH₂-cyclopropyl |
| 338 | CH₂—c-Hex | CH₂CH₂ | CH₂CH₂ | acetyl |
| 339 | CH₂—c-Hex | CH₂CH₂ | CH₂CH₂ | CO₂—t-Bu |
| 340 | CH₂—c-Hex | CH₂CH₂ | CH₂CH₂ | CH₂—Ph |
| 341 | CH₂—c-Hex | CH₂CH₂ | CH₂ | H |
| 342 | CH₂—c-Hex | CH₂CH₂ | CH₂ | CH₃ |
| 343 | CH₂—c-Hex | CH₂CH₂ | CH₂ | CH₂CH₃ |
| 344 | CH₂—c-Hex | CH₂CH₂ | CH₂ | CH₂CH₂CH₃ |
| 345 | CH₂—c-Hex | CH₂CH₂ | CH₂ | isopropyl |
| 346 | CH₂—c-Hex | CH₂CH₂ | CH₂ | cyclopropyl |
| 347 | CH₂—c-Hex | CH₂CH₂ | CH₂ | CH₂-cyclopropyl |
| 348 | CH₂—c-Hex | CH₂CH₂ | CH₂ | acetyl |
| 349 | CH₂—c-Hex | CH₂CH₂ | CH₂ | CO₂—t-Bu |
| 350 | CH₂—c-Hex | CH₂CH₂ | CH₂ | CH₂—Ph |
| 351 | CH₂—c-Hex | CH₂CH₂CH₂ | — | H |
| 352 | CH₂—c-Hex | CH₂CH₂CH₂ | — | CH₃ |
| 353 | CH₂—c-Hex | CH₂CH₂CH₂ | — | CH₂CH₃ |
| 354 | CH₂—c-Hex | CH₂CH₂CH₂ | — | CH₂CH₂CH₃ |
| 355 | CH₂—c-Hex | CH₂CH₂CH₂ | — | isopropyl |
| 356 | CH₂—c-Hex | CH₂CH₂CH₂ | — | cyclopropyl |
| 357 | CH₂—c-Hex | CH₂CH₂CH₂ | — | CH₂-cyclopropyl |
| 358 | CH₂—c-Hex | CH₂CH₂CH₂ | — | acetyl |
| 359 | CH₂—c-Hex | CH₂CH₂CH₂ | — | CO₂—t-Bu |
| 360 | CH₂—c-Hex | CH₂CH₂CH₂ | — | CH₂—Ph |
| 361 | (CH₂)₃CH₃ | CH₂ | CH₂ | H |
| 362 | (CH₂)₃CH₃ | CH₂ | CH₂ | CH₃ |
| 363 | (CH₂)₃CH₃ | CH₂ | CH₂ | CH₂CH₃ |
| 364 | (CH₂)₃CH₃ | CH₂ | CH₂ | CH₂CH₂CH₃ |
| 365 | (CH₂)₃CH₃ | CH₂ | CH₂ | isopropyl |
| 366 | (CH₂)₃CH₃ | CH₂ | CH₂ | cyclopropyl |
| 367 | (CH₂)₃CH₃ | CH₂ | CH₂ | CH₂-cyclopropyl |
| 368 | (CH₂)₃CH₃ | CH₂ | CH₂ | acetyl |
| 369 | (CH₂)₃CH₃ | CH₂ | CH₂ | CO₂—t-Bu |
| 370 | (CH₂)₃CH₃ | CH₂ | CH₂ | CH₂—Ph |
| 371 | (CH₂)₃CH₃ | CH₂ | CH₂CH₂ | H |
| 372 | (CH₂)₃CH₃ | CH₂ | CH₂CH₂ | CH₃ |
| 373 | (CH₂)₃CH₃ | CH₂ | CH₂CH₂ | CH₂CH₃ |
| 374 | (CH₂)₃CH₃ | CH₂ | CH₂CH₂ | CH₂CH₂CH₃ |
| 375 | (CH₂)₃CH₃ | CH₂ | CH₂CH₂ | isopropyl |
| 376 | (CH₂)₃CH₃ | CH₂ | CH₂CH₂ | cyclopropyl |
| 377 | (CH₂)₃CH₃ | CH₂ | CH₂CH₂ | CH₂-cyclopropyl |
| 378 | (CH₂)₃CH₃ | CH₂ | CH₂CH₂ | acetyl |
| 379 | (CH₂)₃CH₃ | CH₂ | CH₂CH₂ | CO₂—t-Bu |
| 380 | (CH₂)₃CH₃ | CH₂ | CH₂CH₂ | CH₂—Ph |
| 381 | (CH₂)₃CH₃ | — | CH₂CH₂CH₂ | H |
| 382 | (CH₂)₃CH₃ | — | CH₂CH₂CH₂ | CH₃ |
| 383 | (CH₂)₃CH₃ | — | CH₂CH₂CH₂ | CH₂CH₃ |
| 384 | (CH₂)₃CH₃ | — | CH₂CH₂CH₂ | CH₂CH₂CH₃ |
| 385 | (CH₂)₃CH₃ | — | CH₂CH₂CH₂ | isopropyl |
| 386 | (CH₂)₃CH₃ | — | CH₂CH₂CH₂ | cyclopropyl |
| 387 | (CH₂)₃CH₃ | — | CH₂CH₂CH₂ | CH₂-cyclopropyl |
| 388 | (CH₂)₃CH₃ | — | CH₂CH₂CH₂ | acetyl |
| 389 | (CH₂)₃CH₃ | — | CH₂CH₂CH₂ | CO₂—t-Bu |
| 390 | (CH₂)₃CH₃ | — | CH₂CH₂CH₂ | CH₂—Ph |
| 391 | (CH₂)₃CH₃ | CH₂CH₂ | CH₂CH₂ | H |
| 392 | (CH₂)₃CH₃ | CH₂CH₂ | CH₂CH₂ | CH₃ |
| 393 | (CH₂)₃CH₃ | CH₂CH₂ | CH₂CH₂ | CH₂CH₃ |
| 394 | (CH₂)₃CH₃ | CH₂CH₂ | CH₂CH₂ | CH₂CH₂CH₃ |
| 395 | (CH₂)₃CH₃ | CH₂CH₂ | CH₂CH₂ | isopropyl |
| 396 | (CH₂)₃CH₃ | CH₂CH₂ | CH₂CH₂ | cyclopropyl |
| 397 | (CH₂)₃CH₃ | CH₂CH₂ | CH₂CH₂ | CH₂-cyclopropyl |
| 398 | (CH₂)₃CH₃ | CH₂CH₂ | CH₂CH₂ | acetyl |
| 399 | (CH₂)₃CH₃ | CH₂CH₂ | CH₂CH₂ | CO₂—t-Bu |
| 400 | (CH₂)₃CH₃ | CH₂CH₂ | CH₂CH₂ | CH₂—Ph |
| 401 | (CH₂)₃CH₃ | CH₂CH₂ | CH₂ | H |
| 402 | (CH₂)₃CH₃ | CH₂CH₂ | CH₂ | CH₃ |
| 403 | (CH₂)₃CH₃ | CH₂CH₂ | CH₂ | CH₂CH₃ |
| 404 | (CH₂)₃CH₃ | CH₂CH₂ | CH₂ | CH₂CH₂CH₃ |
| 405 | (CH₂)₃CH₃ | CH₂CH₂ | CH₂ | isopropyl |
| 406 | (CH₂)₃CH₃ | CH₂CH₂ | CH₂ | cyclopropyl |
| 407 | (CH₂)₃CH₃ | CH₂CH₂ | CH₂ | CH₂-cyclopropyl |
| 408 | (CH₂)₃CH₃ | CH₂CH₂ | CH₂ | acetyl |
| 409 | (CH₂)₃CH₃ | CH₂CH₂ | CH₂ | CO₂—t-Bu |
| 410 | (CH₂)₃CH₃ | CH₂CH₂ | CH₂ | CH₂—Ph |
| 411 | (CH₂)₃CH₃ | CH₂CH₂CH₂ | — | H |
| 412 | (CH₂)₃CH₃ | CH₂CH₂CH₂ | — | CH₃ |
| 413 | (CH₂)₃CH₃ | CH₂CH₂CH₂ | — | CH₂CH₃ |
| 414 | (CH₂)₃CH₃ | CH₂CH₂CH₂ | — | CH₂CH₂CH₃ |
| 415 | (CH₂)₃CH₃ | CH₂CH₂CH₂ | — | isopropyl |
| 416 | (CH₂)₃CH₃ | CH₂CH₂CH₂ | — | cyclopropyl |
| 417 | (CH₂)₃CH₃ | CH₂CH₂CH₂ | — | CH₂-cyclopropyl |
| 418 | (CH₂)₃CH₃ | CH₂CH₂CH₂ | — | acetyl |
| 419 | (CH₂)₃CH₃ | CH₂CH₂CH₂ | — | CO₂—t-Bu |
| 420 | (CH₂)₃CH₃ | CH₂CH₂CH₂ | — | CH₂—Ph |

—: single bond
Ph: Phenyl
t-Bu: tert. Butyl
4-F-Bz: 4-Fluorobenzyl
4-Cl-Bz: 4-Chlorobenzyl
3-F-Bz: 3-Fluorobenzyl
2-F-Bz: 2-Fluorobenzyl
c-Hex: Cyclohexyl The invention in particular relates to the compounds of formula I which are selected from the group consisting of:

N-(4-amino-3,4-dioxo-1-phenylbutan-2-yl)-2-(3-(morpholinomethyl)-1H-pyrazol-1-yl)nicotinamide;
N-(4-amino-3,4-dioxo-1-phenylbutan-2-yl)-2-(3-((2,6-dimethylmorpholino)methyl)-1H-pyrazol-1-yl)nicotinamide;
N-(4-amino-3,4-dioxo-1-phenylbutan-2-yl)-2-(3-((cis-2,6-dimethylmorpholino)methyl)-1H-pyrazol-1-yl)nicotinamide;
N-(4-amino-3,4-dioxo-1-phenylbutan-2-yl)-2-(3-((trans-2,6-dimethylmorpholino)-methyl)-1H-pyrazol-1-yl)nicotinamide;
N-(4-amino-3,4-dioxo-1-phenylbutan-2-yl)-2-(3-((4,4-difluoropiperidin-1-yl)methyl)-1H-pyrazol-1-yl)nicotinamide;
N-(4-amino-3,4-dioxo-1-phenylbutan-2-yl)-2-(5-benzyl-4,5,6,7-tetrahydro-2H-pyrazolo[4,3-c]pyridin-2-yl)nicotinamide;
N-(4-amino-3,4-dioxo-1-phenylbutan-2-yl)-2-(3-((4-phenylpiperidin-1-yl)methyl)-1H-pyrazol-1-yl)nicotinamide;
2-(3-((2H-benzo[b][1,4]oxazin-4(3H)-yl)methyl)-1H-pyrazol-1-yl)-N-(4-amino-3,4-dioxo-1-phenylbutan-2-yl)nicotinamide;
N-(4-amino-3,4-dioxo-1-phenylbutan-2-yl)-2-(3-(piperidin-1-ylmethyl)-1H-pyrazol-1-yl)nicotinamide;
2-(3-((2H-benzo[b][1,4]oxazin-4(3H,4aH,5H,6H,7H,8H,8aH)-yl)methyl)-1H-pyrazol-1-yl)-N-(4-amino-3,4-dioxo-1-phenylbutan-2-yl)nicotinamide;
2-(3-((2H-benzo[b][1,4]oxazin-4(3H,4aHS,5H,6H,7H,8H,8aHS)-yl)methyl)-1H-pyrazol-1-yl)-N-(4-amino-3,4-dioxo-1-phenylbutan-2-yl)nicotinamide;
2-(3-((2H-benzo[b][1,4]oxazin-4(3H,4aHS,5H,6H,7H,8H,8aHR)-yl)methyl)-1H-pyrazol-1-yl)-N-(4-amino-3,4-dioxo-1-phenylbutan-2-yl)nicotinamide;
N-(4-amino-3,4-dioxo-1-phenylbutan-2-yl)-2-(3-((2-phenylmorpholino)methyl)-1H-pyrazol-1-yl)nicotinamide;
N-(4-amino-3,4-dioxo-1-phenylbutan-2-yl)-2-(3-(pyrrolidin-1-ylmethyl)-1H-pyrazol-1-yl)nicotinamide;
N-(4-amino-3,4-dioxo-1-phenylbutan-2-yl)-2-(3-(azetidin-1-ylmethyl)-1H-pyrazol-1-yl)nicotinamide;
N-(4-amino-3,4-dioxo-1-phenylbutan-2-yl)-2-(3-((4-(trifluoromethyl)piperidin-1-yl)methyl)-1H-pyrazol-1-yl)nicotinamide;
N-(4-amino-3,4-dioxo-1-phenyl-2-butanyl)-2-{3-[(5,5-difluorohexahydrocyclopenta[c]pyrrol-2(1H)-yl)methyl]-1H-pyrazol-1-yl}nicotinamide;
N-(4-amino-3,4-dioxo-1-phenylbutan-2-yl)-2-(3-((dihydro-1H-furo[3,4-c]pyrrol-5(3H,6H,6aH)-yl)methyl)-1H-pyrazol-1-yl)nicotinamide;
N-(4-amino-3,4-dioxo-1-phenylbutan-2-yl)-2-(3-(indolin-1-ylmethyl)-1H-pyrazol-1-yl)nicotinamide;
N-(4-amino-3,4-dioxo-1-phenylbutan-2-yl)-2-(3-((methyl(phenyl)amino)methyl)-1H-pyrazol-1-yl)nicotinamide;
N-(4-amino-3,4-dioxo-1-phenyl-2-butanyl)-2-[3-(2-oxa-7-azaspiro[3.5]non-7-ylmethyl)-1H-pyrazol-1-yl]nicotinamide;
N-(4-amino-3,4-dioxo-1-phenyl-2-butanyl)-2-{3-[(diethylamino)methyl]-1H-pyrazol-1-yl}nicotinamide;
N-(4-amino-3,4-dioxo-1-phenylbutan-2-yl)-2-(3-(isoindolin-2-ylmethyl)-1H-pyrazol-1-yl)nicotinamide;
N-(4-amino-3,4-dioxo-1-phenyl-2-butanyl)-2-(3-{[cyclohexyl(methyl)amino]methyl}-1H-pyrazol-1-yl)nicotinamide;
N-(4-amino-3,4-dioxo-1-phenyl-2-butanyl)-2-(3-{[benzyl(methyl)amino]methyl}-1H-pyrazol-1-yl)nicotinamide;
N-(4-amino-3,4-dioxo-1-phenyl-2-butanyl)-2-[3-(3,4-dihydro-2(1H)-isoquinolinylmethyl)-1H-pyrazol-1-yl]nicotinamide;
N-(4-amino-3,4-dioxo-1-phenylbutan-2-yl)-2-(3-((4-tert-butylpiperidin-1-yl)methyl)-1H-pyrazol-1-yl)nicotinamide;
N-(4-amino-3,4-dioxo-1-phenylbutan-2-yl)-2-(3-((4-methylpiperidin-1-yl)methyl)-1H-pyrazol-1-yl)nicotinamide;
N-(4-amino-3,4-dioxo-1-phenylbutan-2-yl)-2-(3-((methyl((4-(trifluoromethyl)cyclohexyl)methyl)amino)methyl)-1H-pyrazol-1-yl)nicotinamide;
N-(4-amino-3,4-dioxo-1-phenylbutan-2-yl)-2-(3-((cyclopropyl(methyl)amino)methyl)-1H-pyrazol-1-yl)nicotinamide;
N-(4-amino-3,4-dioxo-1-phenyl-2-butanyl)-2-(3-{[(6R)-6-(4-fluorophenyl)-3-azabicyclo[3.2.0]hept-3-yl]methyl}-1H-pyrazol-1-yl)nicotinamide;
N-(4-amino-3,4-dioxo-1-phenylbutan-2-yl)-2-(3-((phenylamino)methyl)-1H-pyrazol-1-yl)nicotinamide;
N-(4-amino-3,4-dioxo-1-phenyl-2-butanyl)-2-{3-[(3-phenyl-1-pyrrolidinyl)methyl]-1H-pyrazol-1-yl}nicotinamide;
N-(4-amino-3,4-dioxo-1-phenyl-2-butanyl)-2-(3-{[5-(trifluoromethyl)-1,3-dihydro-2H-isoindol-2-yl]methyl}-1H-pyrazol-1-yl)nicotinamide;
N-(4-amino-3,4-dioxo-1-phenyl-2-butanyl)-2-{3-[(5-fluoro-1,3-dihydro-2H-isoindol-2-yl)methyl]-1H-pyrazol-1-yl}nicotinamide;
N-(4-amino-3,4-dioxo-1-phenyl-2-butanyl)-2-{3-[(4-phenyl-1-piperazinyl)methyl]-1H-pyrazol-1-yl}nicotinamide;
N-(4-amino-3,4-dioxo-1-phenyl-2-butanyl)-2-{3-[(4-fluoro-1,3-dihydro-2H-isoindol-2-yl)methyl]-1H-pyrazol-1-yl}nicotinamide;
N-(4-amino-3,4-dioxo-1-phenyl-2-butanyl)-2-{3-[(1,1-dioxido-4-thiomorpholinyl)methyl]-1H-pyrazol-1-yl}nicotinamide;
N-(4-amino-3,4-dioxo-1-phenyl-2-butanyl)-2-{3-[1-(1,3-dihydro-2Hisoindol-2-yl)ethyl]-1H-pyrazol-1-yl}nicotinamide;
N-(4-amino-3,4-dioxo-1-phenyl-2-butanyl)-2-{3-[(1-oxo-1,3-dihydro-2H-isoindol-2-yl)methyl]-1H-pyrazol-1-yl}nicotinamide;
N-(1-amino-1,2-dioxo-3-heptanyl)-2-[3-(1-piperidinylmethyl)-1Hpyrazol-1-yl]nicotinamide;
N-(1-amino-1,2-dioxo-3-heptanyl)-2-{3-[(4,4-difluoro-1-piperidinyl)methyl]-1H-pyrazol-1-yl}nicotinamide;
N-(1-amino-1,2-dioxo-3-heptanyl)-2-[3-(1,3-dihydro-2H-isoindol-2-ylmethyl)-1H-pyrazol-1-yl]nicotinamide;
N-(4-amino-3,4-dioxo-1-phenyl-2-butanyl)-2-(5-benzyl-4,5,6,7-tetrahydro-2H-pyrazolo[4,3-c]pyridin-2-yl)nicotinamide;
N-(4-amino-3,4-dioxo-1-phenyl-2-butanyl)-2-[5-(cyclopropylmethyl)-4,5,6,7-tetrahydro-2H-pyrazolo[4,3-c]pyridin-2-yl]nicotinamide;
N-(4-amino-3,4-dioxo-1-phenyl-2-butanyl)-2-(4,5,6,7-tetrahydro-2Hpyrazolo[4,3-c]pyridin-2-yl)nicotinamide;
tert-butyl 2-(3-(4-amino-3,4-dioxo-1-phenylbutan-2-ylcarbamoyl)pyridin-2-yl)-4,6-dihydropyrrolo[3,4-c]pyrazole-5(2H)-carboxylate;
N-(4-amino-3,4-dioxo-1-phenyl-2-butanyl)-2-(5,6-dihydropyrrolo[3,4-c]pyrazol-2(4H)-yl)nicotinamide;
tert-butyl 2-(3-(4-amino-3,4-dioxo-1-phenylbutan-2-ylcarbamoyl)pyridin-2-yl)-2,4,5,7-tetrahydro-6H-pyrazolo[3,4-c]pyridine-6-carboxylate;
N-(4-amino-3,4-dioxo-1-phenyl-2-butanyl)-2-(4,5,6,7-tetrahydro-pyrazolo[3,4-c]pyridin-2-yl)nicotinamide;
tert-butyl 2-(3-(4-amino-3,4-dioxo-1-phenylbutan-2-ylcarbamoyl)pyridin-2-yl)-2,5,6,7-tetrahydro-4H-pyrazolo[4,3-b]pyridine-4-carboxylate;
N-(4-amino-3,4-dioxo-1-phenyl-2-butanyl)-2-(4,5,6,7-tetrahydro-pyrazolo[4,3-b]pyridin-2-yl)nicotinamide;

N-(4-amino-3,4-dioxo-1-phenyl-2-butanyl)-2-(4-benzyl-4, 5,6,7-tetrahydro-2H-pyrazolo[4,3-b]pyridin-2-yl)nicotinamide;

N-(4-amino-3,4-dioxo-1-phenyl-2-butanyl)-2-[3-(1-methyl-4-piperidinyl)-1H-pyrazol-1-yl]nicotinamide;

N-(4-amino-3,4-dioxo-1-phenyl-2-butanyl)-2-(6-ethyl-4,5, 6,7-tetrahydro-2H-pyrazolo[3,4-c]pyridin-2-yl)nicotinamide;

the tautomers thereof, the hydrates thereof, the prodrugs thereof and the pharmaceutically suitable salts thereof.

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", $5^{th}$ edition, Wiley & Sons and the literature cited therein, and R. Larock, "Comprehensive Organic Transformations", $2^{nd}$ edition, Weinheim, 1999 and the literature cited therein. The carboxamide compounds of the invention of the general formula I are advantageously prepared by the methods described below and/or in the experimental section.

The compounds of the formula I can be prepared in analogy to the schemes and methods described in WO 99/54305, pp. 6-10 and in WO 2008/080969, pp. 65-70. An important access to compounds of the formula I is depicted in scheme 1.

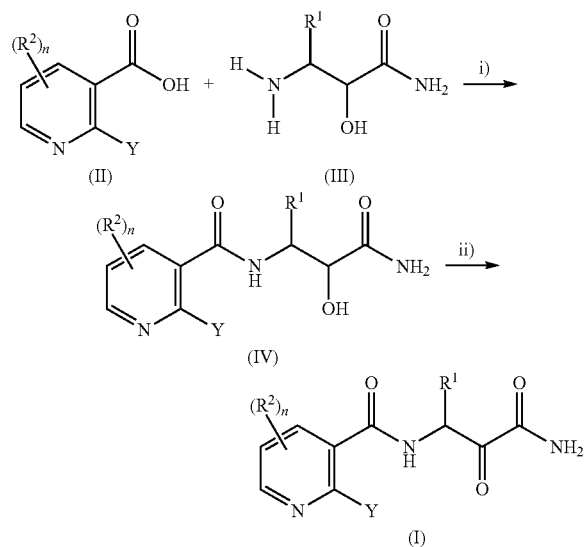

In scheme 1, $R^1$, $R^2$, Y and n exhibit the aforementioned meanings.

In a first step i), a carboxylic acid II is converted by reaction with an amino hydroxy amide III into a corresponding hydroxy diamide IV. In this connection, conventional peptide coupling methods are ordinarily used, as are described for example in R. C. Larock, Comprehensive Organic Transformations, VCH Publisher, 1989, pages 972-976, or in Houben-Weyl, Methoden der organischen Chemie, $4^{th}$ edition, E5, Chap. V. It may be advantageous firstly to activate the carboxylic acid II. For this purpose, for example, the carboxylic acid II is reacted with a coupling agent, e.g. a carbodiimide such as dicyclohexylcarbodiimide (DCC), CDI (carbonyldiimidazole), carbonyldipyrazole, DCI (diisopropylcarbodiimide) or 1-ethyl-3-(3-dimethylaminopropyl)carbodiimide (EDC), preferably in the presence of hydroxybenzotriazole (HOBt), nitrophenol, pentafluorophenol, 2,4,5-trichlorophenol or N-hydroxysuccinimide, to obtain an activated ester IIa. It may further be advantageous to prepare the activated ester IIa in the presence of a base, for example a tertiary amine. Further suitable coupling agents for step I are those mentioned for step iii) in Scheme 3 below, such as benzotriazole derivatives, pyridinotriazole derivatives and phosphonium activators. The activated ester IIa is subsequently reacted with the amino hydroxy amide of the formula III or its hydrohalide salt to give the hydroxy diamide IV. The reaction normally takes place in anhydrous inert solvents such as chlorinated hydrocarbons, e.g. dichloromethane or dichloroethane, ethers, e.g. tetrahydrofuran or 1,4-dioxane, or carboxamides, e.g. N,N-dimethylformamide, N,N-dimethylacetamide or N-methylpyrrolidone. Step i) is ordinarily carried out at temperatures in the range from −20° C. to +25° C.

Subsequently, in a second step ii), the hydroxy diamide compound IV is oxidized to the carboxamide compound I' of the invention. Various conventional oxidation reactions are suitable for this (see R. C. Larock, Comprehensive Organic Transformations, VCH Publisher, 1989, page 604 et seq.) such as, for example, Swern oxidation and Swern analogous oxidations (T. T. Tidwell, Synthesis 1990, pp. 857-870) or Pfitzner-Moffatt oxidation. Suitable oxidizing agents are dimethyl sulfoxide (DMSO) in combination with dicyclohexylcarbodiimide or 1-ethyl-3-(3-dimethylaminopropyl) carbodiimide, dimethyl sulfoxide in combination with the pyridine-$SO_3$ complex or dimethyl sulfoxide in combination with oxalyl chloride, sodium hypochloride/TEMPO (S. L. Harbenson et al., J. Med. Chem. 1994, 37, 2918-2929) or hypervalent iodine compounds (periodinane), such as 2-iodoxybenzoic acid (IBX) (J. Org. Chem. 1995, 60, 7272) or the Dess-Martin periodinane (J. Org. Chem. 1983, 48, 4155). Depending on the oxidizing agent used, the oxidation of the hydroxy amide compound IV takes place at temperatures of from −50 to +35° C.

The amino hydroxy amides III can be obtained by purchase or can be prepared by processes disclosed in the literature, e.g. the compounds III are accessible via the synthesis described in S. L. Harbenson et al., J. Med. Chem. 1994, 37, 2918-2929 or J. P. Burkhardt et al., Tetrahedron Lett. 1988, 29, 3433-3436.

The 3-(S)-diastereomers III' of the propanamide derivatives III which are deuterated in the 3-position, can be synthesized starting from alkinol X in analogy to a 9-step process described by F. Maltais et al., J. Med. Chem. 2009, 52 (24), 7993-8001 (DOI 10.1021/jm901023f), as shown below. According to this process chiral resolution of the intermediately obtained racemic mixture is achieved via amidation with deoxycholic acid. By employing compounds III' in the respective synthetic routes of scheme 1, compounds I which are S-configurated at the carbon atom carrying the radical $R^1$ are accessible.

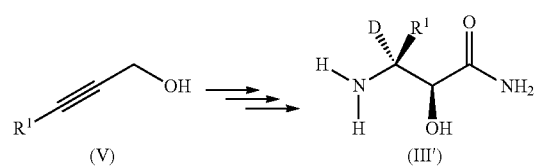

The carboxylic acid II can be prepared by hydrolyzing the corresponding carboxylic ester VI with acids or bases under generally customary conditions (see scheme 2). The hydrolysis preferably takes place with bases such as alkali metal or alkaline earth metal hydroxides, for example lithium hydroxide, sodium hydroxide or potassium hydroxide in aqueous medium, such as a mixture of water and organic solvents, e.g. alcohols such as methanol or ethanol, ethers such as tetrahydrofuran or dioxane, at room temperature or elevated temperature such as 25-100° C.

Scheme 2:

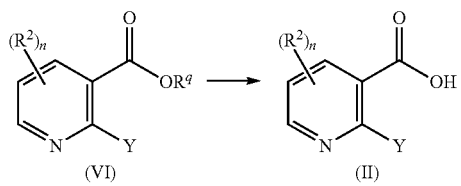

In formulae II and VI, $R^2$, Y and n have the aforementioned meanings. In formula VI, $R^q$ is alkyl, preferably $C_1$-$C_6$-alkyl.

The carboxylic ester of the formula VI can advantageously be obtained by reacting the carboxylic ester of the general formula VII with a Y-H, see scheme 3.

Scheme 3:

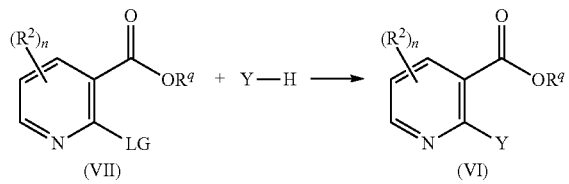

In scheme 3, LG represents a nucleophilically displaceable leaving group. Examples of suitable nucleophilically displaceable leaving groups are halogen, e.g. chlorine or bromine, or sulfonates like mesylate or tosylate. $R^q$ is alkyl, preferably $C_1$-$C_6$-alkyl. $R^2$, Y and n have the aforementioned meanings.

As shown in scheme 3, an ester VII is reacted with an appropriate pyrazole compound of the formula Y-H, where Y is as defined above and where Y is in particular a radical Y2, where the hydrogen atom of Y-H is located on the pyrazole nitrogen. The reaction is ordinarily carried out under conventional conditions in the presence of a base in an inert solvent at elevated temperature. It may be advantageous, where appropriate, to carry out the reaction in the presence of catalytically active amounts of a transition metal, in particular of a metal of group 10 or 11 in the periodic table.

The reaction is preferably carried out at elevated temperature without diluent or in an inert solvent such as an ether, e.g. tetrahydrofuran or dioxane, carboxamides such as N,N-dimethylformamide, N,N-dimethylacetamide or N-methylpyrrolidone, or an aromatic hydrocarbon such as benzene, toluene or o-, m- or p-xylene. The reaction takes place in the presence of inorganic or organic bases and of a crown ether. Suitable inorganic bases are alkali metal or alkaline earth metal amides such as sodium amide, alkali metal or alkaline earth metal carbonates such as potassium carbonate or cesium carbonate or alkali metal hydrides such as sodium hydride. Suitable organic bases are tertiary amines, such as, for example, trimethylamine or triethylamine. A suitable crown ether is 18-crown-6. A Cu(I) salt such as, for example, CuI, CuCN, $Cu_2O$ is added, where appropriate, as catalyst (see, for example, U.S. Pat. No. 4,826,835 and WO 88/00468).

The nicotinic acid ester derivatives VII and the pyrazole compounds can be purchased or can be prepared by conventional methods.

The nicotinic acid ester derivatives VI, where Y is a radical Y-1, may also be prepared from nicotinic acid ester derivatives of the formula VIII or IX (see schemes 4a and 4b):

Scheme 5a:

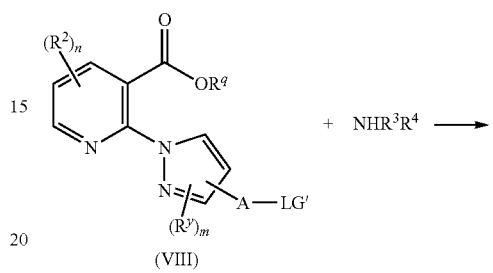

+ $NHR^3R^4$ ⟶

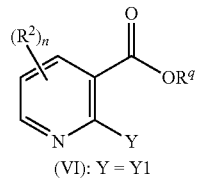

Scheme 5b:

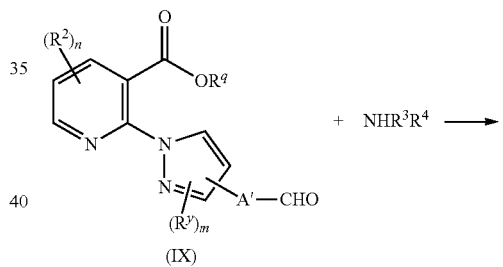

+ $NHR^3R^4$ ⟶

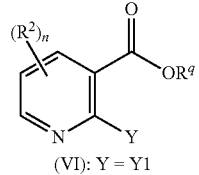

In Schemes 5a and 5b, A, $R^2$, $R^3$, $R^4$, $R^q$, $R^y$, m and n are as defined above. A' is $(CH_2)_{p-1}$ with p being 1, 2, 3 or 4, where one or two hydrogen atoms may be replaced by a radical $R^6$, where A is attached to the 3- or 4-position of the pyrazole radical and where $R^6$ is as defined above and in particular hydrogen. LG' is represents a nucleophilically displaceable leaving group. Examples of suitable nucleophilically displaceable leaving groups are halogen, e.g. chlorine or bromine, or sulfonates like mesylate or tosylate.

The reaction depicted in scheme 5a can be performed by conventional nucleophilic substitution reactions as described e.g. in R. Larock, "Comprehensive Organic Transformations", $2^{nd}$ edition, Weinheim, 1999, pp. 397-400.

The reaction depicted in scheme 5b can be performed by conventional reductive amination reactions as described e.g. in R. Larock, "Comprehensive Organic Transformations", $2^{nd}$ edition, Weinheim, 1999, pp. 421-425.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

If individual compounds I are not obtainable by the routes described above, they can be prepared by derivatization of other compounds I.

The compounds of the invention exhibit extremely low Ki values in relation to the inhibition of calpain and thus permit efficient inhibition of calpain, especially calpain I, at low serum levels. The compounds of the invention ordinarily exhibit Ki values in relation to the inhibition of calpain in vitro of <1500 nM, preferably <800 nM, in particular <400 nM and specifically ≤250 nM. The compounds of the invention are therefore particularly suitable for the treatment of disorders associated with an elevated calpain activity.

In addition, the compounds of the invention are selective calpain inhibitors, i.e. the inhibition of other cysteine proteases such as cathepsin B, cathepsin K, cathepsin L or cathepsin S takes place only at concentrations which are distinctly higher than the concentrations necessary for inhibition of calpain. Accordingly, the compounds of the invention ought to show distinctly fewer side effects than the prior art compounds which are comparatively unselective in relation to inhibition of calpain and likewise inhibit other cysteine proteases.

Compounds preferred according to the invention accordingly have a selectivity in relation to inhibition of cathepsin B, expressed in the form of the ratio of the Ki for inhibition of cathepsin B to the Ki for inhibition of calpain of ≥5, in particular ≥9 and specifically ≥30.

Compounds preferred according to the invention accordingly have a selectivity in relation to inhibition of cathepsin K, expressed in the form of the ratio of the Ki for inhibition of cathepsin K to the Ki for inhibition of calpain of ≥5, in particular ≥9 and specifically ≥30.

Compounds preferred according to the invention accordingly have a selectivity in relation to inhibition of cathepsin L, expressed in the form of the ratio of the Ki for inhibition of cathepsin L to the Ki for inhibition of calpain of ≥5, in particular ≥10 and specifically ≥50.

Compounds preferred according to the invention accordingly have a selectivity in relation to inhibition of cathepsin S, expressed in the form of the ratio of the Ki for inhibition of cathepsin S to the Ki for inhibition of calpain of ≥5, in particular ≥10 and specifically ≥50.

In addition, the compounds of the present invention feature an improved stability in the cytosole of human cells, which markedly contributes to their good overall metabolic stability. The cytosolic stability can be measured for example by incubating a solution of a compound of the invention with liver cytosole from particular species (for example rat, dog, monkey or human) and determining the half-life of the compound under these conditions. It is possible to conclude from larger half-lives that the metabolic stability of the compound is improved. The stability in the presence of human liver cytosole is of particular interest because it makes it possible to predict the metabolic degradation of the compound in the human liver. Compounds with enhanced cytosolic stability therefore are likely to be degraded at reduced rates in the liver. Slower metabolic degradation in the liver in turn can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

Accordingly, due to their improved cytosolic stability the compounds of the invention remain in the cytosol for extended periods, i.e. have a decreased cytosolic clearance, and therefore ought to show enhanced human pharmacokinetics.

Compounds preferred according to the invention accordingly have a cytosolic clearance in human liver cytosol of ≤30 μl/min/mg, in particular of ≤15 μl/min/mg.

The improved cytosolic stability of the compounds according to the present invention is probably primarily due to their reduced susceptibility to aldo-keto reductases (AKRs) which mediate the metabolic degradation of compounds having a carbonyl group in the liver cytosole of humans and monkeys. Thus, the AKR-catalyzed reduction of the ketoamides of formula I should be less pronounced than that of less stable ketoamides. Hence, the ratio of the concentration of the parent compound, i.e. the ketamide of formula I, to the concentration of the metabolite, i.e. the hydroxyamide stemming form the ketoamide, is a measure for the stability of the compounds of the invention.

Compounds preferred according to the invention accordingly have, after an incubation in human hepatocytes for 4 hours, a concentration ratio of the hydroxyamide metabolite to their corresponding parent compound of formula I of ≤5, in particular ≤2 and specifically ≤0.5.

Owing to their inhibitory effect on calpain, their selectivity for calpain in comparison with other cysteine proteases and their cytosolic stability the compounds of the present invention, including their tautomers, their hydrates and their pharmaceutically suitable salts are particularly suitable for the treatment of a disorder or of a condition which is associated with an elevated calpain activity as are described for example in the prior art cited at the outset.

Disorders associated with an elevated calpain activity are in particular neurodegenerative disorders, especially those neurodegenerative disorders occuring as a result of a chronic brain supply deficit, of an ischemia (stroke) or of a trauma such as brain trauma, and the neurodegenerative disorders Alzheimer's disease, Parkinson's disease, amyotrophic lateral sclerosis and Huntington's disease, also multiple sclerosis and the damage to the nervous system associated therewith, especially damage to the optic nerve (optic neuritis) and the nerves which control the movement of the eye. Accordingly, preferred embodiments of the invention relate to the treatment of neurodegenerative disorders, especially of the aforementioned neurodegenerative disorders in humans, and to the use of the compounds of the invention of the formula I, their tautomers and their pharmaceutically suitable salts for the manufacture of a medicament for the treatment of these disorders.

Disorders associated with an elevated calpain activity also include epilepsy. Accordingly, preferred embodiments of the invention relate to the treatment of epilepsy in humans, and to the use of the compounds of the invention for the manufacture of a medicament for the treatment of epilepsy.

The disorders or conditions associated with an elevated calpain activity also include pain and painful conditions. Accordingly, preferred embodiments of the invention relate to the treatment of pain and painful conditions in mammals, especially in humans, and to the use of the compounds of the invention for the manufacture of a medicament for the treatment of pain and painful conditions.

The disorders or conditions associated with an elevated calpain activity also include damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty. Accordingly, preferred embodiments of the invention relate to the treatment of diseases or conditions associated with damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty in mammals, especially in humans, and to the use of the compounds of the invention for the manufacture of a medicament for the treatment of these disorders.

It has further emerged that inhibition of calpain brings about cytotoxic effects on tumor cells. Accordingly, the compounds of the invention are suitable for the chemotherapy of tumors and metastasis thereof. Preferred embodiments of the invention therefore relate to the use of the compounds of the invention in the therapy of tumors and metastases, and to their use for the manufacture of a medicament for the therapy of tumors and metastases.

It has further been found that various impairments associated with an HIV disorder, especially nerve damage (HIV-induced neurotoxicity), are mediated by calpain and therefore inhibition of calpain allows such impairments to be treated or alleviated. Accordingly, the compounds of the invention are suitable for the treatment of HIV patients. Preferred embodiments of the invention therefore relate to the use of the compounds of the invention for the treatment of HIV-infected patients, especially the treatment of those impairments caused by an HIV-induced neurotoxicity, and to their use for the manufacture of a medicament for the treatment of HIV patients.

It has further been found that the release of interleukin-I, TNF or beta-amyloid peptides (A$\beta$ or A$\beta$-peptides) can be reduced or completely inhibited by calpain inhibitors. Accordingly, impairments or disorders associated with an elevated interleukin-I, TNF or A$\beta$ level can be treated by using the compounds of the invention of the formula I, their tautomers and their pharmaceutically suitable salts. Preferred embodiments of the invention therefore relate to the use of the compounds of the invention for the treatment of impairments or disorders associated with an elevated interleukin-I, TNF or A$\beta$ level such as rheumatism, rheumatoid arthritis and to their use for the manufacture of a medicament for the treatment of such impairments or disorders.

It has further emerged that inhibition of calpain is suitable for the treatment of protozoan infection (protist infection) like malaria or toxoplasmosis (Li et al., *Mol Biochem Parasitol.* 2007; 155(1): 26-32; Jung et al. Archives of Pharmacal Research (2009), 32(6), 899-906). Hence, the compounds of the present invention are particularly suitable for treating protozoan infections like malaria or toxoplasmosis and to their use for the manufacture of a medicament for the treatment of such impairments or disorders.

Besides their improved cytosolic stability the compounds of the present invention are also distinguished by a good stability against degradation in liver microsomes. The microsomal stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). Their good microsomal stability contributes to the enhanced overall metabolic stability of the compounds of the invention.

The compounds of the present invention are further distinguished by exhibiting an improved pharmacological activity, compared with the carboxamide compounds disclosed in the prior art, in patients or relevant animal models allowing prognostic statements for use in treatment.

The present invention also relates to pharmaceutical compositions (i.e. medicaments) which comprise at least one compound of the present invention and, where appropriate, one or more suitable drug carriers.

These drug carriers are chosen according to the pharmaceutical form and the desired mode of administration.

The compounds of the present invention can be used to manufacture pharmaceutical compositions for oral, sublingual, subcutaneous, intramuscular, intravenous, topical, intratracheal, intranasal, transdermal or rectal administration, and be administered to animals or humans in unit dose forms, mixed with conventional pharmaceutical carriers, for the prophylaxis or treatment of the above impairments or diseases.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient may vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day, so that a daily dose of from 0.5 to 25000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

The following examples illustrate the invention without restricting it. Depending on the management of the reaction and working up, the compounds of the invention are present as mixtures of compounds of the formula I and of the corresponding hydrates of the formula I-H. Conversion into the pure carbonyl compounds generally takes place by treating the substances with HCl in an inert solvent.

Abbreviations: EDC for N-(3-dimethylaminopropyl)-N'-ethylcarbodiimide hydrochloride; DMSO for dimethyl sulfoxide; MTB for methyl tert.butyl ether; TFA for trifluoroacetic acid.

I. PREPARATION EXAMPLES

The intermediates used were either commercially available or prepared according to the procedures described in WO 2008/080969, WO 2011/076811 and WO 2011/076812.

Example A

Ethyl 2-(3-formyl-1H-pyrazol-1-yl)nicotinate

To ethyl 2-chloronicotinate (8 g, 43.1 mmol) und 1H-pyrazole-3-carbaldehyde (4.6 g, 47.9 mmol) in N,N-dimethylformamide (80 mL) $K_2CO_3$ (12 g, 87 mmol), 18-CROWN-6 (0.5 g, 1.892 mmol) und KI (0.4 g, 2.410 mmol) were added, the mixture heated to 120° C. for 1 hr and then stirred overnight at room temperature.

The mixture then was concentrated, 250 mL of dichloromethane added, washed subsequently with water and brine, dried ($MgSO_4$), filtered and concentrated to give 11.2 g of a yellow oil. Purification by chromatography over silica gel (eluent $CH_2Cl_2$+0-6% methanol) and evaporation of the combined product fractions gave 8.3 g of the title compound as amorphous solid.

ESI-MS $[M+H]^+$: 246.1. $^1$H-NMR (400 MHz, DMSO), δ[ppm]: 9.96 (s), 8.77 (m, 1H), 8.67 (m, 1H), 8.26 (m, 1H), 7.67 (m, 1H), 7.06 (d, 1H), 4.25 (q, 2H), 1.12 (t, 3H).

Example B

Ethyl 2-(3-(hydroxymethyl)-1H-pyrazol-1-yl)nicotinate

To ethyl 2-(3-formyl-1H-pyrazol-1-yl)nicotinate (6 g, 9.79 mmol) in ethanol (100 mL) at 10° C. $NaBH_4$ (0.741 g, 19.57 mmol) was added and stirred at 25° C. for 1 hr. For work up the mixture was poured into 200 mL of ice water, extracted twice with ethyl acetate, the combined organic layers subsequently washed with water and brine, dried ($MgSO_4$), filtered and concentrated to give 7.2 g of a yellow oil. Purification by chromatography over silica gel (eluent $CH_2Cl_2$+0-10% methanol) gave 2.36 g of the corresponding title compound as clear oil; ESI-MS $[M+H]^+$: 248.1.

Example C

Ethyl 2-(3-(chloromethyl)-1H-pyrazol-1-yl)nicotinate

To a solution of ethyl 2-(3-(hydroxymethyl)-1H-pyrazol-1-yl)nicotinate (3.76 g, 13.69 mmol) in dichloromethane (100 mL) thionyl chloride (1.1 mL, 15.07 mmol) was added dropwise under stirring. After the reaction was completed, the mixture was concentrated and purified by chromatography over silica gel (eluent $CH_2Cl_2$+0-5% methanol) to give 3.7 g of the title compound as clear oil; ESI-MS $[M+H]^+$: 266.1. $^1$H-NMR (400 MHz, DMSO), δ[ppm]: 8.64 (dd, 1H), 8.49 (d, 1H), 8.13 (dd, 1H), 7.53 (dd, 1H), 6.65 (d, 2H), 4.23 (q, 2H), 1.17 (t, 3H).

I.2. PREPARATION OF COMPOUNDS OF THE GENERAL FORMULA I

Example 1

N-(4-Amino-3,4-dioxo-1-phenylbutan-2-yl)-2-(3-(morpholinomethyl)-1H-pyrazol-1-yl)nicotinamide

1.1 Ethyl 2-(3-(morpholinomethyl)-1H-pyrazol-1-yl)nicotinate

To a solution of ethyl 2-(3-formyl-1H-pyrazol-1-yl)nicotinate (400 mg, 1.631 mmol) and morpholine (220 μl, 2.53 mmol) in acetonitrile (25 mL) $NaCNBH_4$ (130 mg, 2.069 mmol) was added, and the pH adjusted to 5-6 by adding glacial acetic acid (110 μL, 1.922 mmol). The mixture was stirred at room temperature for 1 h, another portion of $NaCNBH_4$ (30 mg, 0.477 mmol) added and stirred for 2 hrs. For work up the mixture was concentrated, dissolved in 100 mL of dichloromethane, washed subsequently with water and brine, dried ($MgSO_4$), filtered off and concentrated to give 710 mg of the crude title product. Purification by chromatography over silica gel ($CH_2Cl_2$/3%-5% methanol) and concentration yielded 518 mg of the title compound as clear oil; ESI-MS $[M+H]^+$: 317.20.

1.2 2-(3-(Morpholinomethyl)-1H-pyrazol-1-yl)nicotinic acid

To ethyl 2-(3-(morpholinomethyl)-1H-pyrazol-1-yl)nicotinate (370 mg, 1.170 mmol) in methanol (20 mL) and water (2 mL) NaOH (2m solution; 1.7 mL) was added and the mixture heated to reflux for 90 min. The reaction mixture was concentrated, taken up in water, 1.7 mL of 2n HCl added and concentrated again. The obtained solid was treated with 20 mL of acetone, the remainder filtered off and dried to give 295 mg of the acid as off-white amorphous solid; ESI-MS $[M+H]^+$: 289.2.

1.3 N-(4-Amino-3-hydroxy-4-oxo-1-phenylbutan-2-yl)-2-(3-(morpholinomethyl)-1H-pyrazol-1-yl)nicotinamide N-(3-Dimethylaminopropyl)-N'-ethylcarbodiimide hydrochloride (EDC) (280 mg, 1.461 mmol mmol), 1-hydroxybenzotriazole hydrate (220 mg, 1.437 mmol) and triethylamine (Et₃N) (2204) were successively added to a suspension of 2-(3-(morpholinomethyl)-1H-pyrazol-1-yl)nicotinic acid (350 mg, 1.214 mmol) and 3-amino-2-hydroxy-4-phenylbutanamide (260 mg, 1.339 mmol) in CH₂Cl₂ (40 mL) at 5° C., and the mixture was stirred at 5° C. for about 5 minutes. A pH of 8 was adjusted by adding 50 μL of Et₃N, the mixture stirred for 1 hour at 5° C. and then overnight at room temperature. Dichloromethane (50 mL) was added, washed subsequently with water and brine, dried (MgSO₄) and concentrated in vacuo to give 430 mg of a yellow oil, which was purified by chromatography over silica gel (eluent CH₂Cl₂/methanol) to give 260 mg of an amorphous white solid; ESI-MS [M+H]⁺: 465.2

1.4 N-(4-Amino-3,4-dioxo-1-phenylbutan-2-yl)-2-(3-(morpholinomethyl)-1H-pyrazol-1-yl)nicotinamide To a solution of N-(4-amino-3-hydroxy-4-oxo-1-phenylbutan-2-yl)-2-(3-(morpholinomethyl)-1H-pyrazol-1-yl)nicotinamide (70 mg, 0.151 mmol) in DMSO (3 mL) EDC (240 mg, 1.252 mmol) and—after stirring for 5 min—2,2-dichloroacetic acid (50 μL, 0.609 mmol) were added, and the mixture stirred for 15 min at room temperature. 60 mL of a 1:1 mixture of brine and sat. NaHCO₃-solution (60 mL) was added, the stirring continued for 10 min, extracted with ethylacetate (3×50 mL), the combined organic layers dried (MgSO₄), filtered off and concentrated in vacuo to give 170 mg of the crude product as yellow oil. Treatment with 15 mL of methyl-tert.butylether (MTB) and further purification of the precipitate formed by chromatography over silica gel (CH₂Cl₂/methanol) afforded 15 mg of the title compound as amorphous white solid; ESI-MS [M+H]⁺: 463.2. ¹H-NMR (400 MHz, DMSO), δ[ppm]: 8.95 (d, 1H), 8.51 (m, 1H), 8.30 (d, 1H), 8.05 (s, 1H), 7.82 (m, 1H), 7.70 (m, 1H), 7.44 (m, 1H), 7.30 (m, 5H), 6.38 (d, 1H), 5.38 (m, 1H), 3.53 (m, 4H), 3.15 and 2.88 (each dd, 1H), 2.29 (m, 4H).

Example 2

N-(4-Amino-3,4-dioxo-1-phenylbutan-2-yl)-2-(3-((2,6-dimethylmorpholino)methyl)-1H-pyrazol-1-yl)nicotinamide (Mixture of Cis and Trans Diastereomer)

2.1 Ethyl 2-(3-((2,6-dimethylmorpholino)methyl)-1H-pyrazol-1-yl)nicotinate (Mixture of Cis and Trans Diastereomer)

Ethyl 2-(3-(chloromethyl)-1H-pyrazol-1-yl)nicotinate (650 mg, 2.446 mmol), 2,6-dimethylmorpholine (0.482 mL, 3.91 mmol) and K₂CO₃ (1082 mg, 7.83 mmol) in acetonitrile (25 mL) were stirred over night at room temperature. The mixture was concentrated, the remaining solid partitioned between 60 mL of water and dichloromethane, the organic layer separated, dried (MgSO₄), filtered and concentrated again to yield 870 mg of the title compound as clear oil; ESI-MS [M+H]⁺: 345.2.

2.2 Sodium 2-(3-((2,6-dimethylmorpholino)methyl)-1H-pyrazol-1-yl)nicotinic acid To ethyl 2-(3-((2,6-dimethylmorpholino)methyl)-1H-pyrazol-1-yl)nicotinate (870 mg, 2.021 mmol) in ethanol (30 mL) 2 molar NaOH (1.4 mL, 2.80 mmol) was added, and the mixture heated to reflux. After completion of the reaction the mixture was concentrated in vacuo, co-evaporated twice with acetone, and the obtained solid dried. Treatment with n-pentane and drying afforded 820 mg of the title compound as sodium salt, which was used in the next steps without further purification.

2.3 N-(4-Amino-3-hydroxy-4-oxo-1-phenylbutan-2-yl)-2-(3-((2,6-dimethyl-morpholino)methyl)-1H-pyrazol-1-yl)nicotinamide Coupling of sodium 2-(3-((2,6-dimethylmorpholino)methyl)-1H-pyrazol-1-yl)nicotinate (400 mg, 0.946 mmol) and 3-amino-2-hydroxy-4-phenylbutanamide (220 mg, 1.135 mmol) according to the procedure described for example 1.3 and work-up gave 448 mg of the crude product, which further purified by treatment with a mixture of 30 mL of n-pentane/MTB (10 mL). Filtration and drying gave 388 mg of amorphous white solid; ESI-MS [M+H]⁺: 493.2.

2.4 N-(4-Amino-3,4-dioxo-1-phenylbutan-2-yl)-2-(3-((2,6-dimethylmorpholino)-methyl)-1H-pyrazol-1-yl)nicotinamide The mixture of N-(4-amino-3-hydroxy-4-oxo-1-phenylbutan-2-yl)-2-(3-((2,6-dimethylmorpholino)methyl)-1H-pyrazol-1-yl)nicotinamide (200 mg, 0.406 mmol) and 2-iodobenzoic acid (303 mg, 0.487 mmol) in DMSO (6 mL) was stirred over night at room temperature, then cooled to 15° C., and quenched by addition of 15% aqueous NaHCO₃-solution (15 mL), water (10 mL) and CH₂Cl₂ (20 mL). The organic layer was separated, washed with water and tried to give 160 mg of a mixture of title compound and starting material, which was treated again with 200 mg of 2-iodobenzoic acid and quenched following the procedure described. 110 mg of the crude product were purified by chromatography over silica gel (eluent CH₂Cl₂+0-12% methanol) to afford the title compound as two individual diastereomers.

Example 2a (tlc CH₂Cl₂/methanol 9:1 Rf: 0.28): 15 mg, ESI-MS [M+H]⁺: 491.2. ¹H-NMR (400 MHz, DMSO), δ[ppm]: 8.89 (m, 1H), 8.51 (m, 1H), 8.31 (m, 1H), 8.00 (m, 1H), 7.77 (m, 1H), 7.71 (m, 1H), 7.29 (m, 5H), 6.37 (m, 1H), 5.38 (m, 1H), 3.85 (m, 2H), 3.16 (overlapping with water), 2.89 (m, 1H), 2.34 (m 2H), 2.02 (m, 2H), 1.10 (m, 6H).

Example 2b (tlc CH₂Cl₂/methanol 9:1 Rf: 0.32): 31 mg, ESI-MS [M+H]⁺: 491.2. ¹H-NMR (400 MHz, DMSO), δ[ppm]: 8.90 (m, 1H), 8.51 (m, 1H), 8.32 (m, 1H), 8.04 (m, 1H), 7.82 (m, 1H), 7.77 (m, 1H), 7.46 (m, 1H), 7.29 (m, 4H), 7.23 (m, 1H), 6.38 (m, 1H), 5.38 (m, 1H), 3.48 (m, 2H), 3.31 (overlapping with water), 3.18 and 2.90 (each m, 1H), 2.62 (, 2H), 1.58 (m, 2H), 1.01 (m, 6H).

Example 3

N-(4-Amino-3,4-dioxo-1-phenylbutan-2-yl)-2-(3-((4,4-difluoropiperidin-1-yl)methyl)-1H-pyrazol-1-yl)nicotinamide trifluoroacetate

3.1 Ethyl 2-(3-((4,4-difluoropiperidin-1-yl)methyl)-1H-pyrazol-1-yl)nicotinate The mixture of ethyl 2-(3-(chloromethyl)-1H-pyrazol-1-yl)nicotinate (500 mg, 1.882 mmol), 4,4-difluoropiperidine (328 mg, 2.7 mmol), and K$_2$CO$_3$ were stirred at room temperature in acetonitrile (25 mL) until completion of the reaction. The mixture was concentrated, pardoned between water and dichlormethane (60 mL), the organic layer separated, washed twice with water, dried (MgSO$_4$), filtered and dried to give a brown oil, which then was purified by chromatography over silica gel (CH$_2$Cl$_2$+methanol) to yield 620 mg of the title compound as clear oil. ESI-MS [M+H]$^+$: 351.15.

$^1$H-NMR (400 MHz, DMSO), δ[ppm]: 8.65 (m, 1H), 8.48 (m, 1H), 8.15 (m, 1H), 7.45 (m, 1H), 6.51 (m, 1H), 4.25 (q, 2H), 3.65 (d, 1H), 3.25 (d, overlapped with water), 2.5 (overlapped with DMSO), 1.95 (m, 4H).

3.2 2-(3-((4,4-Difluoropiperidin-1-yl)methyl)-1H-pyrazol-1-yl)nicotinic acid, sodium salt Treatment of ethyl 2-(3-((4,4-difluoropiperidin-1-yl)methyl)-1H-pyrazol-1-yl)nicotinate (620 mg, 1.770 mmol) in ethanol (30 mL) with 1.2 mL of a 2M NaOH, concentration of the reaction mixture and drying of the obtained solid gave 610 mg of the acid as sodium salt as an amorphous solid; ESI-MS [M+H]$^+$: 323.1.

3.3 N-(4-Amino-3-hydroxy-4-oxo-1-phenylbutan-2-yl)-2-(3-((4,4-difluoropiperidin-1-yl)methyl)-1H-pyrazol-1-yl)nicotinamide Coupling of sodium 2-(3-((4,4-difluoropiperidin-1-yl)methyl)-1H-pyrazol-1-yl)nicotinate (310 mg, 0.900 mmol) and 3-amino-2-hydroxy-4-phenylbutanamide (227 mg, 1.171 mmol) in N,N-dimethylformamide (20 mL) according to example 1.3 and work-up gave 449 mg of the title compound; ESI-MS [M+H]$^+$: 499.2.

3.4 N-(4-Amino-3,4-dioxo-1-phenylbutan-2-yl)-2-(3-((4,4-difluoropiperidin-1-yl)methyl)-1H-pyrazol-1-yl)nicotinamide trifluoroacetate To a solution of N-(4-amino-3-hydroxy-4-oxo-1-phenylbutan-2-yl)-2-(3-((4,4-difluoropiperidin-1-yl)methyl)-1H-pyrazol-1-yl)nicotinamide (200 mg, 0.401 mmol) in DMSO (5 mL) and dichloromethane (25 ml) EDC (615 mg, 3.21 mmol) and—after stirring for 5 min—2,2-dichloroacetic acid (120 μL, 1.455 mmol) were added, and the mixture stirred for 5 min at room temperature. 20 ml of a cooled sat. NaHCO$_3$-solution were added, the organic layer separated and washed with brine (3×), dried (MgSO$_4$), filtered off, and 2.1 eq. of 1M HCl in diethylether added to the filtrate. After stirring the precipitate formed was filtered, washed with MTB and dried to give an amorphous solid, which was further purified by prep. HPLC (column: xTerra prepMS C18 19×150 mm 5 μM; eluent: water+0.1% TFA/methanol+0.1% TFA; flow: 15 mL/min). Lyophilisation of the combined product fractions afforded 71 mg of a white amorphous solid; ESI-MS [M+H]$^+$: 497.2. $^1$H-NMR (400 MHz, DMSO), δ[ppm]: 9.03 (m, 1H), 8.58 (m, 1H), 8.40 (m, 1H), 8.08 (m, 1H), 7.82 (m, 2H), 7.55 (m, 1H), 7.28 (m, 5H), 6.62 (m, 1H), 5.35 (m, 1H), 4.32 and 4.10 (each m 1H), 3.65 (broad, overlapping with water), 3.14 and 2.84 (each dd, 1H), 2.26 (broad, 4H).

Example 4

N-(4-Amino-3,4-dioxo-1-phenylbutan-2-yl)-2-(5-benzyl-4,5,6,7-tetrahydro-2H-pyrazolo[4,3-c]pyridin-2-yl)nicotinamide

4.1 Ethyl 2-(5-benzyl-4,5,6,7-tetrahydro-2H-pyrazolo[4,3-c]pyridin-2-yl)nicotinate The mixture of 5-benzyl-4,5,6,7-tetrahydro-2H-pyrazolo[4,3-c]pyridine (1.0 g, 4.69 mmol), ethyl 2-chloronicotinate (1.55 g, 8.35 mmol), K$_2$CO$_3$ (1.7 g, 12.30 mmol), 18-CROWN-6 (0.2 g, 0.757 mmol) and KI (0.13 g, 0.783 mmol) in N,N-dimethylformamide (15 mL) was heated to 140° C. under stirring. After completion of the reaction the mixture was concentrated, the remainder dissolved in 250 mL of dichloromethane, washed subsequently with water (3×30 mL) and brine, dried (MgSO$_4$), filtered and concentrated to give 2.21 g of a brown oil, which was purified by chromatography over silica gel (eluent CH$_2$Cl$_2$/methanol). 200 mg of the title compound was obtained as a white amorphous solid; ESI-MS [M+H]$^+$: 363.2.

4.2 2-(5-Benzyl-4,5,6,7-tetrahydro-2H-pyrazolo[4,3-c]pyridin-2-yl)nicotinic acid, sodium salt Treatment of ethyl 2-(5-benzyl-4,5,6,7-tetrahydro-2H-pyrazolo[4,3-c]pyridin-2-yl)nicotinate (110 mg, 0.304 mmol) in ethanol (10 mL) with 0.5 mL of 1m NaOH and and work-up afforded 106 mg of the title compound as sodium salt; ESI-MS [M+H]$^+$: 335.2.

4.3 N-(4-Amino-3-hydroxy-4-oxo-1-phenylbutan-2-yl)-2-(5-benzyl-4,5,6,7-tetrahydro-2H-pyrazolo[4,3-c]pyridin-2-yl)nicotinamide Coupling of sodium 2-(5-benzyl-4,5,6,7-tetrahydro-2H-pyrazolo[4,3-c]pyridin-2-yl)nicotinate (106 mg, 0.297 mmol) and 3-amino-2-hydroxy-4-phenylbutanamide (80 mg, 0.412 mmol) in N,N-dimethylformamide (10 mL) according to example 1.3 and work-up gave 197 mg of the title compound a amorphous solid; ESI-MS [M+H]$^+$: 511.2.

4.4 N-(4-Amino-3,4-dioxo-1-phenylbutan-2-yl)-2-(5-benzyl-4,5,6,7-tetrahydro-2H-pyrazolo[4,3-c]pyridin-2-yl)nicotinamide To a solution of N-(4-amino-3-hydroxy-4-oxo-1-phenylbutan-2-yl)-2-(5-benzyl-4,5,6,7-tetrahydro-2H-pyrazolo[4,3-c]pyridin-2-yl)nicotinamide (45 mg, 0.088 mmol) in DMSO (1200 μL) at room temperature, EDC (160 mg, 0.835 mmol) was added, and after 5 min of stirring 2,2-dichloroacetic acid (40 μL, 0.487 mmol). The mixture was stirred for 45 min at room temperature, and then 10 mL of brine and 10 mL of saturated aqueous NaHCO$_3$-solution were added, the precipitate formed filtered off and dried in vacuo. The yellow solid obtained was crystallized from 2-propanol, the resulting precipitate washed and treated with MTB and n-pentane to afford 27 mg of an off-white amorphous solid; ESI-MS [M+H]$^+$: 509.2. $^1$H-NMR (400 MHz, DMSO), δ[ppm]: 8.86 (m, 1H), 8.47 (m, 1H), 8.07 (m, 1H), 7.98 (m, 1H), 7.76 (m, 1H), 7.65 (m, 1H), 7.35-7.18 (m, 11H), 5.33 (m, 1H), 4.05 (m, 1H), 3.68 (s, 2H), 3.45-3.16 (m, overlapping with water), 2.91 (dd, 1H), 2.72 (m, 4H).

Applying the routes and procedures described above the following examples were prepared:

Example 5

N-(4-Amino-3,4-dioxo-1-phenylbutan-2-yl)-2-(3-((4-phenylpiperidin-1-yl)methyl)-1H-pyrazol-1-yl)nicotinamide

5.1 N-(4-Amino-3-hydroxy-4-oxo-1-phenylbutan-2-yl)-2-(3-((4-phenylpiperidin-1-yl)methyl)-1H-pyrazol-1-yl)nicotinamide 500 mg of a clear oil was obtained; ESI-MS [M+H]$^+$: 509.2.

5.2 N-(4-Amino-3,4-dioxo-1-phenylbutan-2-yl)-2-(3-((4-phenylpiperidin-1-yl)methyl)-1H-pyrazol-1-yl)nicotinamide To a solution of N-(4-amino-3-hydroxy-4-oxo-1-phenylbutan-2-yl)-2-(3-((4-phenylpiperidin-1-yl)methyl)-1H-pyrazol-1-yl)nicotinamide (100 mg, 0.186 mmol) in dichloromethane (3 mL) at room temperature DMSO (300 µL), N,N'-dichyclohexyl-carbodiimide (380 mg, 1.842 mmol) and 2,2-dichloroacetic acid (40 µL, 0.487 mmol) were added, and the mixture stirred for 1.5 h at room temperature. After completion of the reaction the mixture was filtered, the filtrate diluted with 30 mL of water, extracted with ethylacetate, the aqueous layer then adjusted to pH 8 by adding $NaHCO_3$, then extracted again with ethyl acetate (3×30 mL), the combined organic layers washed with brine, dried ($MgSO_4$), filtered and concentrated to give 80 mg of a yellow amorphous solid. Purification by chromatography over silica gel ($CH_2Cl_2$/methanol) and concentration afforded 25 mg of the title compound as white amorphous solid; ESI-MS $[M+H]^+$: 537.2.

Example 6

2-(3-((2H-Benzo[b][1,4]oxazin-4(3H)-yl)methyl)-1H-pyrazol-1-yl)-N-(4-amino-3,4-dioxo-1-phenylbutan-2-yl)nicotinamide

6.1 2-(3-((2H-Benzo[b][1,4]oxazin-4(3H)-yl)methyl)-1H-pyrazol-1-yl)-N-(4-amino-3-hydroxy-4-oxo-1-phenylbutan-2-yl)nicotinamide 358 mg of a yellow amorphous solid; mixture of diastereomers; ESI-MS $[M+H]^+$: 513.2

6.2 2-(3-((2H-Benzo[b][1,4]oxazin-4(3H)-yl)methyl)-1H-pyrazol-1-yl)-N-(4-amino-3,4-dioxo-1-phenylbutan-2-yl)nicotinamide Oxidation of 2-(3-((2H-benzo[b][1,4]oxazin-4(3H)-yl)methyl)-1H-pyrazol-1-yl)-N-(4-amino-3-hydroxy-4-oxo-1-phenylbutan-2-yl)nicotinamide (210 mg, 0.410 mmol) in DMSO (6 mL) with 2-iodobenzoic acid as described for example 2.4 gave 220 mg of a yellow solid, which was purified by chromatography over silica gel (eluent $CH_2Cl_2$+0-15% methanol). After concentration the obtained solid was recrystallized from 2-propanol to give 78 mg of the title compound as an amorphous solid; ESI-MS $[M+H]^+$: 511.2. $^1$H-NMR (400 MHz, DMSO), δ[ppm]: 8.97 (m, 1H), 8.55 (m, 1H), 8.29 (m, 1H), 8.09 (m, 1H), 7.84 (m, 1H), 7.70 (m, 1H), 7.44 (m, 1H), 7.31 (m, 4H), 7.22 (m, 1H), 6.82 (m, 1H), 6.70 (m, 1H), 6.61 (m, 1H), 6.50 (m, 1H), 6.34 (m, 1H), 5.44 (m, 1H), 4.26 (d, 1H), 4.20 (d, 1H), 4.12 (m, 2H), 3.25 (m, 3H), 2.88 (dd, 1H).

Example 7

N-(4-Amino-3,4-dioxo-1-phenylbutan-2-yl)-2-(3-(piperidin-1-ylmethyl)-1H-pyrazol-1-yl)nicotinamide hydrochloride

7.1 N-(4-Amino-3-hydroxy-4-oxo-1-phenylbutan-2-yl)-2-(3-(piperidin-1-ylmethyl)-1H-pyrazol-1-yl)nicotinamide 1960 mg of a yellow amorphous solid was obtained; mixture of diastereomers; ESI-MS $[M+H]^+$: 463.2.

7.2 N-(4-Amino-3,4-dioxo-1-phenylbutan-2-yl)-2-(3-(piperidin-1-ylmethyl)-1H-pyrazol-1-yl)nicotinamide hydrochloride Oxidation of N-(4-amino-3-hydroxy-4-oxo-1-phenylbutan-2-yl)-2-(3-(piperidin-1-ylmethyl)-1H-pyrazol-1-yl)nicotinamide (200 mg, 0.432 mmol) according to the procedure described in example 3.4 and treatment of the obtained crude product with diisopropylether afforded the title compound as white amorphous solid; 78 mg; ESI-MS $[M+H]^+$: 461.2.

Example 8

2-(3-((2H-Benzo[b][1,4]oxazin-4(3H,4aH,5H,6H,7H,8H,8aH)-yl)methyl)-1H-pyrazol-1-yl)-N-(4-amino-3,4-dioxo-1-phenylbutan-2-yl)nicotinamide trifluoroacetate (Mixtures of Diastereomer)

8.1 2-(3-((2H-Benzo[b][1,4]oxazin-4(3H,4aH,5H,6H,7H,8H,8aH)-yl)methyl)-1H-pyrazol-1-yl)-N-(4-amino-3-hydroxy-4-oxo-1-phenylbutan-2-yl)nicotinamide The reaction was carried out in analogy to example 1.3. After completion of the reaction the mixture was concentrated, subsequently 30 mL of water, 10 mL of sat. $NaHCO_3$-solution and 30 mL of dichloromethane added. The remaining solid was filtered off and dried to give 120 mg of a white amorphous solid (diastereomere 1: tlc $CH_2Cl_2$/methanol 9:1 Rf: 0.37); ESI-MS $[M+H]^+$: 519.3. The organic layer was separated, washed, dried and concentrated, and the remaining solid purified by chromatography over silica gel (eluent $CH_2Cl_2$+0-15% methanol) to give 320 mg of a white amorphous solid (diastereomere 2 and 3: tlc $CH_2Cl_2$/methanol 9:1 Rf: 0.29 and 0.27); ESI-MS $[M+H]^+$: 519.3.

8.2.a 2-(3-((2H-Benzo[b][1,4]oxazin-4(3H,4aH,5H,6H,7H,8H,8aH)-yl)methyl)-1H-pyrazol-1-yl)-N-(4-amino-3,4-dioxo-1-phenylbutan-2-yl)nicotinamide trifluoroacetate, diastereomere 1, Oxidation of 2-(3-((2H-benzo[b][1,4]oxazin-4(3H,4aH,5H,6H,7H,8H,8aH)-yl)methyl)-1H-pyrazol-1-yl)-N-(4-amino-3-hydroxy-4-oxo-1-phenylbutan-2-yl)nicotinamide (diastereomers 2 and 3: 200 mg, 0.386 mmol) as described in example 3.4, purification of the crude product by prep. HPLC and lyophilisation afforded the title compound as white amorphous solid; ESI-MS $[M+H]^+$: 517.2.

8.2.b 2-(3-((2H-Benzo[b][1,4]oxazin-4(3H,4aH,5H,6H,7H,8H,8aH)-yl)methyl)-1H-pyrazol-1-yl)-N-(4-amino-3,4-dioxo-1-phenylbutan-2-yl)nicotinamide trifluoroacetate, diastereomere 2

Oxidation of 2-(3-((2H-benzo[b][1,4]oxazin-4(3H,4aH,5H,6H,7H,8H,8aH)-yl)methyl)-1H-pyrazol-1-yl)-N-(4-amino-3-hydroxy-4-oxo-1-phenylbutan-2-yl)nicotinamide (diastereomer 1: 115 mg, 0.222 mmol) as described in example 3.4, purification of the crude product by prep. HPLC and lyophilisation afforded 53 mg of the title compound as white amorphous solid; ESI-MS $[M+H]^+$: 517.2. $^1$H-NMR (400 MHz, DMSO), δ [ppm]: 10.10 (broad), 9.00 (m, 1H), 8.58 (m, 1H), 8.43 (m, 1H), 8.10 (m, 1H), 7.86 (m, 1H), 7.77

(m, 1H), 7.56 (m, 1H), 7.28 (m, 5H), 6.67 (m, 1H), 5.37 (m, 1H), 4.23 (m, 1H), 3.86 (m, 1H), 3.69 (m, 1H), 3.3-3.02 (m, overlapping with water), 2.86 (m, 2H), 2.51-2.34 (m, overlapping with DMSO), 1.91-1.64 (m, 3H) 1.26 (m, 4H).

Example 9

N-(4-Amino-3,4-dioxo-1-phenylbutan-2-yl)-2-(3-((2-phenylmorpholino)methyl)-1H-pyrazol-1-yl)nicotinamide trifluoroacetate 9.1 N-(4-Amino-3-hydroxy-4-oxo-1-phenylbutan-2-yl)-2-(3-((2-phenylmorpholino)methyl)-1H-pyrazol-1-yl)nicotinamide 892 mg, mixture of diastereomers; ESI-MS [M+H]$^+$: 541.2.

9.2 N-(4-Amino-3,4-dioxo-1-phenylbutan-2-yl)-2-(3-((2-phenylmorpholino)methyl)-1H-pyrazol-1-yl)nicotinamide trifluoroacetate Oxidation of N-(4-amino-3-hydroxy-4-oxo-1-phenylbutan-2-yl)-2-(3-((2-phenylmorpholino)methyl)-1H-pyrazol-1-yl)nicotinamide (200 mg, 0.370 mmol) as described in example 3.4, purification of the crude product by prep. HPLC and lyophilisation afforded the title compound as white amorphous solid; 51 mg, ESI-MS [M+H]$^+$: 539.2.

$^1$H-NMR (400 MHz, DMSO), δ[ppm]: 9.09 (m, 1H), 8.58 (m, 1H), 8.49 (m, 1H), 8.14 (m, 1H), 7.90 (m, 1H), 7.77 (m, 1H), 7.54 (m, 1H), 7.50-7.20 (m, 10H), 6.65 (m, 1H), 5.36 (m, 1H), 4.77 (m, 1H), 4.31-2.78 (m).

Example 10

N-(4-Amino-3,4-dioxo-1-phenylbutan-2-yl)-2-(3-(pyrrolidin-1-ylmethyl)-1H-pyrazol-1-yl)nicotinamide trifluoroacetate 10.1 N-(4-Amino-3-hydroxy-4-oxo-1-phenylbutan-2-yl)-2-(3-(pyrrolidin-1-ylmethyl)-1H-pyrazol-1-yl)nicotinamide 343 mg, mixture of diastereomers; ESI-MS [M+H]$^+$: 449.2.

10.2 N-(4-Amino-3,4-dioxo-1-phenylbutan-2-yl)-2-(3-(pyrrolidin-1-ylmethyl)-1H-pyrazol-1-yl)nicotinamide trifluoroacetate Oxidation of N-(4-amino-3-hydroxy-4-oxo-1-phenylbutan-2-yl)-2-(3-(pyrrolidin-1-ylmethyl)-1H-pyrazol-1-yl)nicotinamide (190 mg, 0.424 mmol) as described in example 3.4, purification of the crude product by prep. HPLC and lyophilisation afforded the title compound as white amorphous solid; 22 mg, ESI-MS [M+H]$^+$: 447.2.

$^1$H-NMR (400 MHz, DMSO), δ[ppm]: 10.67 (broad), 9.09 (m, 1H), 8.58 (m, 1H), 8.42 (m, 1H), 8.17 (m, 1H), 7.92 (m, 1H), 7.77 (m, 1H), 7.54 (m, 1H), 7.32 (m, 5H), 6.64 (m, 1H), 5.41 (m, 1H), 4.41 (broad), 4.27 and 4.10 (each d, 1H), 3.18 (dd, 1H), 3.04 (m, 2H), 2.84 (dd, 1H), 1.85 (m, 4H).

Example 11

N-(4-Amino-3,4-dioxo-1-phenylbutan-2-yl)-2-(3-(azetidin-1-ylmethyl)-1H-pyrazol-1-yl)nicotinamide trifluoroacetate 11.1 N-(4-Amino-3-hydroxy-4-oxo-1-phenylbutan-2-yl)-2-(3-(azetidin-1-ylmethyl)-1H-pyrazol-1-yl)nicotinamide 274 mg, mixture of diastereomers; ESI-MS [M+H]$^+$: 435.2.

11.2 N-(4-Amino-3,4-dioxo-1-phenylbutan-2-yl)-2-(3-(azetidin-1-ylmethyl)-1H-pyrazol-1-yl)nicotinamide trifluoroacetate Oxidation of N-(4-amino-3-hydroxy-4-oxo-1-phenylbutan-2-yl)-2-(3-(azetidin-1-ylmethyl)-1H-pyrazol-1-yl)nicotinamide (255 mg, 0.587 mmol) as described in example 3.4, purification of the crude product by prep. HPLC and lyophilisation afforded the title compound as white amorphous solid; 14 mg, ESI-MS [M+H]$^+$: 433.2. $^1$H-NMR (400 MHz, DMSO), δ[ppm]: 10.74 (broad), 9.09 (m, 1H), 8.57 (m, 1H), 8.42 (m, 1H), 8.20 (m, 1H), 7.94 (m, 1H), 7.75 (m, 1H), 7.53 (m, 1H), 7.31 (m, 5H), 6.58 (m, 1H), 5.45 (m, 1H), 4.24 (broad), 4.11 and 4.00 (each d, 1H), 3.85 (m, 4H), 3.17 (dd, 1H), 2.83 (dd, 1H), 2.37 (m, 1H), 2.30 (m, 1H).

Example 12

N-(4-Amino-3,4-dioxo-1-phenylbutan-2-yl)-2-(3-((4-(trifluoromethyl)piperidin-1-yl)methyl)-1H-pyrazol-1-yl)nicotinamide trifluoroacetate 12.1 N-(4-Amino-3-hydroxy-4-oxo-1-phenylbutan-2-yl)-2-(3-((4-(trifluoromethyl)piperidin-1-yl)methyl)-1H-pyrazol-1-yl)nicotinamide 70 mg, mixture of diastereomers; ESI-MS [M+H]$^+$: 531.2.

12.2 N-(4-Amino-3,4-dioxo-1-phenylbutan-2-yl)-2-(3-((4-(trifluoromethyl)piperidin-1-yl)methyl)-1H-pyrazol-1-yl)nicotinamide trifluoroacetate Oxidation of N-(4-amino-3-hydroxy-4-oxo-1-phenylbutan-2-yl)-2-(3-((4-(trifluoromethyl)piperidin-1-yl)methyl)-1H-pyrazol-1-yl)nicotinamide (200 mg, 0.377 mmol) as described in example 3.4, purification of the crude product by prep. HPLC and lyophilisation afforded the title compound as white amorphous solid; 25 mg, ESI-MS [M+H]$^+$: 529.2. $^1$H-NMR (400 MHz, DMSO), δ[ppm]: 10.36 (broad), 9.10 (m, 1H), 8.58 (m, 1H), 8.43 (m, 1H), 8.15 (m, 1H), 7.92 (m, 1H), 7.81 (m, 1H), 7.55 (m, 1H), 7.31 (m, 5H), 6.65 (m, 1H), 5.36 (m, 1H), 4.23 and 4.03 (each d, 1H), 3.50 (m, 1H), 3.40 (m, 1H), 3.14 (dd, 1H), 2.91 (m, 2H), 2.74 (m, 1H), 2.59 (m, 1H), 2.03 and 1.73 (each m, 2H).

Example 13

N-(4-amino-3,4-dioxo-1-phenyl-2-butanyl)-2-{3-[(5,5-difluorohexahydrocyclopenta[c]pyrrol-2(1H)-yl)methyl]-1H-pyrazol-1-yl}nicotinamide trifluoroacetate

13.1 N-(4-Amino-3-hydroxy-4-oxo-1-phenylbutan-2-yl)-2-(3-((5,5-difluorohexahydrocyclopenta[c]pyrrol-2(1H)-yl)methyl)-1H-pyrazol-1-yl)nicotinamide 200 mg, mixture of diastereomers; ESI-MS [M+H]$^+$: 525.2.

13.2 N-(4-amino-3,4-dioxo-1-phenyl-2-butanyl)-2-{3-[(5,5-difluorohexahydrocyclopenta[c]pyrrol-2(1H)-yl)methyl]-1H-pyrazol-1-yl}nicotinamide trifluoroacetate Oxidation of N-(4-amino-3-hydroxy-4-oxo-1-phenylbutan-2-yl)-2-(3-((5,5-difluorohexahydrocyclopenta[c]pyrrol-2(1H)-yl)methyl)-1H-pyrazol-1-yl)nicotinamide (124 mg, 0.236 mmol) as described in example 3.4, purification of the crude product by prep. HPLC and lyophilisation afforded the title compound as white amorphous solid; 61 mg, ESI-MS [M+H]$^+$: 523.2. $^1$H-NMR (400 MHz, DMSO), δ[ppm]: 10.15 (broad), 8.97 (m, 1H), 8.59 (m, 1H), 8.43 (m, 1H), 8.08 (m, 1H), 7.84 (m, 2H), 7.53 (m, 1H), 7.28 (m, 5H), 6.61 (m, 1H), 5.37 (m, 1H), 4.10 (m, 1H), 3.75 (m, 1H), 3.18 (m, overlapping with water), 3.10-2.75 (m, 3H), 2.35 (m, 4H), 2.13 (m, 3H).

Example 14

N-(4-Amino-3,4-dioxo-1-phenylbutan-2-yl)-2-(3-((dihydro-1H-furo[3,4-c]pyrrol-5(3H,6H,6aH)-yl)methyl)-1H-pyrazol-1-yl)nicotinamide trifluoroacetate

14.1 N-(4-Amino-3-hydroxy-4-oxo-1-phenylbutan-2-yl)-2-(3-((dihydro-1H-furo[3,4-c]pyrrol-5(3H,6H,6aH)-yl)methyl)-1H-pyrazol-1-yl)nicotinamide 655 mg, mixture of diastereomers; ESI-MS [M+H]$^+$: 491.2.

14.2 N-(4-Amino-3,4-dioxo-1-phenylbutan-2-yl)-2-(3-((dihydro-1H-furo[3,4-c]pyrrol-5(3H,6H,6aH)-yl)methyl)-1H-pyrazol-1-yl)nicotinamide trifluoroacetate Oxidation of N-(4-amino-3-hydroxy-4-oxo-1-phenylbutan-2-yl)-2-(3-((dihydro-1H-furo[3,4-c]pyrrol-5(3H,6H,6aH)-yl)methyl)-1H-pyrazol-1-yl)nicotinamide (205 mg, 0.418 mmol) as described in example 3.4, purification of the crude product by prep. HPLC and lyophilisation afforded the title compound as white amorphous solid (mixture of diastereomeres); 113 mg, ESI-MS [M+H]$^+$: 489.0.

Example 15

N-(4-Amino-3,4-dioxo-1-phenylbutan-2-yl)-2-(3-(indolin-1-ylmethyl)-1H-pyrazol-1-yl)nicotinamide

15.1 N-(4-Amino-3-hydroxy-4-oxo-1-phenylbutan-2-yl)-2-(3-(indolin-1-ylmethyl)-1H-pyrazol-1-yl)nicotinamide 482 mg, mixture of diastereomers; ESI-MS [M+H]$^+$: 497.25.

15.2 N-(4-Amino-3,4-dioxo-1-phenylbutan-2-yl)-2-(3-(indolin-1-ylmethyl)-1H-pyrazol-1-yl)nicotinamide Oxidation of N-(4-amino-3-hydroxy-4-oxo-1-phenylbutan-2-yl)-2-(3-(indolin-1-ylmethyl)-1H-pyrazol-1-yl)nicotinamide (200 mg, 0.403 mmol) as described in example 3.4, purification of the crude product by prep. HPLC and lyophilisation afforded the title compound as white amorphous solid; 38 mg, ESI-MS [M+H]$^+$: 495.20. $^1$H-NMR (400 MHz, DMSO), δ[ppm]: 8.93 (m, 1H), 8.51 (m, 1H), 8.29 (m, 1H), 8.03 (m, 1H), 7.79 (m, 1H), 7.72 (m, 1H), 7.43 (m, 1H), 7.28 (m, 5H), 7.21 (m, 1H), 6.97 (m, 2H), 6.59 (m, 2H), 6.35 (m, 1H), 5.41 (m, 1H), 4.09 (m, 2H), 3.19 (m, overlapping with water) 2.92-2.85 (m, 3H).

Example 16

16.1 N-(4-Amino-3-hydroxy-4-oxo-1-phenylbutan-2-yl)-2-(3-((methyl(phenyl)amino)methyl)-1H-pyrazol-1-yl)nicotinamide 677 mg, mixture of diastereomers; ESI-MS [M+H]$^+$: 485.2.

16.2 N-(4-Amino-3,4-dioxo-1-phenylbutan-2-yl)-2-(3-((methyl(phenyl)amino)methyl)-1H-pyrazol-1-yl)nicotinamide Oxidation of N-(4-amino-3-hydroxy-4-oxo-1-phenylbutan-2-yl)-2-(3-((methyl(phenyl)amino)methyl)-1H-pyrazol-1-yl)nicotinamide (200 mg, 0.413 mmol) as described in example 1.4. The reaction was quenched by addition of 50 mL of a sat. NaHCO$_3$-solution at 4° C., the precipitate formed was isolated and crystallized from 2-propanole to give 61 mg of a white amorphous solid; ESI-MS [M+H]$^+$: 483.2. $^1$H-NMR (400 MHz, DMSO), δ[ppm]: 8.95 (m, 1H), 8.51 (m 1H), 8.26 (m, 1H), 8.01 (m, 1H), 7.87 (m, 1H), 7.71 (m, 1H), 7.42 (m, 1H), 7.31 (m, 4H), 7.25 (m, 1H), 7.13 (m, 2H), 6.75 (m, 2H), 6.60 (m, 1H), 6.22 (m, 1H), 5.45 (m, 1H), 4.29 (s, 2H), 3.18 (dd, 1H), 2.89 (m, 4H).

Example 17

2-(3-(2-Oxa-7-azaspiro[3.5]nonan-7-ylmethyl)-1H-pyrazol-1-yl)-N-(4-amino-3,4-dioxo-1-phenylbutan-2-yl)nicotinamide trifluoroacetate

17.1 2-(3-(2-Oxa-7-azaspiro[3.5]nonan-7-ylmethyl)-1H-pyrazol-1-yl)-N-(4-amino-3-hydroxy-4-oxo-1-phenylbutan-2-yl)nicotinamide 36 mg, mixture of diastereomers; ESI-MS [M+H]$^+$: 505.3.

17.2 2-(3-(2-Oxa-7-azaspiro[3.5]nonan-7-ylmethyl)-1H-pyrazol-1-yl)-N-(4-amino-3,4-dioxo-1-phenylbutan-2-yl)nicotinamide trifluoroacetate Oxidation of 2-(3-(2-oxa-7-azaspiro[3.5]nonan-7-ylmethyl)-1H-pyrazol-1-yl)-N-(4-amino-3-hydroxy-4-oxo-1-phenylbutan-2-yl)nicotinamide (180 mg, 0.357 mmol) as described in example 3.4, purification of the crude product by prep. HPLC and lyophilisation afforded the title compound as white amorphous solid; 44 mg, ESI-MS [M+H]$^+$: 502.3.

Example 18

18.1 N-(4-Amino-3-hydroxy-4-oxo-1-phenylbutan-2-yl)-2-(3-((diethylamino)methyl)-1H-pyrazol-1-yl)nicotinamide 478 mg, mixture of diastereomers; ESI-MS [M+H]$^+$: 451.2.

18.2 N-(4-Amino-3,4-dioxo-1-phenylbutan-2-yl)-2-(3-((diethylamino)methyl)-1H-pyrazol-1-yl)nicotinamide trifluoroacetate Oxidation of N-(4-amino-3-hydroxy-4-oxo-1-phenylbutan-2-yl)-2-(3-((diethylamino)methyl)-1H-pyrazol-1-yl)nicotinamide (250 mg, 0.555 mmol) as described in example 3.4, purification of the crude product by prep. HPLC and lyophilisation afforded the title compound as white amorphous solid; 48 mg, ESI-MS [M+H]$^+$: 449.2.

Example 19

N-(4-Amino-3,4-dioxo-1-phenylbutan-2-yl)-2-(3-(isoindolin-2-ylmethyl)-1H-pyrazol-1-yl)nicotinamide

19.1 N-(4-Amino-3-hydroxy-4-oxo-1-phenylbutan-2-yl)-2-(3-(isoindolin-2-ylmethyl)-1H-pyrazol-1-yl)nicotinamide 240 mg, mixture of diastereomers; ESI-MS [M+H]$^+$: 497.2.

19.2 N-(4-Amino-3,4-dioxo-1-phenylbutan-2-yl)-2-(3-(isoindolin-2-ylmethyl)-1H-pyrazol-1-yl)nicotinamide Oxidation of N-(4-amino-3-hydroxy-4-oxo-1-phenylbutan-2-yl)-2-(3-(isoindolin-2-ylmethyl)-1H-pyrazol-1-yl)nicotinamide (1.05 g, 2.115 mmol) as described in example 1.4, treatment of the crude product with ethyl acetate gave the title compound as white amorphous solid; 421 mg, ESI-MS [M+H]$^+$: 495.2. $^1$H-NMR (400 MHz, DMSO), δ [ppm]: 8.97 (m, 1H), 8.55 (m, 1H), 8.32 (m, 1H), 8.03 (m, 1H), 7.79 (m, 1H), 7.72 (m, 1H), 7.42 (m, 1H), 7.29-7.15 (m, 9H), 6.47 (m, 1H), 5.42 (m, 1H), 3.80 (s, 4H), 3.68 (m, 2H), 3.15 and 2.87 (each dd, 1H).

Example 20

N-(4-Amino-3,4-dioxo-1-phenylbutan-2-yl)-2-(3-((cyclohexyl(methyl)amino)methyl)-1H-pyrazol-1-yl)nicotinamide trifluoroacetate

20.1 N-(4-Amino-3-hydroxy-4-oxo-1-phenylbutan-2-yl)-2-(3-((cyclohexyl(methyl)-amino)methyl)-1H-pyrazol-1-yl)nicotinamide 816 mg, mixture of diastereomers; ESI-MS [M+H]$^+$: 491.2.

20.2 N-(4-Amino-3,4-dioxo-1-phenylbutan-2-yl)-2-(3-((cyclohexyl(methyl)amino)methyl)-1H-pyrazol-1-yl)nicotinamide trifluoroacetate Oxidation of N-(4-amino-3-hydroxy-4-oxo-1-phenylbutan-2-yl)-2-(3-((cyclohexyl(methyl)amino)methyl)-1H-pyrazol-1-yl)nicotinamide (200 mg, 0.408 mmol) as described in example 3.4, purification of the crude product by prep. HPLC and lyophilisation afforded the title compound as white amorphous solid; 78 mg, ESI-MS [M+H]$^+$: 489.2.

Example 21

N-(4-Amino-3,4-dioxo-1-phenylbutan-2-yl)-2-(3-((benzyl(methyl)amino)methyl)-1H-pyrazol-1-yl)nicotinamide trifluoroacetate

21.1 N-(4-Amino-3-hydroxy-4-oxo-1-phenylbutan-2-yl)-2-(3-((benzyl(methyl)amino)methyl)-1H-pyrazol-1-yl)nicotinamide 874 mg, mixture of diastereomers; ESI-MS [M+H]$^+$: 499.2.

21.2 N-(4-Amino-3,4-dioxo-1-phenylbutan-2-yl)-2-(3-((benzyl(methyl)amino)methyl)-1H-pyrazol-1-yl)nicotinamide trifluoroacetate Oxidation of N-(4-amino-3-hydroxy-4-oxo-1-phenylbutan-2-yl)-2-(3-((benzyl(methyl)amino)methyl)-1H-pyrazol-1-yl)nicotinamide (200 mg, 0.401 mmol) as described in example 3.4, purification of the crude product by prep. HPLC and lyophilisation afforded the title compound as white amorphous solid; 105 mg, ESI-MS [M+H]$^+$: 497.2. $^1$H-NMR (400 MHz, DMSO), δ [ppm]: 9.97 (broad), 8.99 (m, 1H), 8.61 (m, 1H), 8.45 (m, 1H), 8.07 (m, 1H), 7.80 (m, 2H), 7.50 (m, 7H), 7.19 (m, 5H), 6.65 (m, 1H), 5.34 (m, 1H), 4.38-3.90 (m, 4H), 3.10 and 2.76 (each dd, 1H), 2.55 (s, overlapping with DMSO).

Example 22

N-(4-Amino-3,4-dioxo-1-phenylbutan-2-yl)-2-(3-((3,4-dihydroisoquinolin-2(1H)-yl)methyl)-1H-pyrazol-1-yl)nicotinamide

22.1 N-(4-Amino-3-hydroxy-4-oxo-1-phenylbutan-2-yl)-2-(3-((3,4-dihydroisoquinolin-2(1H)-yl)methyl)-1H-pyrazol-1-yl)nicotinamide 690 mg, mixture of diastereomers; ESI-MS [M+H]$^+$: 511.2.

22.2 N-(4-Amino-3,4-dioxo-1-phenylbutan-2-yl)-2-(3-((3,4-dihydroisoquinolin-2(1H)-yl)methyl)-1H-pyrazol-1-yl)nicotinamide Oxidation of N-(4-amino-3-hydroxy-4-oxo-1-phenylbutan-2-yl)-2-(3-((3,4-dihydroisoquinolin-2(1H)-yl)methyl)-1H-pyrazol-1-yl)nicotinamide (200 mg, 0.392 mmol) as described in example 1.4, recrystallization of the crude product from CH$_2$Cl$_2$/MTB gave the title compound as white amorphous solid; 52 mg, ESI-MS [M+H]$^+$: 509.2. $^1$H-NMR (400 MHz, DMSO), δ[ppm]: 8.98 (m, 1H), 8.59 (m, 1H), 8.42 (m, 1H), 8.07 (m, 1H), 7.83 (m, 1H), 7.74 (m, 1H), 7.44 (m, 1H), 7.29-7.15 (m, 5H), 7.10-7.00 (m, 4H), 6.43 (m, 1H), 5.43 (m, 1H), 3.48 (m, 4H), 3.17 and 2.91 (each dd, 1H), 2.91 (m, 2H), 2.61 (m, 2H).

Example 23

N-(4-Amino-3,4-dioxo-1-phenylbutan-2-yl)-2-(3-((4-tert-butylpiperidin-1-yl)methyl)-1H-pyrazol-1-yl)nicotinamide

23.1 N-(4-Amino-3-hydroxy-4-oxo-1-phenylbutan-2-yl)-2-(3-((4-tert-butylpiperidin-1-yl)methyl)-1H-pyrazol-1-yl)nicotinamide 670 mg, mixture of diastereomers; ESI-MS [M+H]$^+$: 519.2.

23.2 N-(4-Amino-3,4-dioxo-1-phenylbutan-2-yl)-2-(3-((4-tert-butylpiperidin-1-yl)methyl)-1H-pyrazol-1-yl)nicotinamide Oxidation of N-(4-amino-3-hydroxy-4-oxo-1-phenylbutan-2-yl)-2-(3-((4-tert-butylpiperidin-1-yl)methyl)-1H-pyrazol-1-yl)nicotinamide (200 mg, 0.386 mmol) as described in example 1.4, recrystallization of the crude product from CH$_2$Cl$_2$/MTB gave the title compound as white amorphous solid; 34 mg, ESI-MS [M+H]$^+$: 517.2. $^1$H-NMR (400 MHz, DMSO), δ[ppm]: 8.94 (m, 1H), 8.52 (m, 1H), 8.30 (m, 1H), 8.05 (m, 1H), 7.82 (m, 1H), 7.74 (m, 1H), 7.43 (m, 5H), 6.37 (m, 1H), 5.36 (m, 1H), 3.27 (m, overlapping with water), 2.88 (m, 3H), 1.75 (m, 2H), 1.54 (m, 2 h), 1.15 (m, 2H), 0.82 (m, 11H).

Example 24

N-(4-Amino-3,4-dioxo-1-phenylbutan-2-yl)-2-(3-((4-methylpiperidin-1-yl)methyl)-1H-pyrazol-1-yl)nicotinamide trifluoroacetate

24.1 N-(4-Amino-3-hydroxy-4-oxo-1-phenylbutan-2-yl)-2-(3-((4-methylpiperidin-1-yl)methyl)-1H-pyrazol-1-yl)nicotinamide 265 mg, mixture of diastereomers; ESI-MS [M+H]$^+$: 477.2.

24.2 N-(4-Amino-3,4-dioxo-1-phenylbutan-2-yl)-2-(3-((4-methylpiperidin-1-yl)methyl)-1H-pyrazol-1-yl)nicotinamide trifluoroacetate Oxidation of N-(4-amino-3-hydroxy-4-oxo-1-phenylbutan-2-yl)-2-(3-((4-methylpiperidin-1-yl)methyl)-1H-pyrazol-1-yl)nicotinamide (260 mg, 0.546 mmol) as described in example 3.4, purification of the crude product by prep. HPLC and lyophilisation afforded the title compound as white amorphous solid; 52 mg, ESI-MS [M+H]$^+$: 475.2.

Example 25

25.1 N-(4-Amino-3-hydroxy-4-oxo-1-phenylbutan-2-yl)-2-(3-((methyl((4-(trifluoromethyl)cyclohexyl)methyl)amino)methyl)-1H-pyrazol-1-yl)nicotinamide 529 mg, mixture of diastereomers; ESI-MS [M+H]$^+$: 573.2.

25.2 N-(4-Amino-3,4-dioxo-1-phenylbutan-2-yl)-2-(3-((methyl((4-(trifluoromethyl)cyclohexyl)methyl)amino)methyl)-1H-pyrazol-1-yl)nicotinamide trifluoroacetate Oxidation of N-(4-amino-3-hydroxy-4-oxo-1-phenylbutan-2-yl)-2-(3-((methyl((4-(trifluoromethyl)cyclohexyl)methyl)amino)methyl)-1H-pyrazol-1-yl)nicotinamide (200 mg, 0.349 mmol) as described in example 3.4, purification of the crude product by prep. HPLC and lyophilisation afforded the title compound as white amorphous solid; 108 mg, ESI-MS [M+H]$^+$: 471.2.

Example 26

26.1 N-(4-Amino-3-hydroxy-4-oxo-1-phenylbutan-2-yl)-2-(3-((cyclopropyl(methyl)amino)methyl)-1H-pyrazol-1-yl)nicotinamide 595 mg, mixture of diastereomers; ESI-MS [M+H]$^+$: 449.2.

26.2 N-(4-Amino-3,4-dioxo-1-phenylbutan-2-yl)-2-(3-((cyclopropyl(methyl)amino)methyl)-1H-pyrazol-1-yl)nicotinamide trifluoroacetate Oxidation of N-(4-amino-3-hydroxy-4-oxo-1-phenylbutan-2-yl)-2-(3-((cyclopropyl(methyl)amino)methyl)-1H-pyrazol-1-yl)nicotinamide (200 mg, 0.446 mmol) as described in example 3.4, purification of the crude product by prep. HPLC and lyophilisation afforded the title compound as white amorphous solid; 78 mg, ESI-MS [M+H]$^+$: 447.2.

Example 27

N-(4-Amino-3,4-dioxo-1-phenylbutan-2-yl)-2-(3-(((6R)-6-(4-fluorophenyl)-3-azabicyclo[3.2.0]heptan-3-yl)methyl)-1H-pyrazol-1-yl)nicotinamide trifluoroacetate

27.1 N-(4-Amino-3-hydroxy-4-oxo-1-phenylbutan-2-yl)-2-(3-(((6R)-6-(4-fluorophenyl)-3-azabicyclo[3.2.0]heptan-3-yl)methyl)-1H-pyrazol-1-yl)nicotinamide 516 mg, mixture of diastereomers; ESI-MS [M+H]$^+$: 569.2.

27.2 N-(4-Amino-3,4-dioxo-1-phenylbutan-2-yl)-2-(3-(((6R)-6-(4-fluorophenyl)-3-azabicyclo[3.2.0]heptan-3-yl)methyl)-1H-pyrazol-1-yl)nicotinamide trifluoroacetate Oxidation of N-(4-amino-3-hydroxy-4-oxo-1-phenylbutan-2-yl)-2-(3-(((6R)-6-(4-fluorophenyl)-3-azabicyclo

[3.2.0]heptan-3-yl)methyl)-1H-pyrazol-1-yl)nicotinamide (155 mg, 0.273 mmol) as described in example 3.4, purification of the crude product by prep. HPLC and lyophilisation afforded the title compound as white amorphous solid; 46 mg, ESI-MS [M+H]$^+$: 567.2.

Example 28

N-(4-Amino-3,4-dioxo-1-phenylbutan-2-yl)-2-(3-((phenylamino)methyl)-1H-pyrazol-1-yl)nicotinamide 28.1 N-(4-Amino-3-hydroxy-4-oxo-1-phenylbutan-2-yl)-2-(3-((phenylamino)methyl)-1H-pyrazol-1-yl)nicotinamide 120 mg, mixture of diastereomers; ESI-MS [M+H]$^+$: 471.2.

28.2 N-(4-Amino-3,4-dioxo-1-phenylbutan-2-yl)-2-(3-((phenylamino)methyl)-1H-pyrazol-1-yl)nicotinamide Oxidation of N-(4-amino-3-hydroxy-4-oxo-1-phenylbutan-2-yl)-2-(3-((phenylamino)methyl)-1H-pyrazol-1-yl)nicotinamide (120 mg, 0.255 mmol) as described in example 3.4, purification of the crude product by prep. HPLC and lyophilisation afforded the title compound as white amorphous solid; 3.8 mg, ESI-MS [M+H]$^+$: 469.2. $^1$H-NMR (400 MHz, DMSO), δ[ppm]: 8.96 (m, 1H), 8.52 (m, 1H), 8.29 (m, 1H), 8.05 (m, 1H), 7.85 (m, 1H), 7.71 (m, 1H), 7.45 (m, 1H), 7.21 (m, 6H), 7.06 (m, 2H), 6.56 (m, 1H), 6.36 (m, 1H), 5.42 (m, 1H), 4.08 (m, 2H), 3.19 and 2.90 (each dd, 1H).

Example 29

N-(4-Amino-3,4-dioxo-1-phenylbutan-2-yl)-2-(3-((3-phenylpyrrolidin-1-yl)methyl)-1H-pyrazol-1-yl)nicotinamide 29.1 N-(4-Amino-3-hydroxy-4-oxo-1-phenylbutan-2-yl)-2-(3-((3-phenylpyrrolidin-1-yl)methyl)-1H-pyrazol-1-yl)nicotinamide 668 mg, mixture of diastereomers; ESI-MS [M+H]$^+$: 525.3.

29.2 N-(4-Amino-3,4-dioxo-1-phenylbutan-2-yl)-2-(3-((3-phenylpyrrolidin-1-yl)methyl)-1H-pyrazol-1-yl)nicotinamide Oxidation of N-(4-amino-3-hydroxy-4-oxo-1-phenylbutan-2-yl)-2-(3-((phenylamino)methyl)-1H-pyrazol-1-yl)nicotinamide (120 mg, 0.255 mmol) as described in example 1.4, subsequent crystallization of the crude product from 2-propanole and then from ethylacetate afforded the title compound as white amorphous solid; 80 mg, ESI-MS [M+H]$^+$: 523.3. $^1$H-NMR (400 MHz, DMSO), δ[ppm]: 8.93 (m, 1H), 8.50 (m, 1H), 8.32 (m, 1H), 8.06 (m, 1H), 7.71 (m, 1H), 7.42-7.25 (m, 10H), 6.42 (m, 1H), 5.38 (m, 1H), 3.49 (m, 2H), 3.25 (m, 1H), 3.17 (dd, 1H), 2.88 (m, 2H), 2.63 (m, 2H), 2.39 (m, 1H), 2.21 (m, 1H), 1.72 (m, 1H).

Example 30

N-(4-Amino-3,4-dioxo-1-phenylbutan-2-yl)-2-(3-((5-(trifluoromethyl)isoindolin-2-yl)methyl)-1H-pyrazol-1-yl)nicotinamide trifluoroacetate 30.1 N-(4-Amino-3-hydroxy-4-oxo-1-phenylbutan-2-yl)-2-(3-((5-(trifluoromethyl)isoindolin-2-yl)methyl)-1H-pyrazol-1-yl)nicotinamide 795 mg, mixture of diastereomers; ESI-MS [M+H]$^+$: 565.3.

30.2 N-(4-Amino-3,4-dioxo-1-phenylbutan-2-yl)-2-(3-((5-(trifluoromethyl)isoindolin-2-yl)methyl)-1H-pyrazol-1-yl)nicotinamide trifluoroacetate Oxidation of N-(4-amino-3-hydroxy-4-oxo-1-phenylbutan-2-yl)-2-(3-((5-(trifluoromethyl)isoindolin-2-yl)methyl)-1H-pyrazol-1-yl)nicotinamide (250 mg, 0.443 mmol) as described in example 3.4, purification of the crude product by prep. HPLC and lyophilisation afforded the title compound as white amorphous solid; 162 mg, ESI-MS [M+H]$^+$: 563.2. $^1$H-NMR (400 MHz, DMSO), δ[ppm]: 9.03 (m, 1H), 8.58 (m, 1H), 8.43 (m, 1H), 8.10 (m, 1H), 7.87 (m, 1H), 7.82 (m, 2H), 7.76 (m, 1H), 7.65 (m, 1H), 7.56 (m, 1H), 7.19 (m, 5H), 6.66 (m, 1H), 5.42 (m, 1H), 4.66-4.22 (m, 6 h), 3.14 and 2.80 (each dd, 1H).

Example 31

N-(4-Amino-3,4-dioxo-1-phenylbutan-2-yl)-2-(3-((5-fluoroisoindolin-2-yl)methyl)-1H-pyrazol-1-yl)nicotinamide trifluoroacetate 31.1 N-(4-Amino-3-hydroxy-4-oxo-1-phenylbutan-2-yl)-2-(3-((5-fluoroisoindolin-2-yl)methyl)-1H-pyrazol-1-yl)nicotinamide 319 mg, mixture of diastereomers; ESI-MS [M+H]$^+$: 515.2.

31.2 N-(4-Amino-3,4-dioxo-1-phenylbutan-2-yl)-2-(3-((5-fluoroisoindolin-2-yl)methyl)-1H-pyrazol-1-yl)nicotinamide trifluoroacetate Oxidation of N-(4-amino-3-hydroxy-4-oxo-1-phenylbutan-2-yl)-2-(3-((5-fluoroisoindolin-2-yl)methyl)-1H-pyrazol-1-yl)nicotinamide (319 mg, 0.620 mmol) as described in example 3.4, purification of the crude product by prep. HPLC and lyophilisation afforded the title compound as white amorphous solid; 70 mg, ESI-MS [M+H]$^+$: 513.2. $^1$H-NMR (400 MHz, DMSO), δ[ppm]: 11.11 (broad), 9.05 (m, 1H), 8.59 (m, 1H), 8.43 (m, 1H), 8.10 (m, 1H), 7.88 (m, 1H), 7.82 (m, 1H), 7.55 (m, 1H), 7.45 (m, 1H), 7.31 (m, 1H), 7.20 (m, 6H), 6.66 (m, 1H), 5.41 (m, 1H), 4.75 (m, 2H), 4.46 (m, 2H), 4.25 (m, 2H), 3.14 and 2.81 (each dd, 1H).

Example 32

N-(4-Amino-3,4-dioxo-1-phenylbutan-2-yl)-2-(3-((4-phenylpiperazin-1-yl)methyl)-1H-pyrazol-1-yl) nicotinamide trifluoroacetate 32.1 N-(4-Amino-3-hydroxy-4-oxo-1-phenylbutan-2-yl)-2-(3-((3-phenylpyrrolidin-1-yl)methyl)-1H-pyrazol-1-yl)nicotinamide 860 mg, mixture of diastereomers; ESI-MS [M+H]$^+$: 540.3.

32.2 N-(4-Amino-3,4-dioxo-1-phenylbutan-2-yl)-2-(3-((4-phenylpiperazin-1-yl)methyl)-1H-pyrazol-1-yl)nicotinamide trifluoroacetate Oxidation of N-(4-amino-3-hydroxy-4-oxo-1-phenylbutan-2-yl)-2-(3-((4-phenylpiperazin-1-yl)methyl)-1H-pyrazol-1-yl)nicotinamide (250 mg, 0.463 mmol) as described in example 3.4, purification of the crude product by prep. HPLC and lyophilisation afforded the title compound as white amorphous solid; 156 mg, ESI-MS [M+H]$^+$: 538.2. $^1$H-NMR (400 MHz, DMSO), δ[ppm]: 9.98 (broad), 9.07 (m, 1H), 8.61 (m, 1H), 8.47 (m, 1H), 8.11 (m, 1H), 7.89 (m, 1H), 7.84 (m, 1H), 7.57 (m, 1H), 7.27 (m, 7H), 7.02 (m, 2H), 6.88 (m, 1H), 6.65 (m, 1H), 5.40 (m, 1H), 4.35 (m, 1H), 4.06 (m, 1H), 3.80 (m, 2H), 3.50 (overlapping with water), 3.15 (dd, 1H), 2.96 (m, 2H), 2.86 (dd, 1H).

Example 33

N-(4-Amino-3,4-dioxo-1-phenylbutan-2-yl)-2-(3-((4-fluoroisoindolin-2-yl)methyl)-1H-pyrazol-1-yl) nicotinamide trifluoroacetate 33.1 N-(4-Amino-3-hydroxy-4-oxo-1-phenylbutan-2-yl)-2-(3-((4-fluoroisoindolin-2-yl)methyl)-1H-pyrazol-1-yl)nicotinamide 505 mg, mixture of diastereomers; ESI-MS [M+H]$^+$: 515.2.

33.2 N-(4-Amino-3,4-dioxo-1-phenylbutan-2-yl)-2-(3-((4-fluoroisoindolin-2-yl)methyl)-1H-pyrazol-1-yl)nicotinamide trifluoroacetate Oxidation of N-(4-amino-3-hydroxy-4-oxo-1-phenylbutan-2-yl)-2-(3-((4-fluoroisoindolin-2-yl)methyl)-1H-pyrazol-1-yl)nicotinamide (230 mg, 0.447 mmol)) as described in example 3.4, purification of the crude product by prep. HPLC and lyophilisation afforded the title compound as white amorphous solid; 118 mg, ESI-MS [M+H]$^+$: 513.2. $^1$H-NMR (400 MHz, DMSO), δ[ppm]: 11.15 (broad), 8.99 (m, 1H), 8.59 (m, 1H), 8.43 (m, 1H), 8.07 (m, 1H), 7.78 (m, 2H), 7.54 (m, 1H), 7.45 (m, 1H), 7.20 (m, 8H), 6.66 (m, 1H), 5.39 (m, 1H), 4.85-4.17 (m, 6H), 3.14 and 2.80 (each dd, 1H).

Example 34

N-(4-Amino-3,4-dioxo-1-phenyl-2-butanyl)-2-{3-[(1,1-dioxido-4-thiomorpholinyl)methyl]-1H-pyrazol-1-yl}nicotinamide trifluoroacetate 34.1 N-(4-Amino-3-hydroxy-4-oxo-1-phenyl-2-butanyl)-2-{3-[(1,1-dioxido-4-thiomorpholinyl)methyl]-1H-pyrazol-1-yl}nicotinamide 550 mg, mixture of diastereomers; ESI-MS [M+H]$^+$: 513.2.

34.2 N-(4-Amino-3,4-dioxo-1-phenyl-2-butanyl)-2-{3-[(1,1-dioxido-4-thiomorpholinyl)methyl]-1H-pyrazol-1-yl}nicotinamide trifluoroacetate Oxidation of N-(4-amino-3-hydroxy-4-oxo-1-phenyl-2-butanyl)-2-{3-[(1,1-dioxido-4-thiomorpholinyl)methyl]-1H-pyrazol-1-yl}nicotinamide (150 mg, 0.293 mmol) as described in example 3.4, purification of the crude product by prep. HPLC and lyophilisation afforded the title compound as white amorphous solid; 70 mg, ESI-MS [M+H]$^+$: 511.2. $^1$H-NMR (400 MHz, DMSO), δ[ppm]: 8.94 (m, 1H), 8.58 (m, 1H), 8.33 (m, 1H), 8.04 (m, 1H), 7.81 (m, 1H), 7.75 (m, 1H), 7.48 (m, 1H), 7.30 (m, 4H), 7.24 (m, 1H), 6.48 (m, 1H), 5.36 (m, 1H), 3.56 (overlapping with water), 3.17 (m, 5H), 3.03 (broad), 2.86 (dd, 1H).

Example 35

N-(4-Amino-3,4-dioxo-1-phenylbutan-2-yl)-2-(3-(1-(isoindolin-2-yl)ethyl)-1H-pyrazol-1-yl)nicotinamide trifluoroacetate 35.1 N-(4-Amino-3-hydroxy-4-oxo-1-phenylbutan-2-yl)-2-(3-(1-(isoindolin-2-yl)ethyl)-1H-pyrazol-1-yl)nicotinamide 460 mg, mixture of diastereomers; ESI-MS [M+H]$^+$: 511.2.

35.2 N-(4-Amino-3,4-dioxo-1-phenylbutan-2-yl)-2-(3-(1-(isoindolin-2-yl)ethyl)-1H-pyrazol-1-yl)nicotinamide trifluoroacetate Oxidation of N-(4-amino-3-hydroxy-4-oxo-1-phenylbutan-2-yl)-2-(3-(1-(isoindolin-2-yl)ethyl)-1H-pyrazol-1-yl) nicotinamide (200 mg, 0.392 mmol) as described in example 3.4, purification of the crude product by prep. HPLC and lyophilisation afforded the title compound as white amorphous solid; mixture of diastereomeres, 77 mg, ESI-MS [M+H]$^+$: 509.2.

Example 36

N-(4-Amino-3,4-dioxo-1-phenylbutan-2-yl)-2-(3-((l-oxoisoindolin-2-yl)methyl)-1H-pyrazol-1-yl)nicotinamide 36.1 N-(4-Amino-3-hydroxy-4-oxo-1-phenylbutan-2-yl)-2-(3-((l-oxoisoindolin-2-yl)methyl)-1H-pyrazol-1-yl)nicotinamide 100 mg, mixture of diastereomers; ESI-MS [M+H]$^+$: 511.2.

36.2 N-(4-Amino-3,4-dioxo-1-phenylbutan-2-yl)-2-(3-((1-oxoisoindolin-2-yl)methyl)-1H-pyrazol-1-yl)nicotinamide Oxidation of N-(4-amino-3-hydroxy-4-oxo-1-phenylbutan-2-yl)-2-(3-((1-oxoisoindolin-2-yl)methyl)-1H-pyrazol-1-yl)nicotinamide (100 mg, 0.196 mmol) as described in example 1.4, purification by chromatography over Chromabond-RP C18 (eluent water+0-60% acetonitril+0.5% glacial acetic acid) and recrystallization of the crude product from 2-propanol afforded the title compound as white amorphous solid; 12 mg, ESI-MS [M+H]$^+$: 509.2.

Example 37

N-(1-Amino-1,2-dioxoheptan-3-yl)-2-(3-(piperidin-1-ylmethyl)-1H-pyrazol-1-yl)nicotinamide

37.1 N-(1-Amino-2-hydroxy-1-oxoheptan-3-yl)-2-(3-(piperidin-1-ylmethyl)-1H-pyrazol-1-yl)nicotinamide Coupling with 3-amino-2-hydroxyheptanamide hydrochloride according to the procedure described for example 1.3 afforded 284 mg of the title compound; ESI-MS [M+H]$^+$: 465.2.

37.2 N-(1-Amino-1,2-dioxoheptan-3-yl)-2-(3-(piperidin-1-ylmethyl)-1H-pyrazol-1-yl)nicotinamide Oxidation of N-(1-amino-2-hydroxy-1-oxoheptan-3-yl)-2-(3-(piperidin-1-ylmethyl)-1H-pyrazol-1-yl)nicotinamide (180 mg, 0.378 mmol) as described in example 1.4 and treatment of the crude product with a mixture of ethyl acetate and MTB 1:1, filtering off the remaining solid and drying gave the title compound as white amorphous solid; 63 mg, ESI-MS [M+H]$^+$: 427.2. $^1$H-NMR (400 MHz, DMSO), δ[ppm]: 8.67 (d, 1H), 8.51 (m, 1H), 8.33 (m, 1H), 7.99 (m, 1H), 7.82 (m, 1H), 7.75 (m, 1H), 7.44 (m, 1H), 6.40 (m, 1H), 5.07 (m, 1H), 3.40 (s, 2H), 2.33 (m, 4H), 1.76 (m, 1H), 1.48 (m, 5H), 1.36 (m, 6H), 0.87 (m, 3H).

Example 38

N-(1-Amino-1,2-dioxoheptan-3-yl)-2-(3-((4,4-difluoropiperidin-1-yl)methyl)-1H-pyrazol-1-yl)nicotinamide

38.1 N-(1-Amino-2-hydroxy-1-oxoheptan-3-yl)-2-(3-((4,4-difluoropiperidin-1-yl)methyl)-1H-pyrazol-1-yl)nicotinamide Coupling with 3-amino-2-hydroxyheptanamide hydrochloride according to the procedure described for example 1.3 afforded 340 mg of the title compound; ESI-MS [M+H]$^+$: 429.2.

38.2 N-(1-Amino-1,2-dioxoheptan-3-yl)-2-(3-((4,4-difluoropiperidin-1-yl)methyl)-1H-pyrazol-1-yl)nicotinamide Oxidation of N-(1-amino-2-hydroxy-1-oxoheptan-3-yl)-2-(3-((4,4-difluoropiperidin-1-yl)methyl)-1H-pyrazol-1-yl)nicotinamide (140 mg, 0.301 mmol) as described in example 1.4 and treatment of the crude product with MTB, filtering off the remaining solid and drying gave the title compound as white amorphous solid; 74 mg, ESI-MS [M+H]$^+$: 463.2. $^1$H-NMR (400 MHz, DMSO), δ[ppm]: 8.70 (d, 1H), 8.53 (dd, 1H), 8.31 (m, 1H), 7.99 (m, 1H), 7.82 (m, 1H), 7.75 (m, 1H), 7.45 (m, 1H), 6.43 (m, 1H), 5.07 (m, 1H), 3.53 (s, 2H), 1.94 (m, 4H), 1.74 (m, 1H), 1.50 (m, 1H), 1.31 (m, 4H), 0.87 (m, 3H).

Example 39

N-(1-Amino-1,2-dioxoheptan-3-yl)-2-(3-(isoindolin-2-ylmethyl)-1H-pyrazol-1-yl)nicotinamide

39.1 N-(1-Amino-2-hydroxy-1-oxoheptan-3-yl)-2-(3-(isoindolin-2-ylmethyl)-1H-pyrazol-1-yl)nicotinamide Coupling with 3-amino-2-hydroxyheptanamide hydrochloride according to the procedure described for example 1.3 afforded 463 mg of the title compound; ESI-MS [M+H]$^+$: 463.3.

39.2 N-(1-Amino-1,2-dioxoheptan-3-yl)-2-(3-(isoindolin-2-ylmethyl)-1H-pyrazol-1-yl)nicotinamide Oxidation of the compound of example 39.1 (180 mg, 0.389 mmol) as described in example 1.4 and treatment of the crude product with ethylacetate/MTB, filtering off the remaining solid and drying gave the title compound as white amorphous solid; 77 mg, ESI-MS [M+H]$^+$: 461.2. $^1$H-NMR (400 MHz, DMSO), δ[ppm]: 8.73 (d, 1H), 8.54 (dd, 1H), 8.40 (m, 1H), 8.00 (m, 1H), 7.85 (m, 1H), 7.75 (m, 1H), 7.47 (m, 1H), 7.22 (m, 2H), 7.19 (m, 2H), 6.48 (m, 1H), 5.11 (m, 1H), 3.89 (s, 4H), 3.84 (s, 2H), 1.77 (m, 1H), 1.51 (m, 1H), 1.29 (m, 4H), 0.81 (m, 3H).

Example 40

N-(4-Amino-3,4-dioxo-1-phenylbutan-2-yl)-2-(5-benzyl-4,5,6,7-tetrahydro-2H-pyrazolo[4,3-c]pyridin-2-yl)nicotinamide

40.1 N-(4-Amino-3-hydroxy-4-oxo-1-phenylbutan-2-yl)-2-(5-benzyl-4,5,6,7-tetrahydro-2H-pyrazolo[4,3-c]pyridin-2-yl)nicotinamide Coupling according to the procedure described for example 1.3 and purification of the crude product by chromatography over silica gel (eluent: dichloromethane/methanol) afforded 45 mg of the title compound; ESI-MS [M+H]$^+$: 511.2.

40.2 N-(4-Amino-3,4-dioxo-1-phenylbutan-2-yl)-2-(5-benzyl-4,5,6,7-tetrahydro-2H-pyrazolo[4,3-c]pyridin-2-yl)nicotinamide Oxidation of N-(4-amino-3-hydroxy-4-oxo-1-phenylbutan-2-yl)-2-(5-benzyl-4,5,6,7-tetrahydro-2H-pyrazolo[4,3-c]pyridin-2-yl)nicotinamide (45 mg, 0.088 mmol) as described in example 1.4 and treatment of the crude product with MTB, filtering off the remaining solid and drying gave the title compound as white amorphous solid; 27 mg, ESI-MS [M+H]$^+$: 509.2.

Example 41

N-(4-Amino-3,4-dioxo-1-phenylbutan-2-yl)-2-(5-(cyclopropylmethyl)-4,5,6,7-tetrahydro-2H-pyrazolo[4,3-c]pyridin-2-yl)nicotinamide

41.1 N-(4-Amino-3-hydroxy-4-oxo-1-phenylbutan-2-yl)-2-(5-(cyclopropylmethyl)-4,5,6,7-tetrahydro-2H-pyrazolo[4,3-c]pyridin-2-yl)nicotinamide Coupling according to the procedure described for example 1.3 and purification of the crude product by chromatography over silica gel (eluent: dichloromethane/methanol) afforded 200 mg of the title compound; ESI-MS [M+H]$^+$: 475.2.

41.2 N-(4-Amino-3,4-dioxo-1-phenylbutan-2-yl)-2-(5-(cyclopropylmethyl)-4,5,6,7-tetrahydro-2H-pyrazolo[4,3-c]pyridin-2-yl)nicotinamide Oxidation of N-(4-amino-3-hydroxy-4-oxo-1-phenylbutan-2-yl)-2-(5-(cyclopropylmethyl)-4,5,6,7-tetrahydro-2H-pyrazolo[4,3-c]pyridin-2-yl)nicotinamide (100 mg, 0.211 mmol) as described in example 1.4 and recrystallization of the crude product from 2-propanole gave the title compound as white amorphous solid; 30 mg, ESI-MS [M+H]$^+$: 473.2.

Example 42

N-(4-Amino-3,4-dioxo-1-phenylbutan-2-yl)-2-(4,5,6,7-tetrahydro-2H-pyrazolo[4,3-c]pyridin-2-yl)nicotinamide hydrochloride

42.1 tert-Butyl 2-(3-(4-amino-3-hydroxy-4-oxo-1-phenylbutan-2-ylcarbamoyl)pyridin-2-yl)-6,7-dihydro-2H-pyrazolo[4,3-c]pyridine-5(4H)-carboxylate Coupling according to the procedure described for example 1.3 and purification of the crude product by chromatography over silica gel (eluent: dichloromethane/methanol) afforded 180 mg of the title compound; ESI-MS [M+H]$^+$: 521.2.

42.2 N-(4-Amino-3,4-dioxo-1-phenylbutan-2-yl)-2-(4,5,6,7-tetrahydro-2H-pyrazolo[4,3-c]pyridin-2-yl)nicotinamide hydrochloride Oxidation of tert-butyl 2-(3-(4-amino-3-hydroxy-4-oxo-1-phenylbutan-2-ylcarbamoyl)pyridin-2-yl)-6,7-dihydro-2H-pyrazolo[4,3-c]pyridine-5(4H)-carboxylate (170 mg, 0.327 mmol) as described in example 1.4 gave 105 mg of an amorphous solid; ESI-MS [M+H]$^+$: 519.2.

70 mg of the obtained Boc-protected compound in 10 mL of dichloromethane were treated with 200 μL of 4M HCl in dioxane over night, the mixture concentrated and the obtained solid treated again with dichloromethane gave 39 mg of a white-yellow amorphous solid; ESI-MS [M+H]$^+$: 419.2.

Example 43 tert-Butyl 2-(3-(4-amino-3,4-dioxo-1-phenylbutan-2-ylcarbamoyl)pyridin-2-yl)-4,6-dihydropyrrolo[3,4-c]pyrazole-5(2H)-carboxylate

43.1 tert-Butyl 2-(3-(4-amino-3-hydroxy-4-oxo-1-phenylbutan-2-ylcarbamoyl)pyridin-2-yl)-4,6-dihydropyrrolo[3,4-c]pyrazole-5(2H)-carboxylate Coupling according to the procedure described for example 1.3 and treatment of the obtained crude product with water afforded 90 mg of the title compound; ESI-MS [M+H]$^+$: 507.2.

43.2 tert-Butyl 2-(3-(4-amino-3,4-dioxo-1-phenylbutan-2-ylcarbamoyl)pyridin-2-yl)-4,6-dihydropyrrolo[3,4-c]pyrazole-5(2H)-carboxylate Oxidation of tert-butyl 2-(3-(4-amino-3-hydroxy-4-oxo-1-phenylbutan-2-ylcarbamoyl)pyridin-2-yl)-4,6-dihydropyrrolo[3,4-c]pyrazole-5(2H)-carboxylate (88 mg, 0.174 mmol) as described in example 1.4 and purification by chromatography over Chromabond RP-C18 (eluent: water/acetonitrile) gave 55 mg of an amorphous solid; ESI-MS [M+H]$^+$: 505.2. $^1$H-NMR (400 MHz, DMSO), δ[ppm]: 8.83 (m, 1H), 8.52 (m, 1H), 8.15 (m, 1H), 8.06 (m, 1H), 7.84 (m, 1H), 7.72 (m, 1H), 7.44 (m, 1H), 7.23 (m, 4H), 7.17 (m, 1H), 5.26 (m, 1H), 4.35 (m, 2H), 4.18 (m, 1H), 4.0 (m, 1H), 3.09 (m, 1H), 2.73 (m, 1H), 1.49 (s, 9H).

Example 44

N-(4-Amino-3,4-dioxo-1-phenyl-2-butanyl)-2-(5,6-dihydropyrrolo[3,4-c]pyrazol-2(4H)-yl)nicotinamide hydrochloride To a solution of tert-butyl 2-(3-(4-amino-3,4-dioxo-1-phenylbutan-2-ylcarbamoyl)-pyridin-2-yl)-4,6-dihydropyrrolo[3,4-c]pyrazole-5(2H)-carboxylate (50 mg, 0.099 mmol) in dichloromethane (10 mL) 4004 of 4M HCl in dioxan were added and stirred over night at room temperature. The mixture then was concentrated, the remainder treated with MTB and the remaining solid then further purified by chromatography over Chromabond RP-C18 (eluent: water/acetonitrile) to give 30 mg of the titel compound; ESI-MS [M+H]$^+$: 405.1. $^1$H-NMR (400 MHz, DMSO), δ[ppm]: 10.41 (broad), 8.93 (m, 1H), 8.54 (m, 1H), 8.21 (m, 1H), 8.06 (m, 1H), 7.85 (m, 1H), 7.71 (m, 1H), 7.49 (m, 1H), 7.26 (m, 5H), 5.33 (m, 1H), 4.35-4.16 (m, 5H), 3.12 (m, 1H), 2.84 (m, 1H).

Example 45 tert-Butyl 2-(3-(4-amino-3,4-dioxo-1-phenylbutan-2-ylcarbamoyl)pyridin-2-yl)-2,4,5,7-tetrahydro-6H-pyrazolo[3,4-c]pyridine-6-carboxylate

45.1 tert-Butyl 2-(3-(4-amino-3-hydroxy-4-oxo-1-phenylbutan-2-ylcarbamoyl)pyridin-2-yl)-4,5-dihydro-2H-pyrazolo[3,4-c]pyridine-6(7H)-carboxylate Coupling according to the procedure described for example 1.3 and treatment of the obtained crude product with water afforded 90 mg of the title compound; ESI-MS [M+H]$^+$: 521.2.

45.2 tert-Butyl 2-(3-(4-amino-3,4-dioxo-1-phenylbutan-2-ylcarbamoyl)pyridin-2-yl)-2,4,5,7-tetrahydro-6H-pyrazolo[3,4-c]pyridine-6-carboxylate Oxidation of tert-butyl 2-(3-(4-amino-3-hydroxy-4-oxo-1-phenylbutan-2-ylcarbamoyl)pyridin-2-yl)-4,5-dihydro-2H-pyrazolo[3,4-c]pyridine-6(7H)-carboxylate (170 mg, 0.327 mmol) as described in example 1.4 and purification by chromatography over Chromabond RP-C18 (eluent: water/acetonitrile) gave 84 mg of an amorphous solid; ESI-MS [M+H]$^+$: 519.2.

Example 46

N-(4-Amino-3,4-dioxo-1-phenyl-2-butanyl)-2-(4,5,6,7-tetrahydro-pyrazolo[3,4-c]pyridin-2-yl)nicotinamide hydrochloride To a solution of tert-butyl 2-(3-(4-amino-3,4-dioxo-1-phenylbutan-2-ylcarbamoyl)pyridin-2-yl)-2,4,5,7-tetrahydro-6H-pyrazolo[3,4-c]pyridine-6-carboxylate in dioxane (5 ml) 400 μL of 4M HCl in dioxane were added and stirred over night at room temperature. The mixture then was concentrated, and the remainder purified by chromatography over Chromabond RP-C18 (eluent: water/acetonitrile) to give 24 mg of the title compound; ESI-MS [M+H]$^+$: 419.2.

Example 47 tert-Butyl 2-(3-(4-amino-3,4-dioxo-1-phenylbutan-2-ylcarbamoyl)pyridin-2-yl)-2,5,6,7-tetrahydro-4H-pyrazolo[4,3-b]pyridine-4-carboxylate

47.1 tert-Butyl 2-(3-(4-amino-3-hydroxy-4-oxo-1-phenylbutan-2-ylcarbamoyl)pyridin-2-yl)-6,7-dihydro-2H-pyrazolo[4,3-b]pyridine-4(5H)-carboxylate Coupling according to the procedure described for example 1.3 and treatment of the obtained crude product with water afforded 600 mg of the title compound; ESI-MS [M+H]$^+$: 521.2.

47.2 tert-Butyl 2-(3-(4-amino-3,4-dioxo-1-phenylbutan-2-ylcarbamoyl)pyridin-2-yl)-2,5,6,7-tetrahydro-4H-pyrazolo[4,3-b]pyridine-4-carboxylate Oxidation of the compound from example 47.1 as described in example 1.4 and purification by chromatography over Chromabond RP-C18 (eluent: water/acetonitrile) gave 84 mg of an amorphous solid; ESI-MS [M+H]$^+$: 519.2. $^1$H-NMR (400 MHz, DMSO), δ[ppm]: 8.80 (m, 1H), 8.46 (m, 2H), 7.99 (m, 1H), 7.75 (m, 1H), 7.63 (m, 1H), 7.39 (m, 1H), 7.23 (m, 4H), 5.36 (m, 1H), 3.62 (m, 2H), 3.12 (dd, 1H), 2.87 (dd, 1H), 2.66 (m, 1H), 2.50 (overlapping with DMSO), 1.87 (m, 2H), 1.50 (s, 9H).

Example 48

N-(4-Amino-3,4-dioxo-1-phenyl-2-butanyl)-2-(4,5,6,7-tetrahydro-pyrazolo[4,3-b]pyridin-2-yl)nicotinamide hydrochloride To a solution of the compound from example 47.1 (400 mg, 0.771 mmol) in dichloromethane (25 ml) 1 mL of 4M HCl in dioxane was added and stirred over night at room temperature. The mixture then was filtered, the obtained precipitate washed with dichloromethane and dried to give 346 mg of the title compound; ESI-MS [M+H]$^+$: 419.2. $^1$H-NMR (400 MHz, DMSO), δ[ppm]: 8.95 (m, 1H), 8.53 (m, 1H), 8.46 (m, 1H), 8.06 (m, 1H), 7.78 (m, 1H), 7.72 (m, 1H), 7.46 (m, 1H), 7.22 (m, 5H), 5.35 (m, 1H), 3.31 (m, 2H), 3.14 (dd, 1H), 2.89 (dd, 1H), 2.61 (m, 1H), 2.50 (overlapping with DMSO), 1.98 (m, 2H).

Example 49

N-(4-Amino-3,4-dioxo-1-phenylbutan-2-yl)-2-(4-benzyl-4,5,6,7-tetrahydro-2H-pyrazolo[4,3-b]pyridin-2-yl)nicotinamide

49.1 N-(4-Amino-3-hydroxy-4-oxo-1-phenylbutan-2-yl)-2-(4-benzyl-4,5,6,7-tetrahydro-2H-pyrazolo[4,3-b]pyridin-2-yl)nicotinamide Coupling according to the procedure described for example 1.3 and treatment of the obtained crude product with water afforded 1340 mg of the title compound; ESI-MS [M+H]$^+$: 511.2.

49.2 N-(4-Amino-3,4-dioxo-1-phenylbutan-2-yl)-2-(4-benzyl-4,5,6,7-tetrahydro-2H-pyrazolo[4,3-b]pyridin-2-yl)nicotinamide Oxidation of N-(4-amino-3-hydroxy-4-oxo-1-phenylbutan-2-yl)-2-(4-benzyl-4,5,6,7-tetrahydro-2H-pyrazolo[4,3-b]pyridin-2-yl)nicotinamide (150 mg, 0.294 mmol) as described in example 2.4 and purification by chromatography over silica gel (eluent: dichloromethane/methanol) afforded the title compound as an amorpous solid; 11 mg, ESI-MS [M+H]$^+$: 509.2. $^1$H-NMR (400 MHz, DMSO), δ[ppm]: 8.62 (m, 1H), 8.35 (m, 2H), 7.76 (m, 1H), 7.50 (m, 1H), 7.35-7.12 (m, 12H), 5.85 (s, 1H), 4.36 (m, 1H), 4.20 (s, 2H), 3.20 (m, 2H), 2.93 (m, 2H), 2.71 (m, 3H), 1.94 (m, 2H).

Example 50

N-(4-Amino-3,4-dioxo-1-phenylbutan-2-yl)-2-(3-(1-methylpiperidin-4-yl)-1H-pyrazol-1-yl)nicotinamide

50.1 N-(4-Amino-3-hydroxy-4-oxo-1-phenylbutan-2-yl)-2-(3-(1-methylpiperidin-4-yl)-1H-pyrazol-1-yl)nicotinamide Coupling of 2-(3-(1-methylpiperidin-4-yl)-1H-pyrazol-1-yl)nicotinic acid (360 mg, 1.257 mmol) and 3-amino-2-hydroxy-4-phenylbutanamide (293 mg, 1.509 mmol) in dichloromethane (50 mL) according to the procedure described for example 1.3 and recrystallization from ethylacetate afforded 273 mg of the title compound; ESI-MS [M+H]$^+$: 463.3.

50.2 N-(4-Amino-3,4-dioxo-1-phenylbutan-2-yl)-2-(3-(1-methylpiperidin-4-yl)-1H-pyrazol-1-yl)nicotinamide Oxidation of N-(4-amino-3-hydroxy-4-oxo-1-phenylbutan-2-yl)-2-(3-(1-methylpiperidin-4-yl)-1H-pyrazol-1-yl)nicotinamide (150 mg, 0.324 mmol) as described in example 1.4 and purification by chromatography over silica gel afforded the title compound as an amorpous solid; 18 mg, ESI-MS [M+H]$^+$: 461.2.

Example 51

N-(4-Amino-3,4-dioxo-1-phenylbutan-2-yl)-2-(6-ethyl-4,5,6,7-tetrahydro-2H-pyrazolo[3,4-c]pyridin-2-yl)nicotinamide trifluoroacetate

51.1 N-(4-Amino-3-hydroxy-4-oxo-1-phenylbutan-2-yl)-2-(6-ethyl-4,5,6,7-tetrahydro-2H-pyrazolo[3,4-c]pyridin-2-yl)nicotinamide To a solution of N-(4-amino-3-hydroxy-4-oxo-1-phenylbutan-2-yl)-2-(4,5,6,7-tetrahydro-2H-pyrazolo[3,4-c]pyridin-2-yl)nicotinamide hydrochloride (210 mg, 0.460 mmol) in methanol (15 ml) first acetaldehyde (150 μL, 2.66 mmol) and after 30 minutes NaCN(BH$_4$)$_4$ (40 mg, 0.637 mmol) and glacial acetic acid (20 μL, 0.349 mmol) were added and stirred over night. The mixture was concentrated, 20 mL of water, 10 mL NaHCO$_3$-solution and 20 mL of dichloromethane added, the organic layer separated, washed 2× with water, dried with MgSO$_4$, filtered and concentrated to give 85 mg of an amorphous solid; ESI-MS [M+H]$^+$: 449.2.

51.2 N-(4-Amino-3,4-dioxo-1-phenylbutan-2-yl)-2-(6-ethyl-4,5,6,7-tetrahydro-2H-pyrazolo[3,4-c]pyridin-2-yl)nicotinamide trifluoroacetate Oxidation of N-(4-amino-3-hydroxy-4-oxo-1-phenylbutan-2-yl)-2-(6-ethyl-4,5,6,7-tetrahydro-2H-pyrazolo[3,4-c]pyridin-2-yl)nicotinamide (85 mg, 0.190 mmol) and purification as described in example 3.4 afforded the title compound as an amorpous solid; 18 mg, ESI-MS [M+H]$^+$: 447.2.

II ENZYME INHIBITION IN VITRO

Testing for blockade of the corresponding enzymic activities was carried out by means of kinetic fluorescence assays (excitation 390 nm, emission 460 nm).

Apparent Ki values were calculated from the experimentally determined IC$_{50}$ values by the Cheng-Prussoff relation assuming a reversible competitive enzyme inhibition. The Km values of the substrates used under the assay conditions indicated above were: 90 μM (Z-Phe-Arg-AMC, cathepsin B), 10 μM (Z-Gly-Pro-Arg-AMC, cathepsin K), 2 μM (Z-Phe-Arg-AMC, cathepsin L), and 30 μM (Z-Val-Val-Arg-AMC, cathepsin S). The indicated Ki values are averages of the inhibition constants calculated on the basis of 2 to 4 independent dose-effect plots.

The following assays were used:

1. Calpain I:
20 nM calpain-I—isolated from human erythrocytes (Calbiochem #208713), 100 μM Suc-Leu-Tyr-AMC (Bachem #I-1355) as substrate in buffer with 62 mM imidazole, 0.3 mM CaCl$_2$, 0.10% CHAPS, 0.05% BSA, 1 mM DTT at pH 7.3 and room temperature.

2. Cathepsin B:
0.25 nM cathepsin B—isolated from human liver (Calbiochem #219362), 100 μM Z-Phe-Arg-AMC (Bachem #I-1160) as substrate 50 mM MES, 2 mM EDTA, 0.05% Brij 35, 2.5 mM L-cysteine, pH 6.0, room temperature.

3. Cathepsin K:
3 nM cathepsin K—activated from recombinant human procathepsin K from *E. coli* (Calbiochem #342001), 10 μM Z-Gly-Pro-Arg-AMC (Biomol #P-142) as substrate in 50 mM MES, 2 mM EDTA, 0.05% Brij 35, 2.5 mM L-cysteine, pH 6.0, room temperature.

4. Cathepsin L:
1 nM cathepsin L—isolated from human liver (Calbiochem #219402), 2 μM Z-Phe-Arg-AMC (Bachem #I-1160) as substrate in 50 mM MES, 2 mM EDTA, 0.05% Brij 35, 2.5 mM L-cysteine, pH 6.0, room temperature.

5. Cathepsin S:
0.5 nM recombinant human cathepsin S from *E. coli* (Calbiochem #219343), 20 μM Z-Val-Val-Arg-AMC (Bachem #I-1540) as substrate in 50 mM MES, 2 mM EDTA, 0.05% Brij 35, 2.5 mM L-cysteine, pH 6.0, room temperature.

The results of the in vitro determination are indicated in Table 1. The following abbreviations are used in Table 1:

In the "Calpain activity" column, +++ stands for a calpain Ki (Ki(calpain)) of <250 nM, ++ means 250 nM≤Ki(calpain) of ≤400 nM, + means 400 nM<Ki(Calpain) ≤800 nM and o means 800 nM<Ki(Calpain)≤1000 nM.

The "Sel. cat. B" column indicates the Ki(cathepsin B)/Ki(calpain) ratio. In this connection, +++ means a Ki(cathepsin B)/Ki(calpain) ratio of >30, ++ means 9<Ki(cathepsin B)/Ki(calpain)≤30, and + means 5≤Ki(cathepsin B)/Ki(calpain)≤9 and o means Ki(cathepsin B)/Ki(calpain)<5.

The "Sel. cat. K" column indicates the Ki(cathepsin K)/Ki(calpain) ratio. In this connection, +++ means a Ki(cathepsin K)/Ki(calpain) ratio of >30, ++ means 9<Ki(cathepsin K)/Ki(calpain)≤30, and + means 5≤Ki(cathepsin K)/Ki(calpain)≤9 and o means Ki(cathepsin K)/Ki(calpain)<5.

The "Sel. cat. L" column indicates the Ki(cathepsin L)/Ki(calpain) ratio. In this connection, +++ means a Ki(cathepsin L)/Ki(calpain) ratio of >50, ++ means 10<Ki(cathepsin L)/Ki(calpain)≤50, and + means 5≤Ki(cathepsin L)/Ki(calpain) ≤10 and o means Ki(cathepsin L)/Ki(calpain)<5.

The "Sel. cat. S" column indicates the Ki(cathepsin S)/Ki(calpain) ratio. In this connection, +++ means a Ki(cathepsin S)/Ki(calpain) ratio of >50, ++ means 10<Ki(cathepsin S)/Ki(calpain)≤50, and + means 5≤Ki(cathepsin S)/Ki(calpain) ≤10 and o means Ki(cathepsin S)/Ki(calpain)<5.

TABLE 1

| Example | Calpain activity | Sel cat. B | Sel cat. K | Sel cat. L | Sel cat. S | human cytCL | cyno cytCL |
|---|---|---|---|---|---|---|---|
| 1 | +++ | o | o | + | +++ | ++ | ++ |
| 2a | +++ | o | o | o | +++ | ++ | ++ |
| 2b | +++ | o | o | o | ++ | ++ | ++ |
| 3 | +++ | + | o | ++ | +++ | ++ | ++ |
| 4 | +++ | o | o | + | +++ | + | ++ |
| 5 | +++ | o | o | ++ | +++ | ++ | ++ |
| 6 | +++ | + | ++ | +++ | +++ | + | + |
| 7 | +++ | o | o | o | ++ | ++ | ++ |
| 8a | +++ | o | o | o | +++ | ++ | ++ |
| 8b | +++ | o | o | o | +++ | ++ | ++ |
| 9 | +++ | + | o | + | +++ | + | + |
| 10 | ++ | o | o | o | +++ | ++ | ++ |
| 11 | ++ | o | o | o | +++ | ++ | ++ |
| 12 | +++ | o | o | o | +++ | + | ++ |
| 13 | +++ | o | o | o | +++ | ++ | ++ |
| 14 | +++ | o | o | o | +++ | ++ | ++ |
| 15 | +++ | + | ++ | +++ | ++ | + | + |
| 16 | +++ | + | ++ | +++ | +++ | + | + |
| 17 | +++ | o | o | o | ++ | ++ | ++ |
| 18 | ++ | o | o | o | ++ | ++ | ++ |
| 19 | +++ | o | o | + | +++ | + | ++ |
| 20 | +++ | o | o | o | ++ | ++ | ++ |
| 21 | +++ | o | o | o | +++ | + | ++ |
| 22 | +++ | o | o | + | +++ | + | ++ |
| 23 | +++ | o | o | + | +++ | + | ++ |
| 24 | +++ | o | o | o | +++ | ++ | ++ |
| 25 | +++ | o | o | o | +++ | + | + |
| 26 | +++ | o | o | o | +++ | + | ++ |
| 27 | +++ | o | o | + | +++ | + | + |
| 28 | +++ | + | + | +++ | ++ | + | + |
| 29 | +++ | o | o | o | +++ | + | + |

TABLE 1-continued

| Example | Calpain activity | Sel cat. B | Sel cat. K | Sel cat. L | Sel cat. S | human cytCL | cyno cytCL |
|---|---|---|---|---|---|---|---|
| 30 | +++ | o | o | ++ | +++ | + | + |
| 31 | +++ | o | o | + | +++ | + | ++ |
| 32 | +++ | o | o | ++ | +++ | + | ++ |
| 33 | +++ | o | o | + | +++ | + | + |
| 34 | +++ | o | o | +++ | ++ | ++ | ++ |
| 35 | +++ | + | o | o | +++ | + | ++ |
| 36 | +++ | ++ | ++ | +++ | +++ | + | + |
| 37 | +++ | o | o | o | o | ++ | ++ |
| 38 | +++ | o | o | o | o | + | ++ |
| 39 | +++ | o | o | + | ++ | + | + |
| 40 | +++ | o | o | + | +++ | + | ++ |
| 41 | +++ | o | o | o | ++ | ++ | ++ |
| 42 | +++ | o | o | o | + | ++ | ++ |
| 43 | +++ | o | ++ | +++ | ++ | + | + |
| 44 | +++ | o | o | o | ++ | ++ | ++ |
| 45 | +++ | o | o | ++ | ++ | + | + |
| 46 | +++ | o | o | o | + | ++ | ++ |
| C1* | # | o | o | o | o | ++ | ++ |
| C2** | o | o | o | o | + | + | ++ |

C1*
Calpain activity
Ki > 1000 nM

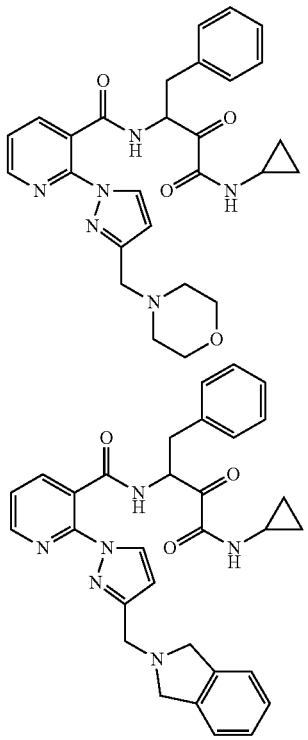

As can be seen from Table 1 the compounds of formula I according to the invention feature improved Calpain activity over related compounds C1 and C2 carrying a cyclopropyl group at the amino nitrogen atom.

III SPECTRIN MOLT-4 ASSAY TO DETERMINE CELLULAR CALPAIN INHIBITION

The following solutions and buffers were employed:
HBS (for 40 ml): 800 μl 1M HEPES; 2.16 ml 100 mM KCl; 4.8 ml 1M NaCl; 3.59 ml 5% glucose; 60 μl 1M $MgSO_4$; 400 μl 100 mM Na pyruvate, 28.19 ml water; pH 7.2-7.5.
lysis buffer (for 20 ml): 400 μl 1M Tris pH 8.2; 2.74 ml 1M NaCl; 520 μl 0.5M EDTA; 2 ml 10% triton X-100; 0.8 ml (=1:25) CompletePlus (1 tablet/2 ml $H_2O$); 200 μl 100 mM Pefabloc; 13.34 ml water, pH 8.2.
TBST (10×) (for 1l): 100 mM Tris (12.1 g); 1.5M NaCl (87 g); 1% Tween 20 (10 g), adjusted to pH 8.

The assay design and procedure were as disclosed by Chatterjee; BMC 1998, 6, pp. 509-522; the $EC_{50}$ values are calculated from the percentage degradation of spectrin as a function of the dose.

Cell culture conditions: the molt-4 cells are maintained in RPMI 1640+Glutamax™ I medium (Gibco) with 10% FCS and 50 μg/ml gentamicin at 37° C., 5% $CO_2$ and split 1:15 twice a week.

Preparation of the molt-4 cells: the cells are washed, counted and taken up in a concentration of $2 \times 10^7$ cells/ml in HBS buffer.

Dilution of the inhibitor substances: all the inhibitors are dissolved in a concentration of $10^{-2}$ M in DMSO. The stock solution is then diluted 1:15 in DMSO (=$6.67 \times 10^{-4}$ M). Thereafter the stock solution diluted 1:15 is diluted 1:4 in DMSO in two steps (=$1.67 \times 10^{-4}$ M and $4.17 \times 10^{-5}$ M). Thereafter, these three solutions are further diluted 1:50 in HBS buffer to give solutions having a concentration of $1.33 \times 10^{-5}$ M, $3.36 \times 10^{-6}$ M and $8.34 \times 10^{-7}$ M.

Test mixture: for each mixture, $10^6$ cells (see above) are introduced into a 1.5 ml Eppendorf tube. To these are added in each case 150 μl of the diluted substances (final conc. 10-5 M; $2.5 \times 10^{-6}$ M and $6.25 \times 10^{-7}$ M) and thoroughly mixed. A negative control and a positive control are used as controls. In this case, initially only 150 μl of HBS buffer is pipetted onto the cells. All the mixtures are incubated at 37° C., 5% $CO_2$ in an incubator for 10 min. Thereafter, except for the negative control, in each case $CaCl_2$ (final conc. 5 mM) and ionomycin (final conc. 5 μM) are added, thoroughly mixed and incubated at 37° C., 5% $CO_2$ in an incubator for 30 min. Then centrifuge at 700 g for 5 min. The supernatants are discarded and the pellets are taken up in 20 μl of lysis buffer. The mixtures are subsequently placed on ice for 30-60 min and then centrifuged at 15000 g for 15 min. The supernatants are removed and put into new Eppendorf tubes. The protein determination is then carried out thereon, e.g. with a MicroBCA assay (Pierce).

SDS-PAGE electrophoresis: 10 μg of total protein from each mixture are put into a new Eppendorf tube and, after pipetting in the same volume of 2× Tris-glycine SDS sample buffer (Invitrogen) and 1/10 volume of 1M DTT, thoroughly mixed and heated at 95° C. for 15 min. The solutions are briefly centrifuged and loaded onto a 6% SDS gel (Invitrogen). The gel is run at 100V with 1× Tris-glycine laemmli buffer (Biomol) until the lower band of the marker has reached the base of the gel.

Western blotting: the gel is removed from the apparatus and blotted onto nitrocellulose in 1× Tris-glycine transfer buffer (Invitrogen) +20% methanol with 1.5 A/$cm^2$ in a Fast-Blot chamber (Biometra) for 30 min. The nitrocellulose filter is removed, briefly washed in TBST buffer and blocked in TBST/5% milk powder for 1 h at RT (room temperature). The blocked nitrocellulose is then incubated with an anti-spectrin Ab (Chemicon) (1:10000 in TBST/5% milk powder) at RT for 3 h or at 4° C. overnight. The nitrocellulose is washed 3× in TBST buffer. It is then incubated with anti-mouse IgG (POD) antibody (Sigma) (1:10000 in TBST/5% milk powder) at room temperature for 1 h.

The nitrocellulose is then washed 5× in TBST buffer. In the next step, 5 ml of prepared solution of the SuperSignal® West Pico chemiluminescence substrate (Pierce) are put on the filter and incubated for 5 min. The nitrocellulose is then taken out of the solution, gently dabbed dry and inserted into a development folder film (Tropix). A digital image analysis system (VersaDoc, Biorad) is used to record and quantify the ECL (QuantityOne), and the percentage degradation of spectrin is calculated from the data. Graph-pad prism is used to fit the percentage spectrum degradation as a function of the dose to a sigmoidal dose-effect plot (top fixed at 100% and bottom at 0%), and the EC 50% is calculated.

IV ASSAY FOR DETERMINING CYTOSOLIC CLEARANCE OF COMPOUNDS OF FORMULA I

For comparison purposes data measured with human liver cytosol were contrasted with those obtained with cynomolgus monkey liver cytosol.

0.5 µM of a compound to be tested was incubated with 1 mg/ml of human liver cytosol as well as monkey liver cytosol at 37° C. in 0.5 M of phosphate buffer at pH 7.5 while shaking (commercial sources: female cynomolgus liver cytosol from Tebu bio, human liver cytosol from BDgentest).

In each case aliquots of 65 µl were taken after 0, 5, 10 and 15 min and transferred into wells of a wellplate which were immediately filled with 130 µl of ethanol to stop the reaction. The samples were kept frozen until analysis on a LC/MS/MS system (Applied Biosystems SCIEX 4000).

Read out parameters were the loss of parent compounds, from which the half life periods ($T_{1/2}$) were calculated from. Based on these data the parameters cytosolic clearance (cytCL), scaled clearance (CLs) and predicted clearance (CLp) were calculated using the following equations:

$$cytCL=(\ln 2/T_{1/2})\times[\text{cytosolic protein}]\times1000 \quad 1)$$

$$CLs=cytCL\times[\text{cytosolic yield}]/1{,}000{,}000\times60 \quad 2)$$

$$CLp=(CLs+\text{hepatic plasma flow})/\text{hepatic plasma flow}/CLs \quad 3)$$

To assess the stability of the compounds tested the clearance ranges were adjusted to the hepatic plasma flow of the different species according to the following scheme:
stable=from 0 to about ⅓ of the hepatic plasma flow;
moderately stable=from about ⅓ to about ⅔ of the hepatic plasma flow;
instable=more than ⅔ of the hepatic plasma flow.

Based on this adjustment the following qualifiers were assigned to evaluate the cytosolic stabilities of the compounds tested:

| cytCL | symbol | human | cynomolgus monkey (cyno) |
|---|---|---|---|
| stable | ++ | 0-14 µl/min/mg | 0-18 µl/min/mg |
| moderately stable | + | 14-70 µl/min/mg | 18-90 µl/min/mg |
| instable | − | >70 µl/min/mg | >90 µl/min/mg |

The cytCL data obtained this way for the compounds of the Examples 1 to 46 are depicted in Table 1 above.

V IN-VITRO ASSAY FOR DETERMINING DEGRADATION OF COMPOUNDS I INTO THE CORRESPONDING HYDROXYAMIDE METABOLITES IN HEPATOCYTES

Each compound to be tested (10 µl) was incubated in monkey and also in human hepatocytes to determine the concentration ratio of hydroxyamide metabolite to the compound of formula I as parent compound. Incubations were carried out at 37° C. for 0 and 4 hours in a 24-well plate, each well holding 0.5 ml hepatocyte medium with about 500,000 cells/ml. At the end of each time point, 1 ml of acetonitrile/ethanol (1/1, v/v) was added to each well to quench the reaction. The solutions were vortexed and mixed thoroughly. An aliquot was subjected to LC-UV-MS/MS analysis at UV wavelength of 254 nm. Identities of compounds I tested and their corresponding hydroxyamide metabolites were confirmed by MS/MS analysis and by comparison with synthetic standards. UV areas for each test compound and its hydroxylamide metabolite were integrated. The concentration ratios of hydroxyamide metabolites to parent compounds (M/P ratios) were determined as ratios of the UV areas of metabolites to those of the compounds I, assuming that extinction coefficients $\epsilon_P$ and $\epsilon_M$ are approximately identical. The M/P ratios obtained this way for incubations were terminated after 4 hours.

VI IN-VIVO DETERMINATION OF THE RATIO OF HYDROXYAMIDE METABOLITE TO THE PARENT COMPOUND I IN PLASMA OF CYNOMOLGUS MONKEYS

The tested compounds were prepared as a solution for either intravenous or oral administration to groups of female cynomolgus monkeys. For intravenous dosing, the compounds were prepared in a 10% DMSO/PEG-400 vehicle at a concentration of 2 mg/ml. For oral dosing, the compounds were prepared in a lipid based vehicle at a concentration of 3 mg/ml. Groups of three monkeys received either a 1 mg/kg (0.5 ml/kg) intravenous dose or a 3 mg/kg (1 ml/kg) oral dose. The intravenous dose was administered as a slow bolus in a saphenous vein; the oral dose was administered by gastric intubation and was followed by ~5 ml water. Serial blood samples were obtained from each animal at selected time points up to 24 hours after drug administration. Plasma was separated from the blood by centrifugation and stored frozen (<-15 C) until analysis. Parent compounds I and the selected metabolites were separated from plasma using protein precipitation with mixture of methanol, acetonitrile and water. The supernatant was evaporated to dryness with a stream of dry nitrogen. The samples were reconstituted with an aliquot of mobile phase, followed by quantification by HPLC-MS/MS. Standard curves for both parent and the selected metabolites were prepared from authentic standards in blank monkey plasma; standards were analyzed simultaneously with the samples. The plasma concentration of each sample was calculated by least squares linear regression analysis of the peak area ratio (parent or metabolite/internal standard) of the spiked plasma standards versus concentration.

Peak plasma concentrations ($C_{max}$) and the time to peak plasma concentration ($T_{max}$) were read directly from the plasma concentration data for each monkey. The plasma concentration data for both parent and metabolite were submitted to multi-exponential curve fitting using WinNonlin. The area under the plasma concentration-time curve from 0 to t hours (time of the last measurable plasma concentration) after dosing ($AUC_{0-t}$) was calculated using the linear trapezoidal rule for the plasma concentration-time profiles. The residual area extrapolated to infinity, determined as the final measured plasma concentration (Ct) divided by the terminal elimination rate constant (β), was added to $AUC_{0-t}$ to produce the total area under the curve ($AUC_{0-inf}$). The apparent total plasma clearance ($CL_p$) was calculated by dividing the administered dose by the $AUC_{0-inf}$. The initial volume of distribution ($V_c$) was calculated as the dose divided by the extrapolated concentration at time=0 ($C_0$). The volume of distribution at steady state, $V_{ss}$, was estimated as a product of the plasma clearance ($CL_p$) and the mean residence time (MRT); the terminal-phase volume of distribution ($V_β$), was derived from the plasma clearance value ($CL_p$) divided by the plasma elimination rate constant (β). The bioavailability was calculated as the dose-normalized $AUC_{0-inf}$ from the oral dose divided by the corresponding value derived from the intravenous dose. Metabolite to parent ratios were calculated as the $C_{max}$ (metabolite)/$C_{max}$ (parent) or AUC(metabolite)/AUC (parent) for the peak concentrations and area under the curve, respectively.

The invention claimed is:
1. A carboxamide compound of the formula I

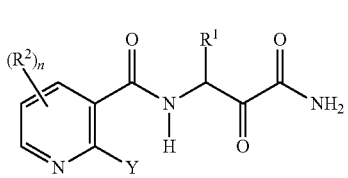

in which
$R^1$ is selected from the group consisting of $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents selected from $R^{1a}$, $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals selected from $R^{1b}$, aryl, hetaryl, aryl-$C_1$-$C_6$-alkyl, aryl-$C_2$-$C_6$-alkenyl, hetaryl-$C_1$-$C_4$-alkyl, and hetaryl-$C_2$-$C_6$-alkenyl, where aryl and hetaryl in the last 6 radicals mentioned may be unsubstituted or may carry 1, 2, 3 or 4 identical or different radicals selected from $R^{1c}$; where
$R^{1a}$ is selected independently of one another from the group consisting of OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, —$NR^{a2}$—$SO_2$—$R^{a4}$, $NR^{a2}$—CO—$R^{a5}$, $SO_2$—$R^{a4}$, and $NR^{a6}R^{a7}$;
$R^{1b}$ is selected independently of one another from the group consisting of OH, SH, COOH, CN, $OCH_2COOH$, halogen, phenyl, which optionally has 1, 2 or 3 substituents selected from $R^{1a}$, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents selected from $R^{1a}$, $COOR^{b1}$, $CONR^{b2}R^{b3}$, $SO_2NR^{b2}R^{b3}$, $NR^{b2}$—$SO_2$—$R^{b4}$, $NR^{b2}$—CO—$R^{b5}$, $SO_2$—$R^{b4}$, and $NR^{b6}R^{b7}$,
in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring;
$R^{1c}$ is selected independently of one another from the group consisting of OH, SH, halogen, $NO_2$, $NH_2$, CN, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents selected from $R^{1a}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals,
aryl, hetaryl, O-aryl, O—$CH_2$-aryl, where the last three radicals mentioned are unsubstituted in the aryl moiety or may carry 1, 2, 3 or 4 $R^{1d}$ radicals, $COOR^{c1}$, $CONR^{c2}R^{c3}$, $SO_2NR^{c2}R^{c3}$, $NR^{c2}$—$SO_2$—$R^{c4}$, $NR^{c2}$—CO—$R^{c5}$, $SO_2$—$R^{c4}$,
—$(CH_2)_p$—$NR^{c6}R^{c7}$ with p=0, 1, 2, 3, 4, 5 or 6, and O—$(CH_2)_q$—$NR^{c6}R^{c7}$ with q=2, 3, 4, 5 or 6; where two radicals $R^{1b}$ or two radicals $R^{1c}$ bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms selected from the group consisting of O, N, and S as ring members;
$R^{1d}$ is selected from the group consisting of halogen, OH, SH, $NO_2$, COOH, $C(O)NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—$C(O)C_1$-$C_6$-alkyl, and $SO_2$—$C_1$-$C_6$-alkyl;
$R^2$ is selected from the group consisting of halogen, $NH_2$, CN, $CF_3$, $CHF_2$, $CH_2F$, O—$CF_3$, O—$CHF_2$, O—$CH_2F$, COOH, $OCH_2COOH$, $C_1$-$C_2$-alkyl, $C_1$-$C_2$-alkoxy, $C_1$-$C_2$-alkoxy-$C_1$-$C_2$-alkyl, $C_1$-$C_2$-alkylthio, and $CH_2NRR'$, where
R and R' are selected independently of one another from the group consisting of hydrogen and $C_1$-$C_4$-alkyl;
n is 0, 1 or 2;
Y is a radical of the formulae Y1 or Y2

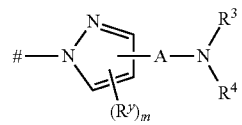

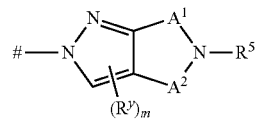

where # indicates the point of attachment of Y to the pyridine ring;
A is $(CH_2)_p$ with p being 1, 2, 3 or 4, where one or two hydrogen atoms may be replaced by a radical $R^6$, where A is attached to the 3- or 4-positon of the pyrazole radical;
$A^1$ is $(CH_2)_q$ with q being 0, 1, 2 or 3, where one or two hydrogen atoms may be replaced by halogen or $C_1$-$C_4$-alkyl;
$A^2$ is $(CH_2)_r$ with r being 0, 1, 2 or 3, where one or two hydrogen atoms may be replaced by halogen or $C_1$-$C_4$-alkyl;
provided that r+q is 2, 3, 4, 5 or 6;
m is 0 or 1;
$R^y$ is selected from the group consisting of halogen, $NH_2$, CN, $CF_3$, $CHF_2$, $CH_2F$, O—$CF_3$, O—$CHF_2$, O—$CH_2F$, COOH, $OCH_2COOH$, $C_1$-$C_2$-alkoxy, $C_1$-$C_2$-alkoxy-$C_1$-$C_2$-alkyl, and $C_1$-$C_2$-alkylthio;
$R^3$ is selected from the group consisting of hydrogen, $C_1$-$C_6$-alkyl, $C_1$-$C_6$-haloalkyl, $C_1$-$C_6$-alkyl which has 1, 2 or 3 substituents selected from $R^{3a}$, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals selected from $R^{3b}$, $C_2$-$C_6$-alkenyl, $C_2$-$C_6$-alkynyl, where alkenyl and alkynyl, in the last 2 radicals mentioned are unsubstituted or have 1, 2 or 3 substituents selected from $R^{3a}$, phenyl, phenyl-$C_1$-$C_4$-alkyl, where phenyl in the last 2 radicals mentioned are unsubstituted or have 1, 2 or 3 substituents selected from $R^{3c}$, and a radical $C(=O)R^{3d}$;

$R^{3a}$ is selected from the group consisting of OH, SH, CN, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, $-NR^{a2}-SO_2-R^{a4}$, $NR^{a2}-CO-R^{a5}$, $SO_2-R^{a4}$, and $NR^{a6}R^{a7}$;

$R^{3b}$ is selected from the group consisting of OH, SH, CN, halogen, $C_1$-$C_6$-alkyl $C_1$-$C_6$-alkoxy, $C_1$-$C_6$-alkylthio, where the alkyl moieties in the last 3 substituents mentioned may be partly or completely halogenated and/or have 1, 2 or 3 substituents selected from $R^{3a}$, phenyl, which optionally has 1, 2 or 3 substituents selected from $R^{3c}$, $COOR^{b1}$, $CONR^{b2}R^{b3}$, $SO_2NR^{b2}R^{b3}$, $NR^{b2}-SO_2-R^{b4}$, $NR^{b2}-CO-R^{b5}$, $SO_2-R^{b4}$ and $NR^{b6}R^{b7}$, or two $R^{3b}$ radicals may together also form a $C_1$-$C_4$-alkylene group, or two $R^{3b}$ radicals bonded to adjacent C atoms of cycloalkyl may form together with the carbon atoms to which they are bonded also a benzene ring;

$R^{3c}$ is selected from the group consisting of halogen, OH, SH, $NO_2$, $C(O)NH_2$, CHO, CN, $NH_2$, $C_1$-$C_6$-alkyl, $C_1$-$C_6$-haloalkyl $C_1$-$C_6$-alkoxy, $C_1$-$C_6$-haloalkoxy, $C_1$-$C_6$-alkylthio, $C_1$-$C_6$-haloalkylthio, $CO-C_1$-$C_6$-alkyl, $CO-O-C_1$-$C_6$-alkyl $NH-C_1$-$C_6$-alkyl, $NH-C(O)C_1$-$C_6$-alkyl, and $SO_2-C_1$-$C_6$-alkyl;

$R^{3d}$ is selected from the group consisting of $C_1$-$C_6$-alkyl, $C_1$-$C_6$-haloalkyl, $C_1$-$C_6$-alkyl, which has 1, 2 or 3 substituents selected from $R^{3a}$, $C_3$-$C_7$-cycloalkyl, $C_3$-$C_7$-cycloalkyl-$C_1$-$C_4$-alkyl, where the cycloalkyl moiety of the last 2 radicals mentioned is unsubstituted or may have 1, 2, 3 or 4 radicals selected from $R^{3b}$, and phenyl, which optionally has 1, 2 or 3 substituents selected from $R^{3c}$;

$R^4$ is selected from the group consisting of hydrogen, $C_1$-$C_6$-alkyl, $C_1$-$C_6$-haloalkyl, $C_1$-$C_6$-alkyl, which has 1, 2 or 3 substituents selected from $R^{4a}$, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals selected from $R^{4b}$, $C_2$-$C_6$-alkenyl, $C_2$-$C_6$-alkynyl, where alkenyl and alkynyl, in the last 2 radicals mentioned are unsubstituted or have 1, 2 or 3 substituents selected from $R^{4a}$, phenyl, and phenyl-$C_1$-$C_4$-alkyl, where phenyl in the last 2 radicals mentioned are unsubstituted or have 1, 2 or 3 substituents selected from $R^{4c}$, where $R^{4a}$ is as defined for $R^{3a}$, $R^{4b}$ is as defined for $R^{3b}$, and $R^{4c}$ is as defined for $R^{3c}$, or the moiety $NR^3R^4$ in formula Y1 is a saturated, N-bound 4-, 5-, 6-, or 7-membered heteromonocyclic or 7-, 8-, 9-, or 10-membered heterobicyclic radical, where said heteromonocyclic and the heterobicyclic radical, in addition to the nitrogen atom, may have 1 or 2 further heteroatoms or heteroatom moieties as ring members, which are selected from the group consisting of O, S, S(O), $S(O)_2$, and $NR^{4d}$, where said heteromonocyclic radical may carry a fused benzene ring and where said heteromonocyclic and the heterobicyclic radical are unsubstituted or may be substituted by 1, 2, 3 or 4 radicals selected from $R^{4e}$;

$R^{4d}$ is selected from the group consisting of hydrogen, $C_1$-$C_6$-alkyl, $C_1$-$C_6$-haloalkyl, $C_1$-$C_6$-alkyl, which has 1, 2 or 3 substituents selected from $R^{4a}$, $C_3$-$C_7$-cycloalkyl, $C_3$-$C_7$-cycloalkyl-$C_1$-$C_4$-alkyl, where the cycloalkyl moiety of the last 2 radicals mentioned is unsubstituted or may have 1, 2, 3 or 4 radicals selected from $R^{4b}$, phenyl, and phenyl-$C_1$-$C_4$-alkyl, where the phenyl ring of the last 2 radicals mentioned is unsubstituted or may have 1, 2 or 3 substituents selected from $R^{4c}$;

$R^{4e}$ is selected from the group consisting of halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $COOR^{b1}$, $CONR^{b2}R^{b3}$, $SO_2NR^{b2}R^{b3}$, $NR^{b2}-SO_2-R^{b4}$, $NR^{b2}-CO-R^{b5}$, $SO_2-R^{b4}$, and phenyl, which optionally has 1, 2 or 3 substituents selected from $R^{4c}$;

$R^5$ has one of the meanings given for $R^3$ or is a radical $COOR^{b1}$;

$R^6$ if present, is selected from halogen or $C_1$-$C_4$-alkyl, or $R^6$ together with $R^4$ forms a bivalent radical $(CH_2)_s$ with s being 1, 2 or 3, where one or two hydrogen atoms may be replaced by halogen or $C_1$-$C_4$-alkyl;

and where $R^{a1}$, $R^{b1}$ and $R^{c1}$ are independently of one another selected from the group consisting of $C_1$-$C_6$-alkyl, $C_1$-$C_6$-haloalkyl, $C_1$-$C_6$-alkyl which has 1, 2 or 3 substituents selected from $R^{1a}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl, and hetaryl-$C_1$-$C_4$-alkyl, where aryl and hetaryl in the last 4 radicals mentioned are unsubstituted or have 1, 2 or 3 substituents selected from $R^{1d}$;

$R^{a2}$, $R^{b2}$ and $R^{c2}$ are independently of one another selected from the group consisting of H, $C_1$-$C_6$-alkyl, $C_1$-$C_6$-haloalkyl, $C_1$-$C_6$-alkyl, which has 1, 2 or 3 substituents selected from $R^{1a}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl, and hetaryl-$C_1$-$C_4$-alkyl, where aryl and hetaryl in the last 4 radicals mentioned are unsubstituted or have 1, 2 or 3 substituents selected from $R^{1d}$;

$R^{a3}$, $R^{b3}$ and $R^{c3}$ are independently of one another selected from the group consisting of H, $C_1$-$C_6$-alkyl, $C_1$-$C_6$-haloalkyl, $C_1$-$C_6$-alkyl, which has 1, 2 or 3 substituents selected from $R^{1a}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl, and hetaryl-$C_1$-$C_4$-alkyl, where aryl and hetaryl in the last 4 radicals mentioned are unsubstituted or have 1, 2 or 3 substituents selected from $R^{1d}$, or the two radicals $R^{a2}$ and $R^{a3}$, or $R^{b2}$ and $R^{b3}$, or $R^{c2}$ and $R^{c3}$ form together with the N atom a 3 to 7-membered, optionally substituted nitrogen heterocycle which may optionally have 1, 2 or 3 further different or identical heteroatoms selected from the group consisting of O, N, and S as ring members;

$R^{a4}$, $R^{b4}$ and $R^{c4}$ are independently of one another selected from the group consisting of $C_1$-$C_6$-alkyl, $C_1$-$C_6$-haloalkyl, $C_1$-$C_6$-alkyl, which has 1, 2 or 3 substituents selected from $R^{1a}$, $C_2$-$C_6$-alkenyl, $C_2$-$C_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl, and hetaryl-C$_1$-C$_4$-alkyl, where aryl and hetaryl in the last 4 radicals mentioned are unsubstituted or have 1, 2 or 3 substituents selected from R$^{1d}$;

R$^{a5}$, R$^{b5}$ and R$^{c5}$ have independently of one another the meanings mentioned for R$^{a1}$, R$^{b1}$ and R$^{c1}$;

R$^{a6}$, R$^{b6}$ and R$^{c6}$ are independently of one another selected from the group consisting of H, C$_1$-C$_6$-alkyl, C$_1$-C$_6$-alkoxy, C$_1$-C$_6$-haloalkyl, C$_1$-C$_6$-alkyl, which has 1, 2 or 3 substituents selected from R$^{1a}$, C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—C$_1$-C$_6$-alkyl, aryl, hetaryl, O-aryl, OCH$_2$-aryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$alkyl), and SO$_2$-(hetaryl-C$_1$-C$_4$-alkyl), where aryl and hetaryl in the last 18 radicals mentioned are unsubstituted or have 1, 2 or 3 substituents selected from R$^{1d}$; and R$^{a7}$, R$^{b7}$ and R$^{c7}$ are independently of one another selected from the group consisting of H, C$_1$-C$_6$-alkyl, C$_1$-C$_6$-haloalkyl, C$_1$-C$_6$-alkyl, which has 1, 2 or 3 substituents selected from R$^{1a}$, C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl, and hetaryl-C$_1$-C$_4$-alkyl, where aryl and hetaryl in the last 4 radicals mentioned are unsubstituted or have 1, 2 or 3 substituents selected from R$^{1d}$, or the two radicals R$^{a6}$ and R$^{a7}$, or R$^{b6}$ and R$^{b7}$, or R$^{c6}$ and R$^{c7}$ form together with the N atom a 3 to 7-membered, optionally substituted nitrogen heterocycle which may optionally have 1, 2 or 3 further different or identical heteroatoms selected from the group consisting of O, N, and S as ring members;

or a tautomer thereof, hydrate thereof, or pharmaceutically suitable salt thereof.

2. The carboxamide compound of claim 1, wherein R$^1$ is selected from the group consisting of:

C$_1$-C$_{10}$-alkyl, which may be partly or completely halogenated and/or have 1, 2 or 3 substituents selected from R$^{1a}$, C$_3$-C$_7$-cycloalkyl-methyl, where the cycloalkyl moiety may have 1, 2, 3 or 4 radicals selected from R$^{1b}$, benzyl, and hetaryl-methyl, where phenyl and hetaryl in the last 2 radicals mentioned may be unsubstituted or carry 1, 2, 3 or 4 identical or different radicals selected from R$^{1c}$.

3. The carboxamide compound of claim 2, wherein R$^1$ is benzyl, which may be unsubstituted or carry 1 or 2 identical or different radicals selected from halogen, C$_1$-C$_2$-alkyl and C$_1$-C$_2$-alkoxy.

4. The carboxamide compound of claim 1, wherein n is 0 or 1 and, when n=1, R$^2$ is selected from the group consisting of F, Cl, CN, CF$_3$, C$_1$-C$_2$-alkyl, and C$_1$-C$_2$-alkoxy.

5. The carboxamide compound of claim 1, wherein m is 0.

6. The carboxamide compound of claim 1, wherein Y is a radical of the formula Y1.

7. The carboxamide compound of claim 6, wherein the moiety A-NR$^3$R$^4$ in formula Y1 is located in the 3-position of the pyrazole ring.

8. The carboxamide compound of claim 6, wherein the moiety A is a bivalent radical of the formula CH—R$^p$(CH$_2$)$_z$, where the carbon atom which carries R$^p$ is bound to the pyrazole ring, and where R$^p$ is hydrogen or methyl, or together with R$^4$ forms a bivalent radical of the formula (CH$_2$)$_s$ with s being 1, 2 or 3, and z is 0, 1 or 2.

9. The carboxamide compound of any of claim 6, wherein R$^3$ is selected from the group consisting of C$_1$-C$_6$-alkyl, C$_1$-C$_6$-haloalkyl, C$_3$-C$_7$-cycloalkyl, C$_3$-C$_7$-cycloalkyl-C$_1$-C$_4$-alkyl, where the cycloalkyl moiety of the last 2 radicals mentioned may have 1, 2, 3 or 4 radicals selected from R$^{3b}$, phenyl, and phenyl-C$_1$-C$_4$-alkyl, where phenyl in the last 2 radicals mentioned are unsubstituted or have 1, 2 or 3 substituents selected from R$^{3c}$, R$^{3b}$ is selected from the group consisting of halogen, C$_1$-C$_6$-alkyl, which may be partly or completely halogenated, and phenyl, which optionally has 1, 2 or 3 substituents selected from R$^{3c}$;

R$^{3c}$ is selected from the group consisting of halogen, OH, SH, NO$_2$, C(O)NH$_2$, CHO, CN, NH$_2$, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, CO—C$_1$-C$_6$-alkyl, CO—O —C$_1$-C$_6$-alkyl, NH—C$_1$-C$_6$-alkyl, NH—C(O)C$_1$-C$_6$-alkyl, and SO$_2$—C$_1$-C$_6$-alkyl; and R$^4$ is selected from the group consisting of hydrogen, C$_1$-C$_6$-alkyl, and C$_1$-C$_6$-haloalkyl.

10. The carboxamide compound of claim 6, wherein the moiety NR$^3$R$^4$ in formula Y1 is a saturated, N-bound 4-, 5-, 6-, or 7-membered heteromonocyclic or 7-, 8-, 9-, or 10-membered heterobicyclic radical, where said heteromonocyclic and the heterobicyclic radical, in addition to the nitrogen atom, may have 1 further heteroatom or heteroatom moiety as ring member, which are selected from the group consisting of O, S, S(O)$_2$, and NR$^{4d}$, where said heteromonocyclic radical may carry a fused benzene ring and where said heteromonocyclic and the heterobicyclic radical are unsubstituted or may be substituted by 1, 2, 3 or 4 radicals selected from R$^{4e}$;

R$^{4d}$ is selected from the group consisting of hydrogen, C$_1$-C$_6$-alkyl, C$_1$-C$_6$-haloalkyl, C$_1$-C$_6$-alkyl, which has 1, 2 or 3 substituents selected from R$^{4a}$, C$_3$-C$_7$-cycloalkyl, C$_3$-C$_7$-cycloalkyl-C$_1$-C$_4$-alkyl, where the cycloalkyl moiety of the last 2 radicals mentioned is unsubstituted or may have 1, 2, 3 or 4 radicals selected from R$^{4b}$, phenyl, and benzyl, where the phenyl ring of the last 2 radicals mentioned is unsubstituted or may have 1, 2 or 3 substituents selected from R$^{4c}$; and R$^{4e}$ is selected from the group consisting of halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, and phenyl.

11. The carboxamide compound of claim 6, wherein the moiety NR$^3$R$^4$ in formula Y1 represents a radical which is selected from the group consisting of 4-morpholinyl, 4-thiomorpholinyl, 1,1-dioxothiomorpholin-4-yl, 2,6-dimethylmorpholin-4-yl, 2-phenylmorpholin-4-yl, 1-azetidinyl, 1-pyrrolidinyl, 3-phenylpyrrolidin-1-yl, 1-azepanyl, 1-piperidinyl, 4-methylpiperidin-1-yl, 4-ethylpiperidin-1-yl, 4-propylpiperazin-1-yl, 4-cyclopropylmethylpiperazin-1-yl, 4-cyclopropylpiperazin-1-yl, 4-phenylpiperidin-1-yl, 4,4-difluoropiperidin-1-yl, 4-(trifluoromethyl)piperidin-1-yl, 4-(tert.-butyl)piperidin-1-yl, 4-methylpiperazin-1-yl, 4-phenylpiperazin-1-yl, dimethylamino, diethylamino, diisopropylamino, N-phenylamino, N-methyl-N-phenylamino, N-cyclopropyl-N-methylamino, N-cyclohexyl-N-methylamino, N-benzyl-N-methylamino, N-cyclohexylmethyl-N-methylamino, N-methyl-N-isopropylamino, N-cyclopropyl-N-phenyl, N-cyclopropyl-N-benzyl, N-(4-trifluoromethylcyclohexyl)methyl-N-methylamino, 3,4-dihydro-2H-1,4-benzoxazin-4-yl, cis-octahydrobenzo-[1,4]oxazin-4-yl, trans-octahydrobenzo[1,4]oxazin-4-yl, 5,5-difluoroocta-hydrocyclopenta[c]pyrrol-2-yl, hexahydrofuro[3,4-c]pyrrol-5-yl, 2,3-dihydroindol-1-yl, 2-oxa-7-azaspiro[3.5]nonane-7-yl, 2,3-dihydro-1H-isoindole-2-yl, 5-trifluoromethyl-2,3-dihydro-1H-isoindole-2-yl, 4-trifluoro-2,3-dihydro-1H-isoindole-2-yl, 2,3-dihydroisoindole-1-one-2-yl, 1,2,3,4-tetrahydroisoquinoline-2-yl, 3-azabicyclo[3.2.0]heptane-3-yl, and 6-(4-fluorophenyl)-3-azabicyclo[3.2.0]heptane-3-yl.

12. The carboxamide compound of claim 8, wherein
$R^3$ is selected from the group consisting of $C_1$-$C_6$-alkyl, $C_1$-$C_6$-haloalkyl, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals selected from $R^{3b}$, phenyl, and phenyl-$C_1$-$C_4$-alkyl, where phenyl in the last 2 radicals mentioned are unsubstituted or have 1, 2 or 3 substituents selected from $R^{3c}$;
$R^{3b}$ is selected from the group consisting of $C_1$-$C_6$-alkyl, which may be partly or completely halogenated, and phenyl, which optionally has 1, 2 or 3 substituents selected from $R^{3c}$;
$R^{3c}$ is selected from the group consisting of halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—$C(O)C_1$-$C_6$-alkyl, and $SO_2$-$C_1$-$C_6$-alkyl; and
wherein $R^p$ together with $R^4$ forms a bivalent radical of the formula $(CH_2)_s$ with s being 1, 2 or 3.

13. The carboxamide compound of claim 12, wherein the moiety A-$NR^3R^4$ in formula Y1 represents a radical which is selected from the group consisting of azetidin-3-yl, pyrrolidin-3-yl, 1-methylpyrrolidin-3-yl, piperidin-3-yl, 1-methylpiperidin-3-yl, piperidin-4-yl, 1-methylpiperidin-4-yl, 1-ethylpiperidin-4-yl, 1-propylpiperidin-4-yl, 1-cyclopropylpiperidin-4-yl, and 1-benzylpiperidin-4-yl.

14. The carboxamide compound of claim 6, having the following formula Ia

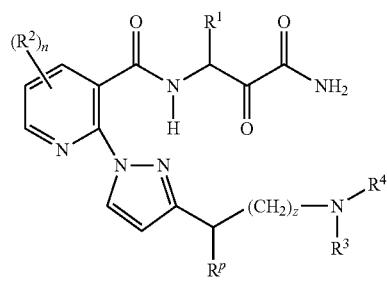

(Ia)

where
$R^p$ is hydrogen, methyl or ethyl, or
$R^p$ together with $R^4$ forms a bivalent radical of the formula $(CH_2)_s$ with s being 1, 2 or 3, and
z is 0, 1 or 2;
or a tautomer thereof, hydrate thereof, or pharmaceutically suitable salt thereof.

15. The carboxamide compound of claim 1, wherein Y is a radical of the formula Y2.

16. The carboxamide compound of claim 15, wherein the moiety $A^1$ is a single bond, $CH_2$, or $CH_2CH_2$, and the moiety $A^2$ is $CH_2$, $CH_2CH_2$, or $CH_2CH_2CH_2$.

17. The carboxamide compound of claim 15, wherein $R^5$ is selected from the group consisting of hydrogen, $C_1$-$C_6$-alkyl, $C_1$-$C_6$-haloalkyl, $C_3$-$C_7$-cycloalkyl, $C_3$-$C_7$-cycloalkyl-$C_1$-$C_4$-alkyl, where the cycloalkyl moiety of the last 2 radicals mentioned may have 1, 2, 3 or 4 radicals selected from $R^{3b}$, phenyl, phenyl-$C_1$-$C_4$-alkyl, where phenyl in the last 2 radicals mentioned are unsubstituted or have 1, 2 or 3 substituents selected from $R^{3c}$, and
a radical $COOR^{b1}$, where
$R^{3b}$ is selected from the group consisting of $C_1$-$C_6$-alkyl, which may be partly or completely halogenated, and phenyl which optionally has 1, 2 or 3 substituents selected from $R^{3c}$;
$R^{3c}$ is selected from the group consisting of halogen, OH, SH, $NO_2$, $C(O)NH_2$, CHO, CN, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NH—$C(O)C_1$-$C_6$-alkyl, and $SO_2$-$C_1$-$C_6$-alkyl; and
$R^{b1}$ is selected from the group consisting of $C_1$-$C_6$-alkyl, $C_3$-$C_7$-cycloalkyl, $C_3$-$C_7$-cycloalkyl-$C_1$-$C_4$-alkyl, phenyl, and phenyl-$C_1$-$C_4$-alkyl, where phenyl in the last 2 radicals mentioned is unsubstituted or has 1, 2 or 3 substituents selected from $R^{1d}$, which are selected from the group consisting of halogen, $C_1$-$C_6$-alkyl, $C_1$-$C_6$-alkoxy, and $C_1$-$C_6$-haloalkyl.

18. The carboxamide compound of claim 15, wherein the radical of the formula Y2 is selected from the group consisting of 4,5,6,7-tetrahydropyrazolo[3,4-c]pyridin-2-yl, 6-($C_1$-$C_4$-alkyl)-4,5,6,7-tetrahydropyrazolo[3,4-c]pyridin-2-yl, 6-(tert.-butoxycarbonyl)-4,5,6,7-tetrahydropyrazolo[3,4-c]pyridin-2-yl, 6-benzyl-4,5,6,7-tetrahydropyrazolo[3,4-c]pyridin-2-yl, 6-cyclopropylmethyl-4,5,6,7-tetrahydropyrazolo[3,4-c]pyridin-2-yl, 4,5,6,7-tetrahydropyrazolo[4,3-c]pyridin-2-yl, 5-($C_1$-$C_4$-alkyl)-4,5,6,7-tetrahydropyrazolo[4,3-c]pyridin-2-yl, 5-(tert.-butoxycarbonyl)-4,5,6,7-tetrahydropyrazolo[4,3-c]pyridin-2-yl, 5-benzyl-4,5,6,7-tetrahydropyrazolo[4,3-c]pyridin-2-yl, 5-cyclopropylmethyl-4,5,6,7-tetrahydropyrazolo[4,3-c]pyridin-2-yl, 2,4,5,6-tetrahydropyrrolo[3,4-c]pyrazol2-yl, 5-($C_1$-$C_4$-alkyl)-2,4,5,6-tetrahydropyrrolo[3,4-c]pyrazol-2-yl, 5-benzyl-2,4,5,6-tetrahydropyrrolo[3,4-c]pyrazol-2-yl, 5-(tert.-butoxycarbonyl)-2,4,5,6-tetrahydropyrrolo[3,4-c]pyrazol-2-yl, 4,5,6,7-tetrahydropyrazolo[4,3-c]pyridin-2-yl, 5-($C_1$-$C_4$-alkyl)-4,5,6,7-tetrahydropyrazolo[4,3-b]pyridin-2-yl, 5-(tert.-butoxycarbonyl)-4,5,6,7-tetrahydropyrazolo[4,3-b]pyridin-2-yl, 5-benzyl-4,5,6,7-tetrahydropyrazolo[4,3-b]pyridin-2-yl, and 5-cyclopropylmethyl-4,5,6,7-tetrahydropyrazolo[4,3-b]pyridin-2-yl.

19. The carboxamide compound of claim 1, having the following formula Ib

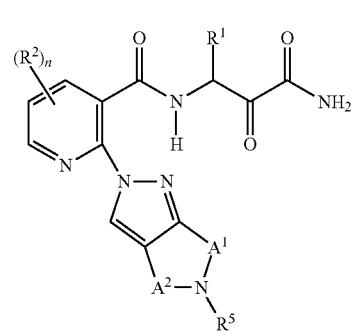

(Ib)

where
$A^1$ is $(CH_2)_q$ with q being 0, 1 or 2; and
$A^2$ is $(CH_2)_r$ with r being 1, 2 or 3;

where q+r is 1, 2 or 3;
or a tautomer thereof, hydrate thereof, or pharmaceutically suitable salt thereof.

20. The carboxamide compound of claim 1 which is selected from the group consisting of:

N-(4-amino-3,4-dioxo-1-phenylbutan-2-yl)-2-(3-(morpholinomethyl)-1H-pyrazol-1-yl)nicotinamide;
N-(4-amino-3,4-dioxo-1-phenylbutan-2-yl)-2-(3-((2,6-dimethylmorpholino)methyl)-1H-pyrazol-1-yl)nicotinamide;
N-(4-amino-3,4-dioxo-1-phenylbutan-2-yl)-2-(3-((cis-2,6-dimethylmorpholino)methyl)-1H-pyrazol-1-yl)nicotinamide;
N-(4-amino-3,4-dioxo-1-phenylbutan-2-yl)-2-(3-((trans-2,6-dimethylmorpholino)-methyl)-1H-pyrazol-1-yl)nicotinamide;
N-(4-amino-3,4-dioxo-1-phenylbutan-2-yl)-2-(3-((4,4-difluoropiperidin-1-yl)methyl)-1H-pyrazol-1-yl)nicotinamide;
N-(4-amino-3,4-dioxo-1-phenylbutan-2-yl)-2-(5-benzyl-4,5,6,7-tetrahydro-2H-pyrazolo[4,3-c]pyridin-2-yl)nicotinamide;
N-(4-amino-3,4-dioxo-1-phenylbutan-2-yl)-2-(3-((4-phenylpiperidin-1-yl)methyl)-1H-pyrazol-1-yl)nicotinamide;
2-(3-((2H-benzo[b][1,4]oxazin-4(3H)-yl)methyl)-1H-pyrazol-1-yl)-N-(4-amino-3,4-dioxo-1-phenylbutan-2-yl)nicotinamide;
N-(4-amino-3,4-dioxo-1-phenylbutan-2-yl)-2-(3-(piperidin-1-ylmethyl)-1H-pyrazol-1-yl)nicotinamide;
2-(3-((2H-benzo[b][1,4]oxazin-4(3H,4aH,5H,6H,7H,8H,8aH)-yl)methyl)-1H-pyrazol-1-yl)-N-(4-amino-3,4-dioxo-1-phenylbutan-2-yl)nicotinamide;
2-(3-((2H-benzo[b][1,4]oxazin-4(3H,4aHS,5H,6H,7H,8H,8aHS)-yl)methyl)-1H-pyrazol-1-yl)-N-(4-amino-3,4-dioxo-1-phenylbutan-2-yl)nicotinamide;
2-(3-((2H-benzo[b][1,4]oxazin-4(3H,4aHS,5H,6H,7H,8H,8aHR)-yl)methyl)-1H-pyrazol-1-yl)-N-(4-amino-3,4-dioxo-1-phenylbutan-2-yl)nicotinamide;
N-(4-amino-3,4-dioxo-1-phenylbutan-2-yl)-2-(3-((2-phenylmorpholino)methyl)-1H-pyrazol-1-yl)nicotinamide;
N-(4-amino-3,4-dioxo-1-phenylbutan-2-yl)-2-(3-(pyrrolidin-1-ylmethyl)-1H-pyrazol-1-yl)nicotinamide;
N-(4-amino-3,4-dioxo-1-phenylbutan-2-yl)-2-(3-(azetidin-1-ylmethyl)-1H-pyrazol-1-yl)nicotinamide;
N-(4-amino-3,4-dioxo-1-phenylbutan-2-yl)-2-(3-((4-(trifluoromethyl)piperidin-1-yl)methyl)-1H-pyrazol-1-yl)nicotinamide;
N-(4-amino-3,4-dioxo-1-phenyl-2-butanyl)-2-{3-[(5,5-difluorohexahydrocyclo-penta[c]pyrrol-2(1H)-yl)methyl]-1H-pyrazol-1-yl}nicotinamide;
N-(4-amino-3,4-dioxo-1-phenylbutan-2-yl)-2-(3-((dihydro-1H-furo[3,4-c]pyrrol-5(3H,6H,6aH)-yl)methyl)-1H-pyrazol-1-yl)nicotinamide;
N-(4-amino-3,4-dioxo-1-phenylbutan-2-yl)-2-(3-(indolin-1-ylmethyl)-1H-pyrazol-1-yl)nicotinamide;
N-(4-amino-3,4-dioxo-1-phenylbutan-2-yl)-2-(3-((methyl(phenyl)amino)methyl)-1H-pyrazol-1-yl)nicotinamide;
N-(4-amino-3,4-dioxo-1-phenyl-2-butanyl)-2-[3-(2-oxa-7-azaspiro[3.5]non-7-ylmethyl)-1H-pyrazol-1-yl]nicotinamide;
N-(4-amino-3,4-dioxo-1-phenyl-2-butanyl)-2-{3-[(diethylamino)methyl]-1H-pyrazol-1-yl}nicotinamide;
N-(4-amino-3,4-dioxo-1-phenylbutan-2-yl)-2-(3-(isoindolin-2-ylmethyl)-1H-pyrazol-1-yl)nicotinamide;
N-(4-amino-3,4-dioxo-1-phenyl-2-butanyl)-2-(3-{[cyclohexyl(methyl)amino]methyl}-1H-pyrazol-1-yl)nicotinamide;
N-(4-amino-3,4-dioxo-1-phenyl-2-butanyl)-2-(3-{[benzyl(methyl)amino]methyl}-1H-pyrazol-1-yl)nicotinamide;
N-(4-amino-3,4-dioxo-1-phenyl-2-butanyl)-2-[3-(3,4-dihydro-2(1H)-isoquinolinylmethyl)-1H-pyrazol-1-yl]nicotinamide;
N-(4-amino-3,4-dioxo-1-phenylbutan-2-yl)-2-(3-((4-tert-butylpiperidin-1-yl)methyl)-1H-pyrazol-1-yl)nicotinamide;
N-(4-amino-3,4-dioxo-1-phenylbutan-2-yl)-2-(3-((4-methylpiperidin-1-yl)methyl)-1H-pyrazol-1-yl)nicotinamide;
N-(4-amino-3,4-dioxo-1-phenylbutan-2-yl)-2-(3-((methyl((4-(trifluoromethyl)cyclohexyl)methyl)amino)methyl)-1H-pyrazol-1-yl)nicotinamide;
N-(4-amino-3,4-dioxo-1-phenylbutan-2-yl)-2-(3-((cyclopropyl(methyl)amino)methyl)-1H-pyrazol-1-yl)nicotinamide;
N-(4-amino-3,4-dioxo-1-phenyl-2-butanyl)-2-(3-{[(6R)-6-(4-fluorophenyl)-3-azabicyclo[3.2.0]hept-3-yl]methyl}-1H-pyrazol-1-yl)nicotinamide;
N-(4-amino-3,4-dioxo-1-phenylbutan-2-yl)-2-(3-((phenylamino)methyl)-1H-pyrazol-1-yl)nicotinamide;
N-(4-amino-3,4-dioxo-1-phenyl-2-butanyl)-2-{3-[(3-phenyl-1-pyrrolidinyl)methyl]-1H-pyrazol-1-yl}nicotinamide;
N-(4-amino-3,4-dioxo-1-phenyl-2-butanyl)-2-(3-{[5-(trifluoromethyl)-1,3-dihydro-2H-isoindol-2-yl]methyl}-1H-pyrazol-1-yl)nicotinamide;
N-(4-amino-3,4-dioxo-1-phenyl-2-butanyl)-2-{3-[(5-fluoro-1,3-dihydro-2H-isoindol-2-yl)methyl]-1H-pyrazol-1-yl}nicotinamide;
N-(4-amino-3,4-dioxo-1-phenyl-2-butanyl)-2-{3-[(4-phenyl-1-piperazinyl)methyl]-1H-pyrazol-1-yl}nicotinamide;
N-(4-amino-3,4-dioxo-1-phenyl-2-butanyl)-2-{3-[(4-fluoro-1,3-dihydro-2H-isoindol-2-yl)methyl]-1H-pyrazol-1-yl}nicotinamide;
N-(4-amino-3,4-dioxo-1-phenyl-2-butanyl)-2-{3-[(1,1-dioxido-4-thiomorpholinyl)methyl]-1H-pyrazol-1-yl}nicotinamide;
N-(4-amino-3,4-dioxo-1-phenyl-2-butanyl)-2-{3-[1-(1,3-dihydro-2Hisoindol-2-yl)ethyl]-1H-pyrazol-1-yl}nicotinamide;
N-(4-amino-3,4-dioxo-1-phenyl-2-butanyl)-2-{3-[(1-oxo-1,3-dihydro-2H-isoindol-2-yl)methyl]-1H-pyrazol-1-yl}nicotinamide;
N-(1-amino-1,2-dioxo-3-heptanyl)-2-[3-(1-piperidinylmethyl)-1Hpyrazol-1-yl]nicotinamide;
N-(1-amino-1,2-dioxo-3-heptanyl)-2-{3-[(4,4-difluoro-1-piperidinyl)methyl]-1H-pyrazol-1-yl1}nicotinamide;
N-(1-amino-1,2-dioxo-3-heptanyl)-2-[3-(1,3-dihydro-2H-isoindol-2-ylmethyl)-1H-pyrazol-1-yl]nicotinamide;
N-(4-amino-3,4-dioxo-1-phenyl-2-butanyl)-2-(5-benzyl-4,5,6,7-tetrahydro-2H-pyrazolo[4,3-c]pyridin-2-yl)nicotinamide;
N-(4-amino-3,4-dioxo-1-phenyl-2-butanyl)-2-[5-(cyclopropylmethyl)-4,5,6,7-tetrahydro-2H-pyrazolo[4,3-c]pyridin-2-yl]nicotinamide;
N-(4-amino-3,4-dioxo-1-phenyl-2-butanyl)-2-(4,5,6,7-tetrahydro-2Hpyrazolo[4,3-c]pyridin-2-yl)nicotinamide;
tert-butyl 2-(3-(4-amino-3,4-dioxo-1-phenylbutan-2-ylcarbamoyl)pyridin-2-yl)-4,6-dihydropyrrolo[3,4-c]pyrazole-5(2H)-carboxylate;
N-(4-amino-3,4-dioxo-1-phenyl-2-butanyl)-2-(5,6-dihydropyrrolo[3,4-c]pyrazol-2(4H)-yl)nicotinamide;

tert-butyl 2-(3-(4-amino-3,4-dioxo-1-phenylbutan-2-yl-carbamoyl)pyridin-2-yl)-2,4,5,7-tetrahydro-6H-pyrazolo[3,4-c]pyridine-6-carboxylate;

N-(4-amino-3,4-dioxo-1-phenyl-2-butanyl)-2-(4,5,6,7-tetrahydro-pyrazolo[3,4-c]pyridin-2-yl)nicotinamide;

tert-butyl 2-(3-(4-amino-3,4-dioxo-1-phenylbutan-2-yl-carbamoyl)pyridin-2-yl)-2,5,6,7-tetrahydro-4H-pyrazolo[4,3-b]pyridine-4-carboxylate;

N-(4-amino-3,4-dioxo-1-phenyl-2-butanyl)-2-(4,5,6,7-tetrahydro-pyrazolo[4,3-b]pyridin-2-yl)nicotinamide;

N-(4-amino-3,4-dioxo-1-phenyl-2-butanyl)-2-(4-benzyl-4,5,6,7-tetrahydro-2H-pyrazolo[4,3-b]pyridin-2-yl)nicotinamide;

N-(4-amino-3,4-dioxo-1-phenyl-2-butanyl)-2[3-(1-methyl-4-piperidinyl)-1H-pyrazol-1-yl]nicotinamide; and N-(4-amino-3,4-dioxo-1-phenyl-2-butanyl)-2-(6-ethyl-4,5,6,7-tetrahydro-2H-pyrazolo[3,4-c]pyridin-2-yl)nicotinamide;

or a tautomer thereof, hydrate thereof, or pharmaceutically suitable salt thereof.

21. The carboxamide compound of claim 1, which has the S configuration at the carbon atom carrying the group R1.

22. A pharmaceutical composition comprising at least one carboxamide compound of claim 1 and a carrier.

\* \* \* \* \*